US008846702B2

(12) United States Patent
Kuduk et al.

(10) Patent No.: US 8,846,702 B2
(45) Date of Patent: *Sep. 30, 2014

(54) PYRANYL ARYL METHYL BENZOQUINAZOLINONE M1 RECEPTOR POSITIVE ALLOSTERIC MODULATORS

(75) Inventors: Scott D. Kuduk, Harleysville, PA (US); Ronald K. Chang, Oreland, PA (US); Thomas J. Greshock, Collegeville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/392,647

(22) PCT Filed: Aug. 26, 2010

(86) PCT No.: PCT/US2010/046733
§ 371 (c)(1),
(2), (4) Date: Feb. 27, 2012

(87) PCT Pub. No.: WO2011/025851
PCT Pub. Date: Mar. 3, 2011

(65) Prior Publication Data
US 2012/0157438 A1  Jun. 21, 2012

(51) Int. Cl.
| | | |
|---|---|---|
| A61K 31/505 | (2006.01) |
| C07D 239/70 | (2006.01) |
| C07D 417/14 | (2006.01) |
| C07D 471/04 | (2006.01) |
| C07D 405/14 | (2006.01) |
| C07D 491/04 | (2006.01) |
| A61K 31/517 | (2006.01) |
| C07D 401/14 | (2006.01) |
| C07D 405/04 | (2006.01) |

(52) U.S. Cl.
CPC ............ *A61K 31/517* (2013.01); *C07D 417/14* (2013.01); *C07D 471/04* (2013.01); *C07D 405/14* (2013.01); *C07D 491/04* (2013.01); *C07D 401/14* (2013.01); *C07D 405/04* (2013.01)
USPC .......................................... 514/267; 544/249

(58) Field of Classification Search
CPC ............................ A61K 31/517; C07D 401/14
USPC .................... 514/210.21, 267, 232.8, 252.16; 544/249, 115
See application file for complete search history.

(56) References Cited

U.S. PATENT DOCUMENTS

2008/0032973 A1   2/2008 Hong et al.
2011/0224198 A1*  9/2011 Beshore et al. ............ 514/228.2
2011/0301167 A1  12/2011 Beshore et al.

FOREIGN PATENT DOCUMENTS

| EA | 7483 | 10/2006 |
|---|---|---|
| RU | 2167877 | 5/1996 |
| WO | WO2011073639 | 9/2004 |
| WO | WO2008002621 | 1/2008 |
| WO | WO2009042177 | 4/2009 |
| WO | WO2010059773 | 5/2010 |
| WO | WO 2010059773 A1 * | 5/2010 |
| WO | WO2010123716 | 10/2010 |
| WO | WO2011041143 | 4/2011 |
| WO | WO2011049731 | 4/2011 |
| WO | WO2011/075371 | 6/2011 |
| WO | WO2011137049 | 11/2011 |

OTHER PUBLICATIONS

Watt, M.L., et al. "Pharmacological Characterization of LY593093, an M1 Muscarinic Acetylcholine Receptor-Selective Partial Orthosteric Agonist." The Journal of Pharmacology and Experimental Therapeutics. vol. 338, No. 3, (2011), pp. 622-632.*
Patani, G.A., et al. "Bioisosterism: A Rational Approach in Drug Design." Chem. Rev. (1996), vol. 96, pp. 3147-3176.*
American Chemical Society (ACS). STN Chemical Abstract Service (CAS) RN Database. © 2013.*
R. M. Eglen et al., "Therapeutic Opportunities from Muscarinic Receptor Research", 2001, pp. 409-414, vol. 22, No. 8, Trends in Pharmacological Sciences.
A. Fisher, Therapeutic Strategies in Alzheimer's Disease: M1 Muscarinic Agonists, 2000, pp. 101-112, vol. 84, Jpn. J. Pharmacol.
T. A. Spalding et al., "Discovery of an Ectopic Activation Site on the M1 Muscarinic Receptor", 2002, pp. 1297-1302, Molecular Pharmacology.

(Continued)

*Primary Examiner* — Andrew D Kosar
*Assistant Examiner* — John S Kenyon
(74) *Attorney, Agent, or Firm* — Sylvia A. Ayler; John C. Todaro

(57) ABSTRACT

The present invention is directed to pyranyl aryl methyl benzoquinazolinone compounds of formula (I) which are M1 receptor positive allosteric modulators and that are useful in the treatment of diseases in which the M1 receptor is involved, such as Alzheimer's disease, schizophrenia, pain or sleep disorders. The invention is also directed to pharmaceutical compositions comprising the compounds, and to the use of the compounds and compositions in the treatment of diseases mediated by the M1 receptor.

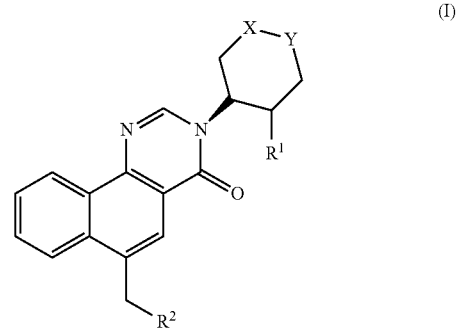

40 Claims, No Drawings

(56) References Cited

OTHER PUBLICATIONS

S. Lazareno et al., "Analogs of WIN 62.577 Define a Second Allosteric Site on Muscarinic Receptors", 2002, pp. 1492-1505, vol. 62, Molecular Pharmacology.

S. Lazareno et al., "Allosteric Interactions of Staurosporine and Other Indolocarbazoles with N-[methyl-3-H] Scopolamine and Acetylcholine at Muscarinic Receptor Subtypes: Identification of a Second Allosteric Site",2000, pp. 194-207, vol. 58, Molecular Pharmacology.

M. P. Caulfield, "Muscarinic Receptors-Characterization, Coupling and Function", 1993, pp. 319-379, vol. 58, Pharma. Ther.

N. J. M. Birdsall et al., "Multiple Allosteric Sites on Muscarinic Receptors", 2001, pp. 2517-2524, vol. 68, Life Sciences.

A. Christopoulos et al., "Allosteric Binding Sites on Cell-Surface Receptors: Novel Targets for Drug Discovery", 2002, pp. 198-210, Natural Reviews, Drug Discovery.

H. Brauner-Osborne et al., "Pharmacology of Muscarinic Acetylcholine Receptor Subtypes (m1-m5): High Throughput Assays in Mammalian Cells". 1996, vol. 295, pp. 93-102, E. Journal of Pharmacology.

Peng et al., Structure and Function Prediction of Human Muscarinic Acetylcholine Receptor 1, Cation-P1 Studies, and Protein Design, PhD Thesis, California Institute of Technology, Pasadena, California, 2005, Abstract, p. 12, pp. 16-39, Figs 1-3; Figs 8-16).

\* cited by examiner

PYRANYL ARYL METHYL BENZOQUINAZOLINONE M1 RECEPTOR POSITIVE ALLOSTERIC MODULATORS

CROSS REFERENCE TO RELATED APPLICATIONS

This application is the National Stage of International Application No. PCT/US2010/046733 filed on Aug. 26, 2010, which claims the benefit under 35 U.S.C. 119(e) of U.S. Provisional Application Nos. 61/238,457, filed Aug. 31, 2009.

FIELD OF THE INVENTION

The invention is directed to a class of pyranyl aryl methyl benzoquinazolinone compounds, their salts, pharmaceutical compositions comprising them and their use in therapy of the human body. In particular, the invention is directed to a class of pyranyl aryl methyl benzoquinazolinone compounds which are muscarinic M1 receptor positive allosteric modulators, and hence are useful in the treatment of Alzheimer's Disease and other diseases mediated by the muscarinic M1 receptor.

BACKGROUND OF THE INVENTION

Alzheimer's Disease is a common neurodegenerative disease affecting the elderly, resulting in progressive memory impairment, loss of language and visuospatial skills, and behavior deficits. Characteristics of the disease include degeneration of cholinergic neurons in the cerebral cortex, hippocampus, basal forebrain, and other regions of the brain, neurofibrillary tangles, and accumulation of the amyloid β peptide (Aβ). Aβ is a 39-43 amino acid produced in the brain by processing of the beta-amyloid precursor protein (APP) by the beta-amyloid protein cleaving enzyme ("beta secretase" or "BACE") and gamma-secretase. The processing leads to accumulation of Aβ in the brain.

Cholinergic neurotransmission involves the binding of acetylcholine either to the nicotinic acetylcholine receptor (nAChR) or to the muscarinic acetylcholine receptor (mAChR). It has been hypothesized that cholinergic hypofunction contributes to the cognitive deficits of patients suffering from Alzheimer's Disease. Consequently, acetyl cholinesterase inhibitors, which inhibit acetylcholine hydrolysis, have been approved in the United States for use in the treatment of the cognitive impairments of Alzheimer's Disease patients. While acetyl cholinesterase inhibitors have provided some cognitive enhancement in Alzheimer's Disease patients, the therapy has not been shown to change the underlying disease pathology.

A second potential pharmacotherapeutic target to counteract cholinergic hypofunction is the activation of muscarinic receptors. Muscarinic receptors are prevalent throughout the body. Five distinct muscarinic receptors (M1-M5) have been identified in mammals. In the central nervous system, muscarinic receptors are involved in cognitive, behavior, sensory, motor and autonomic functions. The muscarinic M1 receptor, which is prevalent in the cerebral cortex, hippocampus and striatum, has been found to have a major role in cognitive processing and is believed to have a role in the pathophysiology of Alzheimer's Disease. See Eglen et al, *TRENDS in Pharmacological Sciences,* 2001, 22:8, 409-414.

In addition, unlike acetyl cholinesterase inhibitors, which are known to provide only symptomatic treatment, M1 agonists also have the potential to treat the underlying disease mechanism of Alzheimer's Disease. The cholinergic hypothesis of Alzheimer's Disease is linked to both β-amyloid and hyperphosphorylated tau protein. Formation of β-amyloid may impair the coupling of the muscarinic receptor with G-proteins. Stimulation of the M1 muscarinic receptor has been shown to increase formation of the neuroprotective αAPPs fragment, thereby preventing the formation of the Aβ peptide. Thus, M1 agonists may alter APP processing and enhance αAPPs secretion. See Fisher, *Jpn J Pharmacol,* 2000, 84:101-112 However, M1 ligands which have been developed and studied for Alzheimer's Disease have produced side effects common to other muscarinic receptor ligands, such as sweating, nausea and diarrhea. See Spalding et al, *Mol Pharmacol,* 2002, 61:6, 1297-1302.

The muscarinic receptors are known to contain one or more allosteric sites, which may alter the affinity with which muscarinic ligands bind to the primary binding or orthosteric sites. See, e.g., S. Lazareno et al, *Mol Pharmacol,* 2002, 62:6, 1491-1505; S. Lazareno et al, *Mol Pharmacol,* 2000, 58, 194-207. See also U.S. 61/199,740, U.S. 61/329,690; 61/286, 122; 61/253,629; 61/247,705; 61/238,457; 61/208,331; and 61/170,744.

Thus the compounds of the invention, which are muscarinic M1 receptor positive allosteric modulators, are believed to be useful in the treatment of Alzheimer's Disease and other diseases mediated by the muscarinic M1 receptor.

SUMMARY OF THE INVENTION

The present invention is directed to pyranyl aryl methyl benzoquinazolinone compounds of generic formula (I)

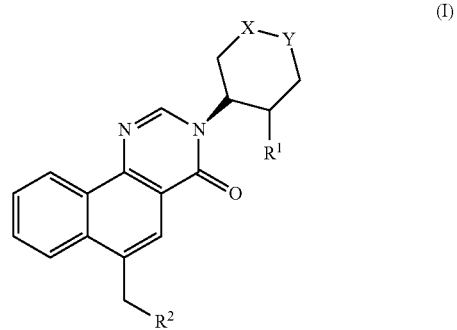

(I)

or a pharmaceutically acceptable salt thereof, which is useful as an M1 receptor positive allosteric modulator.

The invention is further directed to methods of treating a patient (preferably a human) for diseases or disorders in which the M1 receptor is involved, such as Alzheimer's disease, cognitive impairment, schizophrenia, pain disorders and sleep disorders, by administering to the patient a therapeutically effective amount of a compound of general formula (I), or a pharmaceutically acceptable salt thereof. The invention is also directed to pharmaceutical compositions which include an effective amount of a compound of formula (I), or a pharmaceutically acceptable salt thereof, and a pharmaceutically acceptable carrier, and the use of the compounds and pharmaceutical compositions of the invention in the treatment of such diseases.

DETAILED DESCRIPTION OF THE INVENTION

In one embodiment, the invention is directed to quinolinone-pyrazolone compounds of general formula

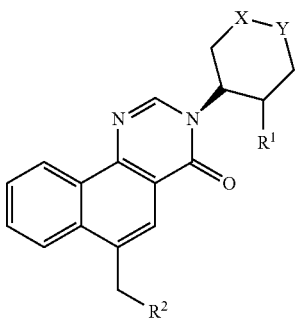

(I)

and pharmaceutically acceptable salts thereof, wherein X—Y is selected from the group consisting of
(1) —O—CR$^A$R$^B$—,
(2) —CR$^A$R$^B$—O—,
(3) —CR$^A$R$^B$—SR$^C$—,
(4) —CR$^A$R$^B$—NR$^C$—, and
(5) —NR$^C$—CR$^A$R$^B$—;
wherein R$^A$ and R$^B$ are each independently selected from the group consisting of,
(a) hydrogen, and
(b) —C$_{1-6}$ alkyl, and
R$^C$ is selected from the group consisting of,
(a) hydrogen,
(b) —C(=O)—C$_{1-6}$ alkyl,
(c) —C$_{1-6}$ alkyl,
(d) —C(=O)—CH$_2$—C$_6$H$_5$,
(e) —S(=O)$_2$—C$_{1-6}$ alkyl;
R$^1$ is selected from the group consisting of
(1) hydrogen, and
(2) hydroxy,
provided that when X—Y is when —O—CR$^A$R$^B$—, —CR$^A$R$^B$—O— or —CR$^A$R$^B$—SR$^C$—, then R$^1$ is hydroxy in the isomeric position:

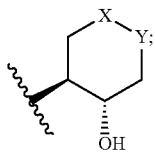

R$^2$ is selected from the group consisting of
(1) —C$_{6-10}$ aryl, or
(2)-heteroaryl, which is an aromatic cyclic group, having from five to twelve ring atoms, the ring atoms selected from C, O, N, N→O or S, at least one of which is O, N, N→O or S,
wherein the aryl or heteroaryl R$^2$ group is optionally substituted with one or more
(a) halogen,
(b) hydroxy,
(c) —NR$^3$R$^4$,
(d) —C$_{1-6}$ alkyl,
(e) —O—C$_{1-6}$ alkyl,
(f) —C$_{2-8}$ alkenyl,
(g) —C(=O)—(O)$_m$—R$^5$,
(h) —C(=O)—NR$^5$,
(i) —S(=O)$_2$—R$^5$,
(j) —SR$^5$,
(k) —CN;
(l) —C$_{6-10}$ aryl,
(m) heteroaryl, which is an aromatic cyclic group, having from five to twelve ring atoms, the ring atoms selected from C, O, N, N→O or S, at least one of which is O, N, N→O or S,
(n) Si(R$^6$)$_3$,
(o)=S,
wherein the alkyl, alkenyl, aryl or heteroaryl moiety is optionally substituted with one or more
(a) halogen,
(b) hydroxyl,
(c) —C$_{1-6}$ alkyl,
(d) —S—R$^6$,
(e) —NR$^8$R$^9$,
(f) —O—C$_{1-6}$ alkyl,
wherein the alkyl moiety is optionally substituted with one or more halogen;
R$^3$ and R$^4$, or R$^8$ and R$^9$, are independently selected from the group consisting of
(1) hydrogen, or
(2) —C$_{1-6}$ alkyl,
wherein the alkyl is optionally substituted with one or more
(a) halogen,
(b) hydroxyl,
(c) —O—C$_{1-6}$ alkyl,
(d) —NR$^{10}$R$^{11}$,
(e) —C(=O)—(O)$_n$—C$_{1-6}$ alkyl,
or R$^3$ and R$^4$, or R$^8$ and R$^9$, are linked together with the nitrogen to which they are attached to form a 4-6 membered carbocyclic ring, wherein one or two of the ring carbon atoms is optionally replaced by a nitrogen, oxygen or sulfur, and the ring is optionally substituted with one or more
(a) halogen,
(b) hydroxyl,
(c) C$_{1-6}$ alkyl,
(d) —O—C$_{1-6}$ alkyl,
(e) —C(=O)—(O)$_n$—C$_{1-6}$ alkyl;
R$^5$ is selected from the group consisting of
(1) hydrogen,
(2) —C$_{1-6}$ alkyl,
(3) —C$_{3-8}$ cycloalkyl,
(4) —C$_{2-8}$ alkenyl, or
(5) —C$_{6-10}$ aryl,
wherein the alkyl, cycloalkyl, alkenyl or aryl is optionally substituted with one or more
(a) halogen,
(b) hydroxyl,
(c) —C$_{1-6}$ alkyl,
(d) —O—C$_{1-6}$ alkyl,
(e) —C$_{3-8}$ cycloalkyl, or
(f) —C$_{6-10}$ aryl;
R$^6$ is selected from the group consisting of
(1) hydrogen, or
(2) —C$_{1-6}$ alkyl;
R$^{10}$ and R$^{11}$ are independently selected from the group consisting of
(1) hydrogen, or
(2) —C$_{1-6}$ alkyl,
wherein the alkyl is optionally substituted with one or more
(a) halogen,
(b) hydroxyl,
(c) —O—C$_{1-6}$ alkyl,
(d) —C(=O)—(O)$_n$—C$_{1-6}$ alkyl,
or R$^{10}$ and R$^{11}$ are linked together with the nitrogen to which they are attached to form a 4-6 membered carbocyclic ring, wherein one or two of the ring carbon atoms is optionally replaced by a nitrogen, oxygen or sulfur, and the ring is optionally substituted with one or more (a) halogen,
(b) hydroxyl,
(c) $C_{1-6}$ alkyl,
(d) —O—$C_{1-6}$ alkyl,
(e) —C(=O)—(O)$_n$—$C_{1-6}$ alkyl;

m is 0 or 1;
n is 0, 1 or 2.

In particular embodiments of the compounds of formula (I), $R^1$ is hydroxy. In particular embodiment, the $R^1$ hydroxy group is in the isomeric position:

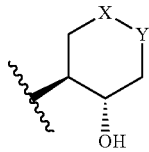

In particular embodiments of the compounds of formula (I), X—Y is —O—$CR^AR^B$— or —$CR^AR^B$—O—, wherein $R^A$ and $R^B$ are each hydrogen.

In other embodiments of the compounds of formula (I), X—Y is —$CR^AR^B$—$SR^C$, $CR^AR^B$—$NR^C$—, or —$NR^C$—$CR^AR^B$—, wherein $R^A$ and $R^B$ are each hydrogen, and $R^C$ is selected from the group consisting of,
(a) hydrogen,
(b) —C(=O)—$C_{1-6}$ alkyl,
(c) —$C_{1-6}$ alkyl,
(d) —C(=O)—$CH_2$—$C_6H_5$, and
(e) —S(=O)$_2$—$C_{1-6}$ alkyl, In particular embodiments of the compounds of formula (I), $R^2$ is —$C_{6-10}$ aryl (for example, phenyl), substituted as described above.

In particular embodiments of the compounds of formula (I), $R^2$ is heteroaryl, which is an aromatic cyclic group, having from five to twelve ring atoms, the ring atoms selected from C, O, N, N→O or S, at least one of which is O, N, N→O or S, substituted as described above.

One exemplary $R^2$ heteroaryl group is heteroaryls having five ring atoms, the ring atoms selected from C, N, N→O and S, wherein one or two of the ring atoms is N, N→O or S (for example, imidazolyl, pyrazolyl, thiazolyl).

Another exemplary $R^2$ heteroaryl group is heteroaryls having six ring atoms, the ring atoms selected from C, N and N→O, wherein one or two of the ring atoms is N or N→O (for example, pyridyl, pyridyl N-oxide, pyrimidinyl). For example, in certain embodiments $R^2$ is pyridyl.

Another exemplary $R^2$ heteroaryl group is fused heteroaryls having nine or ten ring atoms, the ring atoms selected from C, O, N, N→O and S, wherein one, two or three of the ring atoms is O; N, N→O or S (for example, quinoline, benzothiazole, dioxolopyridine, benzothiadiazole, imidazopyridine, pyrrolopyridine and dihydropyrrolopyridine).

In particular embodiments of the compounds of formula (I), when $R^2$ is —$C_{6-10}$ aryl, the aryl is optionally substituted with one or more
(a) halogen,
(b) —$NR^3R^4$,
(c) —O—$C_{1-6}$ alkyl, or
(d) —$C_{1-6}$ alkyl,
(e) —$C_{2-8}$ alkenyl,
(f) —$C_{6-10}$ aryl,
(g) heteroaryl, which is an aromatic cyclic group, having from five to twelve ring atoms, the ring atoms selected from C, O, N, N→O or S, at least one of which is O, N, N→O or S,
wherein the alkyl, alkenyl, aryl or heteroaryl group is optionally substituted with one or more
(i) halogen,
(ii) —$C_{1-6}$ alkyl,
(iii) —$NR^8R^9$,
(iv) —O—$C_{1-6}$ alkyl,
wherein the alkyl moiety is optionally substituted with one or more halogen.

In particular embodiments of the compounds of formula (I), when $R^2$ is a heteroaryl group having five ring atoms, the ring atoms selected from C, N, N→O and S, wherein one or two of the ring atoms is N, N→O or S, the heteroaryl is optionally substituted with one or more
(a) halogen,
(b) —O—$C_{1-6}$ alkyl,
(c) —$C_{1-6}$ alkyl,
(d) —$C_{6-10}$ aryl,
(e) heteroaryl which is an aromatic cyclic group, having from five to twelve ring atoms, the ring atoms selected from C, O, N, N→O or S, at least one of which is O, N, N→O or S,
wherein the alkyl, aryl or heteroaryl moiety is optionally substituted with one or more
(i) halogen,
(ii) —$C_{1-6}$ alkyl,
(iii) —$NR^8R^9$,
(iv) —O—$C_{1-6}$ alkyl,
wherein the alkyl moiety is optionally substituted with one or more halogen.

In particular embodiments of the compounds of formula (I), when $R^2$ is a heteroaryl group having six ring atoms, the ring atoms selected from C, N and N→O, wherein one or two of the ring atoms is N or N→O, the heteroaryl is optionally substituted with one or more
(a) halogen,
(b) hydroxy,
(c) —$NR^3R^4$,
(d) —O—$C_{1-6}$ alkyl,
(e) —$C_{1-6}$ alkyl,
(f) —$C_{2-8}$ alkenyl,
(g) —C(=O)—(O)$_m$—$R^5$,
(h) —C(=O)—$NR^5$,
(i) —S(=O)$_2$—$R^5$,
(j) —$SR^5$,
(k) —CN;
(l) —$C_{6-10}$ aryl,
(m) heteroaryl, which is an aromatic cyclic group, having from five to twelve ring atoms, the ring atoms selected from C, O, N, N→O or S, at least one of which is O, N, N→O or S,
(n) Si($R^6$)$_3$, or
(o)=S,
wherein the alkyl, aryl or heteroaryl moiety is optionally substituted with one or more
(i) halogen,
(ii) hydroxyl
(iii) —$C_{1-6}$ alkyl,
(iv) —S—$R^6$,
(v) —$NR^8R^9$,
(vi) —O—$C_{1-6}$ alkyl,
wherein the alkyl is optionally substituted with one or more halogen.

In particular embodiments of the compounds of formula (I), when $R^2$ is heteroaryl group having nine or ten ring atoms, the ring atoms selected from C, O, N, N→O and S, wherein one, two or three of the ring atoms is N, N→O, O or S, the heteroaryl is optionally substituted with one or more (a) halogen,
(b) —NR³R⁴,
(c) —O—C$_{1-6}$ alkyl,
(d) —C$_{1-6}$ alkyl,
(e) —C$_{6-10}$aryl,
(f) heteroaryl, which is an aromatic cyclic group, having from five to twelve ring atoms, the ring atoms selected from C, O, N, N→O or S, at least one of which is O, N, N→O or S,
wherein the alkyl, aryl or heteroaryl group is optionally substituted with one or more
(i) halogen,
(ii) —C$_{1-6}$ alkyl,
(iii) —NR⁸R⁹,
(iv) —O—C$_{1-6}$ alkyl,
wherein the alkyl moiety is optionally substituted with one or more halogen.

In one embodiment, the invention is directed to methods of treating a patient (preferably a human) for diseases in which the M1 receptor is involved, such as Alzheimer's Disease, cognitive impairment, schizophrenia, pain disorders and sleep disorders, by administering to the patient a therapeutically effective amount of a compound of general formula (I).

The invention is also directed to the use of a compound of formula (I) for treating diseases or disorders in which the M1 receptor is involved, such as Alzheimer's disease, cognitive impairment, schizophrenia, pain disorders and sleep disorders.

The invention is also directed to medicaments or pharmaceutical compositions for treating diseases or disorders in which the M1 receptor is involved, such as Alzheimer's disease, cognitive impairment, schizophrenia, pain disorders and sleep disorders, which comprise a compound of formula (I), or a pharmaceutically acceptable salt thereof, and a pharmaceutically acceptable carrier.

The invention is further directed to a method for the manufacture of a medicament or a composition for treating diseases or disorders in which the M1 receptor is involved, such as Alzheimer's disease, cognitive impairment, schizophrenia, pain disorders and sleep disorders, comprising combining a compound of formula (I) with one or more pharmaceutically acceptable carriers.

Within the genus of compounds of formula (I), there is a sub-genus of compounds of formula (II):

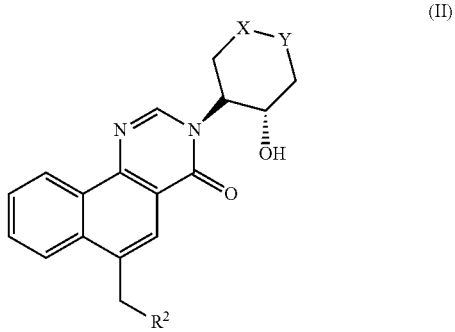

(II)

and pharmaceutically acceptable salts thereof, wherein X, Y and R² are as described above.

In particular embodiments of the compounds of formula (II), X—Y is —O—CR$^A$R$^B$— or —CR$^A$R$^B$—O—, wherein R$^A$ and R$^B$ are each hydrogen.

In other embodiments of the compounds of formula (II), X—Y is —CR$^A$R$^B$—SR$^C$, CR$^A$R$^B$—NR$^C$—, or —NR$^C$—CR$^A$R$^B$—, wherein R$^A$ and R$^B$ are each hydrogen, and R$^C$ is selected from the group consisting of,
(a) hydrogen,
(b) —C(=O)—C$_{1-6}$ alkyl,
(c) —C$_{1-6}$ alkyl,
(d) —C(=O)—CH$_2$—C$_6$H$_5$,
(e) —S(=O)$_2$—C$_{1-6}$ alkyl.

In particular embodiments of the compounds of formula (II), R² is —C$_{6-10}$ aryl (for example, phenyl), substituted as described above.

In particular embodiments of the compounds of formula (II), R² is heteroaryl, which is an aromatic cyclic group, having from five to twelve ring atoms, the ring atoms selected from C, O, N, N→O or S, at least one of which is O, N, N→O or S, substituted as described above.

One exemplary R² heteroaryl group is heteroaryls having five ring atoms, the ring atoms selected from C, N, N→O and S, wherein one or two of the ring atoms is N, N→O or S (for example, imidazolyl, pyrazolyl, thiazolyl).

Another exemplary R² heteroaryl group is heteroaryls having six ring atoms, the ring atoms selected from C, N and N N→O, wherein one or two of the ring atoms is N or N N→O (for example, pyridyl, pyridyl N-oxide, pyrimidinyl). For example, in certain embodiments R² is pyridyl.

Another exemplary R² heteroaryl group is fused heteroaryls having nine or ten ring atoms, the ring atoms selected from C, O, N, N→O and S, wherein one, two or three of the ring atoms is N, N N→O, O or S (for example, quinoline, benzothiazole and pyridinylpyrrole).

In particular embodiments of the compounds of formula (II), when R² is —C$_{6-10}$ aryl, the aryl is optionally substituted with one or more
(a) halogen,
(b) —NR³R⁴,
(c) —O—C$_{1-6}$ alkyl, or
(d) —C$_{1-6}$ alkyl,
(e) —C$_{2-8}$ alkenyl,
(f) —C$_{6-10}$ aryl,
(g) heteroaryl, which is an aromatic cyclic group, having from five to twelve ring atoms, the ring atoms selected from C, O, N, N→O or S, at least one of which is O, N, N→O or S,
wherein the alkyl, alkenyl, aryl or heteroaryl moiety is optionally substituted with one or more
(i) halogen,
(ii) —C$_{1-6}$ alkyl,
(iii) —NR⁸R⁹,
(iv) —O—C$_{1-6}$ alkyl,
wherein the alkyl moiety is optionally substituted with one or more halogen.

In particular embodiments of the compounds of formula (II), when R² is a heteroaryl group having five ring atoms, the ring atoms selected from C, N, N→O and S, wherein one or two of the ring atoms is N, N→O or S, the heteroaryl is optionally substituted with one or more
(a) halogen,
(b) —O—C$_{1-6}$ alkyl,
(c) —C$_{1-6}$ alkyl,
(d) —C$_{6-10}$ aryl,
(e) heteroaryl which is an aromatic cyclic group, having from five to twelve ring atoms, the ring atoms selected from C, O, N, N→O or S, at least one of which is O, N, N→O or S,
wherein the alkyl, aryl or heteroaryl moiety is optionally substituted with one or more
(i) halogen,
(ii) —C$_{1-6}$ alkyl, (iii) —NR$^8$R$^9$,
(iv) —O—C$_{1-6}$ alkyl,
wherein the alkyl moiety is optionally substituted with one or more halogen.

In particular embodiments of the compounds of formula (II), when R$^2$ is a heteroaryl group having six ring atoms, the ring atoms selected from C, N and N→O, wherein one or two of the ring atoms is N or N→O, the heteroaryl is optionally substituted with one or more
(a) halogen,
(b) hydroxy,
(c) —NR$^3$R$^4$,
(d) —O—C$_{1-6}$ alkyl,
(e) —C$_{1-6}$ alkyl,
(f) —C$_{2-8}$ alkenyl,
(g) —C(=O)—(O)$_m$—R$^5$,
(h) —C(=O)—NR$^5$,
(i) —S(=O)$_2$—R$^5$,
(j) —SR$^5$,
(k) —CN;
(l) —C$_{6-10}$ aryl,
(m) heteroaryl, which is an aromatic cyclic group, having from five to twelve ring atoms, the ring atoms selected from C, O, N, N→O or S, at least one of which is O, N, N→O or S,
(n) Si(R$^6$)$_3$
wherein the alkyl, aryl or heteroaryl moiety is optionally substituted with one or more
(i) halogen,
(ii) hydroxyl
(iii) —C$_{1-6}$ alkyl,
(iv) —S—R$^5$,
(v) —NR$^8$R$^9$,
(vi) —O—C$_{1-6}$ alkyl,
wherein the alkyl is optionally substituted with one or more halogen.

In particular embodiments of the compounds of formula (II), when R$^2$ is a heteroaryl group having nine or ten ring atoms, the ring atoms selected from C, O, N, N→O and S, wherein one, two or three of the ring atoms is N, N→O or S, the heteroaryl is optionally substituted with one or more
(a) halogen,
(b) —NR$^3$R$^4$,
(c) —O—C$_{1-6}$ alkyl,
(d) —C$_{1-6}$ alkyl,
(e) —C$_{6-10}$aryl,
(f) heteroaryl, which is an aromatic cyclic group, having from five to twelve ring atoms, the ring atoms selected from C, O, N, N→O or S, at least one of which is O, N, N→O or S,
wherein the alkyl, aryl or heteroaryl moiety is optionally substituted with one or more
(i) -halogen,
(ii) —C$_{1-6}$ alkyl,
(iii) —NR$^8$R$^9$,
(iv) —O—C$_{1-6}$ alkyl,
wherein the alkyl moiety is optionally substituted with one or more halogen.

Within the genus of compounds of formula (I), there is a sub-genus of compounds of formula (III):

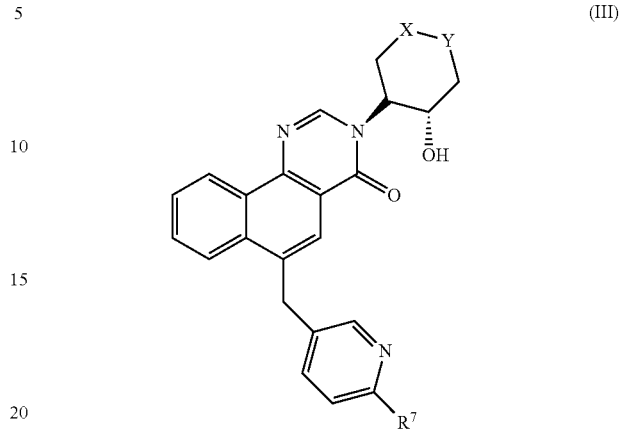

and pharmaceutically acceptable salts thereof, wherein X and Y are as described above, and R$^7$ is selected from the group consisting of
(1) halogen,
(2) hydroxy,
(3) —NR$^3$R$^4$,
(4) —C$_{1-6}$ alkyl,
(5) —O—C$_{1-6}$ alkyl,
(6) —C$_{2-8}$ alkenyl,
(7) —C(=O)—(O)$_m$—R$^5$,
(9) —C(=O)—NR$^5$,
(10) —S(=O)$_2$—R$^5$,
(11) —SR$^5$,
(12) —CN;
(13) —C$_{6-10}$aryl,
(14) heteroaryl, which is an aromatic cyclic group, having from five to twelve ring atoms, the ring atoms selected from C, O, N, N→O or S, at least one of which is O, N, N→O or S,
(15) Si(R$^6$)$_3$,
(16) =S, or
(17) hydrogen,
wherein the alkyl, alkenyl, aryl or heteroaryl moiety is optionally substituted with one or more
(a) halogen,
(b) —C$_{1-6}$ alkyl,
(c) —S—R$^6$,
(d) —NR$^8$R$^9$,
(e) —O—C$_{1-6}$ alkyl,
wherein the alkyl moiety is optionally substituted with one or more halogen.

In particular embodiment of compounds of formula (III), R$^7$ is selected from the group consisting of
(1) halogen,
(2) hydroxy,
(3) —NR$^3$R$^4$,
(4) —C$_{1-6}$ alkyl,
(5) —O—C$_{1-6}$ alkyl,
(6) —S(=O)$_2$—R$^5$, or
(7) —SR$^5$.

In particular embodiments of compounds of formula (III), X—Y is selected from the group consisting of
(1) —O—CR$^A$R$^B$—, or
(2) —CR$^A$R$^B$—O—.

In one embodiment, the compounds of formula (I) are compounds of formula (IV)

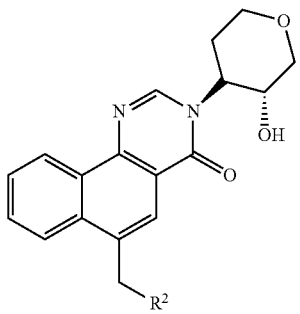

wherein R² is as described above.

In particular embodiments of the compounds of formula (IV), R² is —C₆₋₁₀ aryl (for example, phenyl), substituted as described above.

In particular embodiments of the compounds of formula (IV), R² is heteroaryl, which is an aromatic cyclic group, having from five to twelve ring atoms, the ring atoms selected from C, O, N, N→O or S, at least one of which is O, N, N→O or S, substituted as described above.

One exemplary R² heteroaryl group is heteroaryls having five ring atoms, the ring atoms selected from C, N, N→O and S, wherein one or two of the ring atoms is N, N→O or S (for example, imidazolyl, pyrazolyl, thiazolyl).

Another exemplary R² heteroaryl group is heteroaryls having six ring atoms, the ring atoms selected from C, N and N→O, wherein one or two of the ring atoms is N or N→O (for example, pyridyl, pyridyl N-oxide, pyrimidinyl). For example, in certain embodiments R² is pyridyl.

Another exemplary R² heteroaryl group is fused heteroaryls having nine or ten ring atoms, the ring atoms selected from C, O, N, N→O and S, wherein one, two or three of the ring atoms is N, N→O, O or S (for example, quinoline, benzothiazole, dioxolopyridine, benzothiadiazole, imidazopyridine, pyrrolopyridine and dihydropyrrolopyridine).

In particular embodiments of the compounds of formula (IV), when R² is —C₆₋₁₀ aryl, the aryl is optionally substituted with one or more
(a) halogen,
(b) —NR³R⁴,
(c) —O—C₁₋₆ alkyl, or
(d) —C₁₋₆ alkyl,
(e) —C₂₋₈ alkenyl,
(f) —C₆₋₁₀ aryl,
(g) heteroaryl, which is an aromatic cyclic group, having from five to twelve ring atoms, the ring atoms selected from C, O, N, N→O or S, at least one of which is O, N, N→O or S,
wherein the alkyl, alkenyl, aryl or heteroaryl group is optionally substituted with one or more
(i) halogen,
(ii) —C₁₋₆ alkyl,
(iii) —NR⁸R⁹,
(iv) —O—C₁₋₆ alkyl,
wherein the alkyl is optionally substituted with one or more halogen.

In particular embodiments of the compounds of formula (IV), when R² is a heteroaryl group having five ring atoms, the ring atoms selected from C, N, N→O and S, wherein one or two of the ring atoms is N, N→O or S, the heteroaryl is optionally substituted with one or more (a) halogen,
(b) —O—C₁₋₆ alkyl,
(c) —C₁₋₆ alkyl,
(d) —C₆₋₁₀ aryl,
(e) heteroaryl, which is an aromatic cyclic group, having from five to twelve ring atoms, the ring atoms selected from C, O, N, N→O or S, at least one of which is O, N, N→O or S,
wherein the alkyl, aryl or heteroaryl moiety is optionally substituted with one or more
(i) halogen,
(ii) —C₁₋₆ alkyl,
(iii) —NR⁸R⁹,
(iv) —O—C₁₋₆ alkyl,
wherein the alkyl moiety is optionally substituted with one or more halogen.

In particular embodiments of the compounds of formula (IV), when R² is a heteroaryl group having six ring atoms, the ring atoms selected from C, N and N→O, wherein one or two of the ring atoms is N or N→O, the heteroaryl is optionally substituted with one or more (a) halogen,
(b) hydroxy,
(c) —NR³R⁴,
(d) —O—C₁₋₆ alkyl,
(e) —C₁₋₆ alkyl,
(f) —C₂₋₈ alkenyl,
(g) —C(=O)—(O)ₘ—R⁵,
(h) —C(=O)—NR⁵,
(i) —S(=O)₂—R⁵,
(j) —SR⁵,
(k) —CN;
(l) —C₆₋₁₀ aryl,
(m) heteroaryl, which is an aromatic cyclic group, having from five to twelve ring atoms, the ring atoms selected from C, O, N, N→O or S, at least one of which is O, N, N→O or S,
(n) Si(R⁶)₃, or
(o) =S,
wherein the alkyl, aryl or heteroaryl moiety is optionally substituted with one or more
(iii) halogen,
(iv) hydroxyl
(v) —C₁₋₆ alkyl,
(vi) —S—R⁵,
(b) —NR⁸R⁹,
(vii) —O—C₁₋₆ alkyl,
wherein the alkyl moiety is optionally substituted with one or more halogen.

In particular embodiments of the compounds of formula (II), when R² is a heteroaryl group having nine or ten ring atoms, the ring atoms selected from C, O, N, N→O and S, wherein one, two or three of the ring atoms is N, N→O, O or S, the heteroaryl is optionally substituted with one or more
(a) halogen,
(b) —NR³R⁴,
(c) —O—C₁₋₆ alkyl,
(d) —C₁₋₆ alkyl,
(e) —C₆₋₁₀ aryl,
(f) heteroaryl, which is an aromatic cyclic group, having from five to twelve ring atoms, the ring atoms selected from C, O, N, N→O or S, at least one of which is O, N, N→O or S,
wherein the alkyl, aryl or heteroaryl group is optionally substituted with one or more
(i) halogen,
(ii) —C₁₋₆ alkyl, (iii) —NR$^8$R$^9$,
(iv) —O—C$_{1-6}$ alkyl,
wherein the alkyl moiety is optionally substituted with one or more halogen.

Specific embodiments of formula (I) are described herein as Examples 1-163, including 1-37, as set forth below:

6-[(6-Chloropyridin-3-yl)methyl]-3-[(3R,4S)-3-hydroxytetrahydro-2H-pyran-4-yl]benzo[h]quinazolin-4(3H)-one;
3-[(3R,4S)-3-Hydroxytetrahydro-2H-pyran-4-yl]-6-{[(6-methylthio)pyridin-3-yl]methyl]benzo[h]quinazolin-4(3H)-one;
3-[(3R,4S)-3-Hydroxytetrahydro-2H-pyran-4-yl]-6-[(6-methylpyridin-3-yl)methyl]benzo[h]quinazolin-4(3H)-one;
3-[(3R,4S)-3-Hydroxytetrahydro-2H-pyran-4-yl]-6-{[6-(1-methyl-1H-pyrazol-4-yl)pyridine-3-yl]methyl}benzo[h]quinazolin-4(3H)-one;
3-[(3R,4S)-3-Hydroxytetrahydro-2H-pyran-4-yl]-6-{[6-(1H-pyrazol-1-yl)pyridine-3-yl]methyl}benzo[h]quinazolin-4(3H)-one;
3-[(3R,4S)-3-Hydroxytetrahydro-2H-pyran-4-yl]-6-(pyridine-3-ylmethyl)benzo[h]quinazolin-4(3H)-one;
3-[(3R,4S)-3-Hydroxytetrahydro-2H-pyran-4-yl]-6-[(6-methoxypyridin-3-yl)methyl]benzo[h]quinazolin-4(3H)-one;
5-({3-[(3R,4S)-3-Hydroxytetrahydro-2H-pyran-4-yl]-4-oxo-3,4-dihydrobenzo[h]quinazolin-6-yl}methyl)pyridine-2-carbonitrile;
6-[(6-Ethylpyridin-3-yl)methyl]-3-[(3R,4S)-3-hydroxytetrahydro-2H-pyran-4-yl]benzo[h]quinazolin-4(3H)-one;
6-[(6-Acetylpyridin-3-yl)methyl]-3-[(3R,4S)-3-hydroxytetrahydro-2H-pyran-4-yl]benzo[h]quinazolin-4(3H)-one;
6-{[6-(1-Hydroxy-1-methylethyl)pyridine-3-yl]methyl}-3-[(3R,4S)-3-hydroxytetrahydro-2H-pyran-4-yl]benzo[h]quinazolin-4(3H)-one;
3-[(3R,4S)-3-Hydroxytetrahydro-2H-pyran-4-yl]-6-(4-motpholin-4-ylbenzyl)benzo[h]quinazolin-4(3H)-one;
3-[(3R,4S)-3-Hydroxytetrahydro-2H-pyran-4-yl]-6-{[6-(1,3-thiazol-4-yl)pyridine-3-yl]methyl}benzo[h]quinazolin-4(3H)-one;
6-[(6-Chloro-1-oxidopyridin-3-yl)methyl]-3-[(3R,4S)-3-hydroxytetrahydro-2H-pyran-4-yl]benzo[h]quinazolin-4(3H)-one;
6-[(2-Chloropyridin-4-yl)methyl]-3-[(3R,4S)-3-hydroxytetrahydro-2H-pyran-4-yl]benzo[h]quinazolin-4(3H)-one;
3-[(3R,4S)-3-Hydroxytetrahydro-2H-pyran-4-yl]-6-{[6-(methylsulfonyl)pyridine-3-yl]methyl}benzo[h]quinazolin-4(3H)-one;
3-[(3R,4S)-3-Hydroxytetrahydro-2H-pyran-4-yl]-6-{[6-(methylsulfinyl)pyridine-3-yl]methyl}benzo[h]quinazolin-4(3H)-one;
5-({3-[(3R,4S)-3-Hydroxytetrahydro-2H-pyran-4-yl]4-oxo-3,4-dihydrobenzo[h]quinazolin-6-yl}methyl)pyridine-2-carboxylic acid;
5-({3-[(3R,4S)-3-Hydroxytetrahydro-2H-pyran-4-yl]-4-oxo-3,4-dihydrobenzo[h]quinazolin-6-yl}methyl)-N,N-dimethylpyridine-2-carboxamide;
3-[(3R,4S)-3-Hydroxytetrahydro-2H-pyran-4-yl]-6-{[6-(1-methoxy-1-methylethyl)pyridine-3-yl]methyl}benzo[h]quinazolin-4(3H)-one;
6-{[6-(Hydroxymethyl)pyridine-3-yl]methyl}-3-[(3R,4S)-3-hydroxytetrahydro-2H-pyran-4-yl]benzo[h]quinazolin-4(3H)-one;
6-{[6-(Fluoromethyl)pyridine-3-yl]methyl}-3-[(3R,4S)-3-hydroxytetrahydro-2H-pyran-4-yl]benzo[h]quinazolin-4(3H)-one;
6-{[6-(Difluoromethyl)pyridine-3-yl]methyl}-3-[(3R,4S)-3-hydroxytetrahydro-2H-pyran-4-yl]benzo[h]quinazolin-4(3H)-one;
6-[(2-Chloro-1-oxidopyridin-4-yl)methyl]-3-[(3R,4S)-3-hydroxytetrahydro-2H-pyran-4-yl]benzo[h]quinazolin-4(3H)-one;
6-[(2-Fluoropyridin-4-yl)methyl]-3-[(3R,4S)-3-hydroxytetrahydro-2H-pyran-4-yl]benzo[h]quinazolin-4(3H)-one;
3-[(3R,4S)-3-Hydroxytetrahydro-2H-pyran-4-yl]-6-[(2-methoxypyridin-4-yl)methyl]benzo[h]quinazolin-4(3H)-one;
6-[(6-Ethyoxypyridin-3-yl)methyl]-3-[(3R,4S)-3-hydroxytetrahydro-2H-pyran-4-yl]benzo[h]quinazolin-4(3H)-one;
6-[(6-Hydroxypyridin-3-yl)methyl]-3-[(3R,4S)-3-hydroxytetrahydro-2H-pyran-4-yl]benzo[h]quinazolin-4(3H)-one;
6-{[6-(Difluoromethoxy)pyridine-3-yl]methyl}-3-[(3R,4S)-3-hydroxytetrahydro-2H-pyran-4-yl]benzo[h]quinazolin-4(3H)-one;
6-{[2-(Difluoromethoxy)pyridine-4-yl]methyl}-3-[(3R,4S)-3-hydroxytetrahydro-2H-pyran-4-yl]benzo[h]quinazolin-4(3H)-one;
6-[(3-Bromo-1-methyl-1H-pyrrolo[2,3-b]pyridine-4-yl)methyl]-3-[(3R,4S)-3-hydroxytetrahydro-2H-pyran-4-yl]benzo[h]quinazolin-4(3H)-one;
6-[(1-Ethyl-1H-pyrrolo[2,3-b]pyrdin-4-yl)methyl]-3-[(3R,4S)-3-hydroxytetrahydro-2H-pyran-4-yl]benzo[h]quinazolin-4(3H)-one;
6-[(6-Chloropyridin-3-yl)methyl]-3-[(3R,4S)-3 thiopyran-4-yl]benzo[h]quinazolin-4(3H)-one;
3-[(3S,4S)-4-Hydroxytetrahydro-2H-pyran-3-yl]-6-[(6'-methyl-2,3-bipyridin-5-yl)methyl]benzo[h]quinazolin-4(3H)-one;
rac-6-[(6-Chloropyridin-3-yl)methyl]-3-[(3R,4R)-3-hydroxypiperidin-4-yl]benzo quinazolin-4(3H)-one;
rac-3-[(3R,4R)-1-acetyl-3-hydroxypiperidin-4-yl]-6-[(6-chloropyridin-3-yl)methyl]benzo quinazolin-4(3H)-one;
6-[(6-Chloropyridin-3-yl)methyl]-3-piperidin-4-ylbenzo[h]quinazolin-4(3H)-one;
and pharmaceutically acceptable salts thereof.

The invention is also directed to methods of treating a patient (preferably a human) for diseases or disorders in which the M1 receptor is involved, such as Alzheimer's Disease, cognitive impairment, schizophrenia, pain disorders and sleep disorders, by administering to the patient a therapeutically effective amount of a compound of formulae (II) to (IV), or a pharmaceutically acceptable salt thereof.

The invention is also directed to the use of a compound of formulae (II) to (IV), for treating a disease or disorder in which the M1 receptor is involved, such as Alzheimer's Disease, cognitive impairment, schizophrenia, pain disorders and sleep disorders, by administering to the patient a compound of formulae (II) to (IV), or a pharmaceutically acceptable salt thereof.

The invention is also directed to medicaments or pharmaceutical compositions for the treatment of diseases or disorders in a patient (preferably a human) in which the M1 receptor is involved, such as Alzheimer's Disease, cognitive impairment, schizophrenia, pain disorders, and sleep disorders, which comprise a compound of formulae (II) to (IV), or a pharmaceutically acceptable salt thereof, and a pharmaceutically acceptable carrier.

The invention is also directed to a method for the manufacture of a medicament or a pharmaceutical composition for treating diseases in which M1 receptor is involved, such as Alzheimer's Disease, cognitive impairment, schizophrenia, pain disorders, and sleep disorders, comprising combining a compound of formulae (II) to (IV), or a pharmaceutically acceptable salt thereof, with a pharmaceutically acceptable carrier.

Where a variable occurs more than once in any of formulae (II) to (IV), or in a substituent thereof, the individual occurrences of that variable are independent of each other, unless otherwise specified.

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Preferred alkyl groups for use in the invention are $C_{1-6}$ alkyl groups, having from one to six atoms. Exemplary alkyl groups include methyl, ethyl, n-propyl, isopropyl, n-butyl, isobutyl, tert-butyl, pentyl, hexyl, and the like. $C_0$ alkyl means a bond.

As used herein, the term "alkenyl," by itself or as part of another substituent, means a straight or branched chain hydrocarbon radical having a single carbon-carbon double bond and the number of carbon atoms designated (e.g., $C_{2-10}$ alkenyl means an alkenyl group having from two to ten carbon atoms). Preferred alkenyl groups for use in the invention are $C_{2-6}$ alkenyl groups, having from two to six carbon atoms. Exemplary alkenyl groups include ethenyl and propenyl.

As used herein, the term "cycloalkyl," by itself or as part of another substituent, means a saturated cyclic hydrocarbon radical having the number of carbon atoms designated (e.g., $C_{3-12}$ cycloalkyl means a cycloalkyl group having from three to twelve carbon atoms). The term cycloalkyl as used herein includes mono-, bi- and tricyclic saturated carbocycles, spirocycles, and bridged and fused ring carbocycles.

Preferred cycloalkyl groups for use in the invention are monocyclic $C_{3-8}$ cycloalkyl groups, having from three to eight carbon atoms. Exemplary monocyclic cycloalkyl groups include cyclopropyl, cyclobutyl, cyclopentyl, cyclohexyl and the like. Exemplary bridged cycloalkyl groups include adamantyl and norbornyl. Exemplary fused cycloalkyl groups include decahydronaphthalene.

As used herein, the term "aryl," by itself or as part of another substituent, means an aromatic cyclic hydrocarbon radical. Preferred aryl groups have from six to ten carbons atoms. The term "aryl" includes multiple ring systems as well as single ring systems. Preferred aryl groups for use in the invention include phenyl and naphthyl.

The term "aryl" also includes fused cyclic hydrocarbon rings which are partially aromatic (i.e., one of the fused rings is aromatic and the other is non-aromatic). An exemplary aryl group which is partially aromatic is indanyl.

As used herein, the term "heteroaryl," by itself or as part of another substituent, means a cyclic or polycyclic group having from five to twelve ring atoms selected from C, N, N→O, O and S, wherein at least one ring heteroatom is O, N, N→O or S, and wherein at least one of the constituent rings is aromatic. Exemplary heteroaryl groups for use in the invention include carbazolyl, carbolinlyl, chromenyl, cinnolinyl, furanyl, benzofuranyl, benzofurazanyl, isobenzofuranyl, imidazolyl, benzimidazolyl, benzimidazolonyl, indazolyl, indolyl, isoindolyl, indolinyl, indolazinyl, indynyl, oxadiazolyl, oxazolyl, benzoxazolyl, isoxazolyl, pyranyl, pyrazinyl, pyrazolyl, benzopyrazolyl, pyridazinyl, pyridyl, pyrimidinyl, pyrrolyl, quinolyl, isoquinolyl, tetrazolyl, thiazolyl, isothiazolyl, thiadiazolyl, thienyl, benzothioenyl, benzothiazolyl, quinoxalinyl, triazinyl and triazolyl, and N-oxides thereof.

One subgroup of heteroaryl groups have five ring atoms, the ring atoms selected from C, N, N→O or S, wherein one or two of the ring atoms is N, N→O or S. Exemplary heteroaryl groups in this embodiment are imidazolyl, pyrazolyl and thiazolyl.

Another subgroup of heteroaryl groups have six ring atoms, the ring atoms selected from C, N and N→O, wherein one or two of the ring atoms is N or N→O. Exemplary heteroaryl groups in this embodiment are pyridyl, pyridyl-N-oxide and pyrimidinyl.

Another subgroup of heteroaryl groups have nine or ten ring atoms, the ring atoms selected from C, N, N→O and S, wherein one or two of the ring atoms is N, N→O or S. Exemplary heteroaryl groups in this embodiment are quinoline, benzothiazole, dioxolopyridine, benzothiadiazole, imidazopyridine, pyrrolopyridine and dihydropyrrolopyridine.

The term "heteroaryl" also includes fused cyclic heterocyclic rings which are partially aromatic (i.e., one of the fused rings is aromatic and the other is non-aromatic). An exemplary heteroaryl group which is partially aromatic is benzodioxol.

When a heteroaryl group as defined herein is substituted, the substituent may be bonded to a ring carbon atom of the heteroaryl group, or on a ring heteroatom (i.e., a nitrogen, oxygen or sulfur), which has a valence which permits substitution. Preferably, the substituent is bonded to a ring carbon atom. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment. Preferably, the attachment is at a ring carbon atom.

As used herein, the term "halo" or "halogen" includes fluoro, chloro, bromo and iodo.

The compounds of the invention may have one or more asymmetric centers. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of the compounds of formulae (I) to (IV).

Formulae (I) to (IV) are shown above without a definite stereochemistry. The present invention includes all stereoisomers of formulae (I) to (IV), and pharmaceutically acceptable salts thereof.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers or diastereomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer or diastereomer of a compound may be obtained by stereoselective synthesis using optically pure starting materials or reagents of known configuration by methods well known in the art.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

The compounds of the invention may be prepared according to the following reaction Schemes, in which variables are as defined before or are derived, using readily available starting materials, from reagents and conventional synthetic procedures. It is also possible to use variants which are themselves known to those of ordinary skill in organic synthesis art, but are not mentioned in greater detail.

The present invention also provides a method for the synthesis of compounds useful as intermediates in the preparation of compounds of the invention.

A general synthesis is shown in Scheme 1. Treatment of 2-methyl-1-nitronaphthalene 1 with Bredereck's reagent affords compound 2. Oxidation of 2 with a reagent like potassium permanganate followed by esterification using anhydrous methanol saturated with HCl affords ester 3. Reduction of the nitro group via a catalyst such as palladium on carbon under an atmosphere of hydrogen is followed by bromination with bromine to afford 4. Hydrolysis of 4 using a base such as sodium hydroxide affords acid 5. Amide bond formation with (3R,4S)-4-aminotetrahydro-2H-pyran-3-ol using a coupling reagent such as BOP (Benzotriazolyloxytris(dimethylamino) phosphonium hexafluorophosphate) affords 6. Cyclization of 6 to benzoquinazolinone 7 is mediated by dimethylformamide dimethylacetal. Finally, Negishi cross coupling of 7 with the appropriate zinc reagent using a catalyst such as palladium tetrakis triphenylphosphine in a solvent like THF affords Example 1.

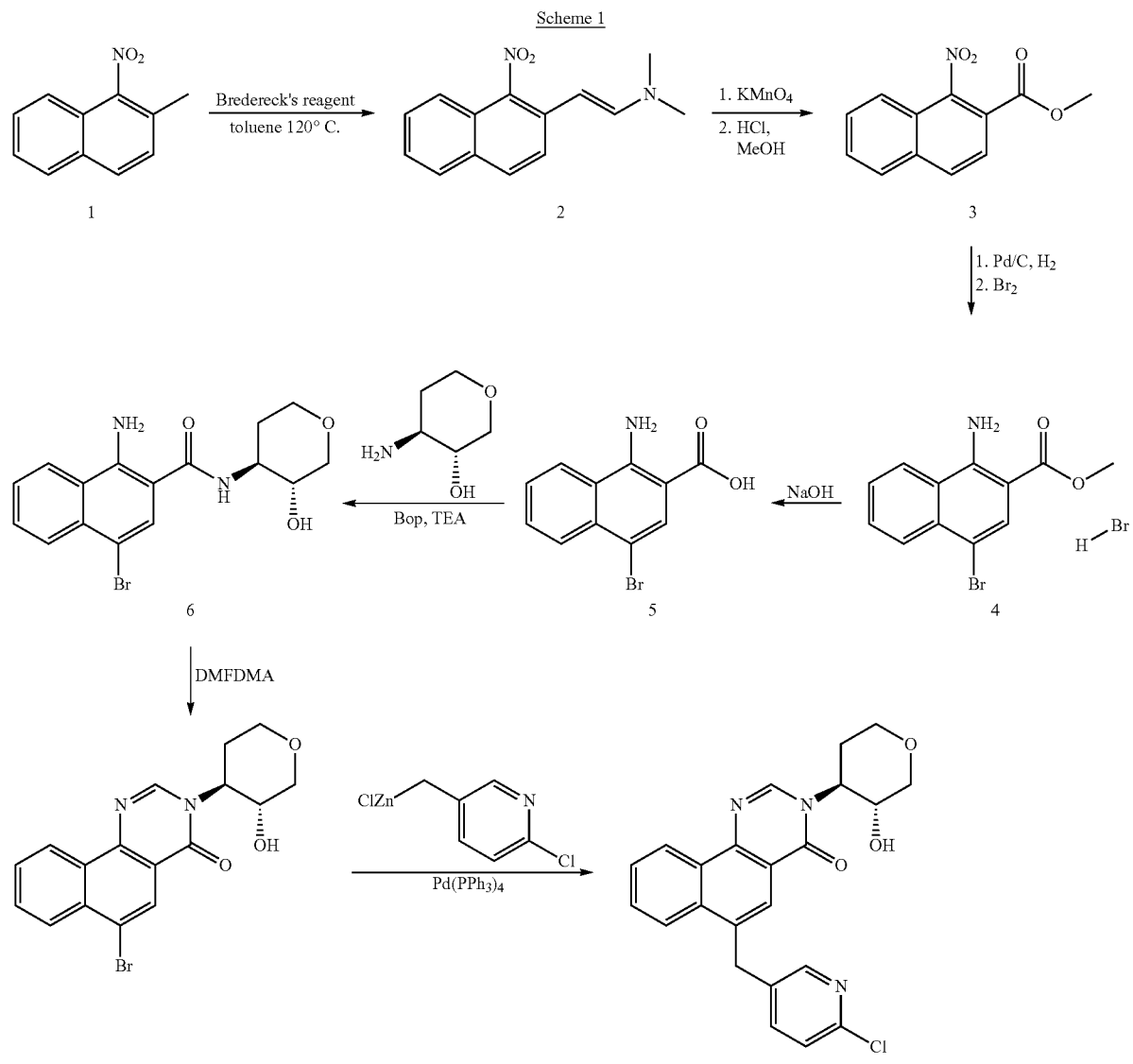

Scheme 2

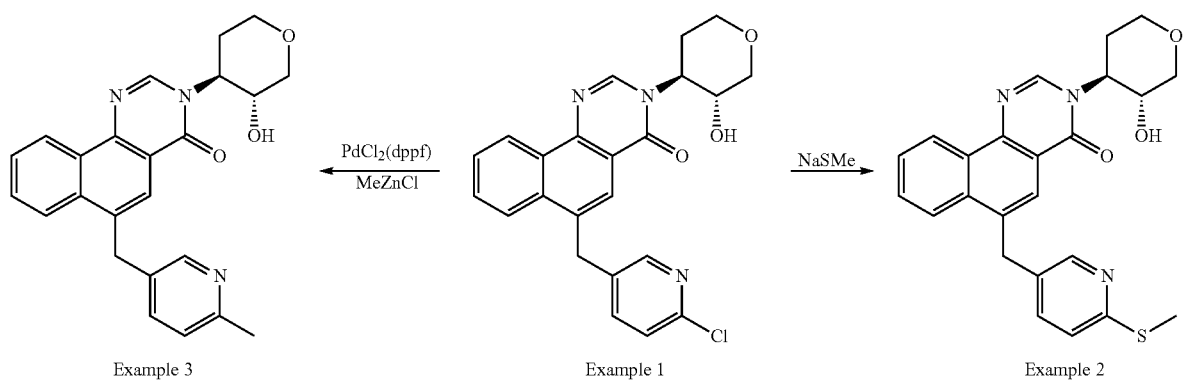

As shown in Scheme 2, Example 1 may be transformed into a number of other examples. Displacement of the chloride with a nucleophile such as sodium thiomethoxide in a solvent like DMSO or DMF at elevated temperature affords Example 2. Transition metal mediated cross-coupling of Example 1 with an organometal such as methylzinc chloride using a catalyst such as palladium in a suitable solvent like THF affords Example 3. A number of other organometals such a boronic acids, boronate esters, potassium fluoroborate salts, and tin reagents may also be employed.

Scheme 3

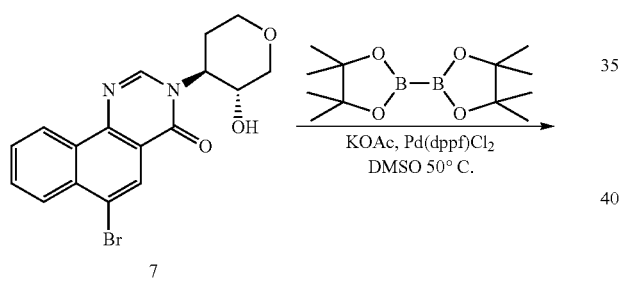

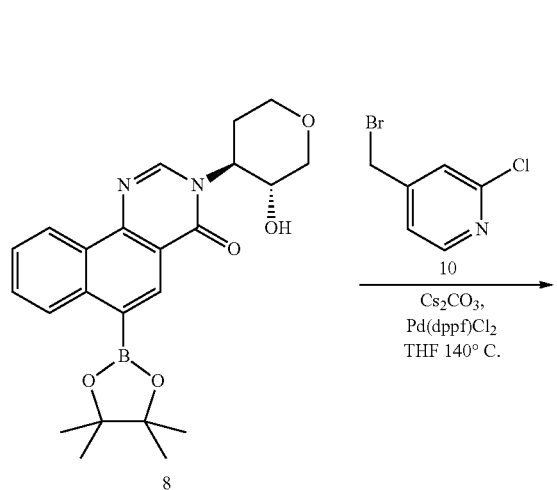

-continued

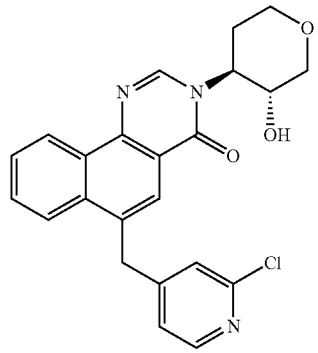

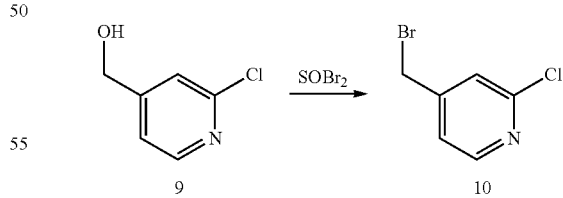

In Scheme 3, intermediate 7 may be converted to boronate ester 8 with pinacol diboron ester using a catalyst such as palladium, a base like potassium acetate in a solvent such as DMSO. Cross-coupling of 8 with bromide 10 using a catalyst like palladium, a base such as cesium carbonate in a solvent like THF affords Example 15. Bromide 10 may be produced from alcohol 9 using a reagent such as thionyl bromide in a solvent like dichloromethane.

Scheme 4
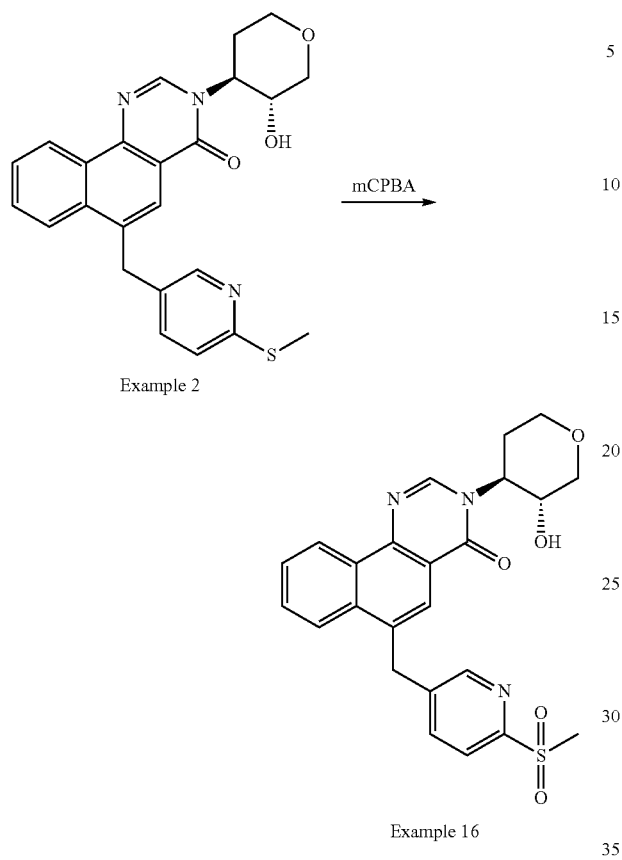
In addition, products may be converted further into other examples. As shown in Scheme 4, oxidation of Example 2 with an oxidant such as meta-chloroperoxybenzoic acids affords Example 16.
Scheme 5
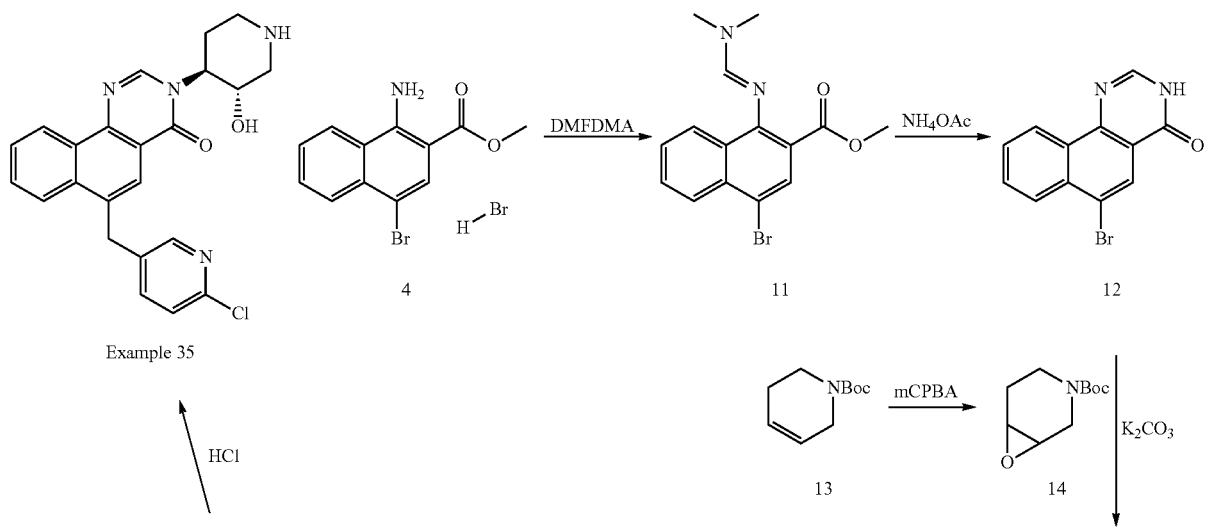

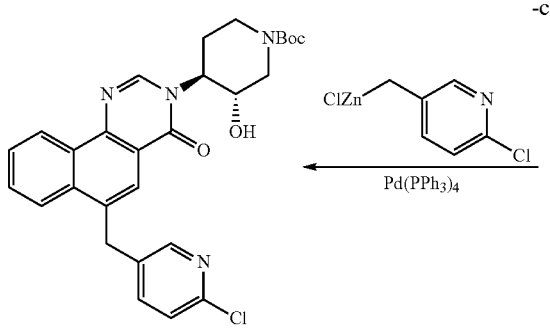

16

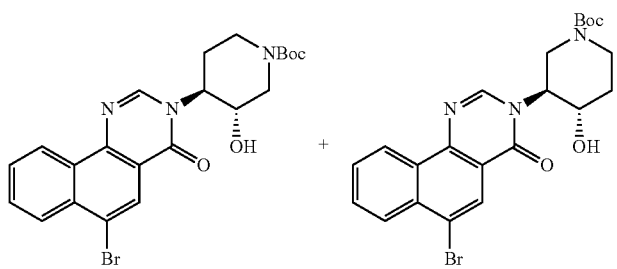

15

In Scheme 5, bromide 4 may be treated with dimethylformamide dimethylacetal to afford 11. Heating 11 with an ammonia source such as ammonium acetate in acetic acid affords benzoquinazolinone 12. Reaction of 12 with epoxide 14 in the presence of a base such as potassium carbonate and a solvent like DMF affords 15 as a mixture of regioisomers which can be separated. Cross-coupling as described in Example 1 affords 16. Removal of the tert-butoxycarbonyl group can be mediated using an acid such as HCl in a solvent like dioxane to afford Example 35.

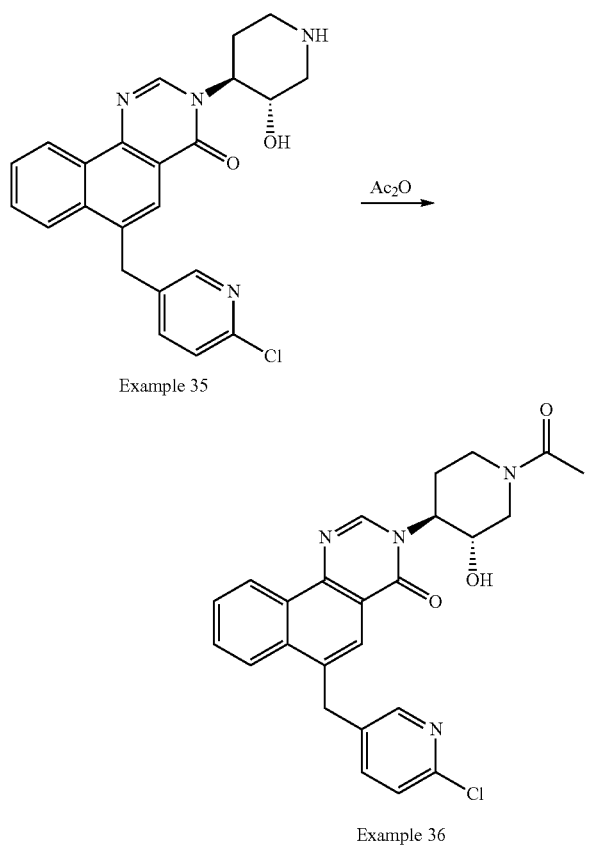

Example 35 can be further functionalized through chemistry off the piperidine ring. For example, acylation can be carried out using a reagent such as acetic anhydride in the presence of a base like triethylamine in a solvent like dichloromethane to afford Example 36

During any of the above synthetic sequences it may be necessary or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973, and T. W. Greene & P/G. M. Wuts, *Protective Groups in Organic Synthesis*, John Wiley & Sons, 1999. The protecting groups may be removed at a convenient sequent stage using methods known from the art.

The term "substantially pure" means that the isolated material is at least 90% pure, and preferably 95% pure, and even more preferably 99% pure as assayed by analytical techniques known in the art.

As used herein, the term "muscarinic M1 receptor" refers to one of the five subtypes of the muscarinic acetylcholine receptor, which is from the superfamily of G-protein coupled receptors. The family of muscarinic receptors is described, for example, in *Pharmacol Ther*, 1993, 58:319-379; *Eur J Pharmacol*, 1996, 295:93-102, and *Mol Pharmacol*, 2002, 61:1297-1302. The muscarinic receptors are known to contain one or more allosteric sites, which may alter the affinity with which muscarinic ligands bind to the primary binding or orthosteric sites. See, e.g., S. Lazareno et al, *Mol Pharmacol*, 2002, 62:6, 1491-1505.

As used herein, the terms "positive allosteric modulator" and "allosteric potentiator" are used interchangeably, and refer to a ligand which interacts with an allosteric site of a receptor to activate the primary binding site. The compounds of the invention are positive allosteric modulators of the muscarinic M1 receptor. For example, a modulator or potentiator may directly or indirectly augment the response produced by the endogenous ligand (such as acetylcholine or xanomeline) at the orthosteric site of the muscarinic M1 receptor in an animal, in particular, a human.

The actions of ligands at allosteric receptor sites may also be understood according to the "allosteric ternary complex model," as known by those skilled in the art. The allosteric ternary complex model is described with respect to the family of muscarinic receptors in Birdsall et al, *Life Sciences*, 2001, 68:2517-2524. For a general description of the role of allosteric binding sites, see Christopoulos, *Nature Reviews: Drug Discovery*, 2002, 1:198-210.

It is believed that the compounds of the invention bind to an allosteric binding site that is distinct from the orthosteric acetylcholine site of the muscarinic M1 receptor, thereby augmenting the response produced by the endogenous ligand acetylcholine at the orthosteric site of the M1 receptor. It is also believed that the compounds of the invention bind to an allosteric site which is distinct from the xanomeline site of the muscarinic M1 receptor, thereby augmenting the response produced by the endogenous ligand xanomeline at the orthosteric site of the M1 receptor.

The term "pharmaceutically acceptable salts" refers to salts prepared from pharmaceutically acceptable non-toxic bases or acids including inorganic or organic bases and inorganic or organic acids. The compounds of the invention may be mono, di or tris salts, depending on the number of acid functionalities present in the free base form of the compound. Free bases and salts derived from inorganic bases include aluminum, ammonium, calcium, copper, ferric, ferrous, lithium, magnesium, manganic salts, manganous, potassium, sodium, zinc, and the like.

Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, trifluoroacetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, para-toluenesulfonic acid, and the like.

The present invention is directed to the use of the compounds of formulae (I) to (III) disclosed herein as M1 allosteric modulators in a patient or subject such as a mammal in need of such activity, comprising the administration of an effective amount of the compound. In addition to humans, a variety of other mammals can be treated according to the method of the present invention.

The compounds of the present invention have utility in treating or ameliorating Alzheimer's disease. The compounds may also be useful in treating or ameliorating other diseases mediated by the muscarinic M1 receptor, such as schizophrenia, sleep disorders, pain disorders (including acute pain, inflammatory pain and neuropathic pain) and cognitive disorders (including mild cognitive impairment). Other conditions that may be treated by the compounds of the invention include Parkinson's Disease, pulmonary hypertension, chronic obstructive pulmonary disease (COPD), asthma, urinary incontinence, glaucoma, schizophrenia, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes, autism and atherosclerosis.

In preferred embodiments, the compounds of the invention are useful in treating Alzheimer's Disease, cognitive disorders, schizophrenia, pain disorders and sleep disorders. For example, the compounds may be useful for the prevention of dementia of the Alzheimer's type, as well as for the treatment of early stage, intermediate stage or late stage dementia of the Alzheimer's type.

Potential schizophrenia conditions or disorders for which the compounds of the invention may be useful include one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketanine and other dissociative anaesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline.

In another specific embodiment, the present invention provides a method for treating schizophrenia or psychosis comprising administering to a patient in need thereof an effective amount of a compound of the present invention. Particular schizophrenia or psychosis pathologies are paranoid, disorganized, catatonic or undifferentiated schizophrenia and substance-induced psychotic disorder. At present, the text revision of the fourth edition of the Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorder. As used herein, the term "schizophrenia or psychosis" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

Examples of combinations of the compounds include combinations with agents for the treatment of schizophrenia, for example in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, aiprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproelone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexyl)hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisuipride, benzhexyl, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

Potential sleep conditions or disorders for which the compounds of the invention may be useful include enhancing sleep quality; improving sleep quality; augmenting sleep maintenance; increasing the value which is calculated from the time that a subject sleeps divided by the tune that a subject is attempting to sleep; decreasing sleep latency or onset (the time it takes to fall asleep); decreasing difficulties in falling asleep; increasing sleep continuity; decreasing the number of awakenings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing daytime alertness; reducing daytime drowsiness; treating or reducing excessive daytime sleepiness; insomnia; hypersomnia; narcolepsy; interrupted sleep; sleep apnea; wakefulness; nocturnal myoclonus; REM sleep interruptions; jet-lag; shift workers' sleep disturbances; dyssomnias; night terror; insomnias associated with depression, emotional/mood disorders, as well as sleep walking and enuresis, and sleep disorders which accompany aging; Alzheimer's sun-downing; conditions associated with circadian rhythmicity as well as mental and physical disorders associated with travel across time zones and with rotating shift-work schedules; conditions due to drugs which cause reductions in REM sleep as a side effect; syndromes which are manifested by non-restorative sleep and muscle pain or sleep apnea which is associated with respiratory disturbances during sleep; and conditions which result from a diminished quality of sleep.

Pain disorders for which the compounds of the invention may be useful include neuropathic pain (such as postherpetic neuralgia, nerve injury, the "dynias", e.g., vulvodynia, phantom limb pain, root avulsions, painful diabetic neuropathy, painful traumatic mononeuropathy, painful polyneuropathy); central pain syndromes (potentially caused by virtually any lesion at any level of the nervous system); postsurgical pain syndromes (eg, postmastectomy syndrome, postthoracotomy syndrome, stump pain); bone and joint pain (osteoarthritis), repetitive motion pain, dental pain, cancer pain, myofascial pain (muscular injury, fibromyalgia); perioperative pain (general surgery, gynecological), chronic pain, dysmennorhea, as well as pain associated with angina, and inflammatory pain of varied origins (e.g. osteoarthritis, rheumatoid arthritis, rheumatic disease, teno-synovitis and gout), headache, migraine and cluster headache, headache, primary hyperalgesia, secondary hyperalgesia, primary allodynia, secondary allodynia, or other pain caused by central sensitization.

Compounds of the invention may also be used to treat or prevent dyskinesias. Furthermore, compounds of the invention may be used to decrease tolerance and/or dependence to opioid treatment of pain, and for treatment of withdrawal syndrome of e.g., alcohol, opioids, and cocaine.

The subject or patient to whom the compounds of the present invention is administered is generally a human being, male or female, in whom M1 allosteric modulation is desired, but may also encompass other mammals, such as dogs, cats, mice, rats, cattle, horses, sheep, rabbits, monkeys, chimpanzees or other apes or primates, for which treatment of the above noted disorders is desired.

The compounds of the present invention may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of combinations of the compounds of the present invention include combinations with anti-Alzheimer's Disease agents, for example beta-secretase inhibitors; alpha 7 nicotinic agonists; ADAM 10 ligands or activators; gamma-secretase inhibitors; gamma secretase modulators; tau phosphorylation inhibitors; glycine transport inhibitors; LXR β agonists; ApoE4 conformational modulators; NR2B antagonists; androgen receptor modulators; blockers of Aβ oligomer formation; 5-HT4 agonists; 5-HT6 antagonists; 5-HT1a antagonists, such as lecozotan; p25/CDK5 inhibitors; NK1/NK3 receptor antagonists; COX-2 inhibitors; HMG-CoA reductase inhibitors; NSAIDs including ibuprofen; vitamin E; anti-amyloid antibodies (including anti-amyloid humanized monoclonal antibodies), such as bapineuzumab; anti-inflammatory compounds such as (R)-flurbiprofen, nitroflurbiprofen; PPAR gamma agonists, such as pioglitazone and rosiglitazone; CB-1 receptor antagonists or CB-1 receptor inverse agonists; antibiotics such as doxycycline and rifampin; N-methyl-D-aspartate (NMDA) receptor antagonists, such as memantine and neramexane; cholinesterase inhibitors such as galantamine, rivastigmine, donepezil, tacrine, phenserine and ladostigil; growth hormone secretagogues such as ibutamoren, ibutamoren mesylate, and capromorelin; histamine $H_3$ receptor antagonists; AMPA agonists or AMPA modulators; PDE IV inhibitors; PDE10A inhibitors; $GABA_A$ inverse agonists; GSK3β inhibitors; neuronal nicotinic agonists; selective M1 agonists; HDAC inhibitors; and microtubule affinity regulating kinase (MARK) ligands; or other drugs that affect receptors or enzymes that either increase the efficacy, safety, convenience, or reduce unwanted side effects or toxicity of the compounds of the present invention.

Examples of combinations of the compounds include combinations with agents for the treatment of pain, for example non-steroidal anti-inflammatory agents, such as aspirin, diclofenac, duflunisal, fenoprofen, flurbiprofen, ibuprofen, indomethacin, ketoprofen, ketorolac, naproxen, oxaprozin, piroxicam, sulindac and tolmetin; COX-2 inhibitors, such as celecoxib, rofecoxib and valdecoxib; CB-2 agonists; VR-1 antagonists; bradykinin B 1 receptor antagonists; sodium channel blockers and antagonists; nitric oxide synthase (NOS) inhibitors (including iNOS and nNOS inhibitors); glycine site antagonists, including lacosamide; neuronal nicotinic agonists; NMDA antagonists; potassium channel openers; AMPA/kainate receptor antagonists; calcium channel blockers, such as ziconotide; GABA-A receptor IO modulators (e.g., a GABA-A receptor agonist); matrix metalloprotease (MMP) inhibitors; thrombolytic agents; opioid analgesics such as codeine, fentanyl, hydromorphone, levorphanol, meperidine, methadone, morphine, oxycodone, oxymorphone, pentazocine, propoxyphene; neutrophil inhibitory factor (NIF); pramipexole, ropinirole, anticholinergics; amantadine; monoamine oxidase B15 ("MAO-B") inhibitors; 5HT receptor agonists or antagonists; mGlu5 antagonists; alpha agonists; neuronal nicotinic agonists; NMDA receptor agonists or antagonists; NKI antagonists; selective serotonin reuptake inhibitors ("SSRI") and/or selective serotonin and norepinephrine reuptake inhibitors ("SSNRI"), such as duloxetine; tricyclic antidepressant drugs, norepinephrine modulators; lithium; valproate; gabapentin; pregabalin; rizatriptan; zolmitriptan; naratriptan and sumatriptan.

The compounds of the present invention may be administered in combination with compounds useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, orexin antagonists, alpha-1 antagonists, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, other orexin antagonists, orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexyl)hydrochloride, COMT inhibitors such as entacapone, MOA-B inhibitors, antioxidants, A2a adenosine receptor antagonists, cholinergic agonists and dopamine receptor agonists such as alentemol, bromocriptine, fenoldopam, lisuride, naxagolide, pergolide and pramipexole.

The term "composition" as used herein is intended to encompass a product comprising specified ingredients in predetermined amounts or proportions, as well as any product which results, directly or indirectly, from combination of the specified ingredients in the specified amounts. This tetra in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients.

In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound, which is a compound of formulae (I) to (VIII), is included in an amount sufficient to produce the desired effect upon the process or condition of diseases. Accordingly, the pharmaceutical compositions of the present invention encompass any composition made by admixing a compound of the present invention and a pharmaceutically acceptable carrier.

The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, or pharmaceutically acceptable salts thereof, may also be administered by controlled release means and/or delivery devices.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient.

Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the active ingredient in a vegetable oil, for example arachis oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, or in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can also be in a form suitable for rectal administration wherein the carrier is a solid. It is preferable that the mixture forms unit dose suppositories. Suitable carriers include cocoa butter and other materials commonly used in the art.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician.

As used herein, the term "treatment" or "treating" means any administration of a compound of the present invention and includes (1) inhibiting the disease in an animal that is experiencing or displaying the pathology or symptomatology of the diseased (i.e., arresting further development of the pathology and/or symptomatology), or (2) ameliorating the disease in an animal that is experiencing or displaying the pathology or symptomatology of the diseased (i.e., reversing the pathology and/or symptomatology).

The compositions containing compounds of the present invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage forms.

The compositions containing compounds of the present invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

When treating or ameliorating a disorder or disease for which compounds of the present invention are indicated, generally satisfactory results are obtained when the compounds of the present invention are administered at a daily dosage of from about 0.1 mg to about 100 mg per kg of animal body weight, preferably given as a single daily dose or in divided doses two to six times a day, or in sustained release form. The total daily dosage is from about 1.0 mg to about 2000 mg, preferably from about 0.1 mg to about 20 mg per kg of body weight. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The amount of active ingredient that may be combined with the carrier materials to produce a single dosage form will vary depending upon the host treated and the particular mode of administration. For example, a formulation intended for the oral administration to humans may conveniently contain from about 0.005 mg to about 2.5 g of active agent, compounded with an appropriate and convenient amount of carrier material. Unit dosage forms will generally contain between from about 0.005 mg to about 1000 mg of the active ingredient, typically 0.005, 0.01 mg, 0.05 mg, 0.25 mg, 1 mg, 5 mg, 25 mg, 50 mg, 100 mg, 200 mg, 300 mg, 400 mg, 500 mg, 600 mg, 800 mg or 1000 mg, administered once, twice or three times a day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the schemes and examples herein. Starting materials are made according to procedures known in the art or as illustrated herein. The following examples are provided so that the invention might be more fully understood.

EXAMPLE 1

6-[(6-Chloropyridin-3-yl)methyl]-3-[(3R,4S)-3-hydroxytetrahydro-2H-pyran-4-yl]benzo[h]quinazolin-4(3H)-one

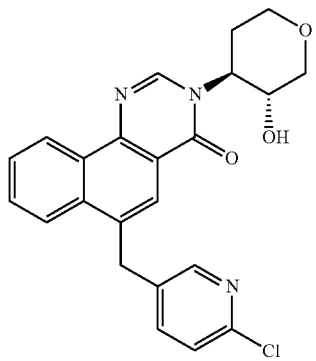

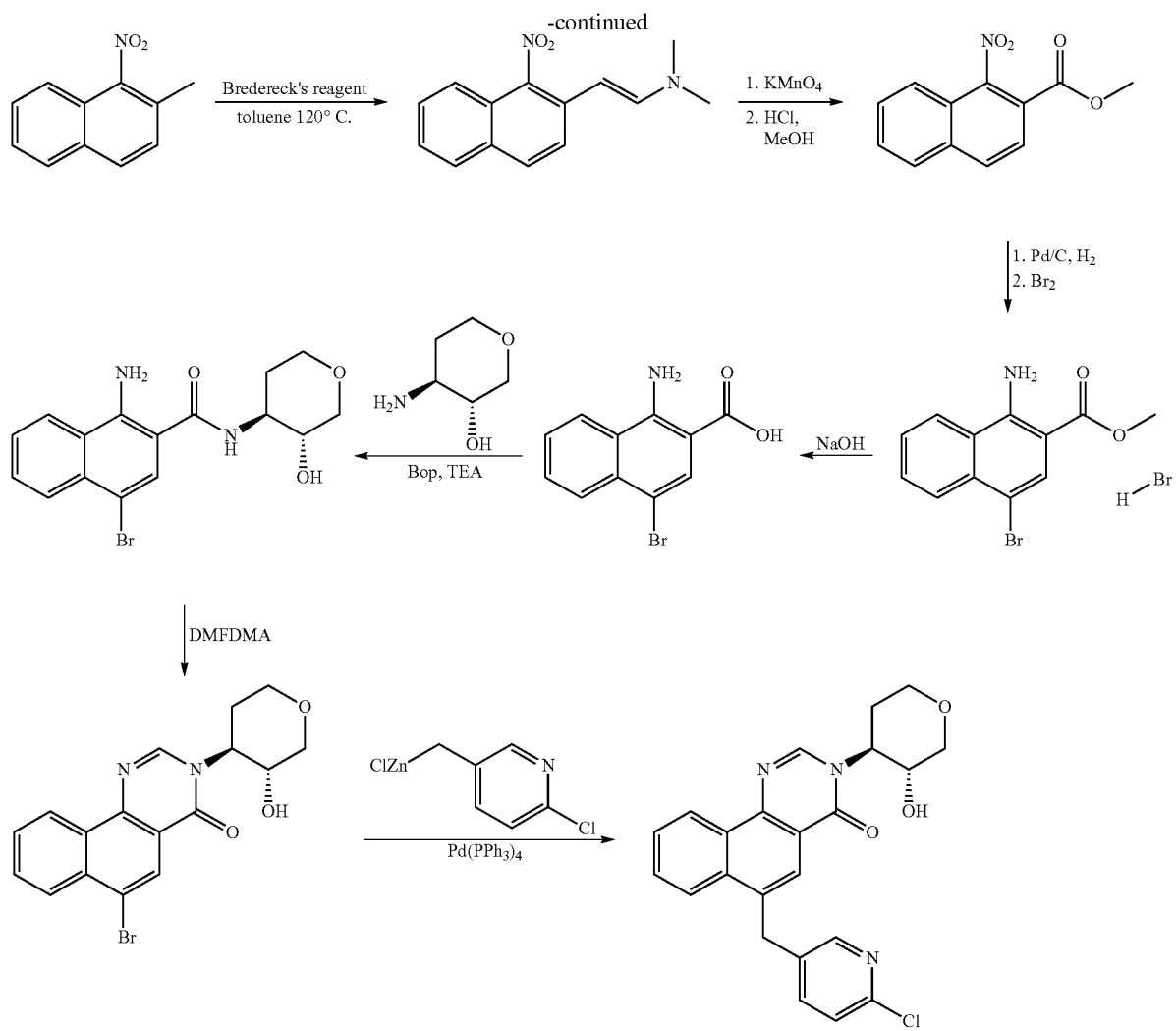

A solution of 2-methyl-1-nitronaphthalane (5.00 g, 26.7 mmol) and tert-butoxybis(dimethylamino)methane (Bredereck's reagent, 8.27 g, 40.1 mmol) in 10 mL of toluene was refluxed at 120° C. for 15 h. Additional tert-butoxybis(dimethylamino)methane (3.76 g, 13.4 mmol) was added and the reaction was refluxed at 120° C. for another 24 h. The mixture was cooled to rt and 50 mL of hexanes was added. After vigorously stirring for 30 min, a brick red solid was collected, washed with additional hexanes, and dried to provide (E)-N,N-dimethyl-2-(1-nitro-2-naphthyl)ethylenamine that gave proton NMR spectra consistent with theory.

To a solution of the above compound (10.0 g, 41.3 mmol) and potassium carbonate (13.7 g, 99.0 mmol) in 300 mL of 1:1 t-BuOH:$H_2O$ was added potassium permanganate (15.7 g, 99.0 mmol) slowly over 30 min. The reaction mixture was stirred at rt for 17 h, and a black precipitate was filtered and washed twice with 100 mL of water. The filtrate was concentrated to 200 mL in volume, and acidified with 6 N HCl to pH ~2. A beige precipitate was collected, washed twice with 100 mL of water, and dried to provide 1-nitro-2-naphthoic acid that gave proton NMR spectra consistent with theory and a mass ion (ES+) of 218.1 for [M+H]$^+$.

A solution of the above compound (32.5 g, 150 mmol) in 150 mL of MeOH was cooled to 0° C. and saturated with gaseous HCl. The solution was warmed to rt and then refluxed at 90° C. for 22 h. The solution was again saturated with $HCl_{(g)}$, refluxed at 90° C. for 20 h, then cooled to rt. The beige precipitate was collected, washed with water and MeOH, and dried to provide methyl 1-nitro-2-naphthoate that gave proton NMR spectra consistent with theory.

To a solution of the above compound (10.0 g, 43.3 mmol) in 250 mL of MeOH and 3 mL of THF was added palladium on carbon (0.100 g, 0.940 mmol). The reaction was placed under an atmosphere of hydrogen (1 atm) for 14 h. The mixture was filtered, the solids were washed with additional MeOH and the filtrate was concentrated in vacuo. The residue was concentrated twice with toluene and dried in vacuo to provide methyl 1-amino-2-naphthoate that gave a mass ion (ES+) of 202.1 for [M+H]$^+$.

To a solution of the above compound (8.70 g, 43.2 mmol) in a 200 mL mixture of 1:1 dioxane: $CCl_4$ at 0° C. was added a solution of bromine (2.23 mL, 43.2 mmol) in 40 mL of 1:1 dioxane: $CCl_4$ dropwise. The mixture was stirred at 0° C. for 2 h, filtered and washed with $Et_2O$, and dried to provide methyl 1-amino-4-bromo-2-naphthoate hydrobromide that gave proton NMR spectra consistent with theory.

To a solution of methyl 1-amino-4-bromo-2-naphthoate hydrobromide (2.00 g, 5.54 mmol) in 20 mL of THF was added sodium hydroxide (11.1 mL, 20% aqueous, 55.4 mmol). The mixture was stirred at 50° C. for 20 h, then heated at 90° C. for 2 h. The solvent was removed in vacuo and hydrochloric acid (1 N aqueous) was added until pH ~2. The beige solid was collected via filtration, washed twice with water, and dried to provide 1-amino-4-bromo-2-naphthoic acid that gave a mass ion (ES+) of 266.0 ($^{79}$Br) for [M+H]$^+$.

Synthesis of
(3R,4S)-4-Aminotetrahydro-2H-pyran-3-ol

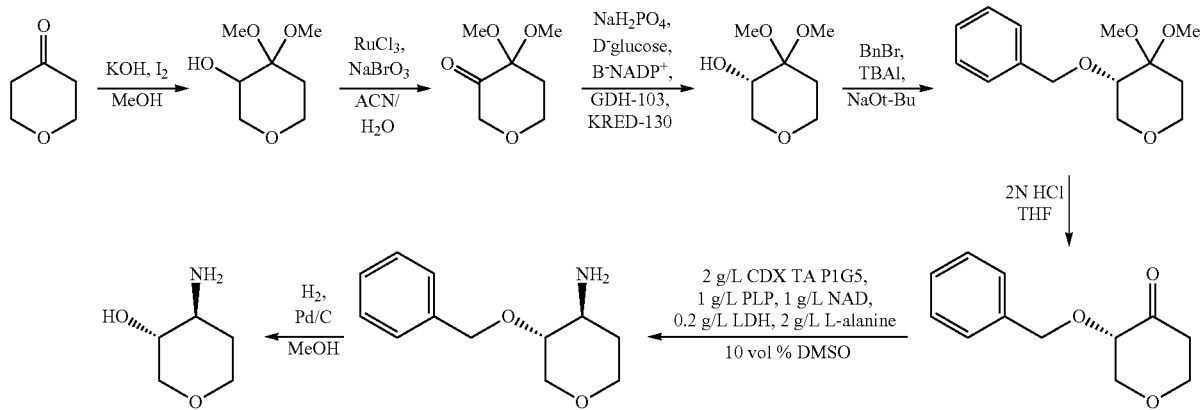

A jacketed flask equipped with an overhead stirrer and a thermocouple was charged with 23.0 L of MeOH, and cooled to 5° C. Potassium hydroxide (1.574 kg, 28.05 mol) was added to the flask, and the resulting solution was aged until homogeneous and recooled to 5° C. Tetrahydro-4H-pyran-4-one (1.00 kg, 10.0 mol) was then added at a steady rate over 20 min, and the resulting solution was aged for 20-30 min. A solution of iodine (2.778 kg, 10.95 mol) in 18.5 L of MeOH was then added via mechanical pump at a steady rate over 90-100 minutes. After an additional 30 min, the solution was warmed to rt and toluene (42.0 L) was added. The resulting slurry was concentrated in vacuo to a volume of ~8.4 L. Additional toluene (8.4 L) was added and the resulting solution was concentrated to a volume of 8.4 L 2x. The resulting slurry was then filtered, and the filter cake was rinsed 2x with toluene (4.0 L). The combined toluene streams were concentrated to ~6 L, and the product is extracted 2x with water (3.0 L) to provide 4,4-dimethyoxytetrahydro-2H-pyran-3-ol.

To a solution of the above compound (1.00 kg, 6.17 mol) in 5 L of water was added acetic acid to pH 5.2-5.4. The mixture was diluted with acetonitrile (4.0 L) and ruthenium trichloride hydrate (6.4 g, 0.028 mol) was added and rinsed in with additional acetonitrile (1.0 L). The flask was placed in a rt water bath and a solution of sodium bromate (650 g, 4.31 mol) in water (1.95 L) was added slowly over ~30 min, keeping the temperature below 30° C. After 2 h, potassium bicarbonate (430 g, 4.30 mol), sodium thiosulfate (1.07 kg, 4.31 mol), potassium chloride (500 g, 6.71 mol) and acetonitrile (5 L) were added sequentially. The layers were separated and the aqueous layer was extracted 3x with acetonitrile (10 L). The combined organic extracts were concentrated to ~4 L. Toluene (5 L) was then added and the mixture reconcentrated to 4 L 4x. The mixture was diluted with toluene (7 L) and filtered to remove solids. The filtercake was washed 3x with toluene (2 L) and the combined filtrate and washes were concentrated to a total volume of 3 L to provide an organic solution of 4,4-dimethoxydihydro-2H-pyran-3(4H)-one. To a 3 L 3-neck RB flask with overhead stirring, thermocouple and heating mantle was added sodium dihydrogenphosphate (96.0 g, 800 mmol) in 1.6 L of water. Sodium hydroxide (29 mL, 50 wt %) was added to pH 7.13, followed by hydrochloric acid (5 mL, 6 N) to pH 7.02.

The above organic solution of 4,4-dimethoxydihydro-2H-pyran-3(4H)-one was extracted 3x with phosphate buffered water (0.55 L). To the combined aqueous extracts was added D-glucose (180 g, 100 mmol), and the solution was heated to 30° C. When the solution exceeded 27° C. upon heating B-NADP+ (1.60 g, 499 mmol), GDH-103 (1.60 g, 499 mmol), and KRED-130 (1.60 g, 499 mmol) were added and the mixture was stirred for 17 h at 30° C. Potassium chloride (200 g, 2.68 mol) and acetonitrile (1.3 L) were added. After 30 min, the reaction mixture was transferred to 6 L sep funnel and additional MeCN (0.67 L) and toluene (0.87 L) were added. The aqueous layer was back extracted 1x with a mixture of acetonitrile (1.95 L) and toluene (0.65 L), and 1x with acetonitrile (1.5 L). The combined organic extracts were concentrated in vacuo to provide (3S)-4,4-dimethoxytetrahydro-2H-pyran-3-ol.

To a 2 L R$^B$ flask with overhead stirring, thermocouple, heating mantle and N$_2$ inlet was added a solution of the above compound (72.0 g, 0.444 mol) in 750 mL of THF. After 15 h, sodium tert-butoxide (48.3 g, 492 mmol) was added in one portion, and the mixture was heated to 35° C. for 1 h, and aged at 22° C. for 1 hr. Tetrabutylammonium iodide (8.19 g, 22.2 mmol) and benzyl bromide (56.5 ml, 466 mmol) were added, and the mixture was heated to 50° C. for 2 h. The solution was cooled to 25° C., and water (750 mL) and MtBE (2.25 L) were added. The organic layer was separated from the aqueous and concentrated in vacuo. The resultant brown oil was purified via silica gel chromatography, eluting with 0-15% ethyl acetate in hexanes to provide (3S)-3-(benzylyoxy)-4,4-dimethoxytetrahydro-2H-pyran.

To a solution of the above compound (61.1 g, 225 mmol) in 300 mL of THF was added 2 N HCl (300 mL, 0.600 mol). After 1.5 h, saturated aqueous potassium carbonate (60 mL) was added via addition funnel to pH 7.4. The aqueous layer was extracted 3x with MtBE (300 mL) and the combined organic extracts were concentrated in vacuo to provide crude (3S)-3-(benzyloxy)tetrahydro-4H-pyran-4-one.

To a solution of L-Alanine (200 g, 2.24 mol), sodium formate (76.0 g, 1.12 mmol), and sodium phosphate dibasic (28.7 g, 202 mmol) in 2.25 L of water adjusted to pH 7.5 was added NAD (2.2 g, 3.21 mmol), pyridoxal-5-phosphate (2.2 g, 8.90 mmol), LDH (0.45 g, 0.22 mol), FDH (4.5 g, 0.20 mol), and TA P1 G5 (4.5 g, 0.22 mol). After all the components were completely dissolved, (3S)-3-(benzyloxy)tetrahydro-4H-pyran-4-one (45 g, 0.22 mol) was added and the pH was adjusted to pH 7.25 with 6 N HCl and aged at 30° C. After 15 h, potassium carbonate (700 g, 5.06 mol) was added slowly, followed by ethyl acetate (2.2 L). The mixture was filtered through a bed of Solka Floc and the cake was washed with ethyl acetate (250 mL). The combined filtrates were separated and the aqueous layer was extracted a second time with ethyl acetate (2 L). The combined organic extracts were concentrated in vacuo to provide crude (3R,4S)-3-(benzyloxy)tetrahydro-2H-pyran-4-amine.

To a solution of the above compound (38.8 g, 0.187 mol) in 730 mL of methanol was added concentrated hydrochloric acid (23.3 mL). The solution was subjected to hydrogenation at 40 psi H$_2$, 25° C. over 5.8 g of 10% Pd/C (5.8 g). After 15 h, the mixture was filtered through solka floc and the filtercake was washed 5× with methanol (100 mL). The combined filtrate and washes were concentrated in vacuo to provide (3R,4S)-4-Aminotetrahydro-2H-pyran-3-ol that gave proton NMR spectra consistent with theory.

To a solution of 1-amino-4-bromo-2-naphthoic acid (0.644 g, 2.42 mmol) in 10 mL of acetonitrile cooled to 0° C. was added (1H-1,2,3-benzotriazol-1-yloxy)[tris(dimethylamino)]-phosphonium hexafluorophosphate (1.82 g, 4.12 mmol), O-(7-azabenzotriazol-1yl)-N,N,N,N'-tetramethyluronium hexafluorophosphate (0.921 g, 2.42 mmol), (3R,4S)-3-hydroxytetrahydro-2H-pyran-4-aminium chloride (0.310 g, 2.02 mmol), and triethylamine (0.84 mL, 6.1 mmol). The reaction was warmed to rt and stirred for 4 h. The mixture was diluted with ethyl acetate, washed with dilute aqueous sodium bicarbonate, dried over sodium sulfate, filtered, and concentrated in vacuo to provide crude 1-amino-4-bromo-N-[(3R,4S)-3-hydroxytetrahydro-2H-pyran-4-yl]-2-naphthamide that gave a mass ion (ES+) of 366.9 ($^{81}$Br) for [M+H]$^+$.

A solution of the above compound (0.737 g, 2.02 mmol) in N,N-dimethylformamide dimethylacetal (2.70 mL, 20.2 mmol) was heated at 85° C. for 3 h. The reaction was cooled to rt, concentrated in vacuo, and dried to provide 6-bromo-3-[(3R,4S)-3-hydroxytetrahydro-2H-pyran-4-yl]benzo[h]quinazolin-4(3H)-one that gave a mass ion (ES+) of 376.8 ($^{81}$Br) for [M+H]$^+$.

To a round bottom flask containing a solution of the above compound (3.65 g, 9.73 mmol) in 20 mL of THF at 0° C. under an atmosphere of nitrogen was added (2-chloro-5-pyridyl)methylzinc chloride (24.3 mL, 0.5 M in THF, 12.2 mmol) and bis(tri-tert-butylphosphine)palladium(0) (3 mol %). The reaction was warmed to rt, stirred for 15 min, then recooled to 0° C. and quenched with water (50 mL). The mixture was diluted with dichloromethane and water, and a beige solid was removed via filtration. The filtrate was extracted 2× with dichloromethane and the combined organic fractions were dried over sodium sulfate, filtered, and concentrated in vacuo. The residue was triturated with dichloromethane, and the resultant white solid was collected via filtration, washed with dichloromethane, and dried to provide the title compound that gave proton NMR spectra consistent with theory and a mass ion (ES+) of 422.1265 for [M+H]$^+$ [Calc'd for C$_{23}$H$_{21}$ClN$_3$O$_3$, [M+H]$^+$=422.1266.]: $^1$H NMR (400 MHz, CDCl$_3$) δ 8.96-8.94 (m, 1H), 8.30 (s, 2H), 7.89 (s, 1H), 7.79 (d, J=7.4 Hz, 1H), 7.67-7.60 (m, 2H), 7.32 (dd, 2.6 Hz, 8.2 Hz, 1H), 7.13 (d, J=8.2 Hz, 1H), 4.86-4.80 (m, 1H), 4.34 (s, 2H), 4.24-4.07 (m, 3H), 3.59-3.53 (m, 1H), 3.34-3.29 (m, 1H), 2.92-2.82 (m, 1H), 2.31-2.22 (m, 1H), 2.02-1.98 (m, 1H).

EXAMPLE 2

3-[(3R,4S)-3-Hydroxytetrahydro-2H-pyran-4-yl]-6-{[(6-methylthio)pyridin-3-yl)methyl]benzo[h]quinazolin-4(3H)-one

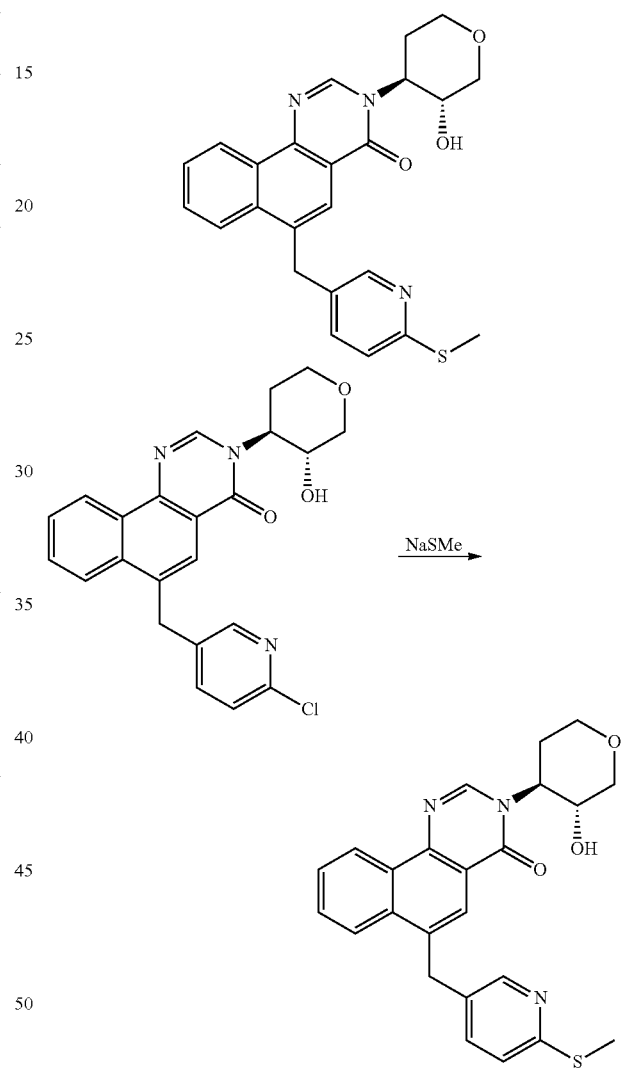

To a solution of 6-[(6-chloropyridin-3-yl)methyl]-3-[(3R,4S)-3-hydroxytetrahydro-2H-pyran-4-yl]benzo[h]quinazolin-4(3H)-one (Example 1, 0.065 g, 0.15 mmol) in 2 mL of MeOH was added sodium thiomethoxide (21.6 mg, 0.308 mmol) and 1 mL of DMF. The mixture was heated in a sealed tube at 100° C. for 24 h. Additional sodium thiomethoxide (0.100 g, 1.43 mmol) was added and the reaction was heated in a sealed tube at 140° C. for 8 hours, cooled to rt, and diluted with dichloromethane and water. The aqueous layer was extracted 3× with dichloromethane and the combined organic fractions were dried over sodium sulfate, filtered, and concentrated in vacuo. The residue was purified via silica gel chromatography, eluting with 0-5% methanol in dichloromethane, to provide the title compound that gave proton NMR spectra consistent with theory and a mass ion (ES+) of 434.1529 for [M+H]+ [Calc'd for $C_{24}H_{23}N_3O_3S$, [M+H]+= 434.1533.]: $^1$H NMR (400 MHz, $CDCl_3$) δ 8.76 (d, J=8.1 Hz, 1H), 8.25 (s, 1H), 8.22 (s, 1H), 7.66 (d, J=7.8 Hz, 1H), 7.61 (s, 1H), 7.58-7.49 (m, 3H), 7.10 (dd, J=2.3 Hz, 8.3 Hz, 1H), 6.94-6.92 (m, 1H), 4.79-4.72 (m, 1H), 4.35 (br s, 1H), 4.25-4.22 (m, 2H), 4.08 (s, 2H), 4.06-4.02 (m, 1H), 3.57-3.51 (m, 1H), 3.36-3.29 (m, 1H), 2.44 (s, 3H), 2.19-2.11 (m, 1H), 1.97-1.90 (m, 1H).

EXAMPLE 3

3-[(3R,4S)-3-Hydroxytetrahydro-2H-pyran-4-yl]-6-[(6-methylpyridin-3-yl)methyl]benzo[h]quinazolin-4(3H)-one

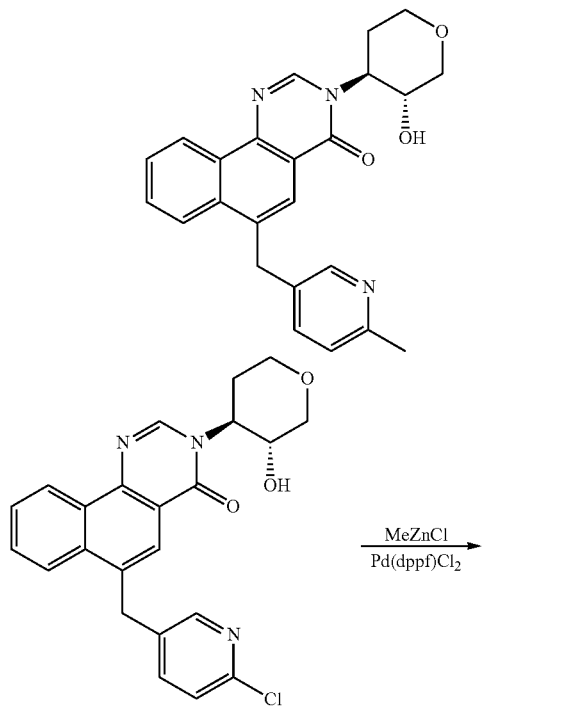

To a solution of 6-[(6-chloropyridin-3-yl)methyl]-3-[(3R,4S)-3-hydroxytetrahydro-2H-pyran-4-yl]benzo[h]quinazolin-4(3H)-one (Example 1, 0.040 g, 0.095 mmol) in 1 mL of THF under an atmosphere of nitrogen was added methyl zinc chloride (0.095 mL, 2 M in THF, 1.90 mmol) and [1,1'-bis(diphenylphosphino)ferrocene]dichloropalladium(II), 1:1 complex with DCM (3 mol %). The reaction was heated at 50° C. for 18 h, cooled to rt, and quenched with water (2 mL). The mixture was filtered through celite and the aqueous layer was extracted 2× with dichloromethane. The combined organic fractions were dried over sodium sulfate, filtered, and concentrated in vacuo. The residue was purified via silica gel chromatography, eluting with 10-60% ethyl acetate in hexanes, to provide the title compound that gave proton NMR spectra consistent with theory and a mass ion (ES+) of 401.46 for [M+H]+: $^1$H NMR (400 MHz, $CDCl_3$) δ 8.92 (d, J=7.5 Hz, 1H), 8.38 (s, 1H), 8.29 (s, 1H), 7.83 (d, J=7.3 Hz, 1H), 7.79 (s, 1H), 7.66-7.59 (m, 2H), 7.15 (d, J=8.1 Hz, 1H), 6.90 (d, J=7.9 Hz, 1H), 4.87-4.78 (m, 1H), 4.26-4.19 (m, 4H), 4.12-4.08 (m, 1H), 3.81 (br s, 1H), 3.61-3.54 (m, 1H), 3.44-3.37 (m, 1H), 2.43 (s, 3H), 2.33-2.23 (m, 1H), 2.03-1.99 (m, 1H).

EXAMPLE 4

3-[(3R,4S)-3-Hydroxytetrahydro-2H-pyran-4-yl]-6-{[6-(1-methyl-1H-pyrazol-4-yl)pyridine-3-yl]methyl}benzo[h]quinazolin-4(3H)-one

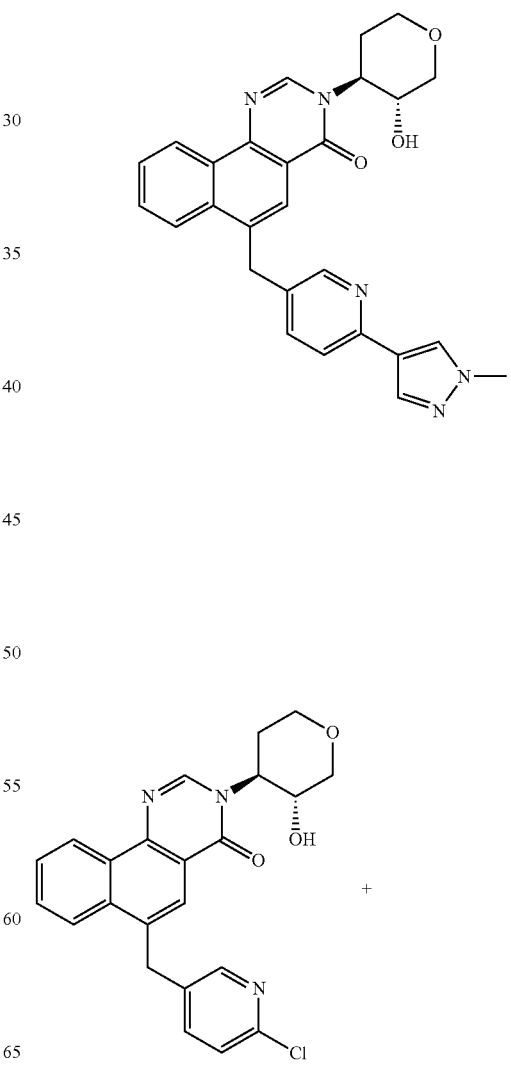

-continued

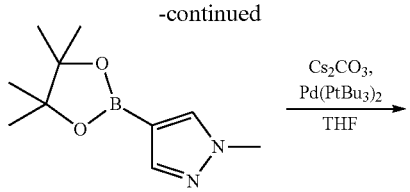 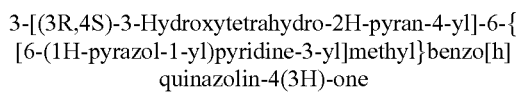

EXAMPLE 5

3-[(3R,4S)-3-Hydroxytetrahydro-2H-pyran-4-yl]-6-{[6-(1H-pyrazol-1-yl)pyridine-3-yl]methyl}benzo[h]quinazolin-4(3H)-one

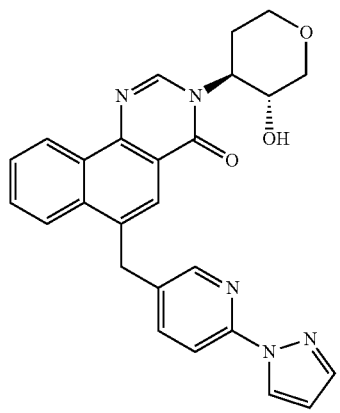

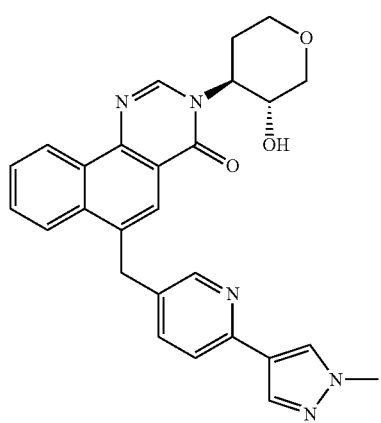

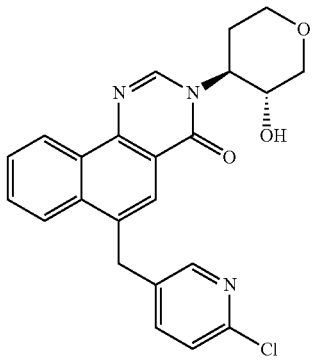

+

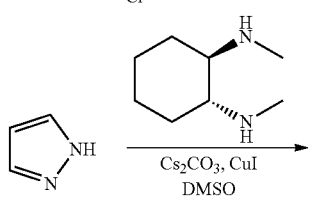

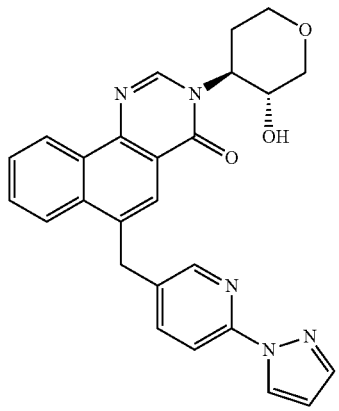

To a solution of 6-[(6-chloropyridin-3-yl)methyl]-3-[(3R,4S)-3-hydroxytetrahydro-2H-pyran-4-yl]benzo[h]quinazolin-4(3H)-one (Example 1, 0.040 g, 0.095 mmol) in 1 mL of THF under an atmosphere of nitrogen was added cesium carbonate (0.19 mL, 1 N aqueous, 0.19 mmol), 1-methyl-4-(4,4,5,5-tetramethyl-1,3,2-dioxaborolan-2-yl)-1H-pyrazole (0.040 g, 0.19 mmol), and bis(tri-tert-butylphosphine)palladium(0) (10 mol %). The reaction was heated at 85° C. for 20 h, and additional 1-methyl-4-(4,4,5,5-tetramethyl-1,3,2-dioxaborolan-2-yl)-1H-pyrazole (0.040 g, 0.19 mmol), and bis(tri-tert-butylphosphine)palladium(0) (10 mol %) were added. After 24 h, the reaction was cooled to rt, diluted with ethyl acetate, and washed with saturated aqueous sodium bicarbonate and brine. The solution was dried over sodium sulfate, filtered, and concentrated in vacuo. The residue was purified via silica gel chromatography, eluting with 0-5% methanol in dichloromethane, to provide the title compound that gave a proton NMR spectra consistent with theory and a mass ion (ES+) of 467.53 for [M+H]+: $^1$H NMR (400 MHz, CD$_3$OD) δ 8.87 (d, J=7.9 Hz, 1H), 8.35 (s, 1H), 8.23 (s, 1H), 7.80-7.78 (m, 2H), 7.72 (s, 2H), 7.66-7.55 (m, 2H), 7.22-7.19 (m, 1H), 7.08 (d, J=8.2 Hz, 1H), 4.80-4.73 (m, 1H), 4.28-4.15 (m, 1H), 4.08-4.04 (m, 1H), 3.85 (s, 3H), 3.61-3.51 (m, 1H), 3.34-3.29 (m, 1H), 2.28-2.18 (m, 1H), 1.99-1.95 (m, 1H).

To a solution of 6-[(6-chloropyridin-3-yl)methyl]-3-[(3R,4S)-3-hydroxytetrahydro-2H-pyran-4-yl]benzo[h]quinazolin-4(3H)-one (Example 1, 0.080 g, 0.19 mmol) and pyrazole (0.052 g, 0.15 mmol) in 2 mL of DMSO under an atmosphere of nitrogen was added potassium carbonate (0.57 mL, 1 N aqueous, 0.57 mmol), trans-N,N'-dimethylcyclohexane-1,2-diamine (21.6 mg, 0.152 mmol), and copper(I) iodide (0.014 g, 0.076 mmol). The mixture was heated at 120° C. for 20 h, cooled to rt, and additional trans-N,N'-dimethylcyclohexane-1,2-diamine (21.6 mg, 0.152 mmol) and copper(I) iodide (0.014 g, 0.076 mmol) were added. The reaction was heated at 150° C. for 24 h, cooled to rt, and diluted with ethyl acetate and water. The aqueous layer was extracted 3× with ethyl acetate, and the combined organic fractions were washed with brine, dried over sodium sulfate, filtered, and concentrated in vacuo. The residue was purified via silica gel chromatography, eluting with 0-5% methanol in dichloromethane, to provide the title compound that gave a proton NMR spectra consistent with theory and a mass ion (ES+) of 453.51 for [M+H]+: 1H NMR (400 MHz, CD3OD) δ 8.93 (d, J=7.3 Hz, 1H), 8.46 (s, 1H), 8.30 (s, 1H), 8.26 (s, 1H), 7.90 (s, 1H), 7.86 (d, J=9.2 Hz, 1H), 7.79 (d, J=8.5 Hz, 1H), 7.66-7.57 (m, 2H), 7.50 (d, J=8.5 Hz, 1H), 6.39 (s, 1H), 6.30 (s, 1H), 4.86-4.84 (m, 1H), 4.36 (s, 2H), 4.23-4.13 (m, 2H), 4.12-4.04 (m, 1H), 3.56-3.50 (m, 1H), 3.34-3.32 (m, 1H), 2.24-2.19 (m, 1H), 2.00-1.97 (m, 1H).

EXAMPLE 6

3-[(3R,4S)-3-Hydroxytetrahydro-2H-pyran-4-yl]-6-(pyridine-3-ylmethyl)benzo[h]quinazolin-4(3H)-one

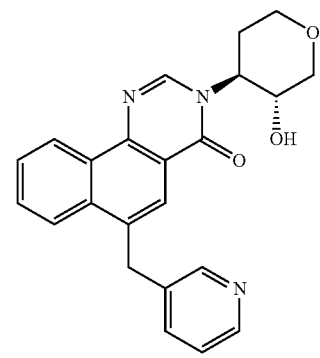

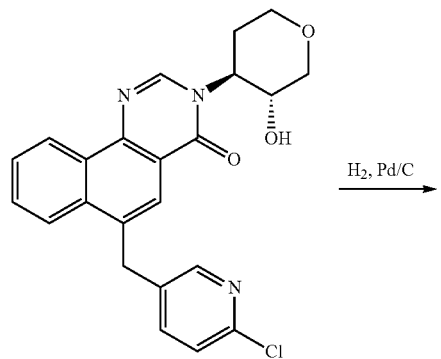

H2, Pd/C →

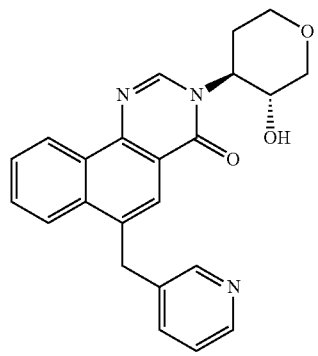

To a solution of 6-[(6-chloropyridin-3-yl)methyl]-3-[(3R,4S)-3-hydroxytetrahydro-2H-pyran-4-yl]benzo[h]quinazolin-4(3H)-one (Example 1, 0.050 g, 0.12 mmol) in 1 mL of methanol and 1 mL of dichloromethane was added palladium on carbon (10 mg, 0.094 mmol). The mixture was placed under an atmosphere of hydrogen (1 atm) for 8 h and was then filtered through a pad of Celite, which was washed with MeOH. The filtrate was concentrated in vacuo to provide the title compound that gave a proton NMR spectra consistent with theory and a mass ion (ES+) of 388.1657 for [M+H]+ [Calc'd for C23H22N3O3, [M+H]+=388.1656]: 1H NMR (400 MHz, d6-DMSO) δ 9.96 (d, J=7.5 Hz, 1H), 8.79 (s, 1H), 8.68 (s, 1H), 8.63 (d, J=4.8 Hz, 1H), 8.15-8.02 (m, 2H), 8.02 (s, 1H), 7.77-7.70 (m, 3H), 4.68 (s, 2H), 4.68 (br s, 1H), 4.13-4.00 (m, 1H), 3.98-3.89 (m, 2H), 3.44-3.38 (m, 1H), 3.13-3.07 (m, 2H), 2.22-2.19 (m, 1H), 1.86-1.83 (m, 1H).

EXAMPLE 7

3-[(3R,4S)-3-Hydroxytetrahydro-2H-pyran-4-yl]-6-[(6-methoxypyridin-3-yl)methyl]benzo[h]quinazolin-4(3H)-one

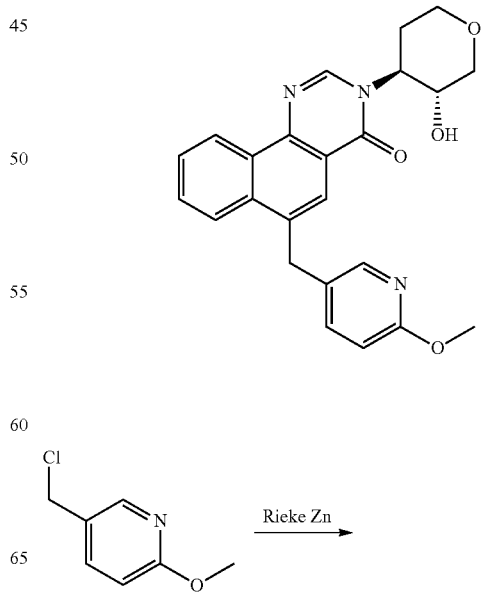

Rieke Zn →

2H), 4.23-4.06 (m, 3H), 3.85 (s, 3H), 3.58-3.53 (m, 1H), 3.31 (t, J=10.3 Hz, 1H), 2.96 (d, J=6.7 Hz, 1H), 2.30-2.20 (m, 1H), 2.01-1.97 (m, 1H).

EXAMPLE 8

5-({3-[(3R,4S)-3-Hydroxytetrahydro-2H-pyran-4-yl]-4-oxo-3,4-dihydrobenzo[h]quinazolin-6-yl}methyl)pyridine-2-carbonitrile

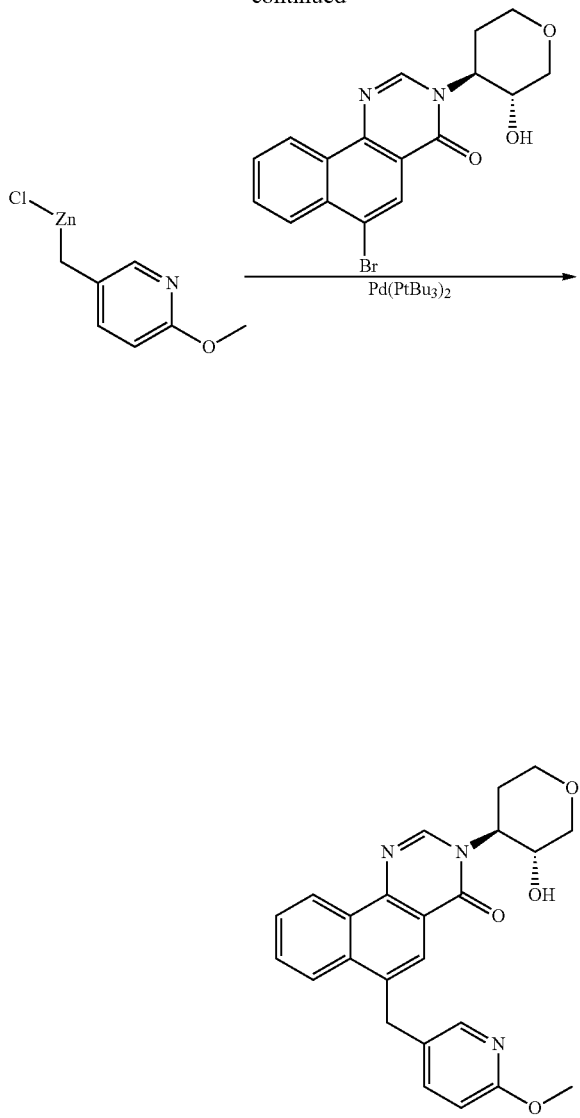

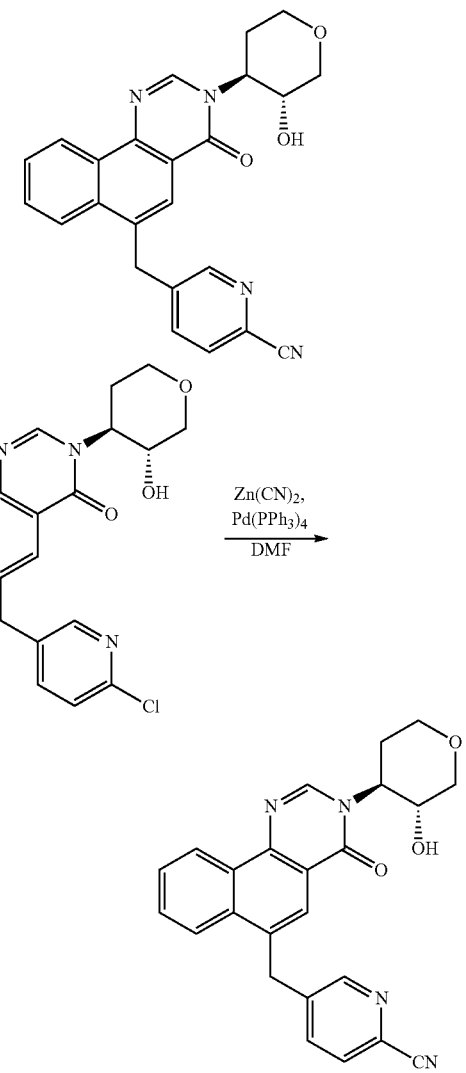

To a solution of 5-(chloromethyl)-2-methoxy pyridine (0.158 g, 0.999 mmol) in 0.5 mL of THF under an atmosphere of nitrogen was added Rieke Zn (1.3 mL, 1.0 mmol, 0.76 M in THF). The mixture was heated to reflux for 18 h, then cooled to 0° C. A solution of 6-bromo-3-[(3R,4S)-3-hydroxytetrahydro-2H-pyran-4-yl]benzo[h]quinazolin-4(3H)-one (see Example 1, 0.125 g, 0.333 mmol) in 0.5 mL of THF was added, followed by bis(tri-tert-butylphosphine)palladium(0) (5.1 mg, 0.010 mmol). The mixture was warmed to rt. After 2 h, the reaction was diluted with dichloromethane and water, and the aqueous layer was extracted with additional dichloromethane. The combined organic fractions were dried over sodium sulfate, filtered, and concentrated in vacuo. The residue was purified via silica gel chromatography, eluting with 0-3% methanol in dichloromethane to provide the title compound that gave proton NMR spectra consistent with theory and a mass ion (ES+) of 418.0 for [M+H]+: 1H NMR (400 MHz, CDCl3) δ 8.94-8.92 (m, 1H), 8.27 (s, 1H), 8.03 (s, 1H), 7.91-7.87 (m, 2H), 7.65-7.61 (m, 2H), 7.29 (dd, J=2.4 Hz, 8.5 Hz, 1H), 6.58 (d, J=8.5 Hz, 1H), 4.86-4.79 (m, 1H), 4.28 (s, To a solution of 6-[(6-chloropyridin-3-yl)methyl]-3-[(3R,4S)-3-hydroxytetrahydro-2H-pyran-4-yl]benzo[h]quinazolin-4(3H)-one (0.100 g, 0.237 mmol) in 1 mL of DMF under an atmosphere of nitrogen was added zinc cyanide (Example 1, 0.084 g, 0.71 mmol) and tetrakis(triphenylphosphine)palladium(0) (13.7 mg, 0.012 mmol). The mixture was heated to 100° C. for 8 h, then at 140° C. for another 15 h. The reaction was cooled to rt, diluted with ethyl acetate, washed 3× with brine, dried over sodium sulfate, filtered, and concentrated in vacuo. The residue was purified via preparative reverse phase HPLC to provide the title compound that gave proton NMR spectra consistent with theory and a mass ion (ES+) of 413.1603 for [M+H]+ [Calc'd for C24H21N4O3, [M+H]+

=413.1608]: $^1$H NMR (400 MHz, CDCl$_3$) δ 8.96-8.94 (m, 1H), 8.56 (s, 1H), 8.29 (s, 1H), 7.98 (s, 1H), 7.78-7.75 (m, 1H), 7.64-7.59 (m, 2H), 7.50 (s, 2H), 4.72-4.69 (m, 1H), 4.49 (s, 2H), 4.11-4.05 (m, 2H), 4.04-3.98 (m, 1H), 3.50-3.47 (m, 1H), 3.29-3.20 (m, 2H), 2.17-2.13 (m, 1H), 2.00-1.95 (m, 1H).

EXAMPLE 9

6-[(6-Ethylpyridin-3-yl)methyl]-3-[(3R,4S)-3-hydroxytetrahydro-2H-pyran-4-yl]benzo[h]quinazolin-4(3H)-one

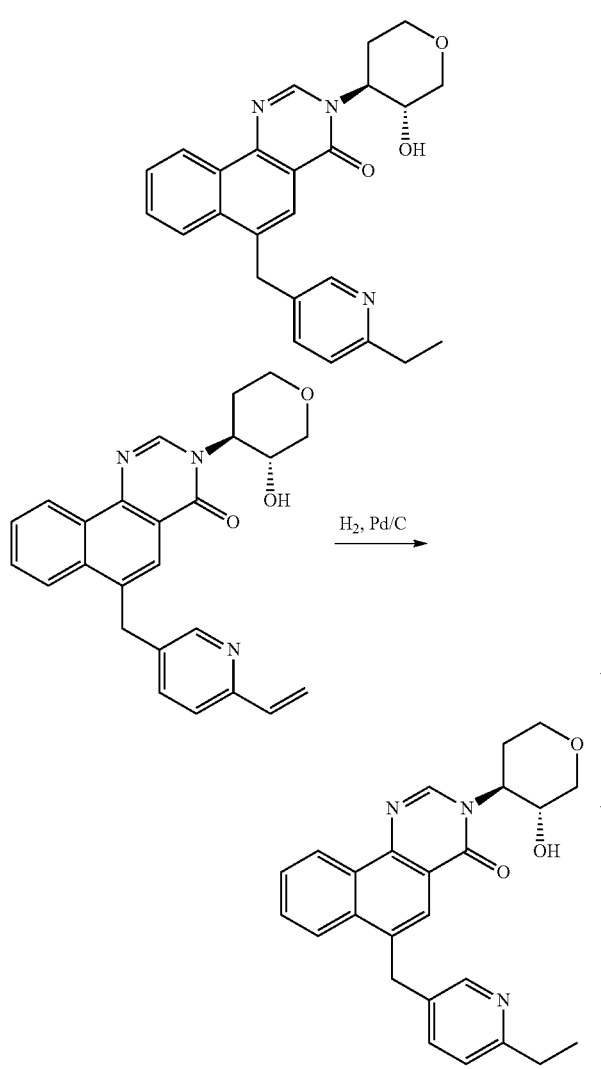

3-[(3R,4S)-3-Hydroxytetrahydro-2H-pyran-4-yl]-6-[(6-vinylpyridin-3-yl)methyl]benzo[h]quinazolin-4(3H)-one was prepared by the procedure described for the synthesis of 3-[(3R,4S)-3-Hydroxytetrahydro-2H-pyran-4-yl]-6-{[6-(1-methyl-1H-pyrazol-4-yl)pyridine-3-yl]methyl}benzo[h]quinazolin-4(3H)-one in Example 4, substituting potassium vinyltrifluoroborate for 1-methyl-4-(4,4,5,5-tetramethyl-1,3,2-dioxaborolan-2-yl)-1H-pyrazole.

To a solution of 3-[(3R,4S)-3-Hydroxytetrahydro-2H-pyran-4-yl]-6-[(6-vinylpyridin-3-yl)methyl]benzo[h]quinazolin-4(3H)-one (0.040 g, 0.097 mmol) in 2 mL of methanol was added palladium on carbon (8.0 mg, 0.075 mmol). The mixture was placed under an atmosphere of hydrogen (1 atm) for 15 h and was then filtered through a pad of Celite, which was washed with MeOH. The filtrate was concentrated in vacuo to provide the title compound that gave a proton NMR spectra consistent with theory and a mass ion (ES+) of 416.1960 for [M+H]$^+$ [Calc'd for C$_{25}$H$_{26}$N$_3$O$_3$, [M+H]$^+$= 416.1969]: $^1$H NMR (400 MHz, CDCl$_3$ δ 8.82 (d, J=7.9 Hz, 1H), 8.44 (s, 1H), 8.34 (s, 1H), 7.65 (d, J=7.6 Hz, 1H), 7.60-7.52 (m, 3H), 737 (d, J=7.7 Hz, 1H), 7.04 (d, J=8.0 Hz, 1H), 4.78-4.71 (m, 1H), 4.29-4.25 (m, 3H), 4.23 (s, 2H), 4.06-3.99 (m, 1H), 3.55 (t, J=11.2 Hz, 1H), 3.38-3.31 (m, 1H), 2.83 (q, J=7.4 Hz, 2H), 2.26-2.19 (m, 1H), 1.97-1.94 (m, 1H), 1.24 (t, J=7.4 Hz, 3H).

EXAMPLE 10

6-[(6-Acetylpyridin-3-yl)methyl]-3-[(3R,4S)-3-hydroxytetrahydro-2H-pyran-4-yl]benzo[h]quinazolin-4(3H)-one

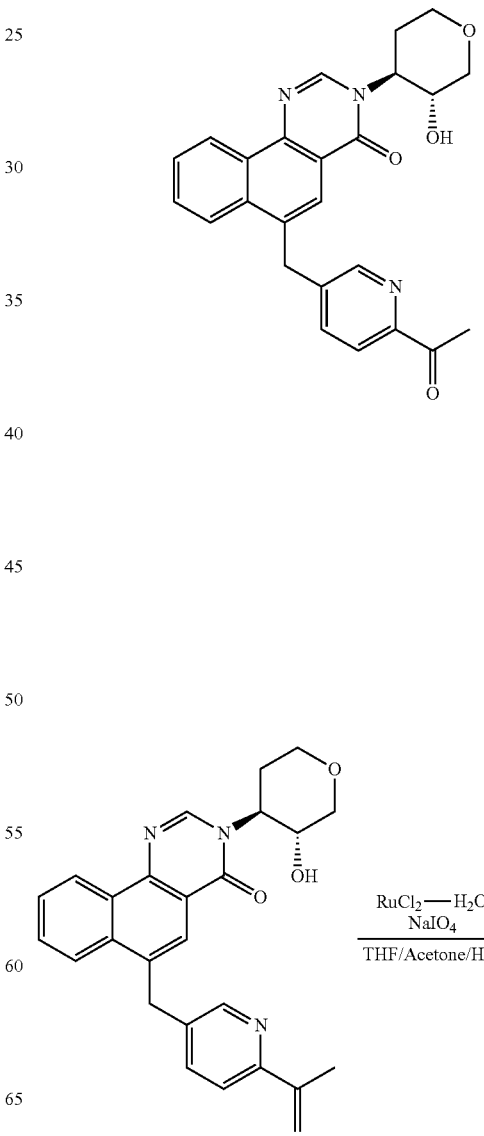

51

-continued

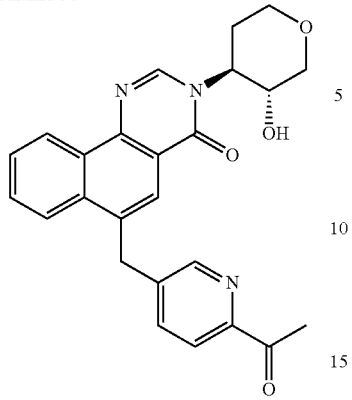

3-[(3R,4S)-3-Hydroxytetrahydro-2H-pyran-4-yl]-6-[(6-isopropenylpyridin-3-yl)methyl]benzo[h]quinazolin-4(3H)-one was prepared by the procedure described for the synthesis of 3-[(3R,4S)-3-Hydroxytetrahydro-2H-pyran-4-yl]-6-{[6-(1-methyl-1H-pyrazol-4-3H)pyridine-3-yl]methyl}benzo[h]quinazolin-4(3H)-one in Example 4, substituting isopropenylboronic acid pinacol ester for 1-methyl-4-(4,4,5,5-tetramethyl-1,3,2-dioxaborolan-2-yl)-1H-pyrazole.

To a solution of 3-[(3R,4S)-3-hydroxytetrahydro-2H-pyran-4-yl]-6-[(6-isopropenylpyridin-3-yl)methyl]benzo[h]quinazolin-4(3H)-one (0.042 g, 0.098 mmol) in a mixture of 1 mL of acetone, 1 mL of THF, and 1 mL of water was added ruthenium(II) chloride hydrate (5.5 mg, 0.025 mmol) and sodium periodate (0.084 g, 0.39 mmol). After 1.5 h, the mixture was diluted with water and extracted 3× with dichloromethane. The combined organic fractions were dried over sodium sulfate, filtered, and concentrated in vacuo. The residue was purified via silica gel chromatography, eluting with 0-5% methanol in dichloromethane to provide the title compound that gave proton NMR spectra consistent with theory and a mass ion (ES+) of 460.1763 for [M+H]$^+$ [Calc'd for C$_{25}$H$_{24}$N$_3$O$_4$, [M+H]$^+$=430.1761]: $^1$H NMR (400 MHz, CDCl$_3$) δ 8.89 (d, J=8.1 Hz, 1H), 8.52 (s, 1H), 8.28 (s, 1H), 7.83 (d, J=8.1 Hz, 1H), 7.78 (s, 1H), 7.71 (d, J=8.4 Hz, 1H), 7.65-7.56 (m, 2H), 7.47-7.45 (m, 1H), 4.84-4.78 (m, 1H), 4.33 (s, 2H), 4.26-4.09 (m, 2H), 4.07-4.05 (m, 1H), 3.70 (br s, 1H), 3.57 (t, J=11.0 Hz, 1H), 3.34 (t, J=10.0 Hz, 1H), 2.64 (s, 3H), 2.25-2.20 (m, 1H), 2.01-1.97 (m, 1H).

EXAMPLE 11

6-{[6-(1-Hydroxy-1-methylethyl)pyridine-3-yl]methyl}-3-[(3R,4S)-3-hydroxytetrahydro-2H-pyran-4-yl]benzo[h]quinazolin-4(3H)-one

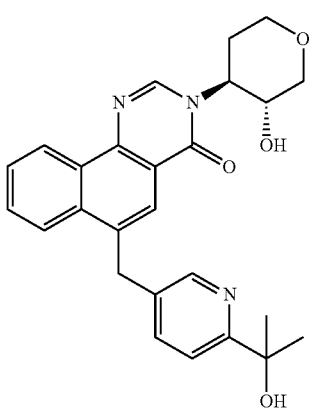

52

-continued

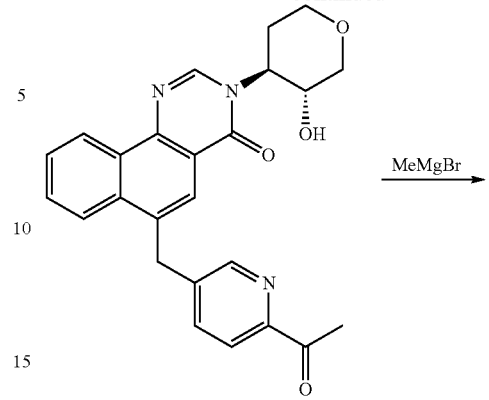

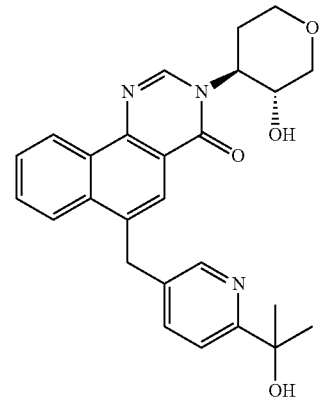

To a solution of 6-[(6-acetylpyridin-3-yl)methyl]-3-[(3R,4S)-3-hydroxytetrahydro-2H-pyran-4-yl]benzo[h]quinazolin-4(3H)-one (Example 10, 0.018 g, 0.042 mmol) in 1 mL of THF at 0° C. was added methylmagnesium bromide (0.035 mL, 3.0 M diethyl ether solution, 0.10 mmol). After 30 min, the mixture was treated with saturated aqueous ammonium chloride and extracted 2× with dichloromethane. The combined organic fractions were dried over sodium sulfate, filtered, and concentrated in vacuo. The residue was purified via silica gel chromatography, eluting with 0-5% methanol in dichloromethane to provide the title compound that gave proton NMR spectra consistent with theory and a mass ion (ES+) of 446.2067 for [M+H]$^+$ [Calc'd for C$_{26}$H$_{28}$N$_3$O$_4$, [M+H]$^+$=446.2074]: $^1$H NMR (400 MHz, CDCl$_3$) δ 8.95-8.93 (m, 1H), 8.40 (s, 1H), 8.29 (s, 1H), 7.85-7.81 (m, 2H), 7.67-7.60 (m, 2H), 7.39 (d, J=8.2 Hz, 1H), 7.18 (d, J=8.2 Hz, 1H), 4.89-4.80 (m, 2H), 4.33 (s, 2H), 4.25-4.04 (m, 3H), 3.60-3.57 (m, 1H), 3.36-3.28 (m, 1H), 2.30-2.15 (m, 1H), 2.02-1.98 (m, 1H), 1.47 (s, 6H).

EXAMPLE 12

3-[(3R,4S)-3-Hydroxytetrahydro-2H-pyran-4-yl]-6-(4-morpholin-4-ylbenzyl)benzo[h]quinazolin-4(3H)-one

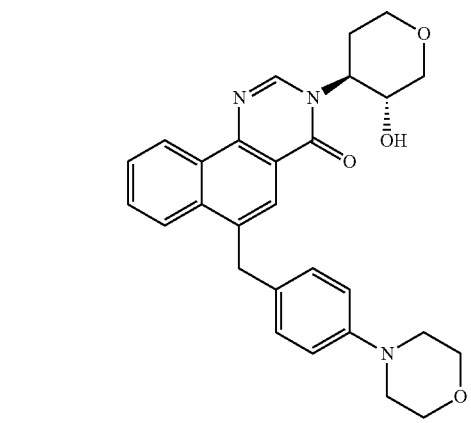

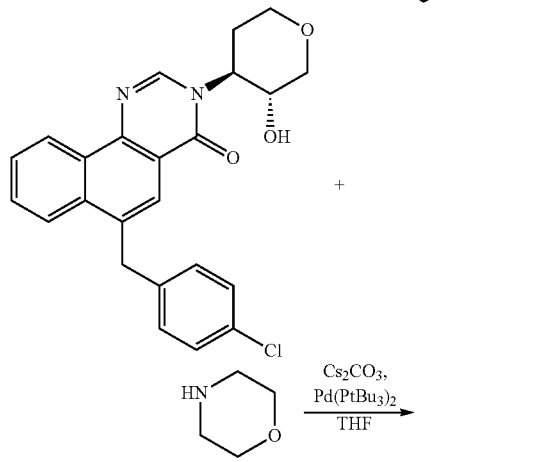

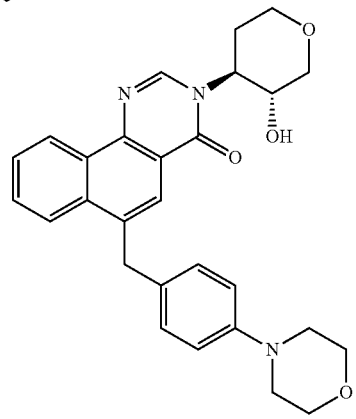

6-(4-Chlorobenzyl)-3-[(3R,4S)-3-hydroxytetrahydro-2H-pyran-4-yl]benzo[h]quinazolin-4(3H)-one was prepared by the procedure described for the synthesis of 6-[(6-chloropyridin-3-yl)methyl]-3-[(3R,4S)-3-hydroxytetrahydro-2H-pyran-4-yl]benzo[h]quinazolin-4(3H)-one in Example 1, substituting 4-chlorobenzylzinc chloride for (2-chloro-5-pyridyl)methylzinc chloride.

To a solution of 6-(4-chlorobenzyl)-3-[(3R,4S)-3-hydroxytetrahydro-2H-pyran-4-yl]benzo[h]quinazolin-4(3H)-one (0.100 g, 0.238 mmol) in 2 mL of DMF under an atmosphere of nitrogen was added morpholine (0.083 g, 0.95 mmol), bis(tri-tert-butylphosphine)palladium(0) (0.012 g, 0.024 mmol), cesium carbonate (0.232 g, 0.713 mmol), and 0.2 mL of water. The mixture was warmed to 65° C. for 5 min, flushed with nitrogen, and irradiated in a microwave reactor at 130° C. for 25 min. The reaction was cooled to rt and diluted with water and dichloromethane. The aqueous layer was reextracted with dichloromethane and the combined organic fractions were dried over sodium sulfate, filtered, and concentrated in vacuo. The residue was purified via silica gel chromatography, eluting with 0-4% methanol in dichloromethane to provide the title compound that gave proton NMR spectra consistent with theory and a mass ion (ES+) of 471.9 for [M+H]$^+$: $^1$H NMR (400 MHz, CDCl$_3$) δ 9.01 (s, 1H), 8.30 (s, 1H), 8.01-7.98 (m, 2H), 7.65-7.59 (m, 2H), 7.07 (d, J=8.7 Hz, 2H), 7.77 (d, J=8.7 Hz, 2H), 4.89-4.82 (m, 1H), 4.35 (s, 2H), 4.22-4.18 (m, 1H), 4.13-4.08 (m, 2H), 3.79 (t, J=4.8 Hz, 4H), 3.59-3.52 (m, 1H), 3.34-3.28 (m, 1H), 3.06 (t, J=4.8 Hz, 4H), 2.66 (br 5, 1H), 2.32-2.22 (m, 1H), 2.03-1.99 (m, 1H).

EXAMPLE 13

3-[(3R,4S)-3-Hydroxytetrahydro-2H-pyran-4-yl]-6-{[6-(1,3-thiazol-4-yl)pyridine-3-yl]methyl}benzo[h]quinazolin-4(3H)-one

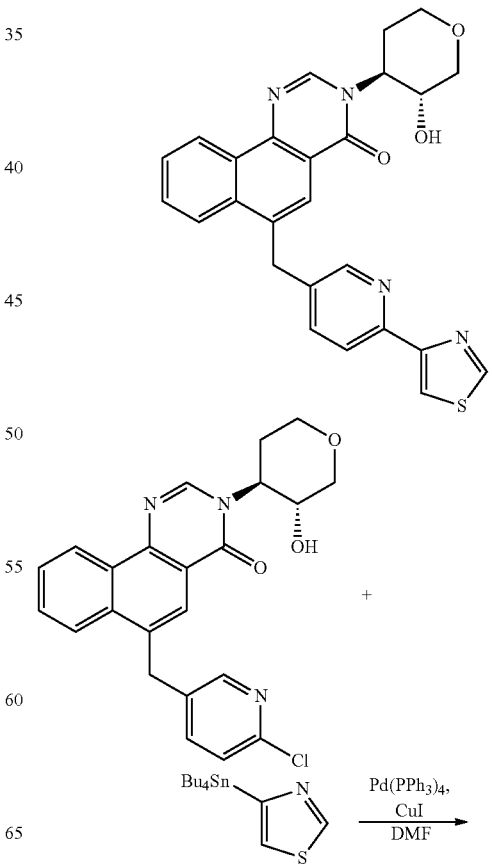

-continued

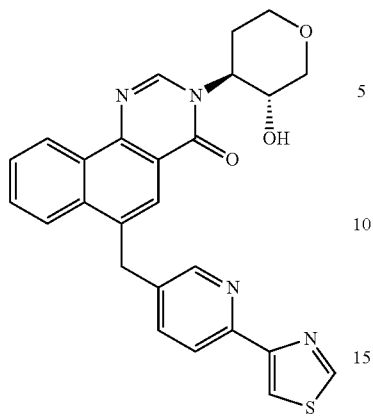

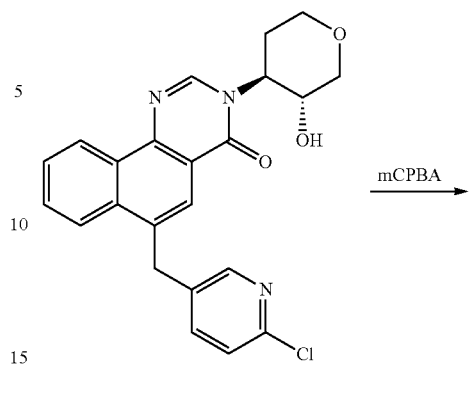

mCPBA →

To a solution of 6-[(6-chloropyridin-3-yl)methyl]-3-[(3R,4S)-3-hydroxytetrahydro-2H-pyran-4-yl]benzo[h]quinazolin-4(3H)-one (Example 1, 0.100 g, 0.237 mmol) in 1 mL of DMF under an atmosphere of nitrogen was added 4-(tributylstannyl)-1,3-thiazole (0.111 g, 0.296 mmol), tetrakis(triphenylphosphine)palladium(0) (0.055 g, 0.047 mmol), and copper(I) iodide (0.018 g, 0.095 mmol). The reaction was heated at 50° C. for 15 h, and then at 140° C. for an additional 6 h. The mixture was cooled to rt, diluted with ethyl acetate, and washed with brine and water. The solution was dried over sodium sulfate, filtered, and concentrated in vacuo. The residue was purified via preparative reverse phase HPLC to provide the title compound that gave a proton NMR spectra consistent with theory and a mass ion (ES+) of 471.1478 for [M+H]$^+$ [Calc'd for $C_{26}H_{23}N_4O_3S$, [M+H]$^+$=471.1485]: $^1$H NMR (400 MHz, CD$_3$OD) δ 9.18 (s, 1H), 9.01 (d, J=8.1 Hz, 1H), 8.62 (s, 1H), 8.58 (s, 1H), 8.54 (s, 1H), 8.39 (d, J=8.4 Hz, 1H), 8.32-8.30 (m, 1H), 8.08 (d, J=8.1 Hz, 1H), 7.98 (s, 1H), 7.76-7.68 (m, 2H), 4.72 (s, 2H), 4.72-4.66 (m, 1H), 4.36-4.24 (m, 1H), 4.09-3.99 (m, 2H), 3.53 (t, J=10.1 Hz, 1H), 3.23 (t, J=10.2 Hz, 1H), 2.36-2.34 (m, 1H), 2.00-1.95 (m, 1H).

EXAMPLE 14

6-[(6-Chloro-1-oxidopyridin-3-yl)methyl]-3-[(3R,4S)-3-hydroxytetrahydro-2H-pyran-4-yl]benzo[h]quinazolin-4(3H)-one

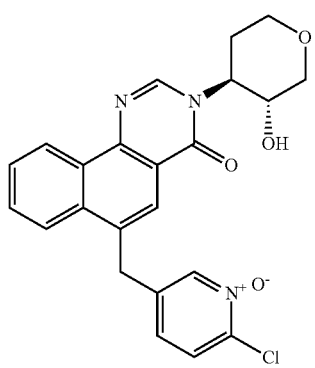

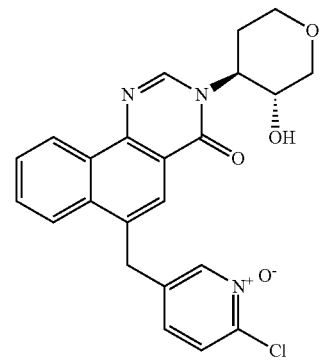

To a solution of -[(6-chloropyridin-3-yl)methyl]-3-[(3R,4S)-3-hydroxytetrahydro-2H-pyran-4-yl]benzo[h]quinazolin-4(3H)-one (Example 1, 0.100 g, 0.237 mmol) in 2 mL of dichloromethane was added m-chloroperbenzoic acid (0.205 g, 1.18 mmol). After 14 days, the mixture was concentrated in vacuo. The residue was purified via preparative reverse phase HPLC to provide the title compound that gave a proton NMR spectra consistent with theory and a mass ion (ES+) of 438.1220 for [M+H]$^+$[Calc'd for $C_{23}H_{21}ClN_3O_4$, [M+H]$^+$=438.1215]: $^1$H NMR (400 MHz, CDCl$_3$) δ 8.79-8.75 (m, 1H), 8.16 (s, 1H), 7.96 (s, 1H), 7.81 (s, 1H), 7.66-7.63 (m, 1H), 7.49-7.43 (m, 2H), 7.24-7.22 (m, 1H), 6.99 (dd, J=1.5 Hz, 8.5 Hz, 1H), 4.49-4.44 (m, 1H), 4.23 (s, 1H), 4.01-3.95 (m, 1H), 3.91-3.87 (m, 1H), 3.84-3.36 (m, 1H), 3.36-3.30 (m, 1H), 3.07-3.02 (m, 1H), 2.08-1.98 (m, 1H), 1.82-1.78 (m, 1H).

EXAMPLE 15

6-[(2-Chloropyridin-4-yl)methyl]-3-[(3R,4S)-3-hydroxytetrahydro-2H-pyran-4-yl]benzo[h]quinazolin-4(3H)-one

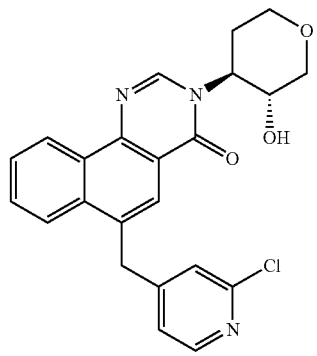

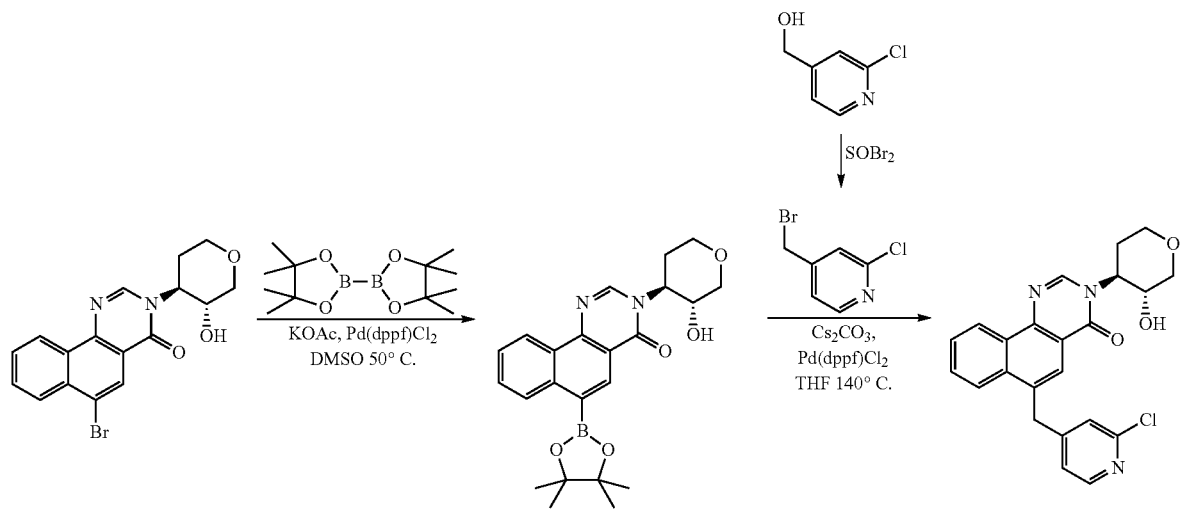

Synthesis of 4-(bromomethyl)-2-chloropyridine

To a solution of 2-chloropyridine-4-methanol (1.02 g, 7.10 mmol) in 15 mL of dichloromethane was added thionyl bromide (1.77 g, 8.53 mmol) dropwise. After 15 min, the reaction was quenched with saturated aqueous ammonium chloride. The organic solution was washed 2× with water, dried over sodium sulfate, filtered, and concentrated in vacuo to provide 4-(bromomethyl)-2-chloropyridine that gave a mass ion (ES+) of 208.0 for [M+H]$^+$.

To a solution of 1-amino-4-bromo-N-[(3R,4S)-3-hydroxytetrahydro-2H-pyran-4-yl]-2-naphthamide (0.800 g, 2.13 mmol) in 10 mL of DMSO under an atmosphere of nitrogen was added potassium acetate (0.628 g, 6.40 mmol), bis(pinacolato)diboron (0.596 g, 2.34 mmol), and [1,1'-bis(diphenylphosphino)ferrocene]dichloro-palladium(II), 1:1 complex with dichloromethane (0.174 g, 0.213 mmol). The mixture was heated at 50° C. for 16 h, cooled to rt, and diluted with water and ethyl acetate. The organic solution was washed 3× with brine, dried over sodium sulfate, filtered, and concentrated in vacuo. The residue was purified via silica gel chromatography, eluting with 0-3% methanol in dichloromethane to provide 3-[(3R,4S)-3-hydroxytetrahydro-2H-pyran-4-yl]-6-(4,4,5,5-tetramethyl-1,3,2-dioxaborolan-2-yl)benzo[h]quinazolin-4(3H)-one that gave proton NMR spectra consistent with theory.

To a solution of the above compound (0.604 g, 1.43 mmol) in 7 mL of THF under an atmosphere of nitrogen was added 4-(bromomethyl)-2-chloropyridine (0.443 g, 2.14 mmol), aqueous cesium carbonate (2 M, 2.14 mL, 4.29 mmol), and [1,1'-bis(diphenylphosphino)ferrocene]dichloro-palladium (II), 1:1 complex with dichloromethane (0.117 g, 0.143 mmol). The mixture was heated at 140° C. for 1 h, cooled to rt, and diluted with dichloromethane. The organic solution was washed 3× with water, dried over sodium sulfate, filtered, and concentrated in vacuo. The resultant shiny was filtered and washed with dichloromethane to provide the title compound that gave proton NMR spectra consistent with theory and a mass ion (ES+) of 422.1264 for [M+H]$^+$ [Calc'd for $C_{23}H_{21}ClN_3O_3$, [M+H]$^+$=422.1266]: $^1$H NMR (400 MHz, CDCl$_3$) δ 9.07-9.04 (m, 1H), 8.36 (s, 1H), 8.25 (d, J=5.0 Hz, 1H), 8.08 (s, 1H), 7.82-7.79 (m, 1H), 7.73-7.66 (m, 2H), 7.13 (s, 1H), 7.04 (d, J=5.3 Hz, 1H), 4.93-4.87 (m, 1H), 4.45 (s, 2H), 4.26-4.12 (m, 3H), 3.60 (t, J=9.8 Hz, 1H), 3.35 (d, J=10.3 Hz, 1H), 2.34 (d, J=4.5 Hz, 1H), 2.32-2.28 (m, 1H), 2.09-2.04 (m, 1H).

EXAMPLE 16

3-[(3R,4S)-3-Hydroxytetrahydro-2H-pyran-4-yl]-6-{[6-(methylsulfonyl)pyridine-3-yl]methyl}benzo[h]quinazolin-4(3H)-one

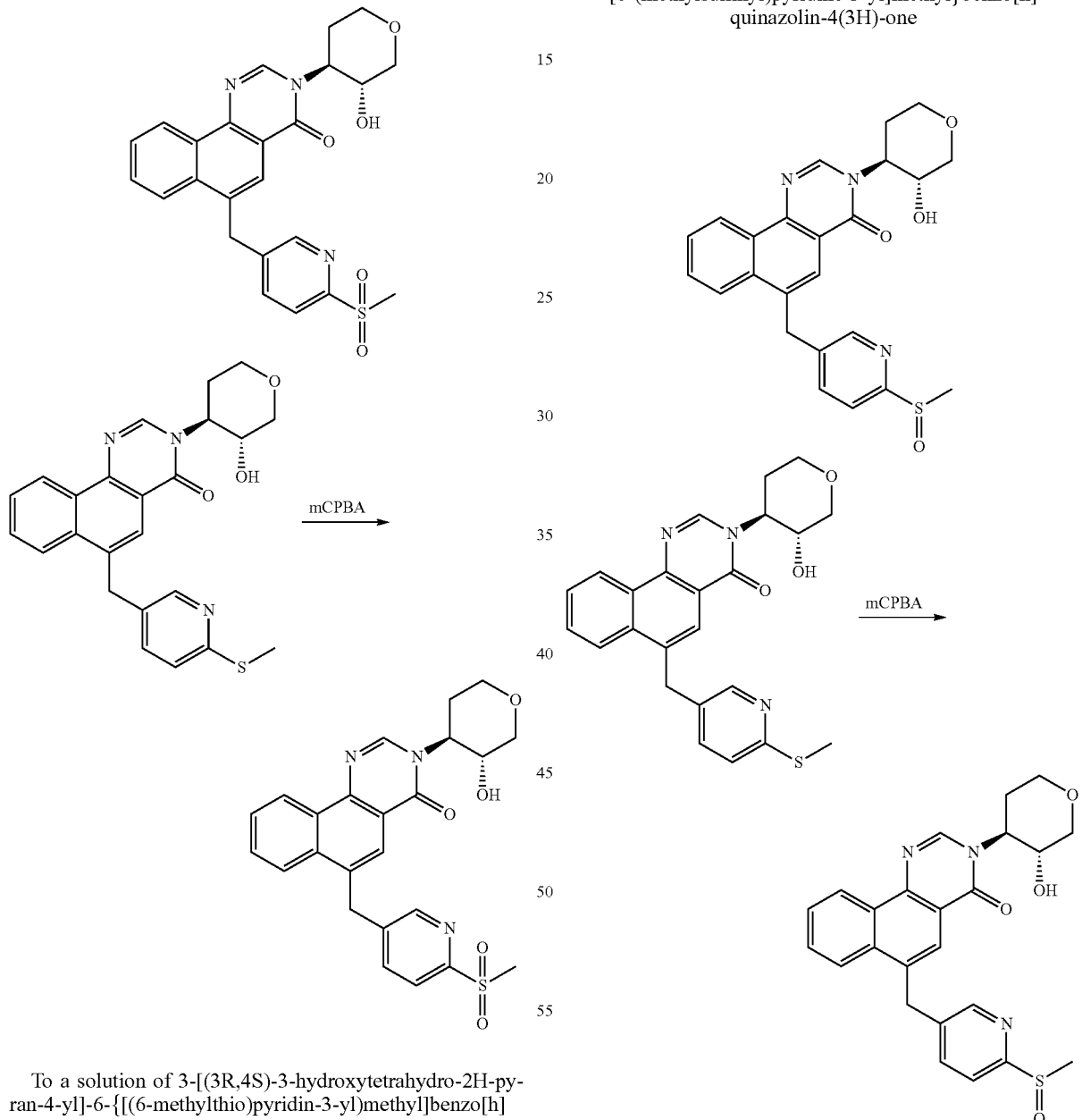

To a solution of 3-[(3R,4S)-3-hydroxytetrahydro-2H-pyran-4-yl]-6-{[(6-methylthio)pyridin-3-yl)methyl]benzo[h]quinazolin-4(3H)-one (Example 2, 0.025 g, 0.058 mmol) in 1 mL of dichloromethane was added m-chloroperbenzoic acid (0.030 g, 0.12 mmol). After 15 h, the mixture was washed 3× with 10% aqueous sodium carbonate, dried over sodium sulfate, filtered, and concentrated in vacuo. The residue was purified via silica gel chromatography, eluting with 0-5% methanol in dichloromethane to provide the title compound that gave proton NMR spectra consistent with theory and a mass ion (ES+) of 466.1446 for [M+H]+ [Calc'd for $C_{24}H_{24}N_3O_5S$, [M+H]+=466.1431]: NMR (400 MHz, CDCl$_3$) δ 8.86 (d, J=8.2 Hz, 1H), 8.57 (s, 1H), 8.27 (s, 1H), 7.87 (d, 8.2 Hz, 1H), 7.66-7.54 (m, 5H), 4.81-4.46 (m, 1H), 4.31 (d, J=3.7 Hz, 2H), 4.27-4.16 (m, 2H), 4.08-4.02 (m, 1H), 3.78 (d, J=6.0 Hz, 1H), 3.59-3.52 (m, 1H), 3.35-3.30 (m, 1H), 3.16 (s, 3H), 2.24-2.13 (m, 1H), 1.99-1.94 (m, 1H).

EXAMPLE 17

3-[(3R,4S)-3-Hydroxytetrahydro-2H-pyran-4-yl]-6-{[6-(methylsulfinyl)pyridine-3-yl]methyl}benzo[h]quinazolin-4(3H)-one

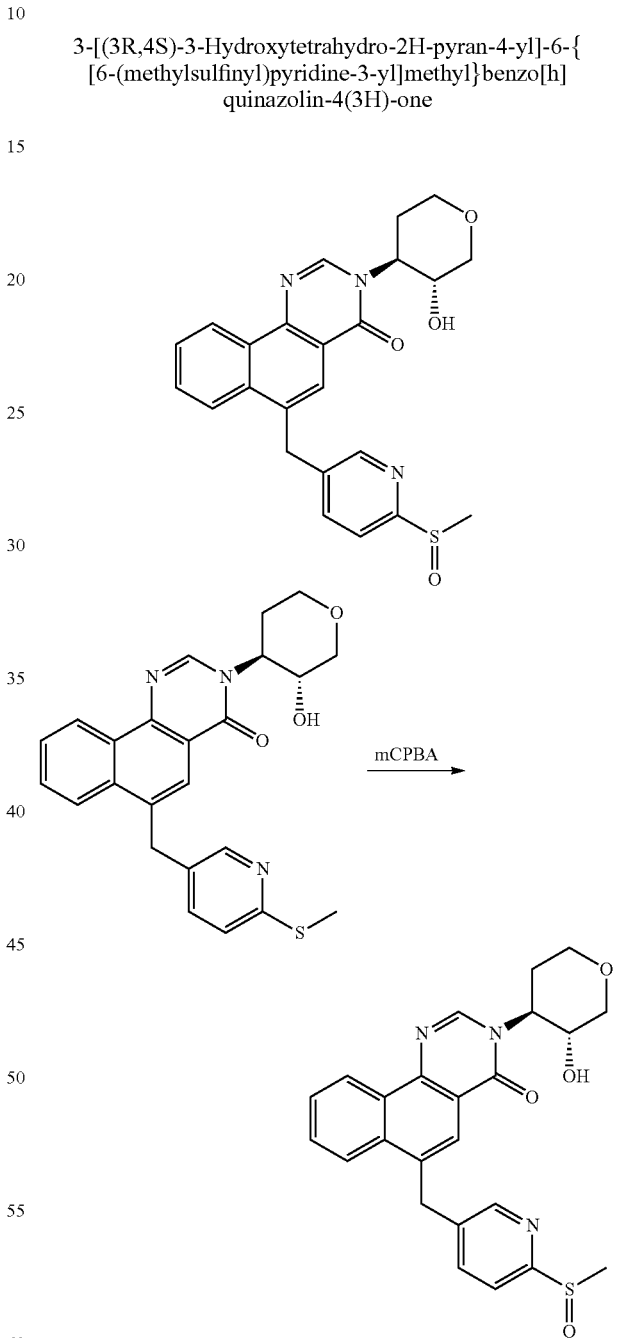

To a solution of 3-[(3R,4S)-3-hydroxytetrahydro-2H-pyran-4-yl]-6-{[(6-methylthio)pyridin-3-yl)methyl]benzo[h]quinazolin-4(3H)-one (Example 2, 0.025 g, 0.058 mmol) in 1 mL of dichloromethane was added m-chloroperbenzoic acid (0.014 g, 0.058 mmol). After 2 h, the mixture was washed 3× with 10% aqueous sodium carbonate, dried over sodium sulfate, filtered, and concentrated in vacuo. The residue was purified via silica gel chromatography, eluting with 0-3% methanol in dichloromethane to provide the title compound that gave proton NMR spectra consistent with theory and a mass ion (ES+) of 450.1495 for [M+H]⁺ [Calc'd for $C_{24}H_{24}N_3O_4S$, [M+H]⁺=450.1482]: ¹H NMR (400 MHz, CDCl₃) δ 8.88 (d, J=8.2 Hz, 1H), 8.42 (s, 1H), 8.28 (s, 1H), 7.77 (d, J=8.2 Hz, 1H), 7.72 (d, J=4.9 Hz, 1H), 7.72-7.54 (m, 4H), 4.80-4.76 (m, 1H), 4.28 (s, 2H), 4.24-4.17 (m, 2H), 4.08-4.04 (m, 1H), 3.90-3.79 (m, 1H), 3.59-3.52 (m, 1H), 3.35-3.30 (m, 1H), 2.75-2.74 (m, 3H), 2.21-2.16 (m, 1H), 2.00-1.95 (m, 1H).

EXAMPLE 18

5-({3-[(3R,4S)-3-Hydroxytetrahydro-2H-pyran-4-yl]-4-oxo-3,4-dihydrobenzo[h]quinazolin-6-yl}methyl)pyridine-2-carboxylic acid

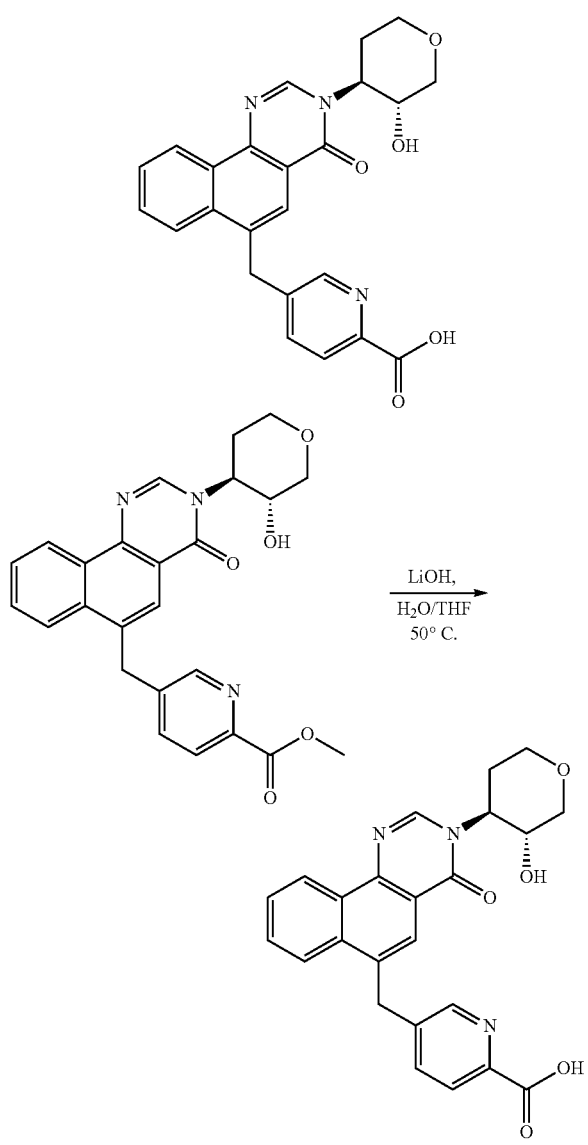

Methyl 5-({3-[(3R,4S)-3-hydroxytetrahydro-2H-pyran-4-yl]-4-oxo-3,4-dihydrobenzo[h]quinazolin-6-yl}methyl)pyridine-2-carboxylate was prepared by the procedure described for the synthesis of 6-[(2-chloropyridin-4-yl)methyl]-3-[(3R,4S)-3-hydroxytetrahydro-2H-pyran-4-yl]benzo[h]quinazolin-4(3H)-one in Example 15, substituting methyl 5-(bromomethyl)pyridine-2-carboxylate for 4-(bromomethyl)-2-chloropyridine.

To a solution of methyl 5-({3-[(3R,4S)-3-hydroxytetrahydro-2H-pyran-4-yl]-4-oxo-3,4-dihydrobenzo[h]quinazolin-6-yl}methyl)pyridine-2-carboxylate (0.150 g, 0.337 mmol) in 2 mL of water and 2 mL of THF was added lithium hydroxide (0.016 g, 0.67 mmol). The mixture was heated to 50° C. for 2 h, cooled to rt, and quenched with saturated aqueous potassium phosphate to pH 5. The aqueous solution was extracted 3× with ethyl acetate and the combined organic fractions were dried over sodium sulfate, filtered, and concentrated in vacuo to provide the title compound that gave proton NMR spectra consistent with theory and a mass ion (ES+) of 432.1560 for [M+H]⁺ [Calc'd for $C_{24}H_{22}N_3O_5$, [M+H]⁺=432.1554]: ¹H NMR (400 MHz, CDCl₃) δ 896-8.94 (m, 1H), 8.70 (s, 1H), 8.67 (s, 1H), 8.13-8.10 (m, 1H), 7.98 (s, 1H), 8.89 (d, J=8.2 Hz, 1H), 7.78-7.67 (m, 3H), 5.26 (d, J=5.3 Hz, 1H), 4.63 (s, 2H), 4.14-4.03 (m, 1H), 3.94-3.88 (m, 2H), 3.41 (t, J=11.0 Hz, 1H), 3.27 (br s, 1H), 3.12-3.08 (m, 2H), 2.28-2.19 (m, 1H), 1.87-1.83 (m, 1H).

EXAMPLE 19

5-({3-[(3R,4S)-3-Hydroxytetrahydro-2H-pyran-4-yl]-4-oxo-3,4-dihydrobenzo[h]quinazolin-6-yl}methyl)-N,N-dimethylpyridine-2-carboxamide

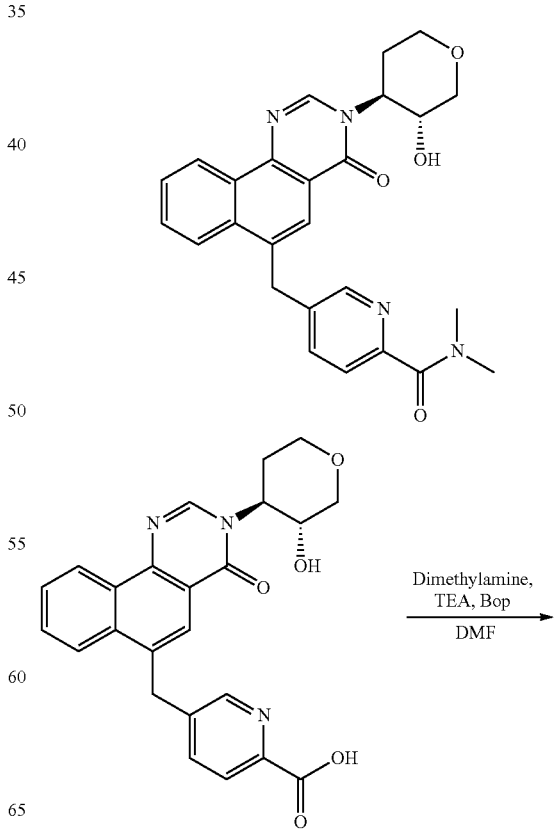

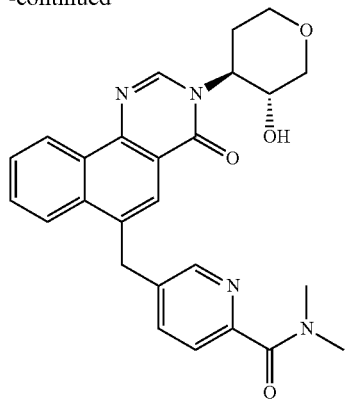

To a solution of 5-({3-[(3R,4S)-3-Hydroxytetrahydro-2H-pyran-4-yl]-4-oxo-3,4-dihydrobenzo[h]quinazolin-6-yl}methyl)pyridine-2-carboxylic acid (Example 18, 0.030 g, 0.070 mmol) in 1 mL of DMF was added dimethylamine (0.087 mL, 0.17 mmol), triethylamine (0.019 mL, 0.14 mmol), and benzotriazol-1-yloxy-tris(dimethylamino)phosphonium hexafluorophosphate (0.046 g, 0.10 mmol). After 1 h, additional dimethylamine (0.17 mL, 0.35 mmol) was added. After 2 h, the mixture was diluted with water and dichloromethane, and the organic solution was dried over sodium sulfate, filtered, and concentrated in vacuo. The residue was purified via silica gel chromatography, eluting with 0-5% methanol in dichloromethane to provide the title compound that gave proton NMR spectra consistent with theory and a mass ion (ES+) of 459.2039 for [M+H]+ [Calc'd for $C_{26}H_{27}N_4O_4$, [M+H]+=459.2027]: $^1$H NMR (400 MHz, CDCl$_3$) δ 8.89-8.87 (m, 1H), 8.41 (s, 1H), 8.28 (s, 1H), 7.76 (s, 1H), 7.70 (d, J=8.4 Hz, 1H), 7.63-7.54 (m, 2H), 7.41 (s, 2H), 4.82-4.75 (m, 1H), 4.34 (br s, 1H), 4.27 (s, 2H), 4.23-4.18 (m, 2H), 4.03 (s, 1H), 3.58-3.51 (m, 1H), 3.34-3.28 (m, 1H), 3.09 (s, 3H), 2.99 (s, 3H), 2.23-2.12 (m, 1H), 2.00-1.91 (m, 1H).

EXAMPLE 20

3-[(3R,4S)-3-Hydroxytetrahydro-2H-pyran-4-yl]-6-{[6-(1-methoxy-1-methylethyl)pyridine-3-yl]methyl}benzo quinazolin-4(3H)-one

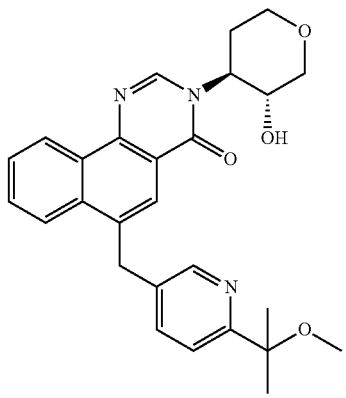

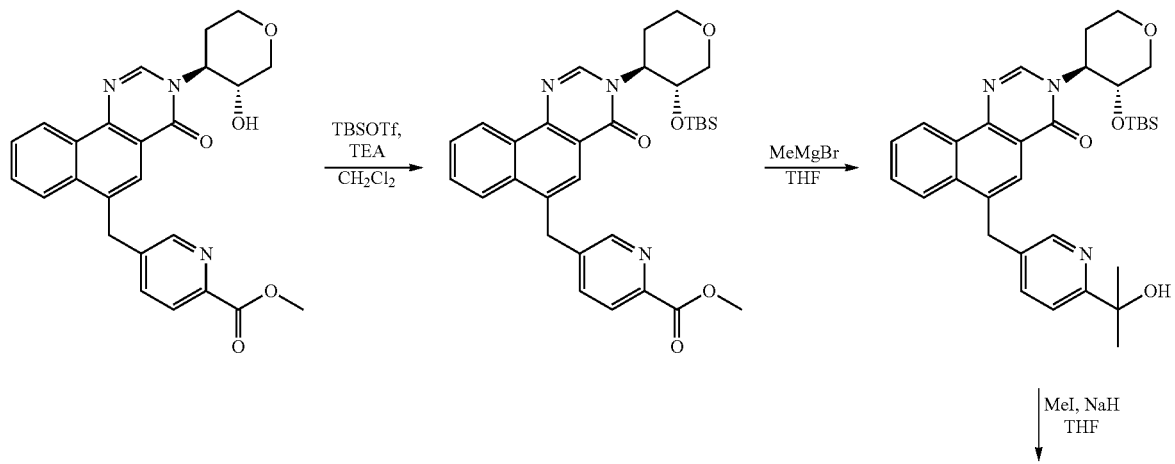

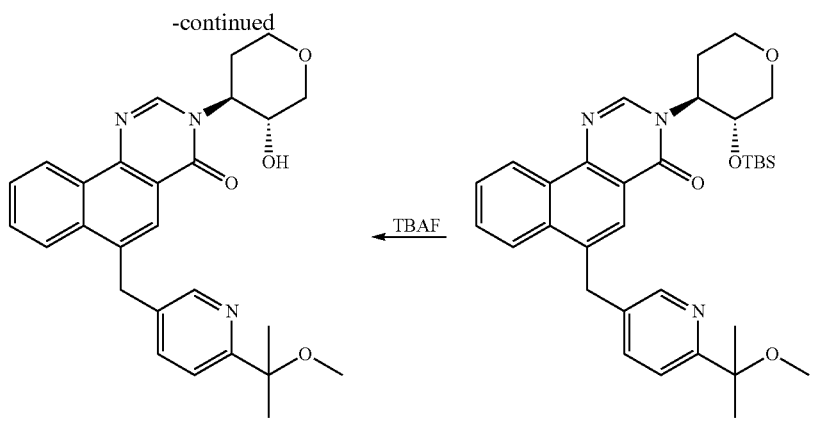

Methyl 5-({3-[(3R,4S)-3-hydroxytetrahydro-2H-pyran-4-yl]-4-oxo-3,4-dihydrobenzo[h]quinazolin-6-yl}methyl)pyridine-2-carboxylate was prepared by the procedure described for the synthesis of 6-[(2-chloropyridin-4-yl)methyl]-3-[(3R,4S)-3-hydroxytetrahydro-2H-pyran-4-yl]benzo[h]quinazolin-4(3H)-one in Example 15, substituting methyl 5-(bromomethyl)pyridine-2-carboxylate for 4-(bromomethyl)-2-chloropyridine.

To a solution of methyl 5-({3-[(3R,4S)-3-hydroxytetrahydro-2H-pyran-4-yl]-4-oxo-3,4-dihydrobenzo[h]quinazolin-6-yl}methyl)pyridine-2-carboxylate (0.255 g, 0.572 mmol) in 6 mL of dichloromethane was added triethylamine (0.087 g, 0.86 mmol) and tert-butydimethylsilyl trifluoromethanesulfonate (0.166 g, 0.630 mmol). After 2 h, the reaction was quenched with saturated aqueous ammonium chloride, and extracted 2× with dichloromethane. The combined organic solution was dried over sodium sulfate, filtered, and concentrated in vacuo to provide methyl 5-{[3-((3R,4S)-3-{[tert-butyl(dimethyl)silyl]oxy}tetrahydro-2H-pyran-4-yl)-4-oxo-3,4-dihydrobenzo[h]quinazolin-6-yl]methyl}pyridine-2-carboxylate title compound that gave a mass ion (ES+) of 560.0 for [M+H]+.

To a solution of the above compound (0.050 g, 0.089 mmol) in 1 mL of THF at 0° C. under an atmosphere of nitrogen was added methylmagnesium bromide (0.089 mL, 3.0 M diethyl ether solution, 0.27 mmol). After 1 h, the mixture was treated with saturated aqueous ammonium chloride and extracted 2× with diethyl ether. The combined organic fractions were dried over sodium sulfate, filtered, and concentrated in vacuo to provide 34(3R,4S)-3-{[tert-butyl(dimethyl)silyl]oxy}tetrahydro-2H-pyran-4-yl)-6-[6-(1-hydroxy-1-methylethyl)pyridine-3-yl]methyl)benzo[h]quinazolin-4(3H)-one that gave proton NMR spectra consistent with theory.

To a solution of the above compound (0.050 g, 0.089 mmol) in 1 mL of THF was added sodium hydride (0.0071 g, 0.18 mmol). After 20 min, iodomethane (0.056 mL, 0.89 mmol) was added. After 15 h, the mixture was treated with saturated aqueous ammonium chloride and extracted 2× with diethyl ether. The combined organic fractions were dried over sodium sulfate, filtered, and concentrated in vacuo to provide 3-((3R,4S)-3-{[tert-butyl(dimethyl)silyl]oxy}tetrahydro-2H-pyran-4-yl)-6-{[6-(1-methoxy-1-methylethyl)pyridine-3-yl]methyl}benzo[h]quinazolin-4(3H)-one gave a mass ion (ES+) of 574.0 for [M+H]+

To a solution of the above compound (0.051 g, 0.089 mmol) in 1 mL of THF was added tetrabutylammonium fluoride (0.223 mL, 0.223 mmol). After 1 h, the mixture was treated with saturated aqueous ammonium chloride and extracted 2× with diethyl ether. The combined organic fractions were dried over sodium sulfate, filtered, and concentrated in vacuo. The residue was purified via silica gel chromatography, eluting with 0-4% methanol in dichloromethane to provide the title compound that gave proton NMR spectra consistent with theory and a mass ion (ES+) of 460.2246 for [M+H]+[Calc'd for $C_{27}H_{30}N_3O_4$, [M+H]+=460.2231]: $^1$H NMR (400 MHz, CDCl$_3$) δ 8.90-8.88 (m, 1H), 8.44 (s, 1H), 8.27 (s, 1H), 7.81-7.79 (m, 2H), 7.64-7.56 (m, 2H), 7.33 (s, 2H), 4.85-4.78 (m, 1H), 4.26 (s, 2H), 4.24-4.06 (m, 4H), 3.58-3.53 (m, 1H), 3.32 (t, J=10.1 Hz, 1H), 3.07 (s, 3H), 2.27-2.16 (m, 1H), 2.00-1.96 (m, 1H), 1.48 (s, 6H).

EXAMPLE 21

6-{[6-(Hydroxymethyl)pyridine-3-yl]methyl}-3-[(3R,4S)-3-hydroxytetrahydro-2H-pyran-4-yl]benzo[h]quinazolin-4(3H)-one

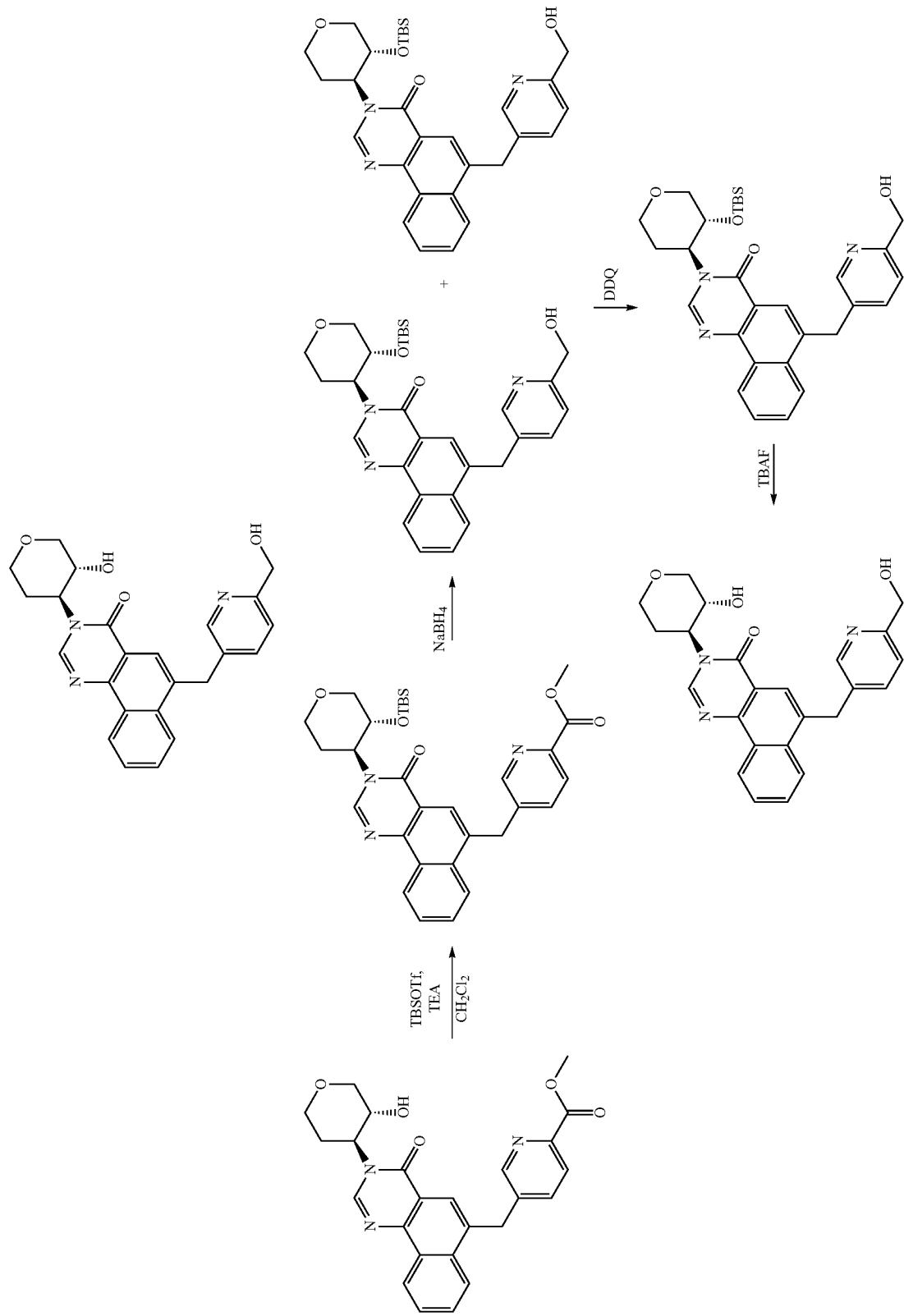

To a solution of methyl 5-{[3-((3R,4S)-3-{[tert-butyl(dimethyl)silyl]oxy}tetrahydro-2H-pyran-4-yl)-4-oxo-3,4-dihydrobenzo[h]quinazolin-6-yl]methyl}pyridine-2-carboxylate (see Example 20, 0.250 g, 0.447 mmol) in 5 mL of ethanol was added sodium borohydride (0.034 g, 0.89 mmol). After 15 h, additional sodium borohydride (0.050 g, 1.32 mmol) was added. After 24 h, the mixture was treated with saturated aqueous ammonium chloride and extracted 2× with dichloromethane. The combined organic fractions were dried over sodium sulfate, filtered, and concentrated in vacuo. To a solution of the residue in 3 mL of chloroform was added 2,3-dichloro-5,6-dicyanobenzoquinone (0.101 g, 0.447 mmol). After 15 min, the mixture was concentrated in vacuo and the residue was purified via silica gel chromatography, eluting with 0-5% methanol in dichloromethane to provide 3-((3R,4S)-3-{[tert-butyl(dimethyl)silyl]oxy}tetrahydro-2H-pyran-4-yl)-6-{[6-(hydroxymethyl)pyridine-3-yl]methyl}benzo[h]quinazolin-4(3H)-one that gave proton NMR spectra consistent with theory and a mass ion (ES+) of 532.0 for [M+H]$^+$.

To a solution of the above compound (0.015 g, 0.028 mmol) in 1 mL of THF was added tetrabutylammonium fluoride (0.070 mL, 0.071 mmol). After 1 h, the mixture concentrated in vacuo and the residue was purified via silica gel chromatography, eluting with 0-5% methanol in dichloromethane to provide the title compound that gave proton NMR spectra consistent with theory and a mass ion (ES+) of 460.2246 for [M+H]$^+$ [Calc'd for $C_{27}H_{30}N_3O_4$, [M+H]$^+$= 460.2231]: $^1$H NMR (400 MHz, CDCl$_3$) δ 8.91-8.89 (m, 1H), 8.40 (s, 1H), 8.27 (s, 1H), 7.79-7.74 (m, 2H), 7.64-7.57 (m, 2H), 7.31-7.29 (m, 1H), 7.04 (d, J=8.0 Hz, 1H), 4.81-4.75 (m, 1H), 4.64 (s, 2H), 4.25 (s, 2H), 4.23-4.16 (m, 2H), 4.09-4.05 (m, 1H), 3.58-3.52 (m, 1H), 3.34-3.29 (m, 1H), 2.87 (br s, 1H), 2.29-2.22 (m, 1H), 2.00-1.95 (m, 1H).

EXAMPLE 22

6-{[6-(Fluoromethyl)pyridine-3-yl]methyl}-3-[(3R,4S)-3-hydroxytetrahydro-2H-pyran-4-yl]benzo[h]quinazolin-4(3H)-one

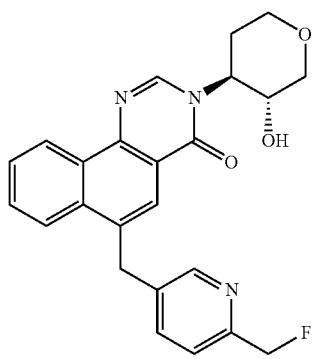

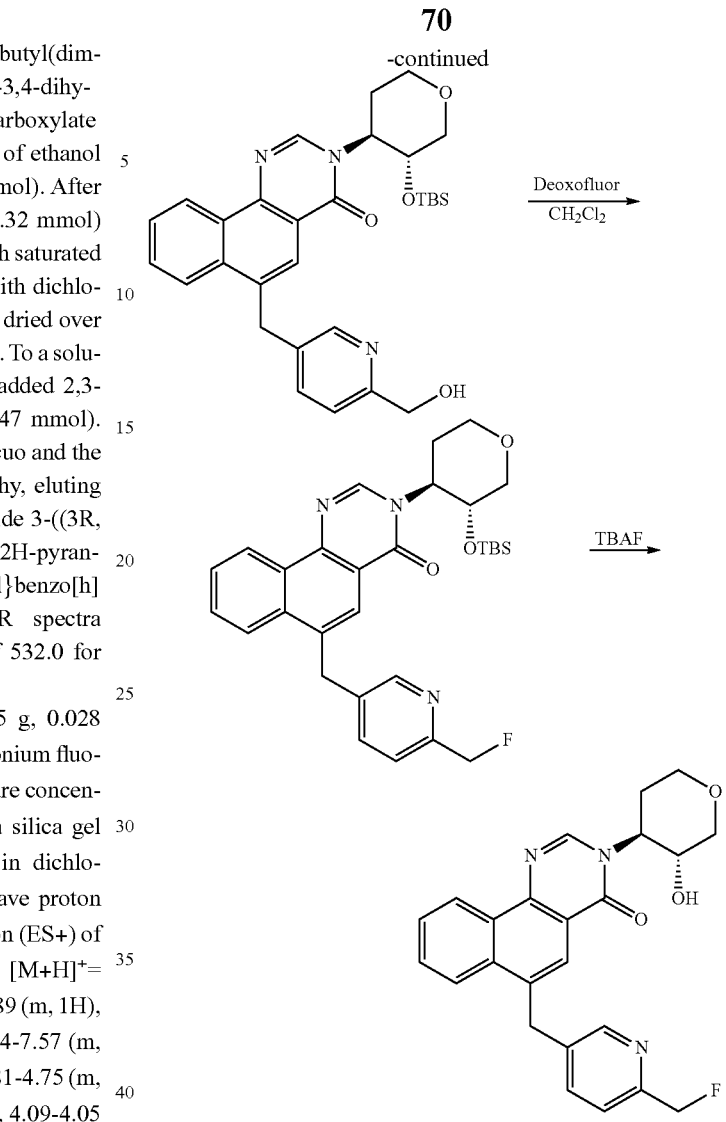

To a solution of 3-((3R,4S)-3-{[tert-butyl(dimethyl)silyl]oxy}tetrahydro-2H-pyran-4-yl)-6-{[6-(hydroxymethyl)pyridine-3-yl]methyl}benzo[h]quinazolin-4(3H)-one (Example 21, 0.035 g, 0.066 mmol) in 1 mL of dichloromethane at −78° C. was added [bis(2-methoxyethyl)amino]sulfur trifluoride (0.015 mL, 0.079 mmol). The reaction was warmed to rt, and after 3 h, the solution was purified via silica gel chromatography, eluting with 0-3% methanol in dichloromethane to provide 3-((3R,4S)-3-{[tert-butyl(dimethyl)silyl]oxy}tetrahydro-2H-pyran-4-yl)-6-{[6-(fluoromethyl)pyridine-3-yl]methyl}benzo[h]quinazolin-4(3H)-one that gave proton NMR spectra consistent with theory and a mass ion (ES+) of 534.0 for [M+H]$^+$.

To a solution of the above compound (0.019 g, 0.035 mmol) in 1 mL of THF was added tetrabutylammonium fluoride (0.089 mL, 0.089 mmol). After 1 h, the mixture was concentrated in vacuo and the residue was purified via silica gel chromatography, eluting with 0-5% methanol in dichloromethane to provide the title compound that gave proton NMR spectra consistent with theory and a mass ion (ES+) of 420.1736 for [M+H]$^+$ [Calc'd for $C_{24}H_{23}N_3O_3$, [M+H]$^+$= 420.1718]: $^1$H NMR (400 MHz, CDCl$_3$) δ 9.02-9.00 (m, 1H), 8.51 (s, 1H), 8.30 (s, 1H), 8.01 (s, 1H), 7.98-7.90 (m, 1H), 7.67-7.64 (m, 2H), 7.49-7.46 (m, 1H), 7.30-7.28 (m, 1H), 5.41 (d, J=47.0 Hz, 2H), 4.89-4.82 (m, 1H), 4.46 (s, 2H), 4.22-4.18 (m, 1H), 4.13-3.88 (m, 2H), 3.56 (t, J=11.1 Hz, 1H), 3.31 (t, J=10.4 Hz, 1H), 2.43-2.34 (m, 1H), 2.33-2.24 (m, 1H), 2.04-2.00 (m, 1H).

EXAMPLE 23

6-{[6-(Difluoromethyl)pyridine-3-yl]methyl}-3-[(3R,4S)-3-hydroxytetrahydro-2H-pyran-4-yl]benzo[h]quinazolin-4(3H)-one methyl}benzo[h]quinazolin-4(3.11)-one (Example 21, 0.075 g, 0.14 mmol) in 1 mL of dichloromethane. After 30 min, triethylamine (0.157 mL, 1.13 mmol) was added, and the reaction was warmed to rt. After 30 min, the mixture was treated with saturated aqueous ammonium chloride and extracted 2× with diethyl ether. The combined organic fractions were dried over sodium sulfate, filtered, and concentrated in vacuo to provide 5-{[3-((3R,4S)-3-{[tert-butyl(dimethyl)silyl]oxy}tetrahydro-2H-pyran-4-yl)-4-oxo-3,4-

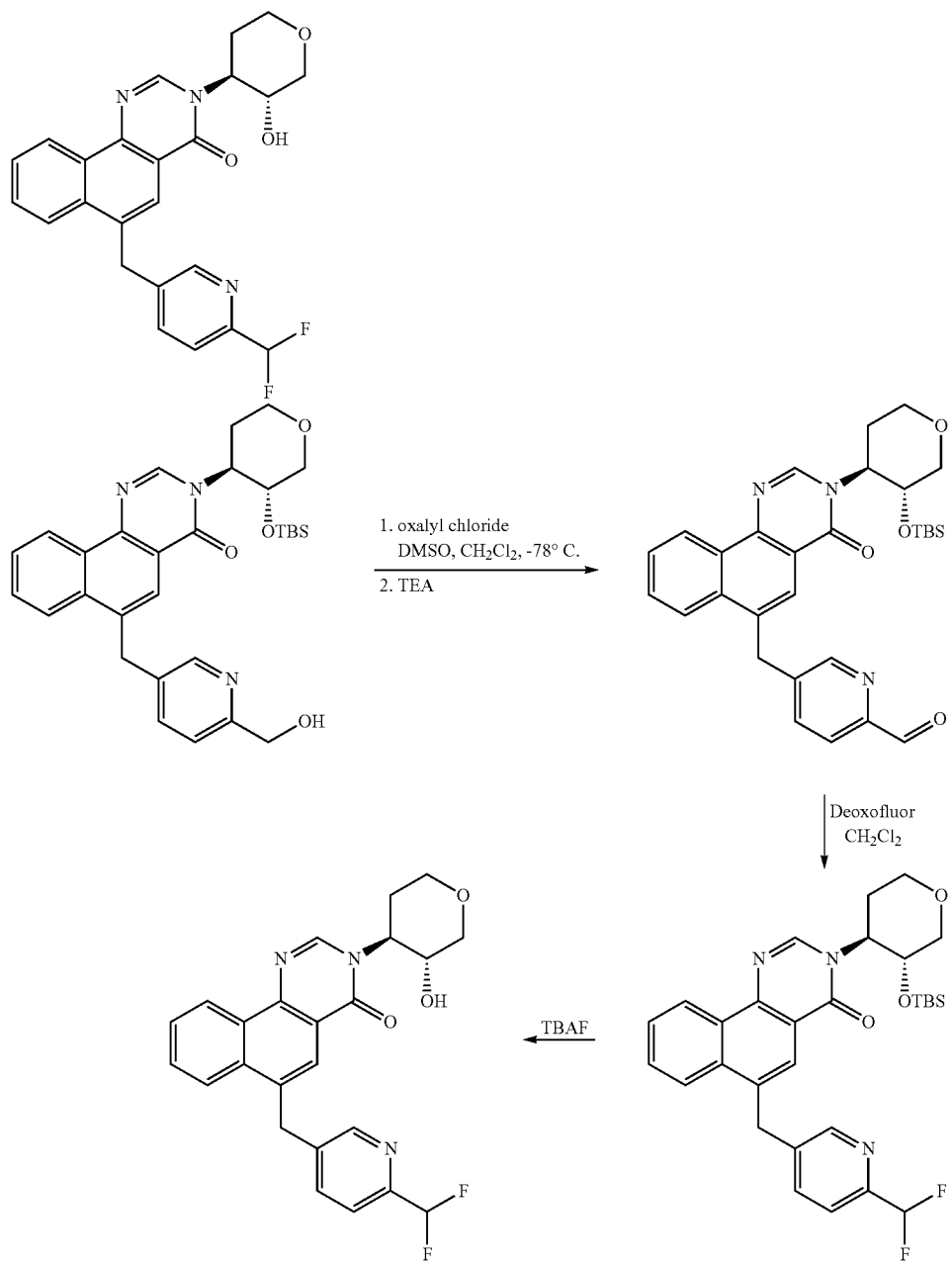

To a solution of dimethylsulfoxide (0.040 mL, 0.56 mmol) in 2 mL of dichloromethane at −78° C. was added oxalyl chloride (0.025 mL, 0.28 mmol). After 30 min, a solution of 3-((3R,4S)-3-{[tert-butyl(dimethyl)silyl]oxy}tetrahydro-2H-pyran-4-yl)-6-{[6-(hydroxymethyl)pyridine-3-yl]

dihydrobenzo[h]quinazolin-6-yl]methyl}pyridine-2-carbaldehyde that gave proton NMR spectra consistent with theory.

To a solution of the above compound (0.050 g, 0.094 mmol) in 1 mL of dichloromethane at −78° C. was added

[bis(2-methoxyethyl)amino]sulfur trifluoride (0.052 mL, 0.28 mmol). The reaction was warmed to rt, and after 4 h, the solution was treated with water and extracted 2× with dichloromethane. The combined organic fractions were dried over sodium sulfate, filtered, and concentrated in vacuo to provide 3-((3R,4S)-3-{[tert-butyl(dimethyl)silyl]oxy}tetrahydro-2H-pyran-4-yl)-6-[6-(difluoromethyl)pyridin-3-yl]methyl}benzo[h]quinazolin-4(3H)-one that gave a mass ion (ES+) of 552.0 for [M+H]$^+$.

To a solution of the above compound (0.052 g, 0.094 mmol) in 1 mL of THF was added tetrabutylammonium fluoride (0.235 mL, 0.235 mmol). After 1 h, the mixture was treated with saturated aqueous ammonium chloride and extracted 2× with dichloromethane. The combined organic fractions were dried over sodium sulfate, filtered, and concentrated in vacuo. The residue was purified via silica gel chromatography, eluting with 0-5% methanol in dichloromethane to provide the title compound that gave proton NMR spectra consistent with theory and a mass ion (ES+) of 438.1642 for [M+H]$^+$ [Calc'd for $C_{24}H_{22}F_2N_3O_3$, [M+H]$^+$= 438.1624]: $^1$H NMR (400 MHz, CDCl$_3$) δ 8.86 (d, J=8.1 Hz, 1H), 8.52 (s, 1H), 8.26 (s, 1H), 7.71 (s, 1H), 7.67 (d, J=8.1 Hz, 1H), 7.64-7.54 (m, 2H), 7.23-6.69 (m, 2H), 6.55 (t, J=55.5 Hz, 1H), 4.83-4.76 (m, 1H), 4.28 (s, 2H), 4.25-4.16 (m, 2H), 4.09-4.05 (m, 1H), 3.75 (br s, 1H), 3.59-3.53 (m, 1H), 3.33 (1, J=10.1 Hz, 1H), 2.24-2.16 (m, 1H), 1.99-1.95 (m, 1H).

EXAMPLE 24

6-[(2-Chloro-1-oxidopyridin-4-yl)methyl]-3-[(3R,4S)-3-hydroxytetrahydro-2H-pyran-4-yl]benzo[h]quinazolin-4(3H)-one

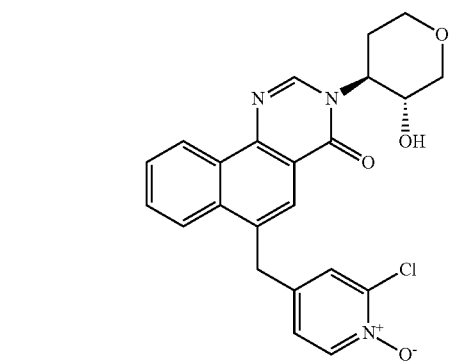

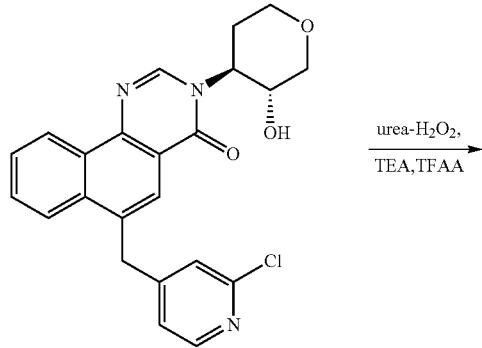

urea-H$_2$O$_2$, TEA,TFAA

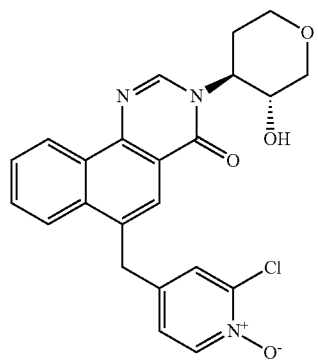

To a solution of 6-[(2-chloropyridin-4-yl)methyl]-3-[(3R,4S)-3-hydroxytetrahydro-2H-pyran-4-yl]benzo[h]quinazolin-4(3H)-one (Example 15, 54.5 mg, 0.129 mmol) in 2 mL of dichloromethane was added urea hydrogen peroxide (60.8 mg, 0.646 mmol), triethylamine (0.090 mL, 0.65 mmol), and trifluoroacetic anhydride (0.036 mL, 0.26 mmol). After 30 min, additional urea hydrogen peroxide (36.5 mg, 0.388 mmol), and triethylamine (0.18 mL, 1.3 mmol), and trifluoroacetic anhydride (0.146 mL, 1.03 mmol) were added. After 3 h, the reaction was cooled to −78° C., treated with 10% aqueous sodium carbonate, and extracted 3× with dichloromethane. The combined organic solutions were dried over sodium sulfate, filtered, and concentrated in vacuo. The residue was suspended in methanol, and the slurry was filtered and washed with additional methanol to provide the title compound that gave proton NMR spectra consistent with theory and a mass ion (ES+) of 438.1214 for [M+H]$^+$ [Calc'd for $C_{23}H_{21}ClN_3O_4$, [M+H]$^+$=438.1215]: $^1$H NMR (400 MHz, d$_6$-DMSO) δ 9.01 (d, J=1.1 Hz, 1H), 8.73 (s, 1H), 8.32 (d, J=6.8 Hz, 1H), 8.14 (d, J=7.7 Hz, 1H), 8.06 (s, 1H), 7.82-7.74 (m, 3H), 7.22-7.20 (m, 1H), 5.31 (d, J=5.5 Hz, 1H), 4.67 (br s, 1H), 4.56 (s, 2H), 4.18 (br s, 1H), 4.00-3.93 (m, 2H), 3.46 (t, J=11.0 Hz, 1H), 3.15 (t, J=10.5 Hz, 1H), 2.24 (br s, 1H), 1.92-1.90 (m, 1H).

EXAMPLE 25

6-[(2-Fluoropyridin-4-yl)methyl]-3-[(3R,4S)-3-hydroxytetrahydro-2H-pyran-4-yl]benzo[h]quinazolin-4(3H)-one

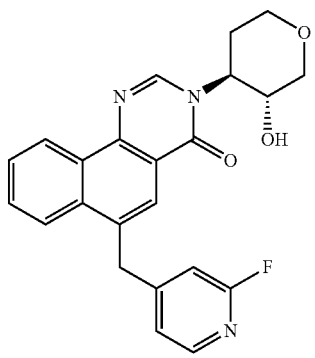

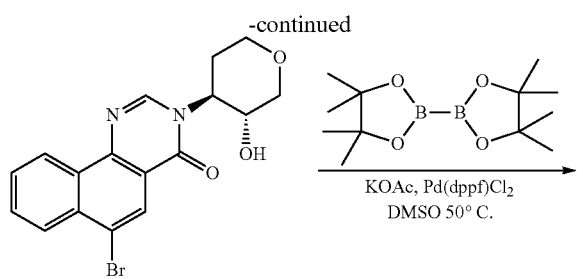

Synthesis of 4-(bromomethyl)-2-fluoropyridine

To a solution of 2-fluoro-4-methylpyridine (0.510 g, 4.59 mmol) in 20 mL of carbon tetrachloride was added N-bromosuccinimide (0.899 g, 5.05 mmol) and benzoyl peroxide (0.148 g, 0.459 mmol). The mixture was heated to 90° C. for 1 h, and then additional benzoyl peroxide (0.074 g, 0.23 mmol) was added. After 20 h, the reaction was diluted with dichloromethane, washed 3× with water, dried over sodium sulfate, filtered, and concentrated in vacuo. The residue was purified via silica gel chromatography, eluting with 0-10% ethyl acetate in hexanes to provide the 4-(bromomethyl)-2-fluoropyridine that gave proton NMR spectra consistent with theory and a mass ion (ES+) of 191.9 ($^{81}$Br) for [M+H]$^+$.

The title compound was prepared by the procedure described for the synthesis of 6-[(2-chloropyridin-4-yl)methyl]-3-[(3R,4S)-3-hydroxytetrahydro-2H-pyran-4-yl]benzo[h]quinazolin-4(3H)-one in Example 15, substituting 4-(bromomethyl)-2-fluoropyridine for 4-(bromomethyl)-2-chloropyridine. The resultant orange solid gave proton NMR spectra consistent with theory and a mass ion (ES+) of 405.9 for [M+H]$^+$: $^1$H NMR (400 MHz, d$_6$-DMSO) δ 9.02-8.99 (m, 1H), 8.73 (s, 1H), 8.11 (d, J=5.6 Hz, 2H), 8.07 (s, 1H), 7.88-7.74 (m, 2H), 7.19 (s, 1H), 7.08 (s, 1H), 5.31 (d, J=5.5 Hz, 1H), 4.65 (s, 2H), 4.18-4.16 (m, 1H), 4.09-3.94 (m, 2H), 3.46 (t, J=11.0 Hz, 1H), 3.22-3.13 (m, 1H), 2.26-2.24 (m, 1H), 1.91-1.87 (m, 1H).

EXAMPLE 26

3-[(3R,4S)-3-Hydroxytetrahydro-2H-pyran-4-yl]-6-[(2-methoxypyridin-4-yl)methyl]benzo[h]quinazolin-4(3H)-one

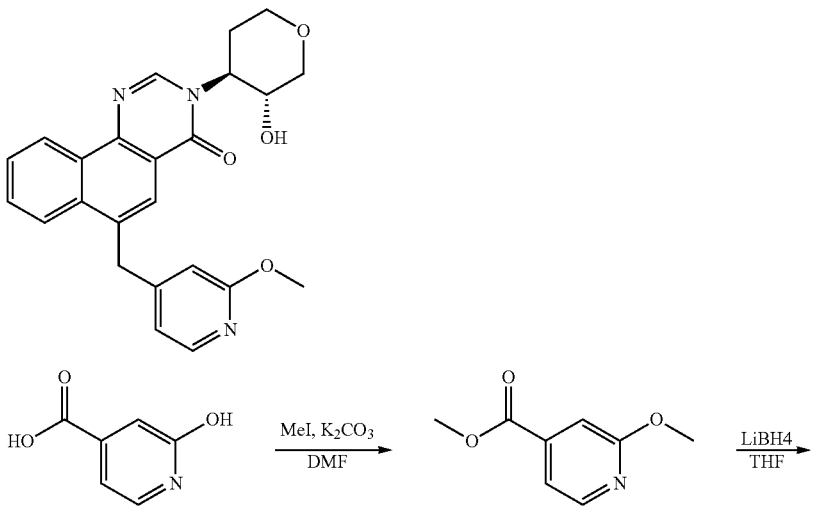

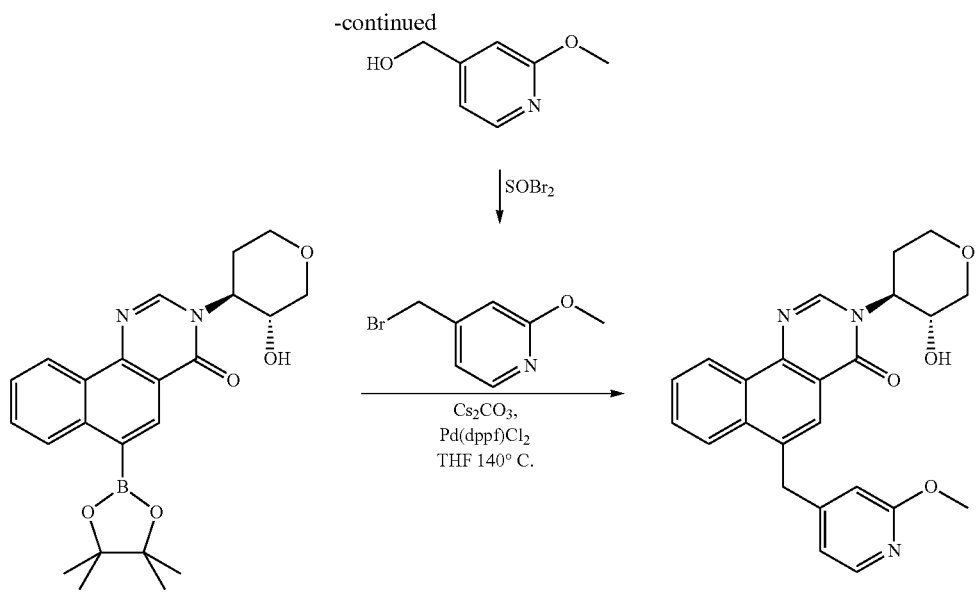

Synthesis of (2-methoxypyridin-4-yl)methanol

To a solution of 2-hydroxyisonicotinic acid (1.05 g, 7.55 mmol) and potassium carbonate (3.23 g, 23.4 mmol) in 7 mL of DMF at 0° C. under an atmosphere of nitrogen was added iodomethane (0.991 mL, 15.8 mmol). The mixture was warmed to rt, and after 14 h, warmed to 40° C. After 3 h, additional iodomethane (0.28 mL, 4.5 mmol) was added. After 20 h, the reaction was diluted with dichloromethane, washed 3× with water, dried over sodium sulfate, filtered, and concentrated in vacuo to provide methyl 2-methoxyisonicotinate that gave proton NMR spectra consistent with theory and a mass ion (ES+) of 168.1 for [M+H]$^+$.

To a solution of the above compound (0.425 g, 2.54 mmol) in 2 mL of THF at 0° C. under an atmosphere of nitrogen was added lithium borohydride (0.089 g, 4.1 mmol). The mixture was warmed to rt, and after 20 h, filtered and washed with dichloromethane. The organic filtrate was concentrated in vacuo and the residue was purified via silica gel chromatography, eluting with 0-5% methanol in dichloromethane to provide (2-methoxypyridin-4-yl)methanol that gave proton NMR spectra consistent with theory.

The title compound was prepared by the procedure described for the synthesis of 6-[(2-chloropyridin-4-yl)methyl]-3-[(3R,4S)-3-hydroxytetrahydro-2H-pyran-4-yl]benzo[h]quinazolin-4(3H)-one in Example 15, substituting (2-methoxypyridin-4-yl)methanol for 2-chloropyridine-4-methanol. The resultant orange solid gave proton NMR spectra consistent with theory and a mass ion (ES+) of 418.1779 for [M+H]$^+$ [Calc'd for $C_{24}H_{24}N_3O_4$, [M+H]$^+$=418.1761]: $^1$H NMR (400 MHz, d$_6$-DMSO) δ 9.01 (d, J=7.7 Hz, 1H), 8.71 (s, 1H), 8.11 (d, J=8.0 Hz, 1H), 8.05 (s, 1H), 7.81-7.74 (m, 2H), 7.56-7.54 (m, 1H), 5.32 (d, J=5.5 Hz, 1H), 4.64 (br s, 1H), 4.37 (s, 2H), 4.17 (br 5, 1H), 4.18-3.97 (m, 2H), 3.51-3.43 (m, 1H), 3.34 (s, 3H), 3.15 (t, J=10.3 Hz, 1H), 2.25 (br s, 1H), 1.91 (d, J=12.0 Hz, 1H).

EXAMPLE 27

6-[(6-Ethyoxypyridin-3-yl)methyl]-3-[(3R,4S)-3-hydroxytetrahydro-2H-pyran-4-yl]benzo[h]quinazolin-4(3H)-one

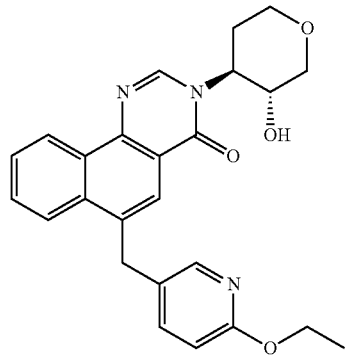

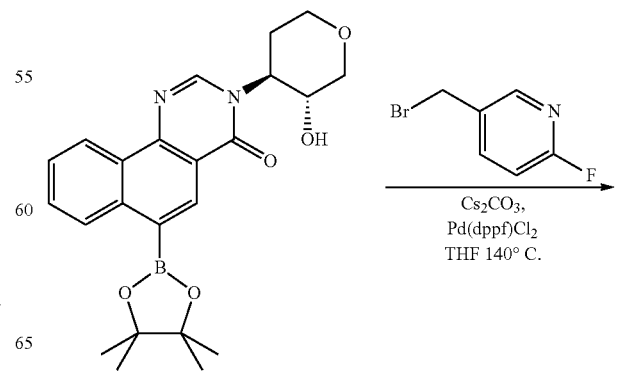

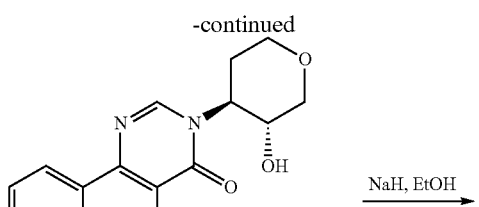

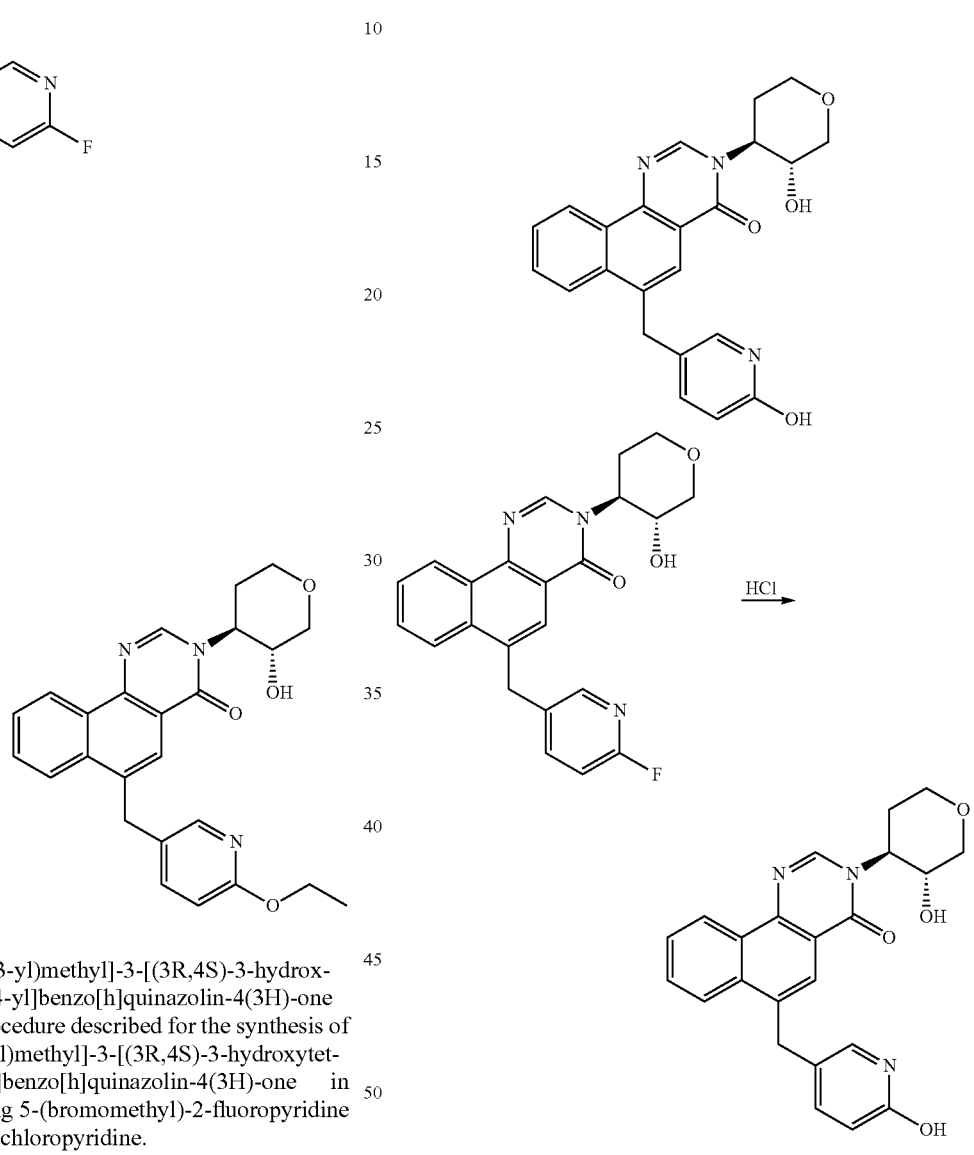

6-[(6-Fluoropyridin-3-yl)methyl]-3-[(3R,4S)-3-hydroxytetrahydro-2H-pyran-4-yl]benzo[h]quinazolin-4(3H)-one was prepared by the procedure described for the synthesis of 6-[(2-chloropyridin-4-yl)methyl]-3-[(3R,4S)-3-hydroxytetrahydro-2H-pyran-4-yl]benzo[h]quinazolin-4(3H)-one in Example 15, substituting 5-(bromomethyl)-2-fluoropyridine for 4-(bromomethyl)-2-chloropyridine.

To a solution of sodium hydride (0.012 g, 0.31 mmol) in 1 mL of DMSO was added ethanol (0.022 mL, 0.37 mmol). After 5 min, 6-[(6-Fluoropyridin-3-yl)methyl]-3-[(3R,4S)-3-hydroxytetrahydro-2H-pyran-4-yl]benzo[h]quinazolin-4(3H)-one (0.050 g, 0.12 mmol) was added. After 4 h, the reaction was diluted with ethyl acetate, washed with water, dried over sodium sulfate, filtered, and concentrated in vacuo. The residue was purified via silica gel chromatography, eluting with 25-75% ethyl acetate in hexanes to provide the title compound that gave proton NMR spectra consistent with theory and a mass ion (ES+) of 432.1916 for [M+H]+ [Calc'd for $C_{25}H_{26}N_3O_4$, [M+H]+=432.1918]: $^1$H NMR (400 MHz, CDCl$_3$) δ 8.92-8.89 (m, 1H), 8.26 (s, 1H), 8.00 (s, 1H), 7.89-7.86 (m, 1H), 7.84 (s, 1H), 7.65-7.58 (m, 2H), 7.29 (s, 1H), 6.55 (s, 1H), 4.86-4.79 (m, 1H), 4.29-4.06 (m, 7H), 3.59-3.52 (m, 1H), 3.33-3.29 (m, 1H), 3.16 (d, J=6.5 Hz, 1H), 2.29-2.19 (m, 1H), 2.01-1.97 (m, 1H), 1.30-1.27 (m, 1H).

EXAMPLE 28

6-[(6-Hydroxypyridin-3-yl)methyl]-3-[(3R,4S)-3-hydroxytetrahydro-2H-pyran-4-yl]benzo[h]quinazolin-4(3H)-one 6-[(6-Fluoropyridin-3-yl)methyl]-3-[(3R,4S)-3-hydroxytetrahydro-2H-pyran-4-yl]benzo[h]quinazolin-4(3H)-one was prepared by the procedure described for the synthesis of 6-[(2-chloropyridin-4-yl)methyl]-3-[(3R,4S)-3-hydroxytetrahydro-2H-pyran-4-yl]benzo[h]quinazolin-4(3H)-one in Example 15, substituting 5-(bromomethyl)-2-fluoropyridine for 4-(bromomethyl)-2-chloropyridine.

A solution of 6-[(6-fluoropyridin-3-yl)methyl]-3-[(3R,4S)-3-hydroxytetrahydro-2H-pyran-4-yl]benzo[h]quinazolin-4(3H)-one (0.100 g, 0.247 mmol) in 2 mL of hydrochloric acid was heated to 100° C. for 4 h. Additional hydrochloric acid (1.5 mL) was added, and after 2 h, the reaction was concentrated in vacuo to provide the title compound that gave proton NMR spectra consistent with theory and a mass ion (ES+) of 404.1604 for [M+H]+ [Calc'd for C23H22N3O4, [M+H]+=404.1605]: 1H NMR (400 MHz, d6-DMSO) δ 8.94 (d, J=8.0 Hz, 1H), 8.66 (s, 1H), 8.18 (d, J=8.0 Hz, 1H), 7.91 (s, 1H), 7.78-7.70 (m, 2H), 7.44-7.41 (m, 2H), 6.40 (d, J=9.0 Hz, 1H), 4.59 (br s, 1H), 4.27 (s, 2H), 4.12 (br s, 1H), 3.94-3.89 (m, 2H), 3.40 (t, J=11.6 Hz, 1H), 3.10 (d, J=10.4 Hz, 1H), 2.19 (br s, 1H), 1.86-1.83 (m, 1H).

EXAMPLE 29

6-{[6-(Difluoromethoxy)pyridine-3-yl]methyl}-3-[(3R,4S)-3-hydroxytetrahydro-2H-pyran-4-yl]benzo[h]quinazolin-4(3H)-one

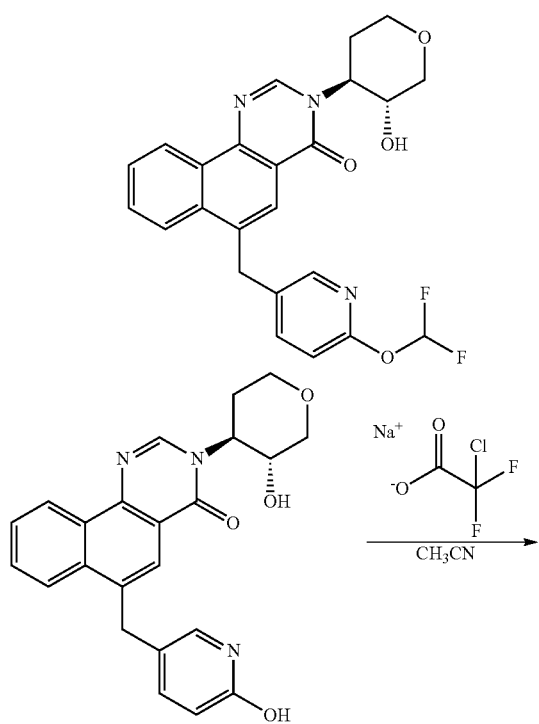

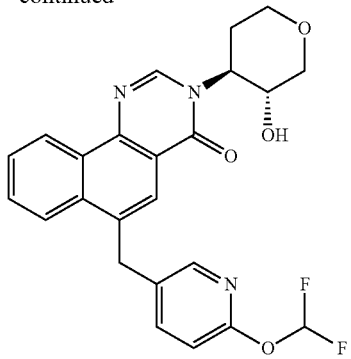

To a solution of 6-[(6-hydroxypyridin-3-yl)methyl]-3-[(3R,4S)-3-hydroxytetrahydro-2H-pyran-4-yl]benzo[h]quinazolin-4(3H)-one (Example 29, 0.025 g, 0.062 mmol) in 1 mL of acetonitrile was added sodium chlorodifluoroacetate (0.010 g, 0.068 mmol). The reaction was heated to reflux under an atmosphere of nitrogen for 4 h, and then DMF (0.310 mL) was added. The mixture was heated to 100° C. for 1 h, cooled to rt, and diluted with ethyl acetate. The organic solution was washed 3× with water, dried over sodium sulfate, filtered, and concentrated in vacuo. The residue was purified via silica gel chromatography, eluting with 0-5% methanol in dichloromethane to provide the title compound that gave proton NMR spectra consistent with theory and a mass ion (ES+) of 454.1573 for [M+H]+ [Calc'd for C24H22F2N3O4, [M+H]+=454.1573]: 1H NMR (400 MHz, CDCl6) δ 8.90-8.88 (m, 1H), 8.26 (s, 1H), 8.03 (s, 1H), 7.77-7.75 (m, 2H), 7.65-7.59 (m, 2H), 7.43-7.40 (m, 1H), 7.37 (t, J=73.2 Hz, 1H), 6.73 (d, J=8.4 Hz, 1H), 4.84-4.77 (m, 1H), 4.25 (s, 2H), 4.22-4.06 (m, 3H), 3.59-3.53 (m, 1H), 3.45 (br s, 1H), 3.35-3.30 (m, 1H), 2.21-1.96 (m, 1H), 2.00-1.96 (m, 1H).

EXAMPLE 30

6-{[2-(Difluoromethoxy)pyridine-4-yl]methyl}-3-[(3R,4S)-3-hydroxytetrahydro-2H-pyran-4-yl]benzo[h]quinazolin-4(3H)-one

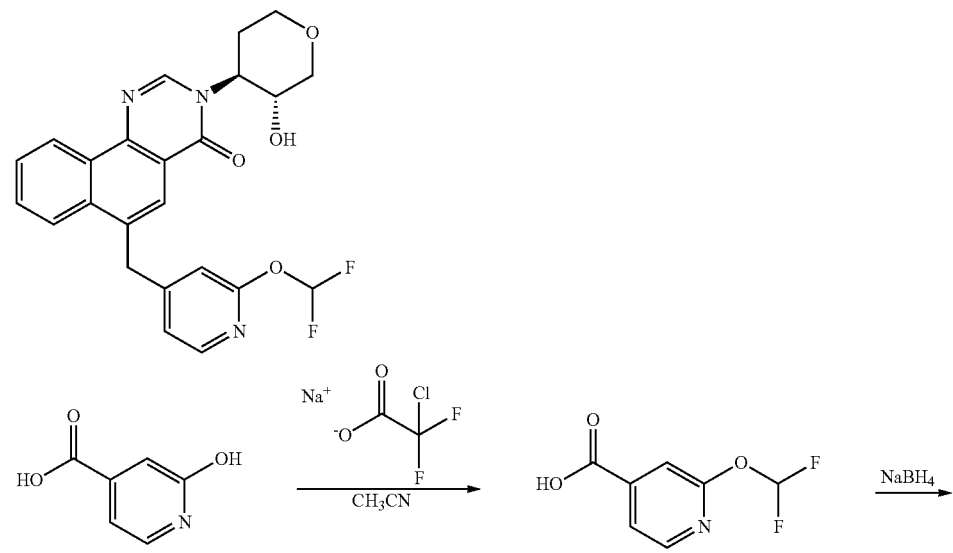

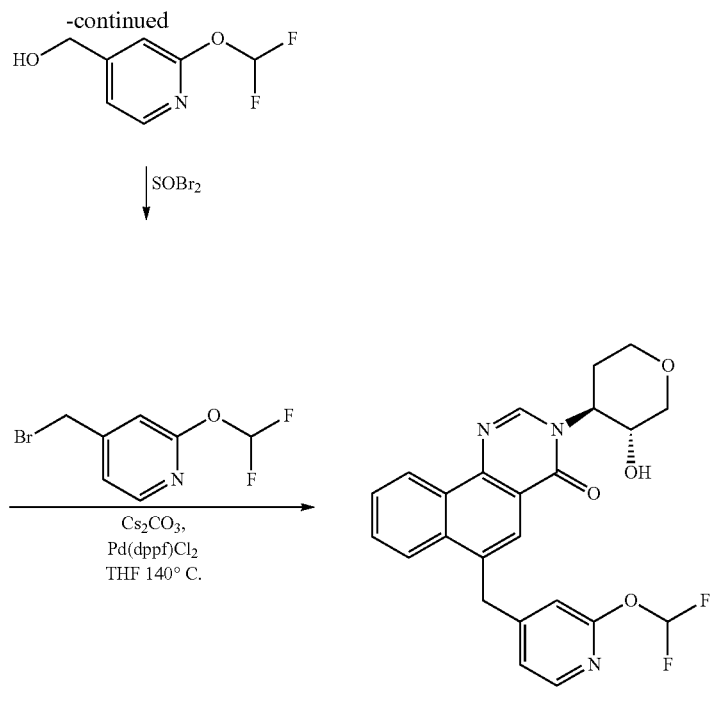

Synthesis of [2-(difluoromethoxy)pyridine-4-yl]methanol

To a solution of 2-hydroxyisonicotinaldehyde (1.00 g, 8.12 mmol) in 25 mL of acetontitrile was added sodium chlorodifluoroacetate (1.86 g, 12.2 mmol). The reaction was heated to reflux for 20 h, cooled to rt, and diluted with ethyl acetate. The organic solution was washed with brine, dried over sodium sulfate, filtered, and concentrated in vacuo. The residue was redissolved in 20 mL of methanol and placed under an atmosphere of nitrogen. Sodium borohydride (0.307 g, 3.12 mmol) was added in 3 portions, and after 2 h, the reaction was treated with brine and diluted extracted 2× with dichloromethane. The combined organic fractions were dried over sodium sulfate, filtered, and concentrated in vacuo to provide 2-(difluoromethoxy)pyridine-4-yl]methanol that gave a mass ion (ES+) of 176.1 for [M+H]$^+$.

The title compound was prepared by the procedure described for the synthesis of 6-[(2-chloropyridin-4-yl)methyl]-3-[(3R,4S)-3-hydroxytetrahydro-2H-pyran-4-yl]benzo[h]quinazolin-4(3H)-one in Example 15, substituting [2-(difluoromethoxy)pyridine-4-yl]methanol for 2-chloropyridine-4-methanol. The resultant white solid gave proton NMR spectra consistent with theory and a mass ion (ES+) of 454.1587 for [M+H]$^+$ [Calc'd for $C_{24}H_{22}F_2N_3O_4$, [M+H]$^+$=454.1573]: $^1$H NMR (400 MHz, d$_6$-DMSO) δ 9.01-8.99 (m, 1H), 8.72 (s, 1H), 8.13-8.11 (m, 2H), 8.07 (s, 1H), 7.82-7.74 (m, 2H), 7.66 (t, J=72.9 Hz, 1H), 7.12 (s, 1H), 6.97 (s, 1H), 5.31 (d, J=5.6 Hz, 1H), 4.63 (br s, 1H), 4.62 (s, 2H), 4.17 (br s, 1H), 4.06-3.93 (m, 2H), 3.49-3.40 (m, 1H), 3.27-3.18 (m, 1H), 2.27 (br s, 1H), 1.99-1.89 (m, 1H).

EXAMPLE 31

6-[(3-Bromo-1-methyl-1H-pyrrolo[2,3-b]pyridine-4-yl)methyl]-3-[(3R,4S)-3-hydroxytetrahydro-2H-pyran-4-yl]benzo[h]quinazolin-4(3H)-one

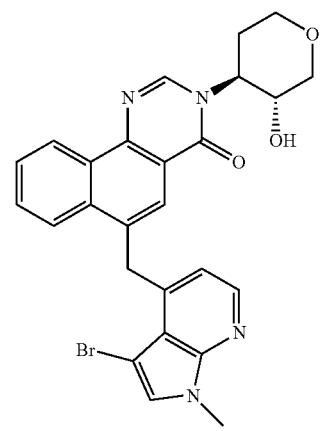

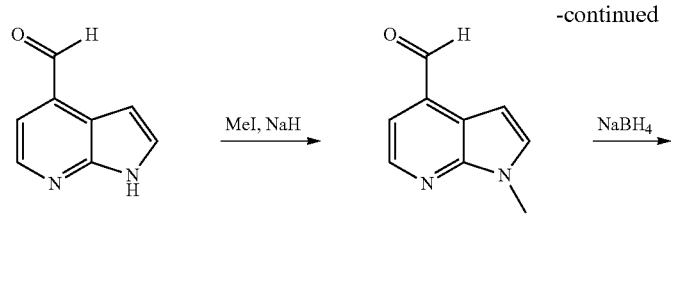

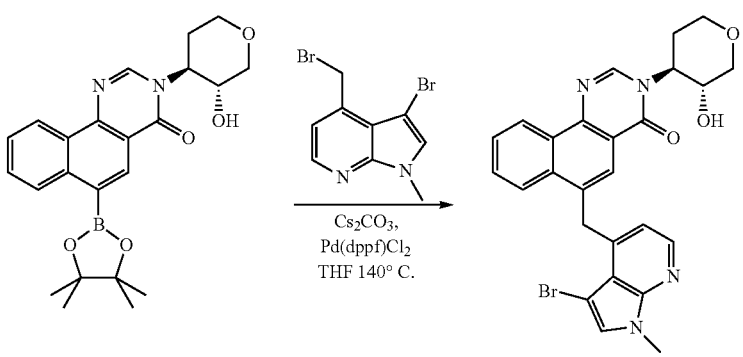

Synthesis of 3-bromo-4-(bromomethyl)-1-methyl-1H-pyrrolo[2,3-b]pyridine

To a solution of 1H-pyrrolo[2,3-b]pyridine-4-carbaldehyde (0.252 g, 1.72 mmol) in 1 mL of DMF under an atmosphere of nitrogen was added sodium hydride (45.5 mg, 1.90 mmol). After 5 min, iodomethane (0.13 mL, 2.1 mmol) was added. After 30 min, the reaction was treated with saturated aqueous ammonium chloride, diluted with water, and extracted 2× with dichloromethane. The combined organic solution was washed 3× with water, dried over sodium sulfate, filtered, and concentrated in vacuo. The residue was purified via silica gel chromatography, eluting with 0-40% ethyl acetate in hexanes to provide 1-methyl-1H-pyrrolo[2,3-b]pyridine-4-carbaldehyde that gave proton NMR spectra consistent with theory and a mass ion (ES+) of 161.2.

To a solution of the above compound (0.136 g, 0.849 mmol) in 5 mL of methanol was added sodium borohydride (9.6 mg, 0.26 mmol). After 2 h, the reaction was treated with saturated aqueous ammonium chloride, diluted with water, and extracted 2× with dichloromethane. The combined organic fractions were washed 3× with water, dried over sodium sulfate, filtered, and concentrated in vacuo. The residue was purified via silica gel chromatography, eluting with 0-40% ethyl acetate in hexanes to provide (1-methyl-1H-pyrrolo[2,3-b]pyridine-4-yl)methanol that gave proton NMR spectra consistent with theory and a mass ion (ES+) of 163.2.

To a solution of the above compound (0.131 g, 0.808 mmol) in 5 mL of dichloromethane at 0° C. was added thionyl bromide (0.336 g, 1.62 mmol) dropwise. After 30 min, the reaction was warmed to rt and quenched with saturated aqueous sodium carbonate. The organic solution was washed 2× with water, dried over sodium sulfate, filtered, and concentrated in vacuo to provide 3-bromo-4-(bromomethyl)-1-methyl-1H-pyrrolo[2,3-b]pyridine that a mass ion (ES+) of 304.9 for [M+H]+.

The title compound was prepared by the procedure described for the synthesis of 6-[(2-chloropyridin-4-yl)methyl]-3-[(3R,4S)-3-hydroxytetrahydro-2H-pyran-4-yl]benzo[h]quinazolin-4(3H)-one in Example 15, substituting 3-bromo-4-(bromomethyl)-1-methyl-1H-pyrrolo[2,3-b]pyridine for 4-(bromomethyl)-2-chloropyridine. The resultant yellow solid gave proton NMR spectra consistent with theory and a mass ion (ES+) of 520.9 ($^{81}$Br) for [M+H]+: $^1$H NMR (400 MHz, d$_6$-DMSO) δ 9.03-9.00 (m, 1H), 8.69 (s, 1H), 8.22-8.19 (m, 2H), 7.84-7.78 (m, 3H), 7.61 (s, 1H), 6.79 (d, J=4.8 Hz, 1H), 5.28 (d, J=5.5 Hz, 1H), 5.07 (s, 2H), 4.56 (br s, 1H), 4.14 (br s, 1H), 3.97-3.90 (m, 2H), 3.85 (s, 3H), 3.44-3.38 (m, 1H), 3.11 (t, J=10.5 Hz, 1H), 2.22 (br s, 1H), 1.87-1.84 (m, 1H).

EXAMPLE 32

6-[(1-Ethyl-1H-pyrrolo[2,3-b]pyrdin-4-yl)methyl]-3-[(3R,4S)-3-hydroxytetrahydro-2H-pyran-4-yl]benzoquinazolin-4(3H)-one

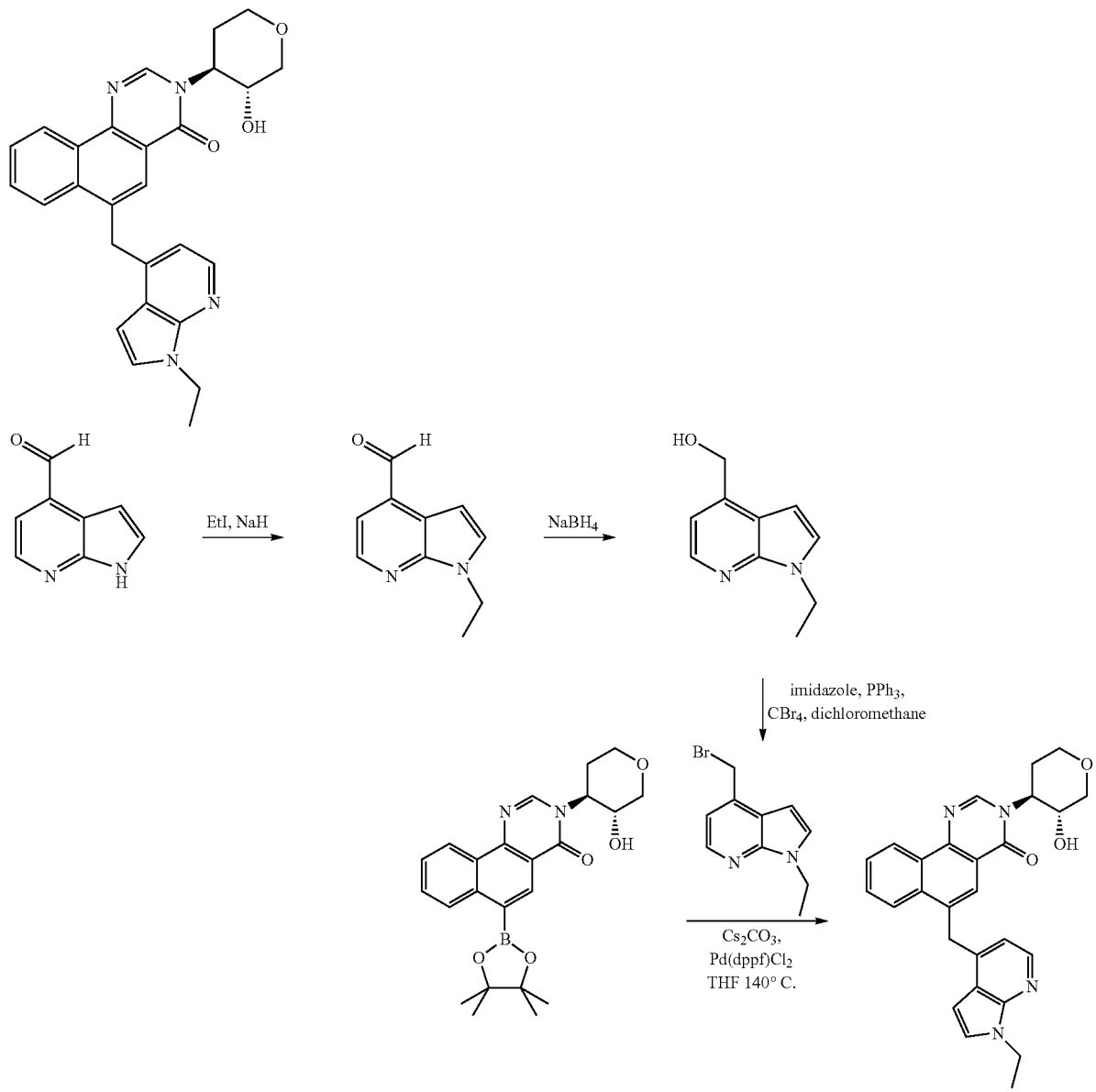

Synthesis of 4-(bromomethyl)-ethyl-1H-pyrrolo[2,3-b]pyridine

To a solution of 1H-pyrrolo[2,3-b]pyridine-4-carbaldehyde (0.413 g, 2.83 mmol) in 5 mL of DMF under an atmosphere of nitrogen was added sodium hydride (74.6 mg, 3.11 mmol). After 5 min, iodoethane (0.529 g, 3.39 mmol) was added. After 30 min, the reaction was treated with saturated aqueous ammonium chloride, diluted with water, and extracted 2× with dichloromethane. The combined organic solution was washed 3× with water, dried over sodium sulfate, filtered, and concentrated in vacuo. The residue was purified via silica gel chromatography, eluting with 0-25% ethyl acetate in hexanes to provide 1-ethyl-M-pyrrolo[2,3-b]pyridine-4-carbaldehyde that gave proton NMR spectra consistent with theory and a mass ion (ES+) of 175.2.

To a solution of the above compound (0.343 g, 1.97 mmol) in 10 mL of methanol was added sodium borohydride (0.022 g, 0.59 mmol). After 30 min, the reaction was treated with saturated aqueous ammonium chloride, diluted with water, and extracted 3× with dichloromethane. The combined organic fractions were washed 3× with water, dried over sodium sulfate, filtered, and concentrated in vacuo to provide (1-ethyl-M-pyrrolo[2,3-b]pyridine-4-yl)methanol that gave proton NMR spectra consistent with theory and a mass ion (ES+) of 177.2.

To a solution of the above compound (0.109 g, 0.619 mmol) in 3 mL of dichloromethane was added triphenylphosphine (0.162 g, 0.619 mmol), imidazole (0.084 g, 1.3 mmol), and carbon tetrabromide (0.226 g, 0.680 mmol). After 30 min, the reaction was treated with saturated aqueous sodium carbonate. The organic solution washed 2× with water, dried over sodium sulfate, filtered, and concentrated in vacuo. The residue was purified via silica gel chromatography, eluting with 0-25% ethyl acetate in hexanes to provide 4-(bromomethyl)-1-ethyl-1H-pyrrolo[2,3-b]pyridine that gave proton NMR spectra consistent with theory and a mass ion (ES+) of 241.1 ($^{81}$Br).

The title compound was prepared by the procedure described for the synthesis of 6-[(2-chloropyridin-4-yl)methyl]-3-[(3R,4S)-3-hydroxytetrahydro-2H-pyran-4-yl]benzo[h]quinazolin-4(3R)-one in Example 15, substituting 4-(bromomethyl)-1-ethyl-1H-pyrrolo[2,3-b]pyridine for 4-(bromomethyl)-2-chloropyridine. The resultant orange solid gave proton NMR spectra consistent with theory and a mass ion (ES+) of 455.2087 for [M+H]$^+$ [Calc'd for C$_{27}$H$_{27}$N$_4$O$_3$, [M+H]$^+$=455.2078]: $^1$H NMR (400 MHz, d$_6$-DMSO) δ 9.01-8.98 (m, 1H), 8.71 (s, 1H), 8.14-8.08 (m, 2H), 8.01 (s, 1H), 7.75-7.71 (m, 2H), 7.56 (s, 1H), 6.74-6.72 (m, 1H), 6.59 (s, 1H), 5.31 (d, J=5.5 Hz, 1H), 4.80 (s, 2H), 4.63 (br s, 1H), 4.28 (q, J=7.2 Hz, 2H), 4.18-4.15 (m, 1H), 3.99-3.92 (m, 1H), 3.42 (t, J=11.1 Hz, 1H), 3.14 (t, J=10.4 Hz, 1H), 2.26 (br s, 1H), 1.91-1.89 (m, 1H), 1.38 (t, J=7.2 Hz, 3H).

EXAMPLE 33

6-[(6-Chloropyridin-3-yl)methyl]-3-[(3R,4S)-3-hydroxytetrahydro-2H-thiopyran-4-yl]benzo[h]quinazolin-4(3H)-one

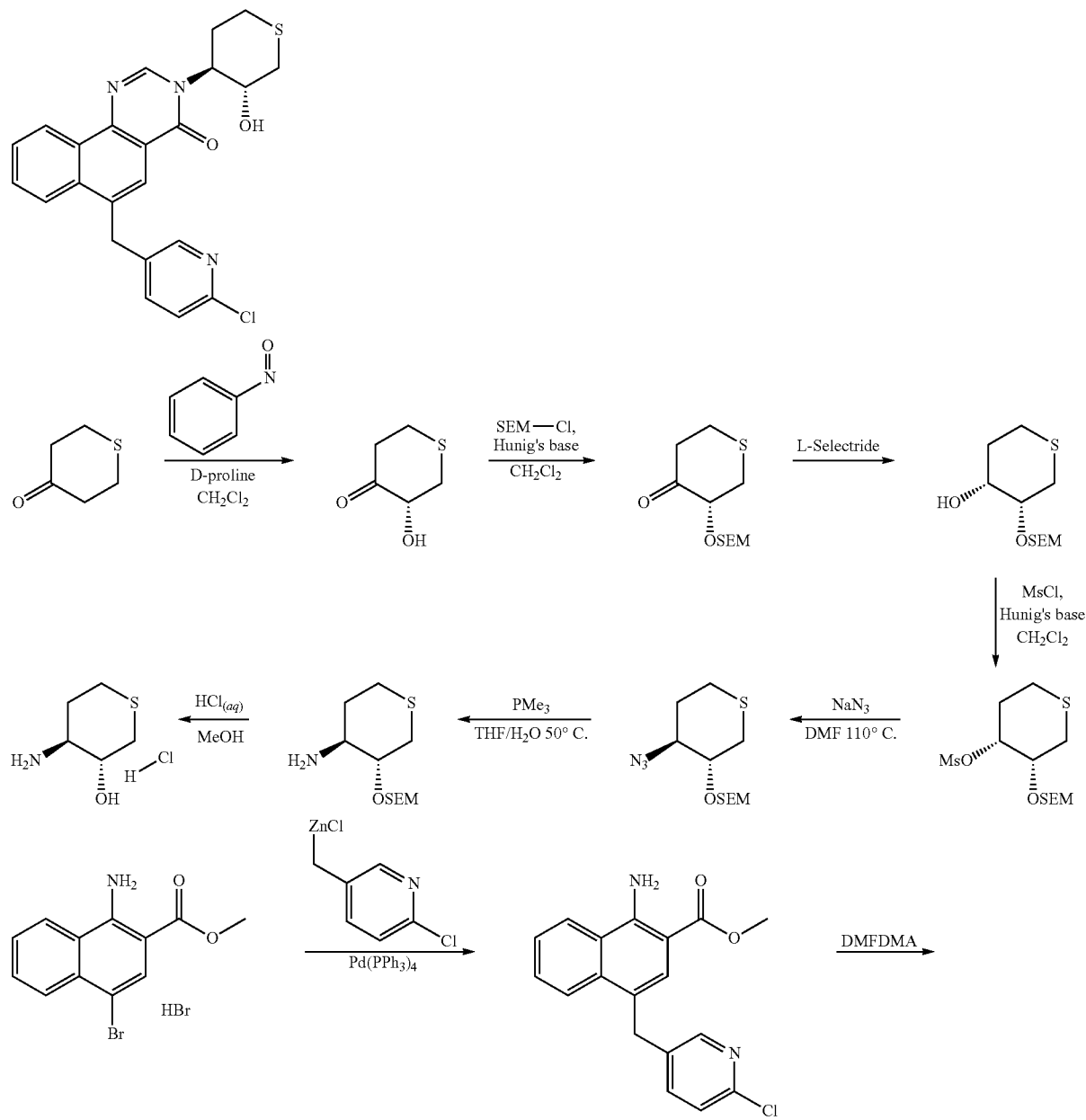

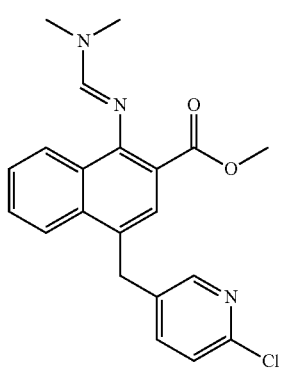
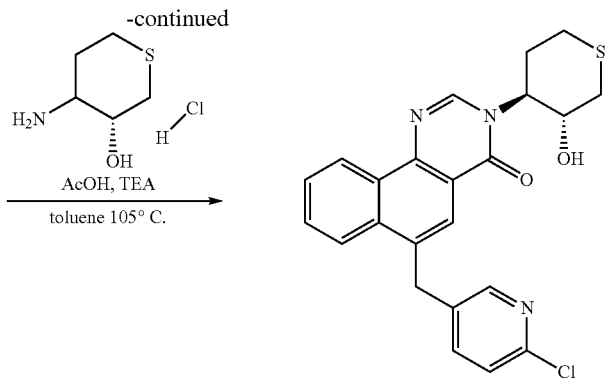

Synthesis of (3R,4S)-4-aminotetrahydro-2H-thiopyran-3-ol hydrochloride

To a solution of tetrahydrothiopyran-4-one (5.00 g, 43.0 mmol) in 200 mL of dichloromethane was added D-proline (0.991 g, 8.61 mmol.) and nitrosobenzene (13.8 g, 0.129 mol). After 15 h, the reaction was treated with water and extracted 2× with dichloromethane. The combined organic solution was dried over sodium sulfate, filtered, and concentrated in vacuo. The residue was purified via silica gel chromatography, eluting with 0-40% ethyl acetate in hexanes to provide (3R)-3-hydroxytetrahydro-4H-thiopyran-4-one.

To a solution of the above compound (0.700 g, 5.30 mmol) in 25 mL of dichloromethane was added N,N-diisopropylethylamine (1.85 mL, 10.6 mmol) and 2-(trimethylsilyl)ethoxymethyl chloride (1.13 mL, 6.35 mmol). After 15 h, the reaction was treated with water and extracted 2× with dichloromethane. The combined organic solution was dried over sodium sulfate, filtered, and concentrated in vacuo. The residue was purified via silica gel chromatography, eluting with 0-15% ethyl acetate in hexanes to provide (3R)-3-{[2-(trimethylsilyl)ethoxy]methoxy)tetrahydro-4H-thiopyran-4-one.

To a solution of the above compound (0.504 g, 1.92 mmol) in 10 mL of TI-IF at −78° C. was added L-Selectride (1.0 M in THF, 2.11 mL, 2.11 mmol). After 1 h, the reaction was treated with 10% aqueous sodium carbonate, warmed to rt, and extracted 2× with diethyl ether. The combined organic solution was dried over sodium sulfate, filtered, and concentrated in vacuo. The residue was purified via silica gel chromatography, eluting with 0-25% ethyl acetate in hexanes to provide (3R,4R)-3-{[2-(trimethylsilyl)ethoxy]methoxy}tetrahydro-2H-thiopyran-4-ol that gave proton NMR spectra consistent with theory.

To a solution of the above compound (0.500 g, 1.89 mmol) in 20 mL of dichloromethane at 0° C. was added N,N-diisopropylethylamine (0.726 mL, 4.16 mmol) and methanesulfonyl chloride (0.18 mL, 2.3 mmol). After 30 min, the reaction was treated with water and extracted 2× with diethyl ether. The combined organic solution was dried over sodium sulfate, filtered, and concentrated in vacuo to provide (3R,4S)-3-{([2-(trimethylsilyl)ethoxy]methoxy}tetrahydro-2H-thiopyran-4-yl methanesulfonate that gave proton NMR spectra consistent with theory.

To a solution of the above compound (0.648 g, 1.89 mmol) in 10 mL of DMF was added sodium azide (0.369 g, 5.67 mmol). The mixture was heated to 110° C. for 15 h, cooled to rt, and diluted with diethyl ether. The organic solution was washed with water, dried over sodium sulfate, filtered, and concentrated in vacuo. The residue was purified via silica gel chromatography, eluting with 0-10% ethyl acetate in hexanes to provide [2-({[(3R,4S)-4-azidotetrahydro-2H-thiopyran-3-yl]oxy}methoxy)ethyl](trimethyl)silane that gave proton NMR spectra consistent with theory.

To a solution of the above compound (0.150 g, 0.518 mmol) in 3 mL of THF and 3 mL of water was added trimethylphosphine (1.0 M in THF, 1.30 mL, 1.30 mmol). The mixture was heated to 50° C. for 15 h, and additional trimethylphosphine was added (1.0 M in THF, 1.30 mL, 1.30 mmol). After 24 h, the reaction was cooled to rt, treated with water, and extracted 2× with dichloromethane. The organic solution was dried over sodium sulfate, filtered, and concentrated in vacuo. The residue was purified via silica gel chromatography, eluting with 0-10% methanol in dichloromethane to provide (3R,4S)-3-{([2-(trimethylsilyl)ethoxy]methoxy}tetrahydro-2H-thiopyran-4-amine that gave proton NMR spectra consistent with theory.

To a solution of the above compound (0.135 g, 0.512 mmol) in 5 mL of methanol was added 3 N HCl (0.85 mL, 2.55 mmol). After 2 h, the reaction was concentrated in vacuo to provide (3R,4S)-4-aminotetrahydro-2H-thiopyran-3-ol hydrochloride that gave proton NMR spectra consistent with theory.

To a solution of methyl 1-amino-4-bromo-2-naphthoate hydrobromide (1.94 g, 5.37 mmol) in 10 mL of THF at 0° C. under an atmosphere of nitrogen was added (2-chloro-5-pyridyl)methylzinc chloride (41.6 mL, 0.5 M in THF, 83.2 mmol) and bis(tri-tert-butylphosphine)palladium(0) (0.177 g, 0.346 mmol). The reaction was warmed to rt, and after 16 h, treated with water (10 mL). The mixture was diluted dichloromethane and water, and a beige solid was removed via filtration. The filtrate was extracted 2× with dichloromethane and the combined organic fractions were dried over sodium sulfate, filtered, and concentrated in vacuo. The residue was purified via silica gel chromatography, eluting with 0-20% ethyl acetate in hexanes provide methyl 1-amino-4-(4-chlorobenzyl)-2-naphthoate that gave a proton NMR spectra consistent with theory and a mass ion (ES+) of 326.1 for [M+H]+.

A solution of the above compound (1.10 g, 3.37 mmol) in N,N-dimethylformamide dimethylacetal (1.35 mL, 10.1 mmol) was heated at 100° C. for 3 h. The reaction was cooled to rt, concentrated in vacuo, and dried to provide methyl 4-[(6-chloropyridin-3-yl)methyl]-1-{[(1E)-(dimethylamino)methylene]amino}-2-naphthoate that gave a mass ion (ES+) of 381.9 for [M+H]+.

To a solution of the above compound (0.025 g, 0.065 mmol) in 1 mL of toluene was added (3R,4S)-4-aminotetrahydro-2H-thiopyran-3-ol hydrochloride (0.013 g, 0.079 mmol) and triethylamine (0.011 mL, 0.082 mmol). After 5 min, acetic acid (0.038 mL, 0.66 mmol) was added, and the reaction was heated to 105° C. for 4 h. The mixture was cooled to rt, concentrated in vacuo, and the residue was purified via silica gel chromatography, eluting with 0-4% methanol in dichloromethane to provide the title compound that gave proton NMR spectra consistent with theory and a mass ion (ES+) of 438.1039 for [M+H]+ [Calc'd for $C_{23}H_{21}ClN_3O_2S$, [M+H]+=438.1038]: $^1$H NMR (400 MHz, $CDCl_3$) δ 8.98-8.94 (m, 1H), 8.30 (s, 1H), 8.26 (s, 1H), 7.93 (s, 1H), 7.83-7.79 (m, 1H), 7.67-7.60 (m, 2H), 7.36-7.30 (m, 1H), 7.71 (d, J=8.3 Hz, 1H), 4.61 (br s, 1H), 4.37 (s, 2H), 4.17 (br s, 1H), 2.95-2.87 (m, 1H), 2.84-2.68 (m, 2H), 2.61-2.34 (m, 1H), 2.02-1.98 (m, 3H).

EXAMPLE 34

3-[(3S,4S)-4-Hydroxytetrahydro-2H-pyran-3-yl]-6-[(6'-methyl-2,3-bipyridin-5-yl)methyl]benzo[h]quinazolin-4(3H)-one

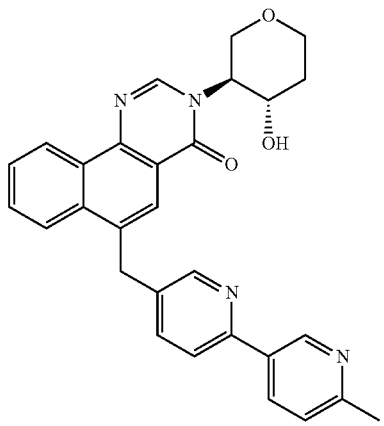

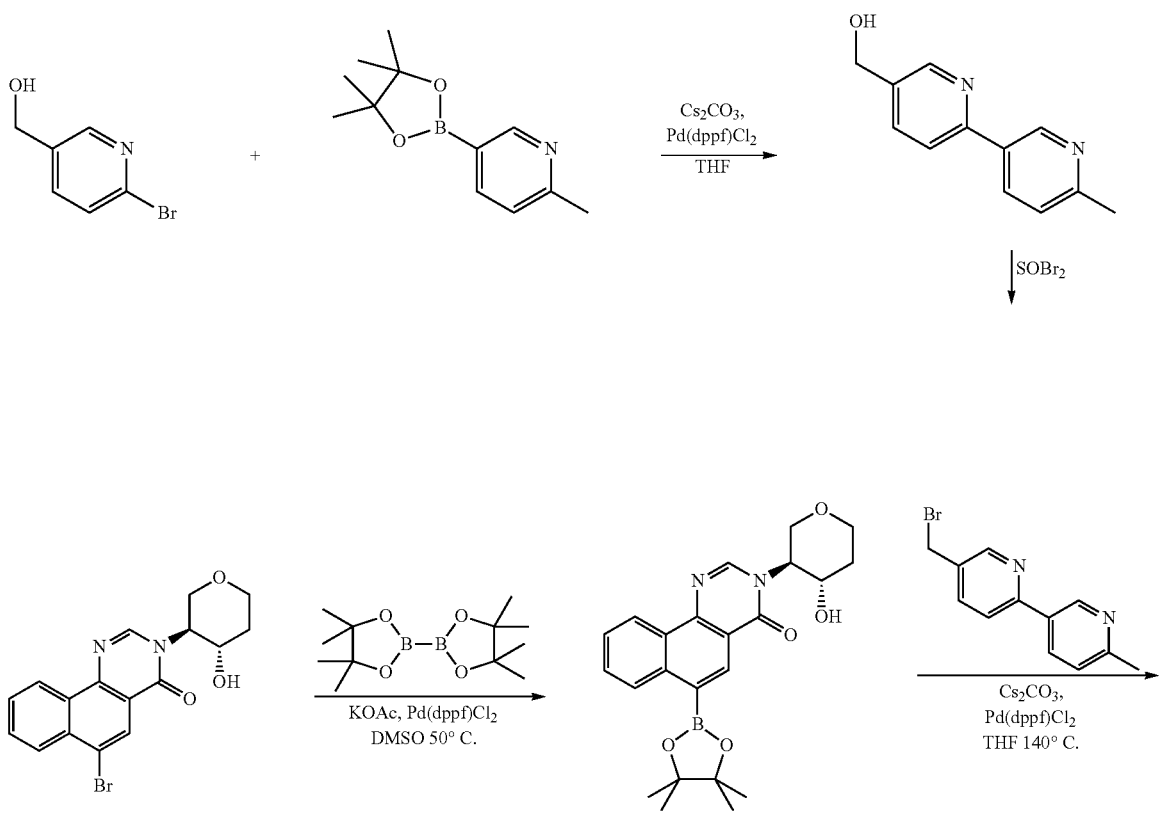

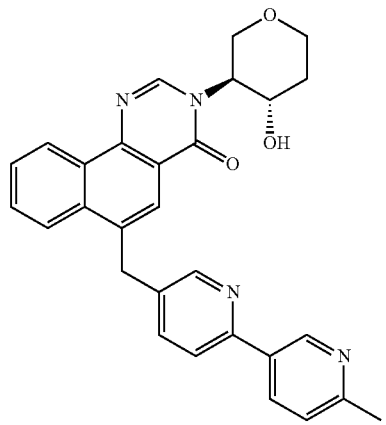

Synthesis of (3S,4S)-3-aminotetrahydro-2H-pyran-4-ol

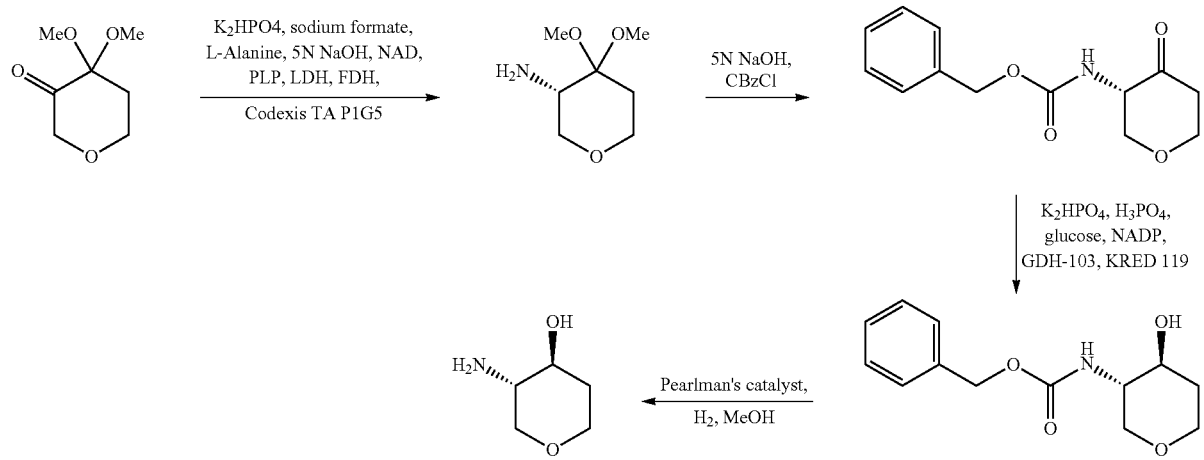

A solution of 4,4-dimethoxydihydro-2H-pyran-3(4H)-one (172 g, 1.07 mol, see Example 1) in 310 mL of toluene was stirred in toluene for 30 min, then extracted 3× with water (270 mL). To the aqueous solution was added potassium dihydrogenphosphate (14.1 g, 0.104 mol), sodium formate (55.1 g, 0.810 mol), and L-Alanine (72.2 g, 0.810 mol). The pH was adjusted to 7.8 with 5N NaOH, and NAD (0.810 g), PLP (0.810 g), LDH (0.162 g), FDH (1.62 g), and Codexis TA P1 G5 (4.05 g) were added. The mixture was heated to 45° C. for 12 h, then cooled to rt. Potassium carbonate (324 g, 2.34 mol) was added, and after 30 min, the mixture was diluted with acetonitrile (810 mL). After 30 min, the reaction was filtered through a pad of solka-floc. The filtrate was partitioned and the aqueous layer was extracted with additional acetonitrile (810 mL). The combined organic fractions were concentrated in vacuo to provide crude (3S)-4,4-dimethoxytetrahydro-2H-pyran-3-amine.

The above residue was redissolved in 700 mL of THF and 254 mL of water, and cooled to 0° C. Sodium hydroxide (5 N, 96 mL, 0.48 mol) was added, and the reaction was retooled to −5° C. Benzyl chloroformate (68.0 mL, 0.476 mol) was added via a syringe pump over 30 min, and the mixture was then warmed to rt. HCl (6 N, 250 mL, 1.50 mol) was added to pH=0.40, and the mixture was stirred with an overhead stirrer. After 2 h, 3M potassium carbonate was added to pH=7.4, and the reaction was diluted with THF (700 mL). A white solid was removed via filtration, and washed with additional THF (100 mL). The combined organic fractions were concentrated in vacuo to provide crude benzyl [(3S)-4-oxotetrahydro-2H-pyran-3-yl]carbamate.

To a solution of potassium dihydrogen phosphate (62.7 g, 0.461 mol) in 3.6 L of water was added phosphoric acid to pH=7.0. To this solution was added glucose (112 g, 0.622 mol), NADP (3.6 g), GDH-103 (1.8 g), KRED 119 (3.6 g), and crude benzyl [(3S)-4-oxotetrahydro-2H-pyran-3-yl]carbamate (103.4 g, 0.4148 mol). After 17 h, the reaction was adjusted to pH 6.5 with 5 N NaOH. A white solid was collected via filtration and washed 2× with water (200 mL). The solid was suspended in 600 mL of toluene and stirred with an overhead stirrer at 105° C. for 1 h, then cooled to rt. A white solid was collected via filtration and washed with toluene (200 mL) to provide benzyl [(3S,4S)-4-hydroxytetrahydro-2H-pyran-3-yl]carbamate.

To a solution of the above compound (90.5 g, 0.360 mol) in 1.8 L of methanol was added palladium hydroxide on carbon (9 g). The mixture was subjected to 40 psi of hydrogen at 25° C. for 15 h, then filtered through solka-floc. The filter cake was washed 3× with methanol (200 mL), and the combined filtrates were concentrated in vacuo to provide crude (3S,4S)-

3-aminotetrahydro-2H-pyran-4-ol that gave proton NMR spectra consistent with theory.

6-Bromo-3-[(3S,4S)-4-hydroxytetrahydro-2H-pyran-3-yl]benzo[h]quinazolin-4(3H)-one was prepared by the procedure described for the synthesis of 1-amino-4-bromo-N-[(3R,4S)-3-hydroxytetrahydro-2H-pyran-4-yl]-2-naphthamide in Example 1, substituting (3S,4S)-3-aminotetrahydro-2H-pyran-4-ol for (3R,4S)-3-hydroxytetrahydro-2H-pyran-4-aminium chloride.

Synthesis of (6'-methyl-2,3'-bipyridin-5-yl)methanol

To a solution of (6-bromo-pyridin-3-yl)-methanol (0.614 g, 3.27 mmol) in 10 mL of THF under an atmosphere of nitrogen was added cesium carbonate (3.27 mL, 2 N aqueous, 6.53 mmol), 2-picoline-5-boronic acid pinacol ester (0.477 g, 2.18 mmol), and [1,1'-bis(diphenylphosphino)-ferrocene]dichloro-palladium(II), 1:1 complex with dichloromethane (0.178 g, 0.218 mmol). The reaction was heated at 85° C. for 1 h, cooled to rt, and diluted with dichloromethane. The organic solution was washed with water, dried over sodium sulfate, filtered, and concentrated in vacuo. The aqueous fraction was concentrated in vacuo, triturated 3× with 20% methanol in dichloromethane, and collected via filtration. The combined solids were purified via silica gel chromatography, eluting with 100% ethyl acetate to provide (6'-methyl-2,3'-bipyridin-5-yl)methanol that gave a proton NMR spectra consistent with theory and a mass ion (ES+) of 201.1 for [M+H]$^+$.

The title compound was prepared by the procedure described for the synthesis of 6-[(2-chloropyridin-4-yl)methyl]-3-[(3R,4S)-3-hydroxytetrahydro-2H-pyran-4-yl]benzo[h]quinazolin-4(3H)-one in Example 15, substituting 6-bromo-3-[(3S,4S)-4-hydroxytetrahydro-2H-pyran-3-yl]benzo[h]quinazolin-4(3H)-one for 1-amino-4-bromo-N-[(3R,4S)-3-hydroxytetrahydro-2H-pyran-4-yl]-2-naphthamide, and (6'-methyl-2,3'-bipyridin-5-yl)methanol for 2-chloropyridine-4-methanol. The resultant tan solid gave proton NMR spectra consistent with theory and a mass ion (ES+) of 479.2073 for [M+H]$^+$ [Calc'd for $C_{29}H_{27}N_4O_3$, [M+H]$^+$=479.2078]: $^1$H NMR (400 MHz, $d_6$-DMSO) δ 9.09 (d, J=2.2 Hz, 1H), 9.01-8.99 (m, 1H), 8.70-8.67 (m, 2H), 8.38-8.24 (m, 2H), 8.01 (s, 1H), 7.92 (d, J=8.1 Hz, 1H), 7.91-7.70 (m, 3H), 7.36 (d, J=8.1 Hz, 1H), 5.29 (br s, 1H), 4.62 (s, 2H), 4.50 (br s, 1H), 4.34 (br s, 1H), 3.93-3.89 (m, 2H), 3.76-3.71 (m, 1H), 3.50 (t, J=11.4 Hz, 1H), 2.50 (s, 3H), 2.05-1.99 (m, 1H), 1.68-1.63 (m, 1H).

EXAMPLE 35 rac-6-[(6-Chloropyridin-3-yl)methyl]-3-[(3R,4R)-3-hydroxypiperidin-4-yl]benzo[h]quinazolin-4(3H)-one

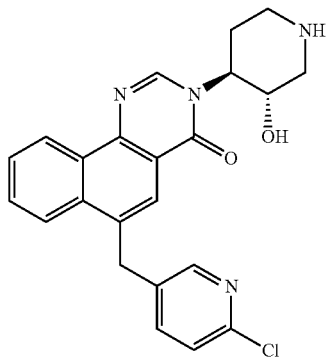

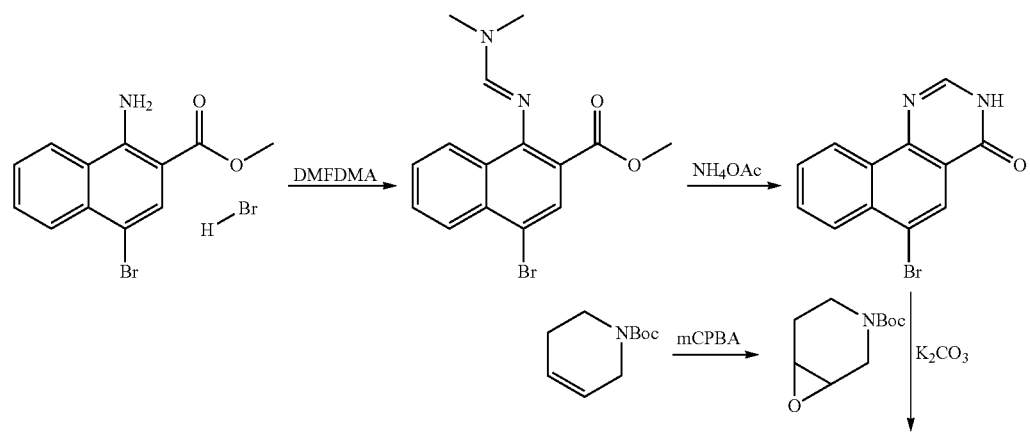

-continued

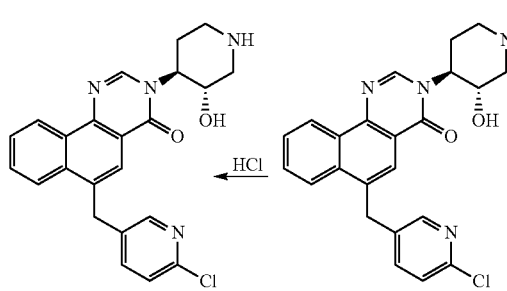

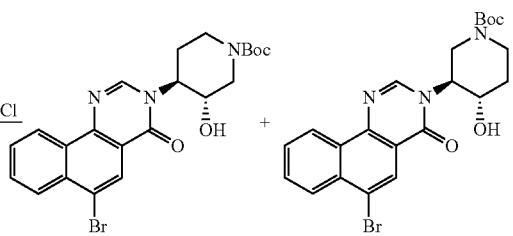

To a solution of N-boc-1,2,3,6-tetrahydropyridine (3.63 g, 21.0 mmol) in 40 mL of dichloromethane was added 3-chloroperoxybenzoic acid (2.75 g, 15.0 mmol). The reaction was stirred at room temperature for 4 h, then washed 3× with saturated aqueous potassium carbonate and once with brine. The solution was dried over sodium sulfate, filtered, and concentrated in vacuo to provide crude tert-butyl 7-oxa-3-azabicyclo[4.1.0]heptane-3-carboxylate that gave a proton NMR spectra consistent with theory.

A solution of methyl 1-amino-4-bromo-2-naphthoate hydrobromide (see Example 1, 3.20 g, 8.86 mmol) in N,N-dimethylformamide dimethylacetal (3.56 mL, 26.6 mmol) was heated at 100° C. for 2 h. Additional N,N-dimethylformamide dimethylacetal (1.19 mL, 8.9 mmol) was added and the solution was heated at 100° C. for an additional 3 h. The reaction was cooled to rt, concentrated, and dried to provide crude methyl 4-bromo-1-{[(1E)-(dimethylamino)methylene]amino}-2-naphthoate that gave a mass ion (ES+) of 337.1 ($^{81}$Br) for [M+H]$^+$.

A solution of the above compound (2.20 g, 6.56 mmol) and ammonium acetate (0.607 g, 7.88 mmol) in 10 mL of acetic acid was heated at 140° C. for 3 h. The reaction was cooled to rt, diluted with 50 mL of water, filtered, washed with water and Et$_2$O, and dried on high vac to provide 6-bromobenzo[h]quinazolin-4(3H)-one that gave a mass ion (ES+) of 276.9 ($^{81}$Br) for [M+H]$^+$.

To a solution of the above compound (0.400 g, 1.45 mmol) in 3 mL of DMF was added tert-butyl 7-oxa-3-azabicyclo[4.1.0]heptane-3-carboxylate (0.579 g, 2.91 mmol) and potassium carbonate (0.402 g, 2.91 mmol). The reaction was stirred at 100° C. for 15 h, cooled to room temperature, and diluted with ethyl acetate and water. A beige solid was removed via filtration, and the organic fraction was washed with water and brine, dried over sodium sulfate, filtered, and concentrated in vacuo. The resultant residue was subjected to purification via column chromatography on silica gel eluted with 0-50% ethyl acetate in hexanes to provide tert-butyl rac-(3R,4R)-4-(6-bromo-4-oxobenzo[h]quinazolin-3(4H)-yl)-3-hydroxypiperidine-1-carboxylate that gave a proton NMR spectra consistent with theory and a mass ion (ES+) of 475.8 ($^{81}$Br) for M+H$^+$, and tert-butyl rac-(3R,4R)-3-(6-bromo-4-oxobenzo quinazolin-3(4H)-yl)-3-hydroxypiperidine-1-carboxylate that gave a proton NMR spectra consistent with theory and a mass ion (ES+) of 475.8 ($^{81}$Br) for M+H$^+$.

To a dry 25 mL round bottom flask containing tert-butyl rac-(3R,4R)-4-(6-bromo-4-oxobenzo[h]quinazolin-3(4H)-yl)-3-hydroxypiperidine-1-carboxylate (0.163 g, 0.344 mmol) under N$_{2(g)}$ was added (2-chloro-5-pyridyl)methylzinc chloride (0.5 M in THF, 2.06 mL, 1.03 mmol) and tetrakis(triphenylphosphine)palladium (0) (10 mol %). The reaction was heated to reflux at 90° C. for 20 h, cooled to room temperature, and diluted with dichloromethane. Hexanes were added to the solution and the resultant beige precipitate was collected via filtration, washed with dichloromethane and hexanes, and dried on high vac to provide crude tert-butyl rac-(3R,4R)-4-[6-[(6-chloropyridin-3-yl)methyl]-4-oxobenzo[h]quinazolin-3(4H)-yl]-3-hydroxypiperidine-1-carboxylate that gave a mass ion (ES+) of 520.9 for M+H$^+$.

To a solution of the above compound (0.180 g, 0.345 mmol) in 5 mL of dichloromethane was added 4 N HCl in dioxane (0.43 mL, 1.7 mmol). After 4 h, additional 4 N HCl in dioxane (0.081 mL, 0.34 mmol) and 5 mL of MeOH were added. After 16 h, the reaction was concentrated in vacuo and ethyl acetate was added to the resultant brown oil. A light yellow solid was collected via filtration and subjected to purification via reverse phase HPLC to provide the title compound that gave a proton NMR spectra consistent with theory and a mass ion (ES+) of 420.9 for M+H$^+$: $^1$H NMR (400 MHz, d$_6$-DMSO) δ9.08-9.06 (m, 1H), 8.38 (s, 1H), 8.29 (s, 1H), 8.14-3.12 (m, 1H), 8.00 (s, 1H), 7.78-7.67 (m, 3H), 7.38 (d, J=8.2 Hz, 1H), 4.80-4.68 (m, 1H), 4.59 (s, 2H), 4.46-4.39 (m, 1H), 3.62-3.52 (m, 2H), 3.22-3.13 (m, 1H), 3.01-2.79 (m, 2H), 2.28-2.22 (m, 1H).

EXAMPLE 36 rac-3-[(3R,4R)-1-acetyl-3-hydroxypiperidin-4-yl]-6-[(6-chloropyridin-3-yl)methyl]benzo[h]quinazolin-4(3H)-one

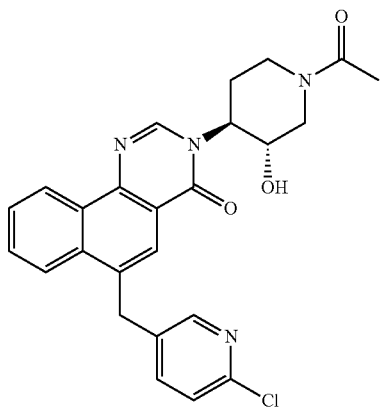

-continued

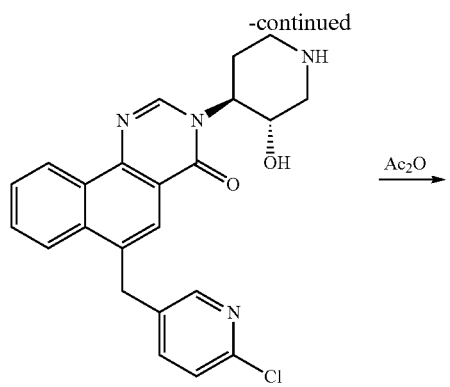

Ac₂O →

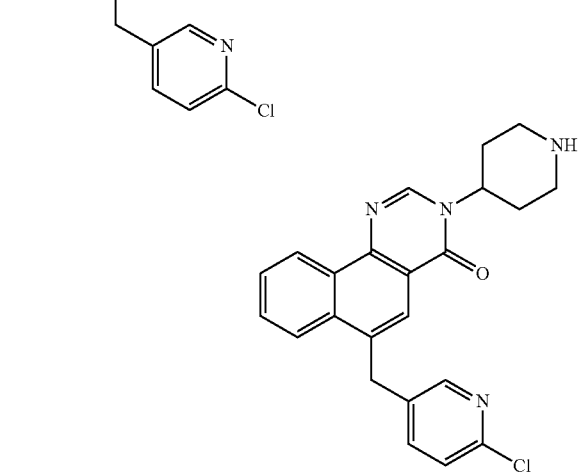

To a solution of rac-6-[(6-chloropyridin-3-yl)methyl]-3-[(3R,4R)-3-hydroxypiperidin-4-yl]benzo[h]quinazolin-4(3H)-one (Example 35, 0.050 g, 0.11 mmol) in 2 mL of dichloromethane at 0° C. was added triethylamine (0.023 mL, 0.16 mmol) and acetic anhydride (0.013 mL, 0.14 mmol). The reaction was stirred at 0° C. for 5 h, quenched with water, and concentrated in vacuo. The resultant residue was subjected to purification via reverse phase HPLC to provide the title compound that gave a proton NMR spectra consistent with theory and a mass ion (ES+) of 462.9 for M+H⁺: ¹H NMR (400 MHz, CDCl₃) p9.01-9.00 (m, 1H), 8.37 (s, 1H), 8.37 (s, 1H), 7.96 (d, J=7.1 Hz, 1H), 7.88 (s, 1H), 7.72-7.68 (m, 2H), 7.41 (d, 8.7 Hz, 1H), 7.22-7.20 (m, 1H), 5.07-5.01 (m, 1H), 4.92-4.67 (m, 2H), 4.44 (s, 2H), 4.23-3.98 (m, 3H), 3.34-3.24 (m, 1H), 3.20-3.11 (m, 1H), 2.22 (s, 3H).

EXAMPLE 37

6-[(6-Chloropyridin-3-yl)methyl]-3-piperidin-4-yl-benzo[h]quinazolin-4(3H)-one

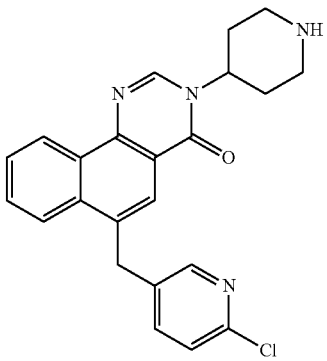

HBr/acetic acid →

Benzyl 4-[6-[(6-chloropyridin-3-yl)methyl]-4-oxobenzo[h]quinazolin-3(4H)-yl]piperidine-1-carboxylate was prepared by the procedure described for 6-[(6-chloropyridin-3-yl)methyl]-3-[(3R,4S)-3-hydroxytetrahydro-2H-pyran-4-yl]benzo[h]quinazolin-4(3H)-one in Example 1, substituting 4-amino-piperidine-1-carboxylic acid benzyl ester for (3R,4S)-3-hydroxytetrahydro-2H-pyran-4-aminium chloride.

A solution of benzyl 4-[6-[(6-chloropyridin-3-yl)methyl]-4-oxobenzo[h]quinazolin-3 (4H)-yl]piperidine-1-carboxylate (0.130 g, 0.241 mmol) in 3 mL of HBr/acetic acid solution (48.0% wt, 264 mmol) was stirred at rt for 3 h. The mixture was concentrated in vacuo and azetroped 3× with toluene. The residue was purified via preparative reverse phase HPLC to provide the title compound that gave proton NMR spectra consistent with theory and a mass ion (ES+) of 404.9 for M+H⁺: ¹H NMR (400 MHz, d₆-DMSO) δ 9.07 (d, J=7.7 Hz, 1H), 8.47 (s, 1H), 8.30 (s, 1H), 8.12 (d, J=7.9 Hz, 1H), 8.11 (s, 1H), 7.80-7.66 (m, 3H), 7.37 (d, J=8.3 Hz, 1), 3.64 (s, 2H), 3.65-3.61 (m, 2H), 3.31-3.23 (m, 2H), 2.62-2.52 (m, 2H), 2.26 (d, J=12.5 Hz, 2H).

The compounds in Table 1 below were prepared according to the general procedures described above (including the particular Examples referenced in the "Synthesis Method" column). Any additional reagents used in the syntheses are either commercially available or may be made from commercially available reagents using conventional reactions well known in the art.

TABLE 1

| Example | Structure | MW | Synthesis Method |
|---|---|---|---|
| 38 | 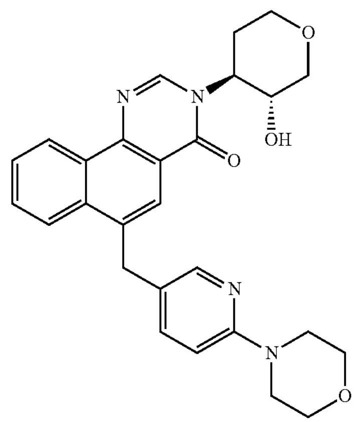 [SMILES: O=c1c2cc(Cc3ccc(N4CCOCC4)nc3)c3ccccc3c2ncn1[C@H]1CCOC[C@@H]1O] | 472.54 | Example 2 |
| 39 | 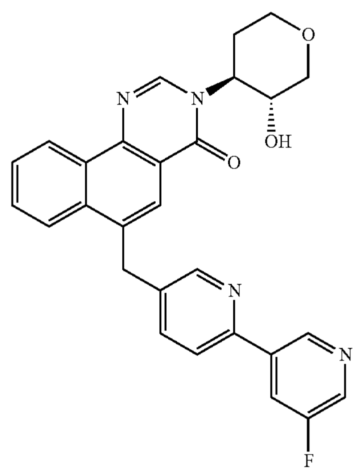 [SMILES: O=c1c2cc(Cc3ccc(-c4cncc(F)c4)nc3)c3ccccc3c2ncn1[C@H]1CCOC[C@@H]1O] | 482.52 | Example 4 |
| 40 | 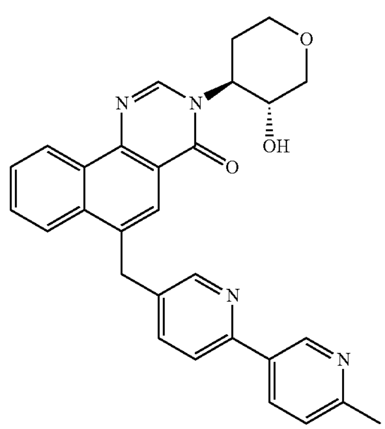 [SMILES: Cc1ccc(-c2ccc(Cc3cc4c(=O)n([C@H]5CCOC[C@@H]5O)cnc4c4ccccc34)cn2)cn1] | 478.56 | Example 4 |

TABLE 1-continued
| Example | Structure | MW | Synthesis Method |
|---|---|---|---|
| 41 | 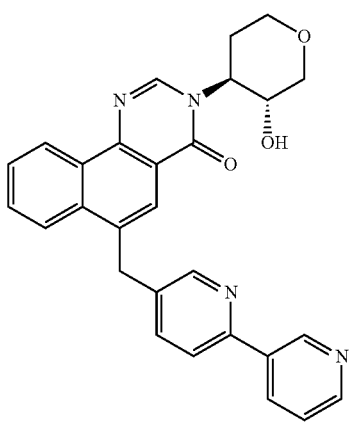 [SMILES: O=c1c2cc(Cc3ccc(-c4cccnc4)nc3)c3ccccc3c2ncn1[C@H]1CCOC[C@@H]1O] | 464.53 | Example 4 |
| 42 | 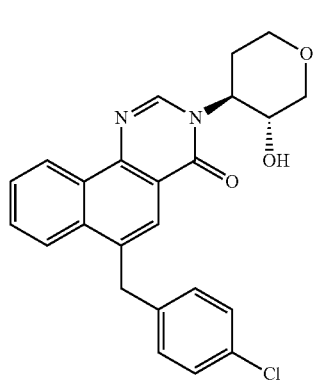 [SMILES: O=c1c2cc(Cc3ccc(Cl)cc3)c3ccccc3c2ncn1[C@H]1CCOC[C@@H]1O] | 420.90 | Example 1 |
| 43 | 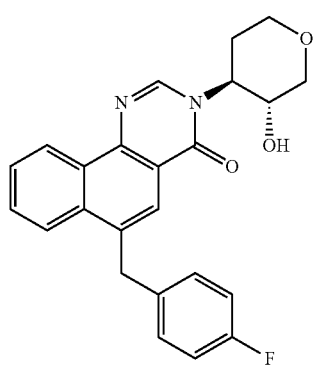 [SMILES: O=c1c2cc(Cc3ccc(F)cc3)c3ccccc3c2ncn1[C@H]1CCOC[C@@H]1O] | 404.45 | Example 1 |
| 44 | 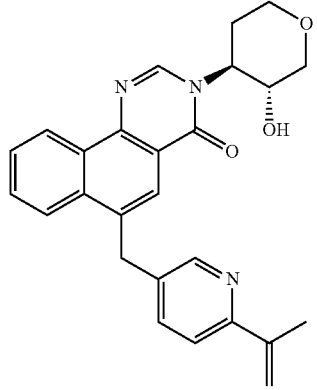 [SMILES: C=C(C)c1ccc(Cc2cc3c(=O)n([C@H]4CCOC[C@@H]4O)cnc3c3ccccc23)cn1] | 427.51 | Example 4 |

TABLE 1-continued

| Example | Structure | MW | Synthesis Method |
|---|---|---|---|
| 45 | 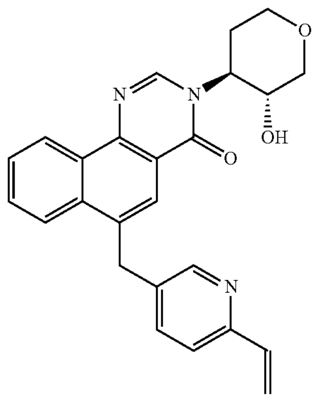 [SMILES: C=Cc1ccc(Cc2cc3c(=O)n([C@H]4CCOC[C@@H]4O)cnc3c3ccccc23)cn1] | 413.48 | Example 4 |
| 46 | 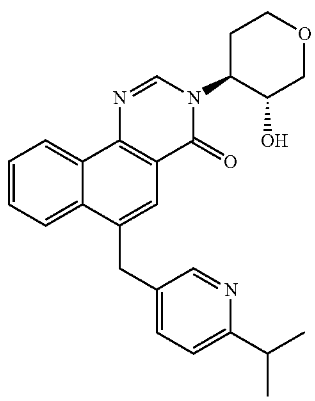 [SMILES: CC(C)c1ccc(Cc2cc3c(=O)n([C@H]4CCOC[C@@H]4O)cnc3c3ccccc23)cn1] | 429.52 | Example 9 |
| 47 | 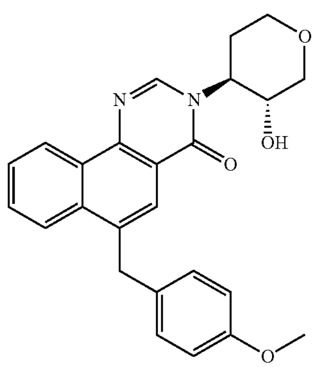 [SMILES: COc1ccc(Cc2cc3c(=O)n([C@H]4CCOC[C@@H]4O)cnc3c3ccccc23)cc1] | 416.48 | Example 1 |
| 48 | 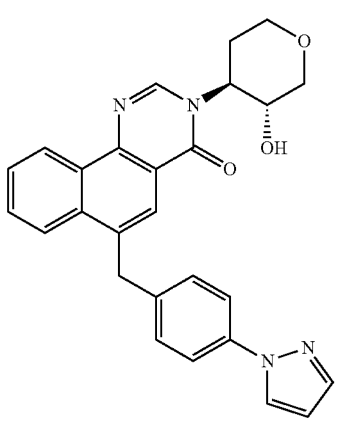 [SMILES: O=c1c2cc(Cc3ccc(-n4cccn4)cc3)c3ccccc3c2ncn1[C@H]1CCOC[C@@H]1O] | 452.52 | Example 5 |

TABLE 1-continued

| Example | Structure | MW | Synthesis Method |
|---|---|---|---|
| 49 | 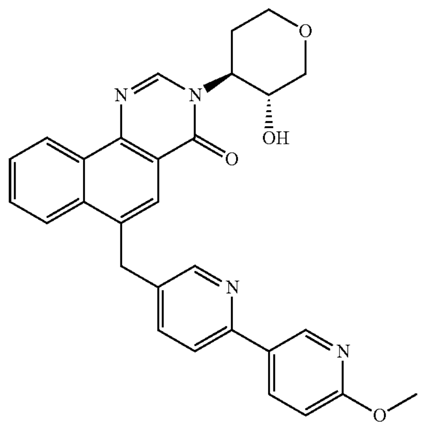 [SMILES: COc1ccc(-c2ccc(Cc3cc4c(=O)n([C@H]5CCOC[C@@H]5O)cnc4c4ccccc34)cn2)cn1] | 494.56 | Example 4 |
| 50 | 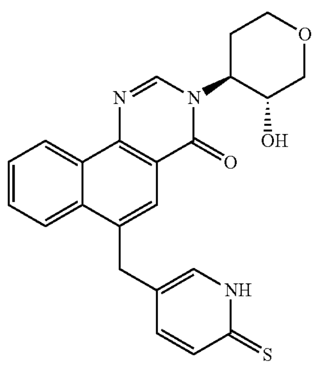 [SMILES: O=c1c2cc(Cc3ccc(=S)[nH]c3)c3ccccc3c2ncn1[C@H]1CCOC[C@@H]1O] | 419.51 | Example 2 |
| 51 | 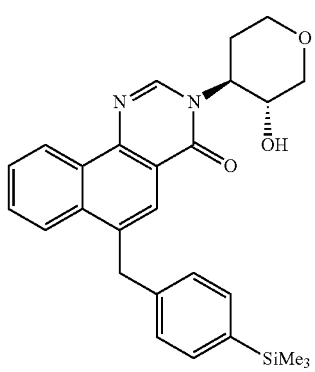 [SMILES: C[Si](C)(C)c1ccc(Cc2cc3c(=O)n([C@H]4CCOC[C@@H]4O)cnc3c3ccccc23)cc1] | 458.64 | Example 15 |
| 52 | 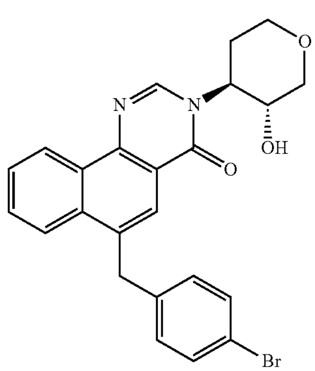 [SMILES: O=c1c2cc(Cc3ccc(Br)cc3)c3ccccc3c2ncn1[C@H]1CCOC[C@@H]1O] | 465.35 | Example 1 |

TABLE 1-continued

| Example | Structure | MW | Synthesis Method |
|---|---|---|---|
| 53 | 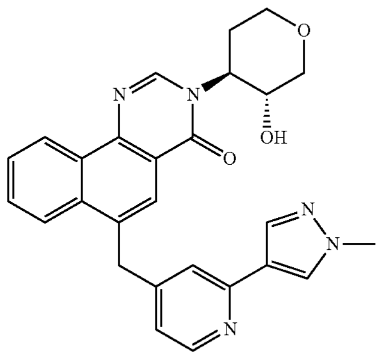 [SMILES: Cn1cc(-c2cc(Cc3cc4c(=O)n([C@H]5CCOC[C@@H]5O)cnc4c4ccccc34)ccn2)cn1] | 467.53 | Example 4 |
| 54 | 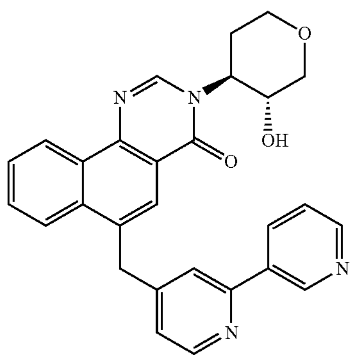 [SMILES: O=c1c2cc(Cc3ccnc(-c4cccnc4)c3)c3ccccc3c2ncn1[C@H]1CCOC[C@@H]1O] | 464.53 | Example 4 |
| 55 | 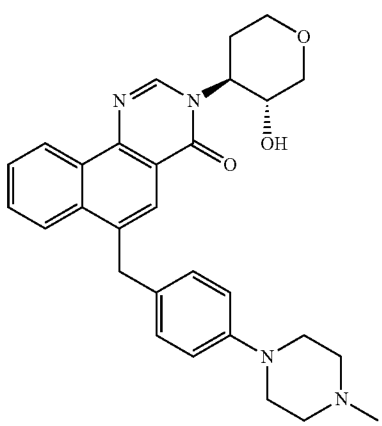 [SMILES: CN1CCN(c2ccc(Cc3cc4c(=O)n([C@H]5CCOC[C@@H]5O)cnc4c4ccccc34)cc2)CC1] | 484.60 | Example 12 |
| 56 | 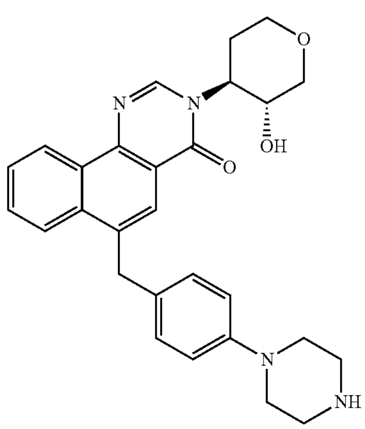 [SMILES: O=c1c2cc(Cc3ccc(N4CCNCC4)cc3)c3ccccc3c2ncn1[C@H]1CCOC[C@@H]1O] | 470.58 | Example 12 |

TABLE 1-continued

| Example | Structure | MW | Synthesis Method |
|---------|-----------|--------|------------------|
| 57 | 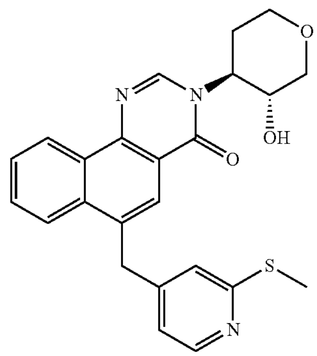 [SMILES: CSc1cc(Cc2cc3c(=O)n([C@H]4CCOC[C@@H]4O)cnc3c3ccccc23)ccn1] | 433.53 | Example 15 |
| 58 | 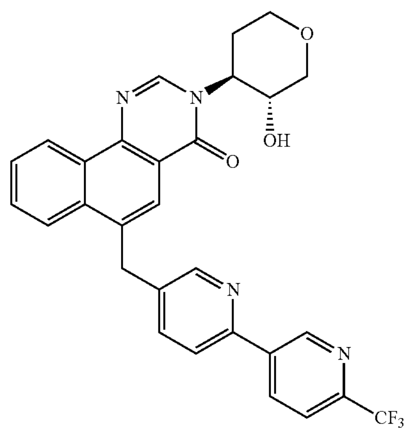 [SMILES: O=c1c2cc(Cc3ccc(-c4ccc(C(F)(F)F)nc4)nc3)c3ccccc3c2ncn1[C@H]1CCOC[C@@H]1O] | 532.53 | Example 4 |
| 59 | 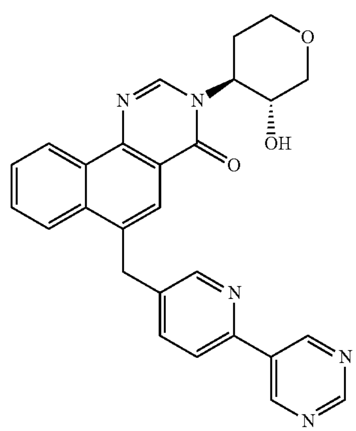 [SMILES: O=c1c2cc(Cc3ccc(-c4cncnc4)nc3)c3ccccc3c2ncn1[C@H]1CCOC[C@@H]1O] | 465.51 | Example 4 |
| 60 | 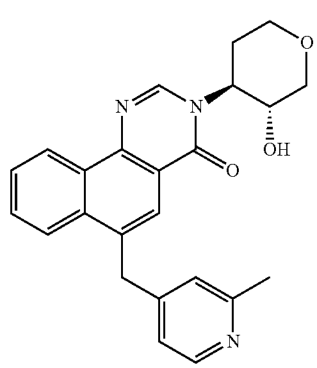 [SMILES: Cc1cc(Cc2cc3c(=O)n([C@H]4CCOC[C@@H]4O)cnc3c3ccccc23)ccn1] | 401.47 | Example 3 |

TABLE 1-continued

| Example | Structure | MW | Synthesis Method |
|---------|-----------|------|------------------|
| 61 | 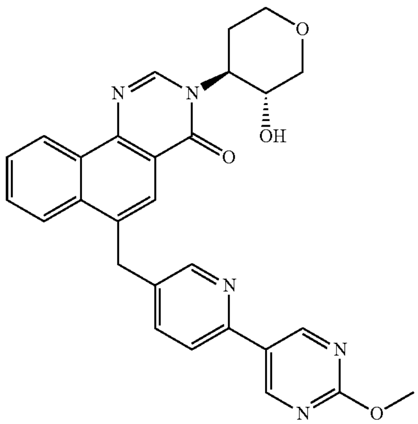 [SMILES: COc1ncc(-c2ccc(Cc3cc4c(=O)n([C@H]5CCOC[C@@H]5O)cnc4c4ccccc34)cn2)cn1] | 495.54 | Example 4 |
| 62 | 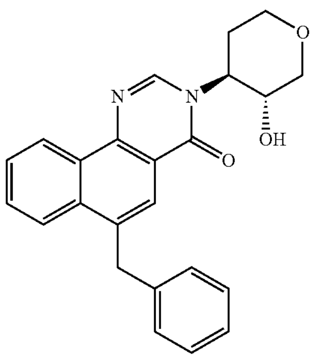 [SMILES: O=c1c2cc(Cc3ccccc3)c3ccccc3c2ncn1[C@H]1CCOC[C@@H]1O] | 386.45 | Example 1 |
| 63 | 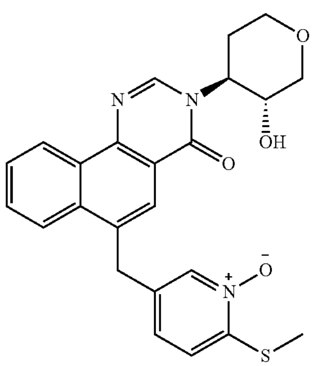 [SMILES: CSc1ccc(Cc2cc3c(=O)n([C@H]4CCOC[C@@H]4O)cnc3c3ccccc23)c[n+]1[O-]] | 449.53 | Example 2 |
| 64 | 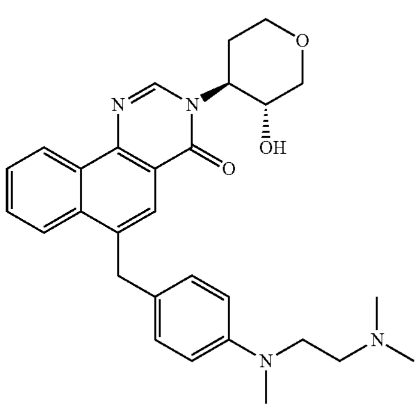 [SMILES: CN(C)CCN(C)c1ccc(Cc2cc3c(=O)n([C@H]4CCOC[C@@H]4O)cnc3c3ccccc23)cc1] | 486.62 | Example 12 |

TABLE 1-continued

| Example | Structure | MW | Synthesis Method |
|---------|-----------|------|------------------|
| 65 | 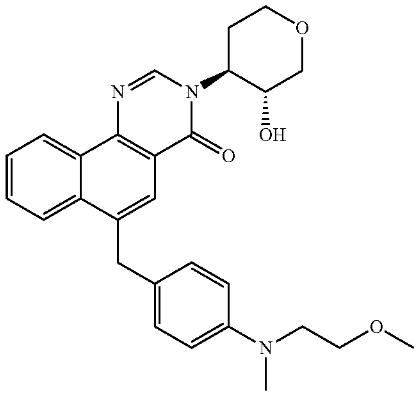 [SMILES: COCCN(C)c1ccc(Cc2cc3c(=O)n([C@H]4CCOC[C@@H]4O)cnc3c3ccccc23)cc1] | 473.58 | Example 12 |
| 66 | 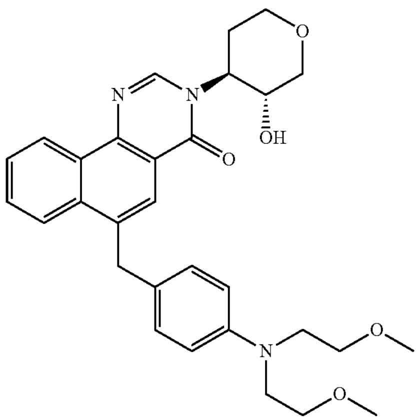 [SMILES: COCCN(CCOC)c1ccc(Cc2cc3c(=O)n([C@H]4CCOC[C@@H]4O)cnc3c3ccccc23)cc1] | 517.63 | Example 12 |
| 67 | 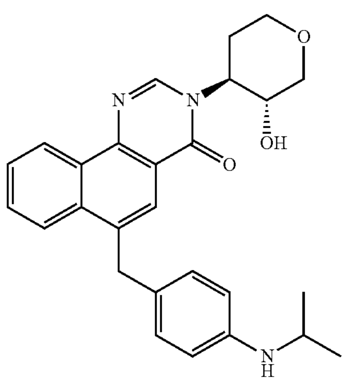 [SMILES: CC(C)Nc1ccc(Cc2cc3c(=O)n([C@H]4CCOC[C@@H]4O)cnc3c3ccccc23)cc1] | 443.55 | Example 12 |
| 68 | 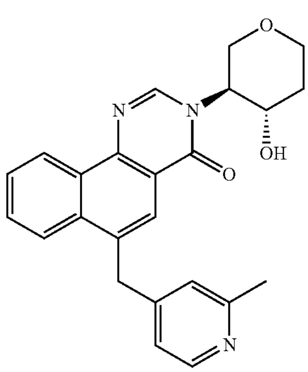 [SMILES: Cc1cc(Cc2cc3c(=O)n([C@H]4COCC[C@@H]4O)cnc3c3ccccc23)ccn1] | 401.47 | Example 15 |

TABLE 1-continued
| Example | Structure | MW | Synthesis Method |
|---------|-----------|------|------------------|
| 69 | 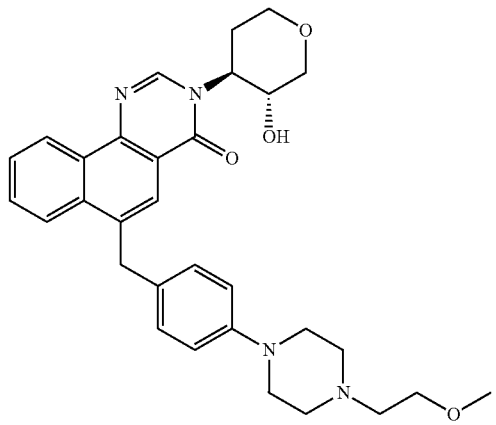 [SMILES: COCCN1CCN(c2ccc(Cc3cc4c(=O)n([C@H]5CCOC[C@@H]5O)cnc4c4ccccc34)cc2)CC1] | 528.66 | Example 12 |
| 70 | 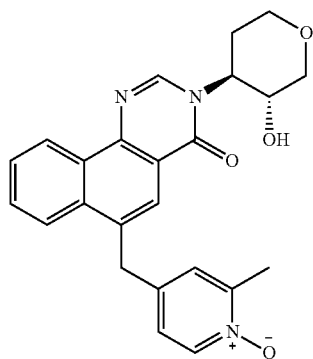 [SMILES: Cc1cc(Cc2cc3c(=O)n([C@H]4CCOC[C@@H]4O)cnc3c3ccccc23)cc[n+]1[O-]] | 417.47 | Example 14 |
| 71 | 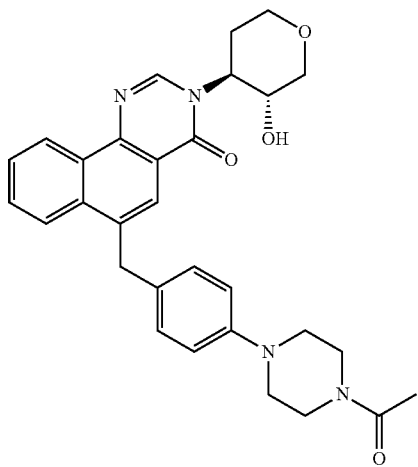 [SMILES: CC(=O)N1CCN(c2ccc(Cc3cc4c(=O)n([C@H]5CCOC[C@@H]5O)cnc4c4ccccc34)cc2)CC1] | 512.61 | Example 12 |

TABLE 1-continued
| Example | Structure | MW | Synthesis Method |
|---------|-----------|-----|------------------|
| 72 | 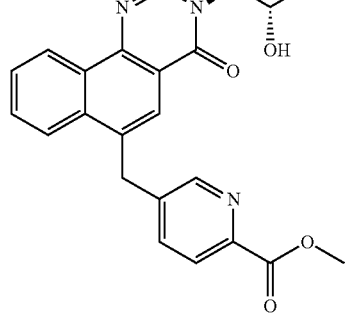 | 445.48 | Example 15 |
| 73 | 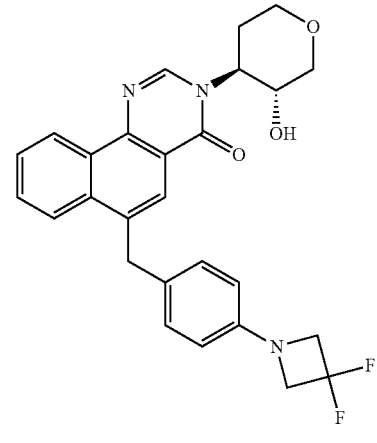 [SMILES: O=c1c2cc(Cc3ccc(N4CC(F)(F)C4)cc3)c3ccccc3c2ncn1[C@H]1CCOC[C@@H]1O] | 477.52 | Example 12 |
| 74 | 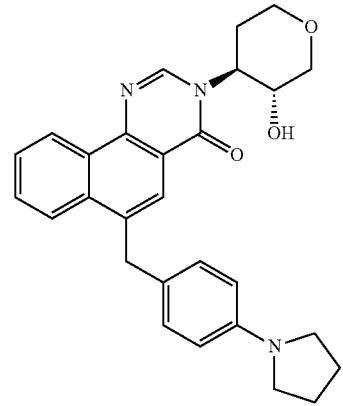 [SMILES: O=c1c2cc(Cc3ccc(N4CCCC4)cc3)c3ccccc3c2ncn1[C@H]1CCOC[C@@H]1O] | 455.56 | Example 12 |

TABLE 1-continued

| Example | Structure | MW | Synthesis Method |
|---------|-----------|------|------------------|
| 75 | 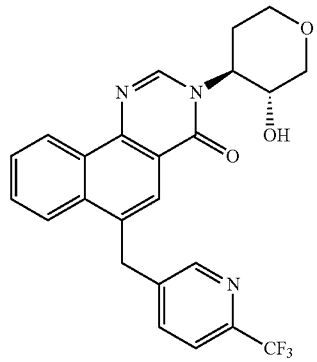 [SMILES: O=c1c2cc(Cc3ccc(C(F)(F)F)nc3)c3ccccc3c2ncn1[C@H]1CCOC[C@@H]1O] | 455.44 | Example 15 |
| 76 | 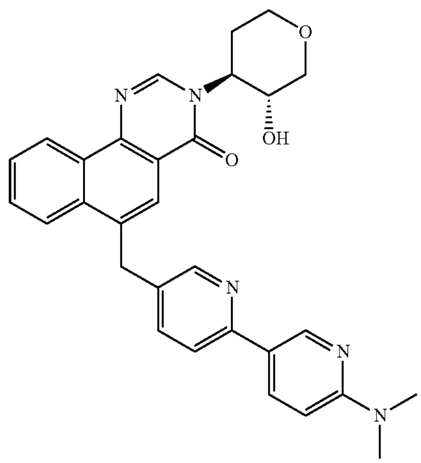 [SMILES: CN(C)c1ccc(-c2ccc(Cc3cc4c(=O)n([C@H]5CCOC[C@@H]5O)cnc4c4ccccc34)cn2)cn1] | 507.60 | Example 4 |
| 77 | 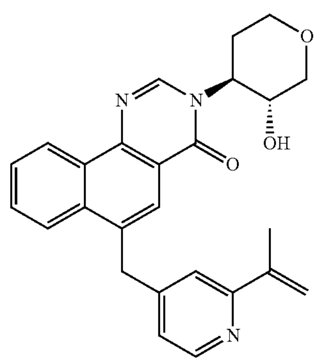 [SMILES: C=C(C)c1cc(Cc2cc3c(=O)n([C@H]4CCOC[C@@H]4O)cnc3c3ccccc23)ccn1] | 427.51 | Example 4 |
| 78 | 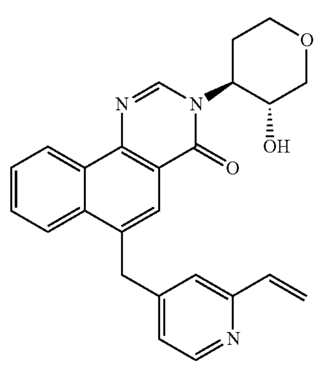 [SMILES: C=Cc1cc(Cc2cc3c(=O)n([C@H]4CCOC[C@@H]4O)cnc3c3ccccc23)ccn1] | 413.48 | Example 4 |

TABLE 1-continued

| Example | Structure | MW | Synthesis Method |
|---------|-----------|--------|------------------|
| 79 | 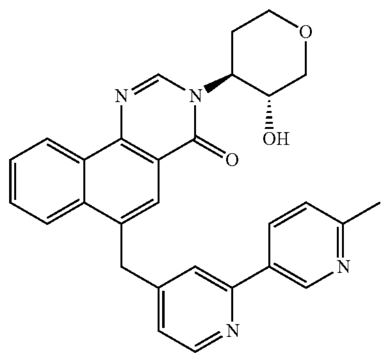 [SMILES: Cc1ccc(-c2cc(Cc3cc4c(=O)n([C@H]5CCOC[C@@H]5O)cnc4c4ccccc34)ccn2)cn1] | 478.56 | Example 4 |
| 80 | 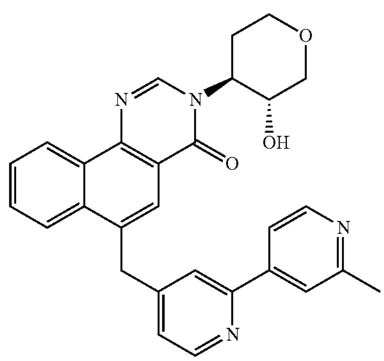 [SMILES: Cc1cc(-c2cc(Cc3cc4c(=O)n([C@H]5CCOC[C@@H]5O)cnc4c4ccccc34)ccn2)ccn1] | 478.56 | Example 4 |
| 81 | 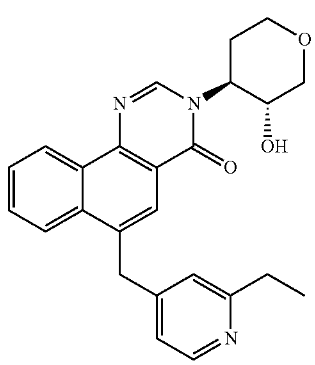 [SMILES: CCc1cc(Cc2cc3c(=O)n([C@H]4CCOC[C@@H]4O)cnc3c3ccccc23)ccn1] | 415.50 | Example 9 |
| 82 | 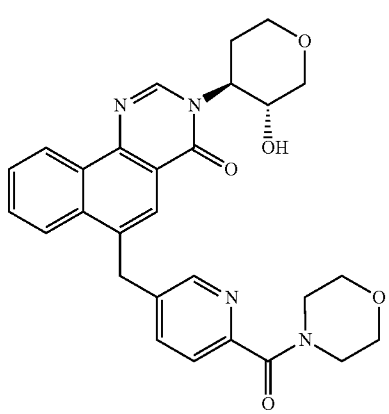 [SMILES: O=C(c1ccc(Cc2cc3c(=O)n([C@H]4CCOC[C@@H]4O)cnc3c3ccccc23)cn1)N1CCOCC1] | 500.56 | Example 19 |

TABLE 1-continued
| Example | Structure | MW | Synthesis Method |
|---|---|---|---|
| 83 | 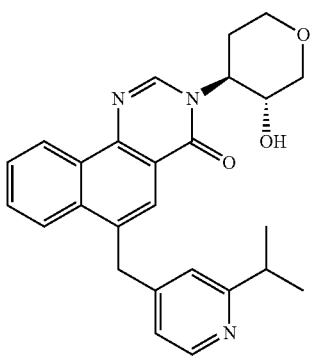 [SMILES: CC(C)c1cc(Cc2cc3c(=O)n([C@H]4CCOC[C@@H]4O)cnc3c3ccccc23)ccn1] | 429.52 | Example 9 |
| 84 | 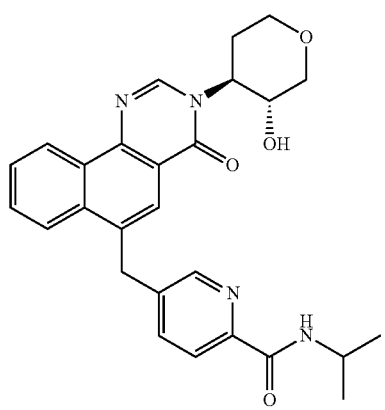 [SMILES: CC(C)NC(=O)c1ccc(Cc2cc3c(=O)n([C@H]4CCOC[C@@H]4O)cnc3c3ccccc23)cn1] | 472.55 | Example 19 |
| 85 | 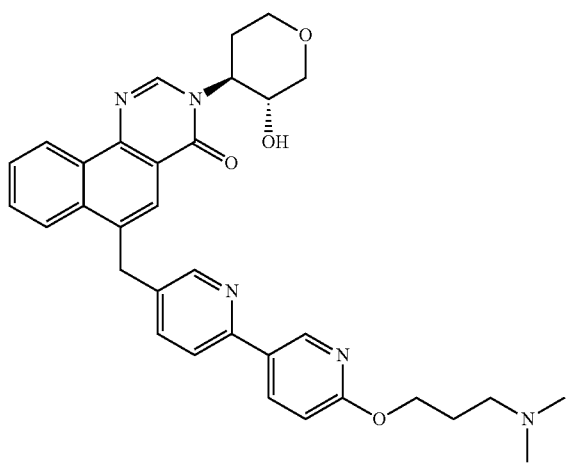 [SMILES: CN(C)CCCOc1ccc(-c2ccc(Cc3cc4c(=O)n([C@H]5CCOC[C@@H]5O)cnc4c4ccccc34)cn2)cn1] | 565.68 | Example 4 |

TABLE 1-continued

| Example | Structure | MW | Synthesis Method |
|---------|-----------|-------|------------------|
| 86 | 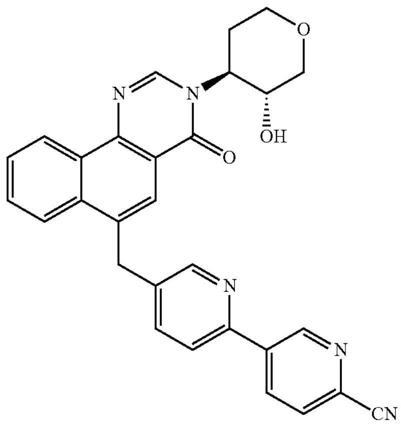 [SMILES: N#Cc1ccc(-c2ccc(Cc3cc4c(=O)n([C@H]5CCOC[C@@H]5O)cnc4c4ccccc34)cn2)cn1] | 489.53 | Example 4 |
| 87 | 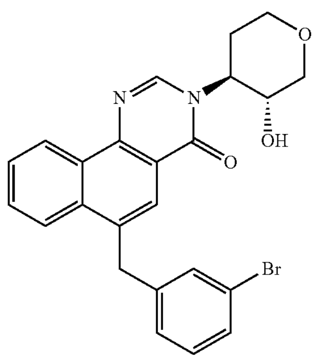 [SMILES: O=c1c2cc(Cc3cccc(Br)c3)c3ccccc3c2ncn1[C@H]1CCOC[C@@H]1O] | 465.35 | Example 15 |
| 88 | 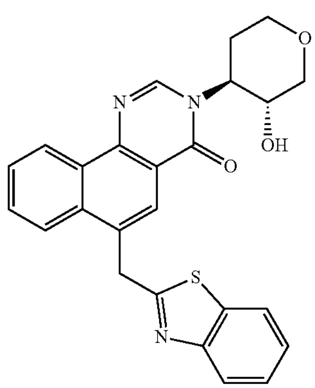 [SMILES: O=c1c2cc(Cc3nc4ccccc4s3)c3ccccc3c2ncn1[C@H]1CCOC[C@@H]1O] | 443.53 | Example 15 |
| 89 | 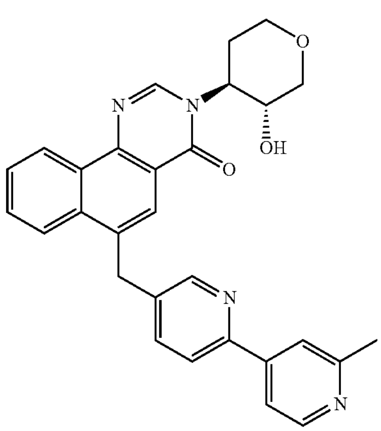 [SMILES: Cc1cc(-c2ccc(Cc3cc4c(=O)n([C@H]5CCOC[C@@H]5O)cnc4c4ccccc34)cn2)ccn1] | 478.56 | Example 4 |

TABLE 1-continued
| Example | Structure | MW | Synthesis Method |
|---|---|---|---|
| 90 | 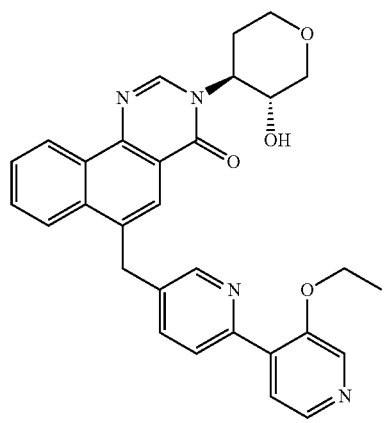 [SMILES: CCOc1cnccc1-c1ccc(Cc2cc3c(=O)n([C@H]4CCOC[C@@H]4O)cnc3c3ccccc23)cn1] | 508.58 | Example 4 |
| 91 | 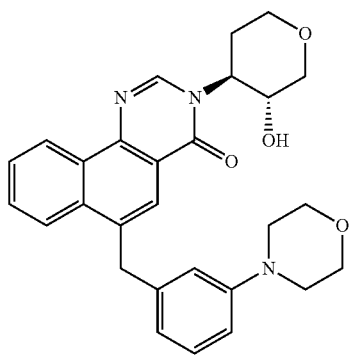 [SMILES: O=c1c2cc(Cc3cccc(N4CCOCC4)c3)c3ccccc3c2ncn1[C@H]1CCOC[C@@H]1O] | 471.56 | Example 12 |
| 92 | 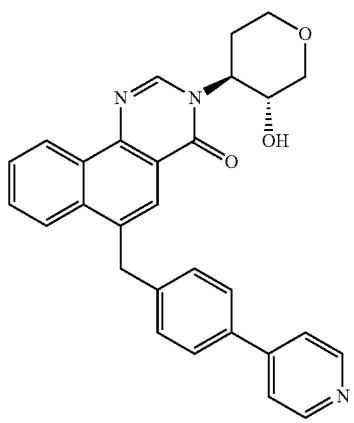 [SMILES: O=c1c2cc(Cc3ccc(-c4ccncc4)cc3)c3ccccc3c2ncn1[C@H]1CCOC[C@@H]1O] | 463.54 | Example 4 |

TABLE 1-continued
| Example | Structure | MW | Synthesis Method |
|---|---|---|---|
| 93 | 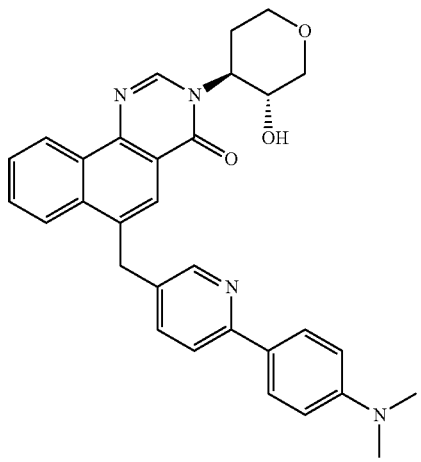 [SMILES: CN(C)c1ccc(-c2ccc(Cc3cc4c(=O)n([C@H]5CCOC[C@@H]5O)cnc4c4ccccc34)cn2)cc1] | 506.61 | Example 4 |
| 94 | 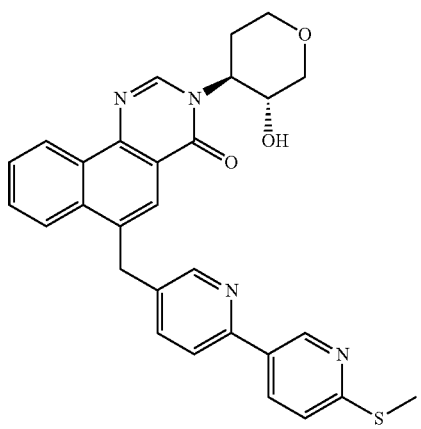 [SMILES: CSc1ccc(-c2ccc(Cc3cc4c(=O)n([C@H]5CCOC[C@@H]5O)cnc4c4ccccc34)cn2)cn1] | 510.62 | Example 4 |
| 95 | 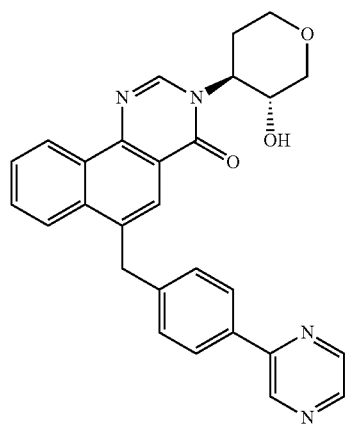 [SMILES: O=c1c2cc(Cc3ccc(-c4cnccn4)cc3)c3ccccc3c2ncn1[C@H]1CCOC[C@@H]1O] | 464.53 | Example 13 |

TABLE 1-continued

| Example | Structure | MW | Synthesis Method |
|---|---|---|---|
| 96 | 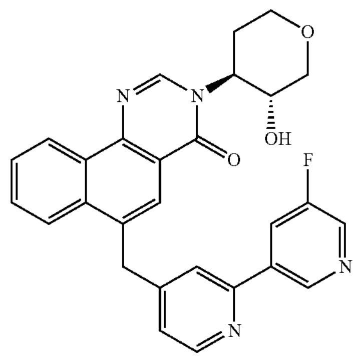 [SMILES: O=c1c2cc(Cc3ccnc(-c4cncc(F)c4)c3)c3ccccc3c2ncn1[C@H]1CCOC[C@@H]1O] | 482.52 | Example 4 |
| 97 | 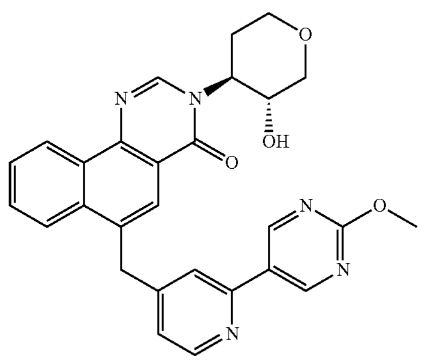 [SMILES: COc1ncc(-c2cc(Cc3cc4c(=O)n([C@H]5CCOC[C@@H]5O)cnc4c4ccccc34)ccn2)cn1] | 495.54 | Example 4 |
| 98 | 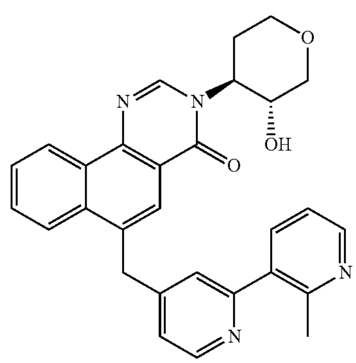 [SMILES: Cc1ncccc1-c1cc(Cc2cc3c(=O)n([C@H]4CCOC[C@@H]4O)cnc3c3ccccc23)ccn1] | 478.56 | Example 4 |
| 99 | 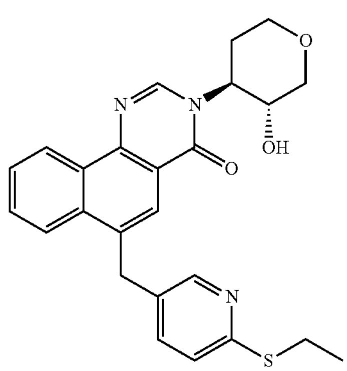 [SMILES: CCSc1ccc(Cc2cc3c(=O)n([C@H]4CCOC[C@@H]4O)cnc3c3ccccc23)cn1] | 447.56 | Example 2 |

TABLE 1-continued

| Example | Structure | MW | Synthesis Method |
|---|---|---|---|
| 100 | 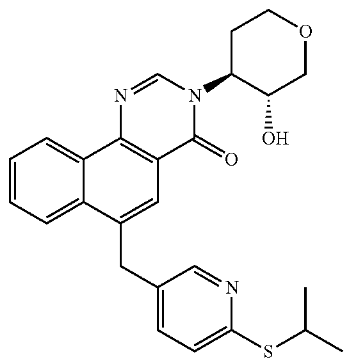 [SMILES: CC(C)Sc1ccc(Cc2cc3c(=O)n([C@H]4CCOC[C@@H]4O)cnc3c3ccccc23)cn1] | 461.59 | Example 2 |
| 101 | 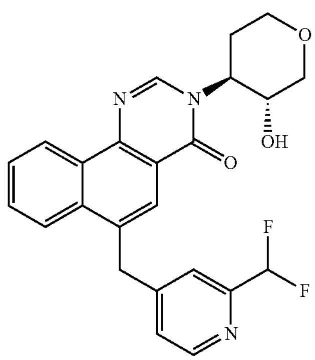 [SMILES: O=c1c2cc(Cc3ccnc(C(F)F)c3)c3ccccc3c2ncn1[C@H]1CCOC[C@@H]1O] | 437.45 | Example 23 |
| 102 | 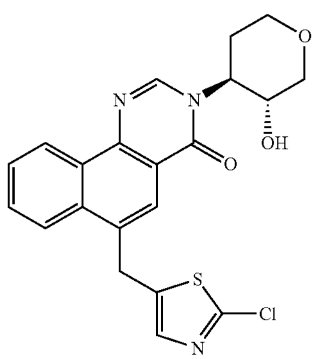 [SMILES: O=c1c2cc(Cc3cnc(Cl)s3)c3ccccc3c2ncn1[C@H]1CCOC[C@@H]1O] | 427.91 | Example 15 |
| 103 | 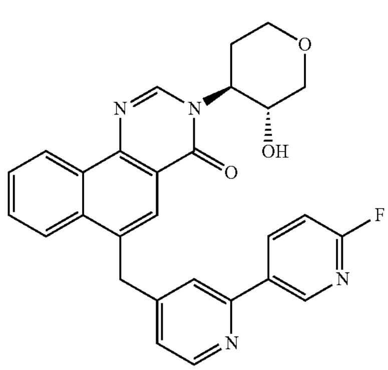 [SMILES: O=c1c2cc(Cc3ccnc(-c4ccc(F)nc4)c3)c3ccccc3c2ncn1[C@H]1CCOC[C@@H]1O] | 482.52 | Example 4 |

TABLE 1-continued
| Example | Structure | MW | Synthesis Method |
|---------|-----------|------|------------------|
| 104 | 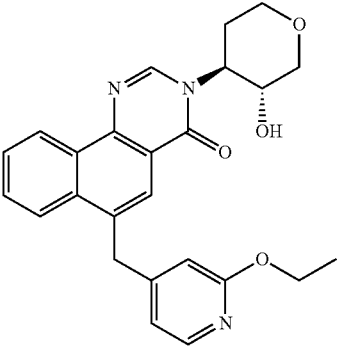 [SMILES: CCOc1cc(Cc2cc3c(=O)n([C@H]4CCOC[C@@H]4O)cnc3c3ccccc23)ccn1] | 431.5 | Example 26 |
| 105 | 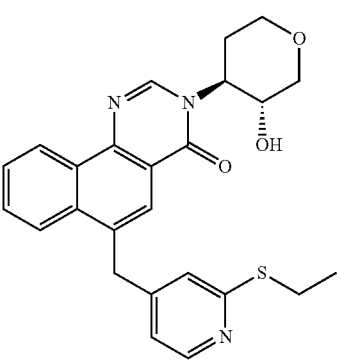 [SMILES: CCSc1cc(Cc2cc3c(=O)n([C@H]4CCOC[C@@H]4O)cnc3c3ccccc23)ccn1] | 447.56 | Example 2 |
| 106 | 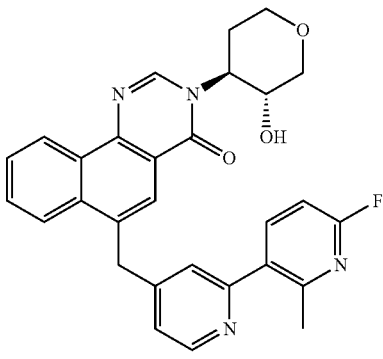 [SMILES: Cc1nc(F)ccc1-c1cc(Cc2cc3c(=O)n([C@H]4CCOC[C@@H]4O)cnc3c3ccccc23)ccn1] | 496.55 | Example 4 |
| 107 | 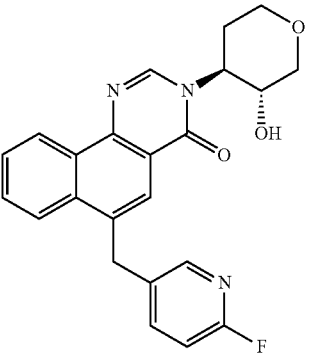 [SMILES: O=c1c2cc(Cc3ccc(F)nc3)c3ccccc3c2ncn1[C@H]1CCOC[C@@H]1O] | 405.43 | Example 15 |

TABLE 1-continued

| Example | Structure | MW | Synthesis Method |
|---|---|---|---|
| 108 | 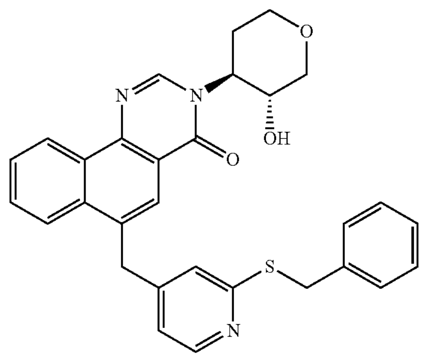 [SMILES: O=c1c2cc(Cc3ccnc(SCc4ccccc4)c3)c3ccccc3c2ncn1[C@H]1CCOC[C@@H]1O] | 509.63 | Example 27 |
| 109 | 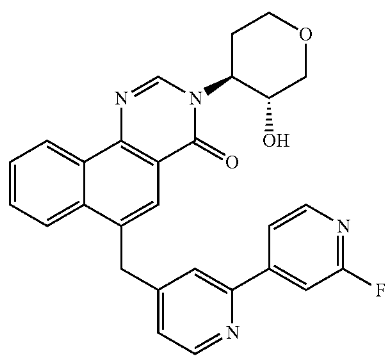 [SMILES: O=c1c2cc(Cc3ccnc(-c4ccnc(F)c4)c3)c3ccccc3c2ncn1[C@H]1CCOC[C@@H]1O] | 482.52 | Example 4 |
| 110 | 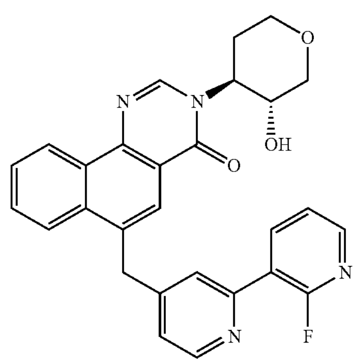 [SMILES: O=c1c2cc(Cc3ccnc(-c4cccnc4F)c3)c3ccccc3c2ncn1[C@H]1CCOC[C@@H]1O] | 482.52 | Example 4 |
| 111 | 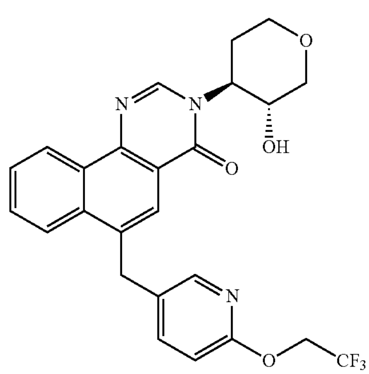 [SMILES: O=c1c2cc(Cc3ccc(OCC(F)(F)F)nc3)c3ccccc3c2ncn1[C@H]1CCOC[C@@H]1O] | 485.47 | Example 27 |

TABLE 1-continued

| Example | Structure | MW | Synthesis Method |
|---------|-----------|------|------------------|
| 112 | 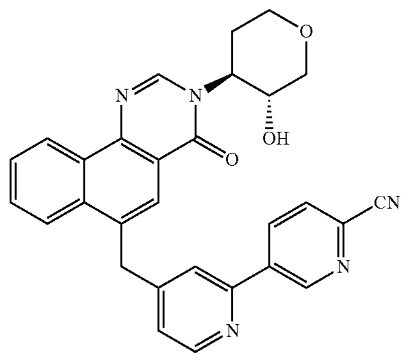 [SMILES: N#Cc1ccc(-c2cc(Cc3cc4c(=O)n([C@H]5CCOC[C@@H]5O)cnc4c4ccccc34)ccn2)cn1] | 489.54 | Example 4 |
| 113 | 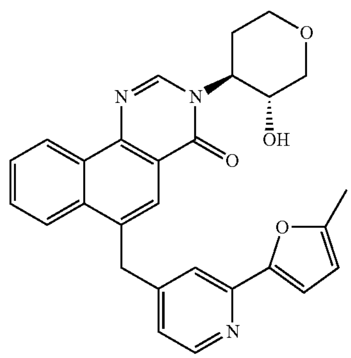 [SMILES: Cc1ccc(-c2cc(Cc3cc4c(=O)n([C@H]5CCOC[C@@H]5O)cnc4c4ccccc34)ccn2)o1] | 467.53 | Example 4 |
| 114 | 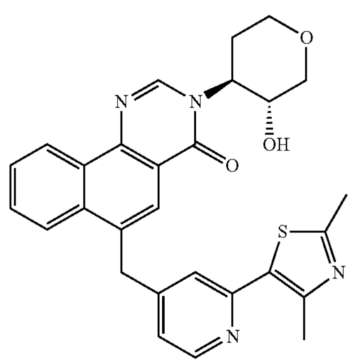 [SMILES: Cc1nc(C)c(-c2cc(Cc3cc4c(=O)n([C@H]5CCOC[C@@H]5O)cnc4c4ccccc34)ccn2)s1] | 498.61 | Example 4 |
| 115 | 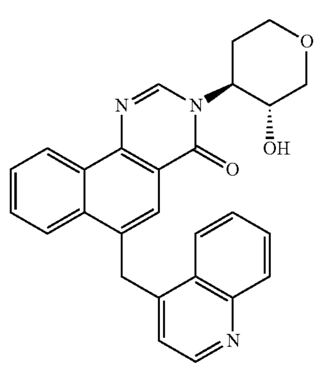 [SMILES: O=c1c2cc(Cc3ccnc4ccccc34)c3ccccc3c2ncn1[C@H]1CCOC[C@@H]1O] | 437.50 | Example 15 |

TABLE 1-continued

| Example | Structure | MW | Synthesis Method |
|---|---|---|---|
| 116 | 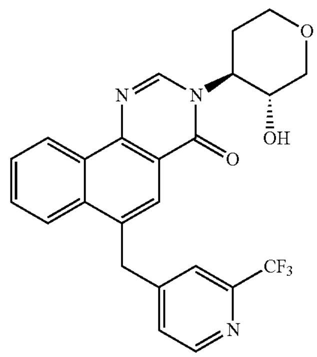 [SMILES: O=c1c2cc(Cc3ccnc(C(F)(F)F)c3)c3ccccc3c2ncn1[C@H]1CCOC[C@@H]1O] | 455.44 | Example 26 |
| 117 | 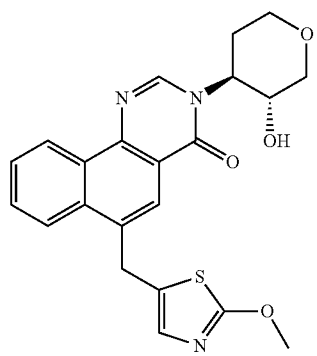 [SMILES: COc1ncc(Cc2cc3c(=O)n([C@H]4CCOC[C@@H]4O)cnc3c3ccccc23)s1] | 423.49 | Example 27 |
| 118 | 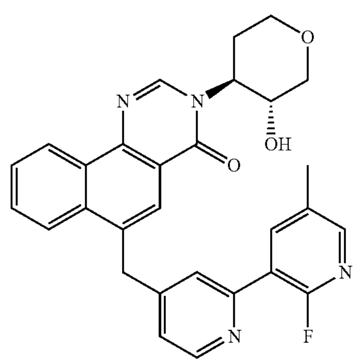 [SMILES: Cc1cnc(F)c(-c2cc(Cc3cc4c(=O)n([C@H]5CCOC[C@@H]5O)cnc4c4ccccc34)ccn2)c1] | 496.55 | Example 4 |
| 119 | 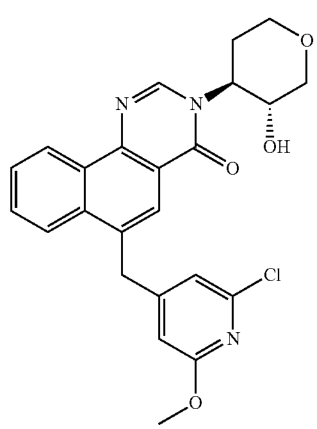 [SMILES: COc1cc(Cc2cc3c(=O)n([C@H]4CCOC[C@@H]4O)cnc3c3ccccc23)cc(Cl)n1] | 451.91 | Example 27 |

TABLE 1-continued

| Example | Structure | MW | Synthesis Method |
|---------|-----------|-----|------------------|
| 120 | 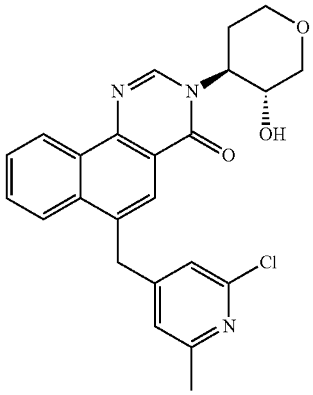 [SMILES: Cc1cc(Cc2cc3c(=O)n([C@H]4CCOC[C@@H]4O)cnc3c3ccccc23)cc(Cl)n1] | 435.91 | Example 26 |
| 121 | 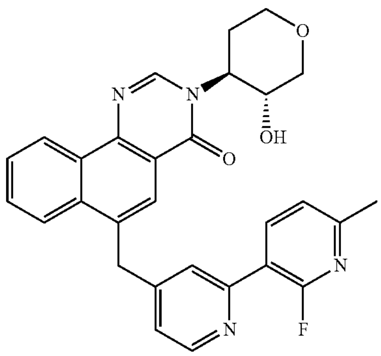 | 496.55 | Example 4 |
| 122 | 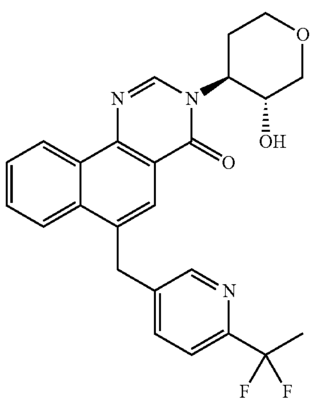 [SMILES: CC(F)(F)c1ccc(Cc2cc3c(=O)n([C@H]4CCOC[C@@H]4O)cnc3c3ccccc23)cn1] | 451.48 | Example 23 |
| 123 | 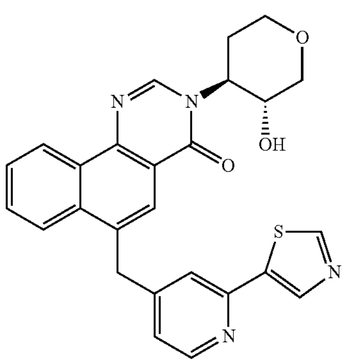 [SMILES: O=c1c2cc(Cc3ccnc(-c4cncs4)c3)c3ccccc3c2ncn1[C@H]1CCOC[C@@H]1O] | 470.55 | Example 4 |

TABLE 1-continued
| Example | Structure | MW | Synthesis Method |
|---|---|---|---|
| 124 | 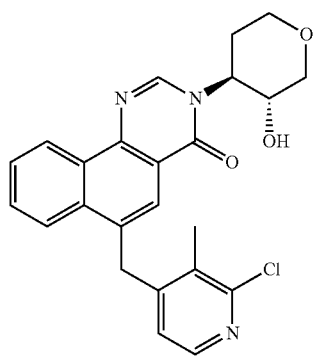 | 435.91 | Example 26 |
| 125 | 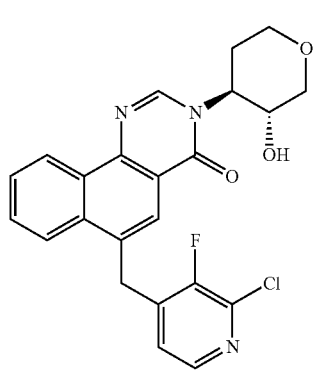 [SMILES: Cc1c(Cc2cc3c(=O)n([C@H]4CCOC[C@@H]4O)cnc3c3ccccc23)ccnc1Cl] | 439.88 | Example 26 |
| 126 | 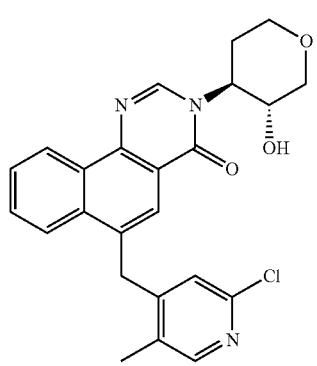 [SMILES: Cc1cnc(Cl)cc1Cc1cc2c(=O)n([C@H]3CCOC[C@@H]3O)cnc2c2ccccc12] | 435.91 | Example 26 |
| 127 | 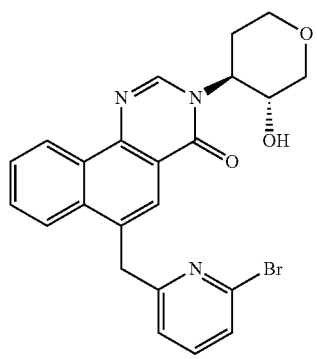 [SMILES: O=c1c2cc(Cc3cccc(Br)n3)c3ccccc3c2ncn1[C@H]1CCOC[C@@H]1O] | 466.34 | Example 15 |

TABLE 1-continued

| Example | Structure | MW | Synthesis Method |
|---|---|---|---|
| 128 | 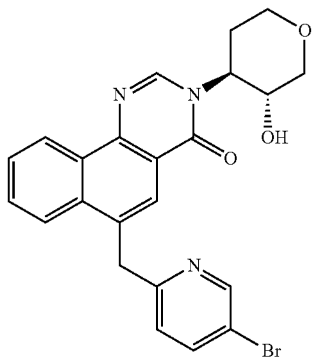 [SMILES: O=c1c2cc(Cc3ccc(Br)cn3)c3ccccc3c2ncn1[C@H]1CCOC[C@@H]1O] | 466.34 | Example 15 |
| 129 | 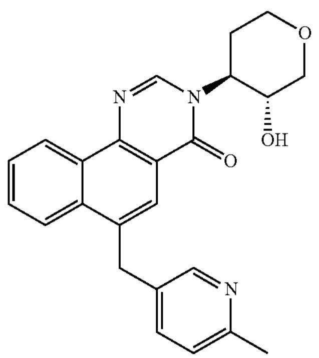 [SMILES: Cc1ccc(Cc2cc3c(=O)n([C@H]4CCOC[C@@H]4O)cnc3c3ccccc23)cn1] | 417.53 | Example 3 |
| 130 | 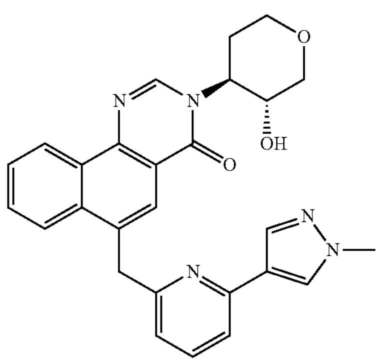 [SMILES: Cn1cc(-c2cccc(Cc3cc4c(=O)n([C@H]5CCOC[C@@H]5O)cnc4c4ccccc34)n2)cn1] | 467.53 | Example 4 |
| 131 | 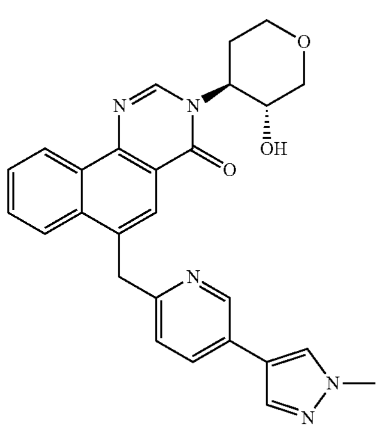 [SMILES: Cn1cc(-c2ccc(Cc3cc4c(=O)n([C@H]5CCOC[C@@H]5O)cnc4c4ccccc34)nc2)cn1] | 467.53 | Example 4 |

TABLE 1-continued

| Example | Structure | MW | Synthesis Method |
|---------|-----------|-------|------------------|
| 132 | 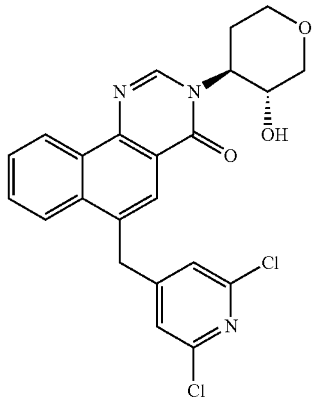 [SMILES: O=c1c2cc(Cc3cc(Cl)nc(Cl)c3)c3ccccc3c2ncn1[C@H]1CCOC[C@@H]1O] | 456.33 | Example 15 |
| 133 | 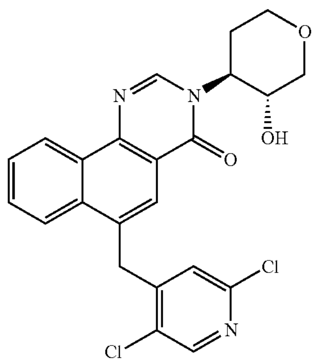 [SMILES: O=c1c2cc(Cc3cc(Cl)ncc3Cl)c3ccccc3c2ncn1[C@H]1CCOC[C@@H]1O] | 456.33 | Example 26 |
| 134 | 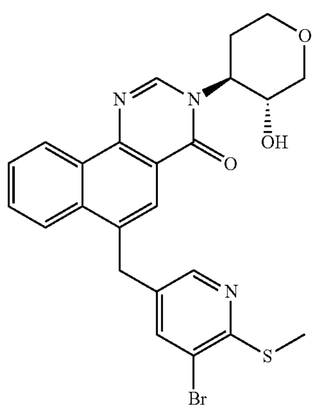 [SMILES: CSc1ncc(Cc2cc3c(=O)n([C@H]4CCOC[C@@H]4O)cnc3c3ccccc23)cc1Br] | 512.43 | Examples 26 |
| 135 | 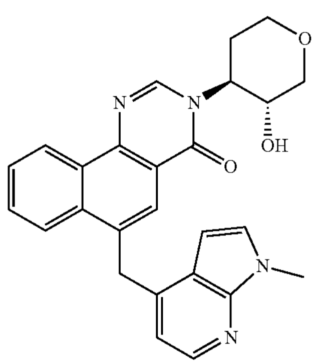 [SMILES: Cn1ccc2c(Cc3cc4c(=O)n([C@H]5CCOC[C@@H]5O)cnc4c4ccccc34)ccnc21] | 440.51 | Example 26 |

TABLE 1-continued

| Example | Structure | MW | Synthesis Method |
|---|---|---|---|
| 136 | 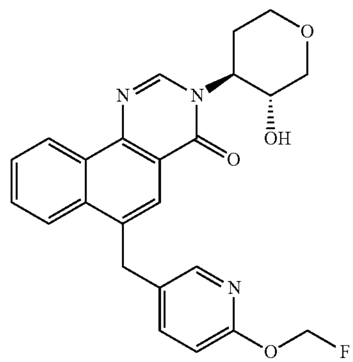 [SMILES: O=c1c2cc(Cc3ccc(OCF)nc3)c3ccccc3c2ncn1[C@H]1CCOC[C@@H]1O] | 435.46 | Example 28 |
| 137 | 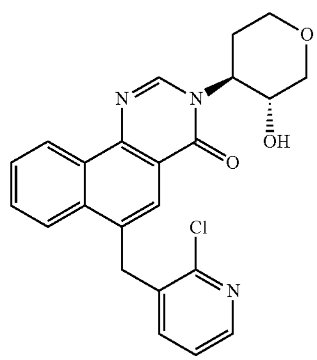 [SMILES: O=c1c2cc(Cc3cccnc3Cl)c3ccccc3c2ncn1[C@H]1CCOC[C@@H]1O] | 421.89 | Example 15 |
| 138 | 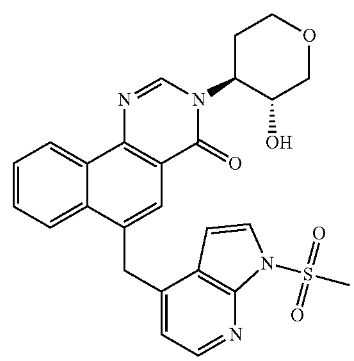 [SMILES: CS(=O)(=O)n1ccc2c(Cc3cc4c(=O)n([C@H]5CCOC[C@@H]5O)cnc4c4ccccc34)ccnc21] | 504.57 | Example 32 |
| 139 | 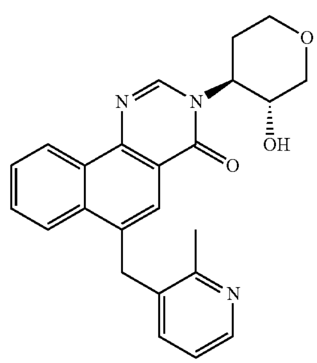 [SMILES: Cc1ncccc1Cc1cc2c(=O)n([C@H]3CCOC[C@@H]3O)cnc2c2ccccc12] | 401.47 | Example 3 |

TABLE 1-continued

| Example | Structure | MW | Synthesis Method |
|---------|-----------|------|------------------|
| 140 | 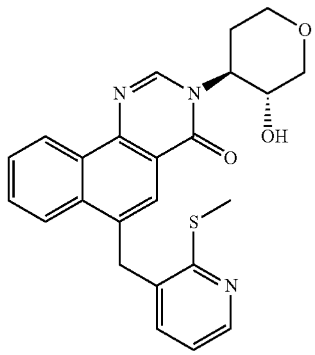 [SMILES: CSc1ncccc1Cc1cc2c(=O)n([C@H]3CCOC[C@@H]3O)cnc2c2ccccc12] | 433.53 | Example 2 |
| 141 | 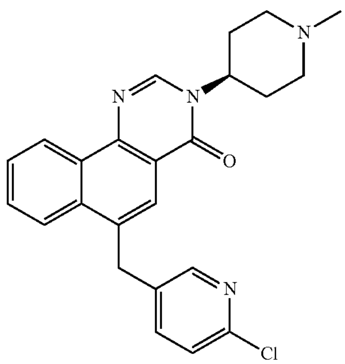 | 418.9 | Example 36 |
| 142 | 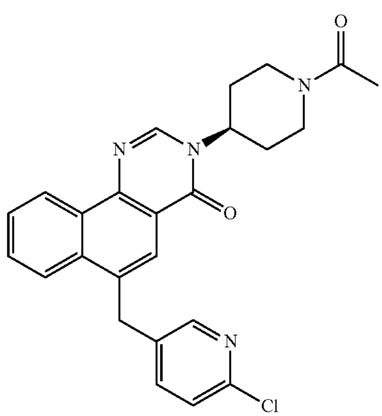 | 446.9 | Example 36 |
| 143 | 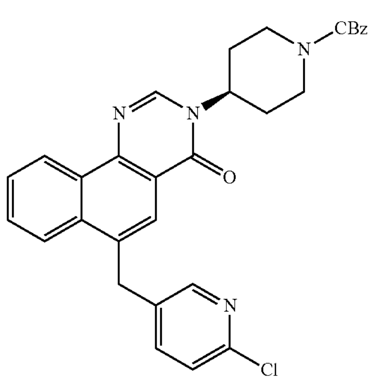 | 538.9 | Example 1 |

TABLE 1-continued

| Example | Structure | MW | Synthesis Method |
|---|---|---|---|
| 144 | 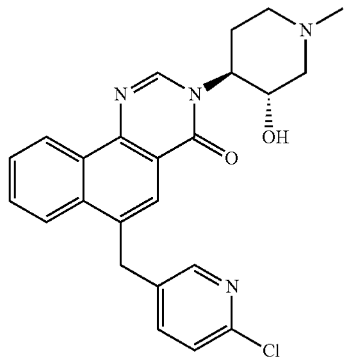 [SMILES: CN1CC[C@H](n2cnc3c(cc(Cc4ccc(Cl)nc4)c4ccccc43)c2=O)[C@@H](O)C1] | 434.9 | Example 36 |
| 145 | 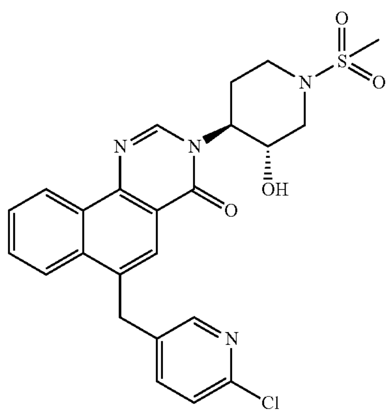 [SMILES: CS(=O)(=O)N1CC[C@H](n2cnc3c(cc(Cc4ccc(Cl)nc4)c4ccccc43)c2=O)[C@@H](O)C1] | 498.9 | Example 36 |
| 146 | 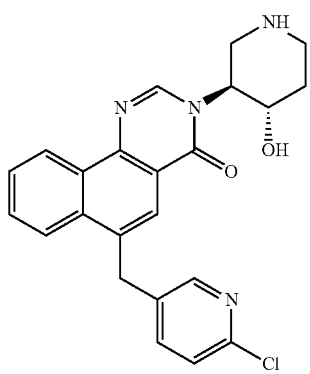 [SMILES: O=c1c2cc(Cc3ccc(Cl)nc3)c3ccccc3c2ncn1[C@H]1CNCC[C@@H]1O] | 420.9 | Example 35 |
| 147 | 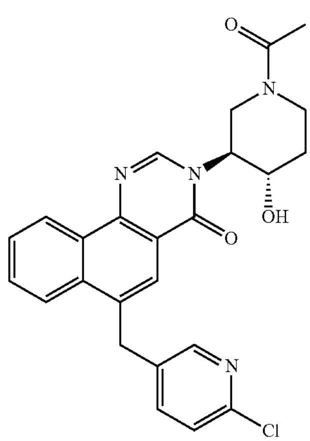 [SMILES: CC(=O)N1CC[C@H](O)[C@@H](n2cnc3c(cc(Cc4ccc(Cl)nc4)c4ccccc43)c2=O)C1] | 462.9 | Example 36 |

TABLE 1-continued
| Example | Structure | MW | Synthesis Method |
|---|---|---|---|
| 148 | 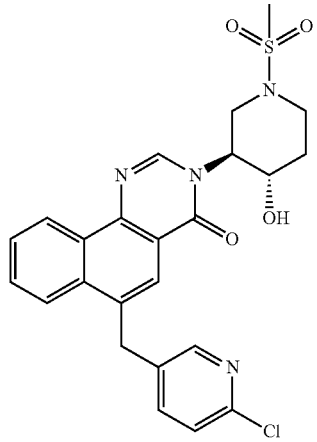 [SMILES: CS(=O)(=O)N1CC[C@H](O)[C@@H](n2cnc3c(cc(Cc4ccc(Cl)nc4)c4ccccc43)c2=O)C1] | 498.8 | Example 36 |
| 149 | 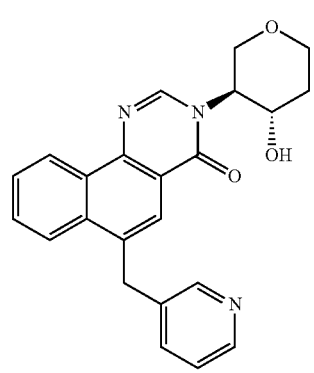 [SMILES: O=c1c2cc(Cc3cccnc3)c3ccccc3c2ncn1[C@H]1COCC[C@@H]1O] | 387.9 | Example 6 |
| 150 | 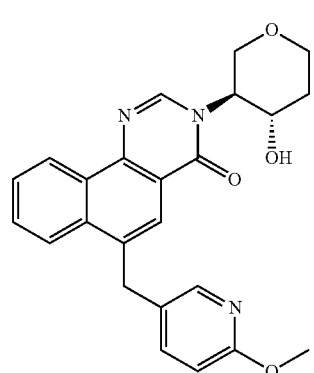 | 417.9 | Example 2 |
| 151 | 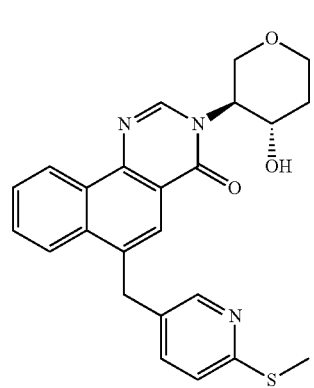 [SMILES: CSc1ccc(Cc2cc3c(=O)n([C@H]4COCC[C@@H]4O)cnc3c3ccccc23)cn1] | 433.9 | Example 2 |

TABLE 1-continued

| Example | Structure | MW | Synthesis Method |
|---|---|---|---|
| 152 | 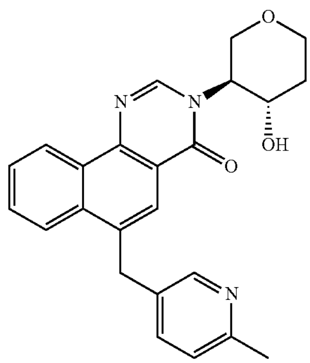 [SMILES: Cc1ccc(Cc2cc3c(=O)n([C@H]4COCC[C@@H]4O)cnc3c3ccccc23)cn1] | 401.9 | Example 3 |
| 153 | 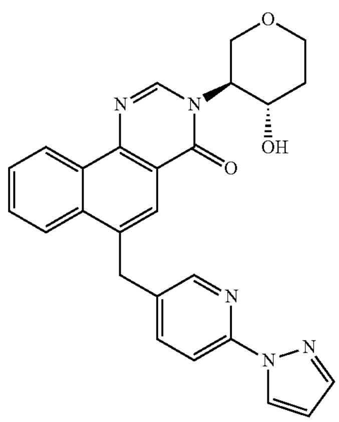 [SMILES: O=c1c2cc(Cc3ccc(-n4cccn4)nc3)c3ccccc3c2ncn1[C@H]1COCC[C@@H]1O] | 453.9 | Example 5 |
| 154 | 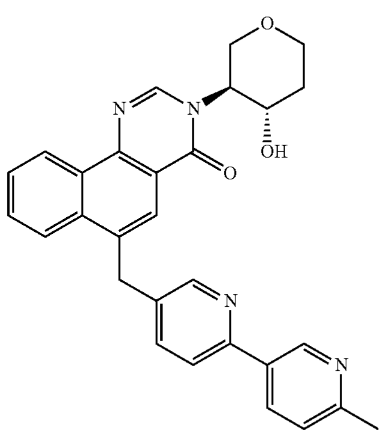 [SMILES: Cc1ccc(-c2ccc(Cc3cc4c(=O)n([C@H]5COCC[C@@H]5O)cnc4c4ccccc34)cn2)cn1] | 478.9 | Example 34 |
| 155 | 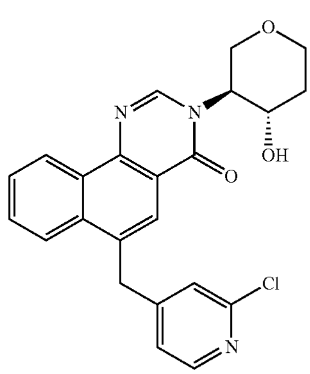 [SMILES: O=c1c2cc(Cc3ccnc(Cl)c3)c3ccccc3c2ncn1[C@H]1COCC[C@@H]1O] | 421.9 | Example 15 |

TABLE 1-continued

| Example | Structure | MW | Synthesis Method |
|---|---|---|---|
| 156 | 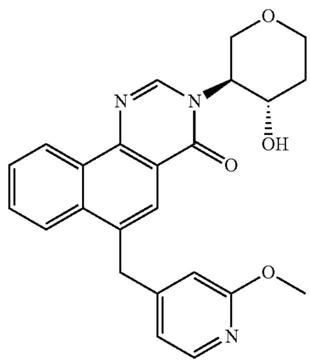 [SMILES: COc1cc(Cc2cc3c(=O)n([C@H]4COCC[C@@H]4O)cnc3c3ccccc23)ccn1] | 417.8 | Example 5 |
| 157 | 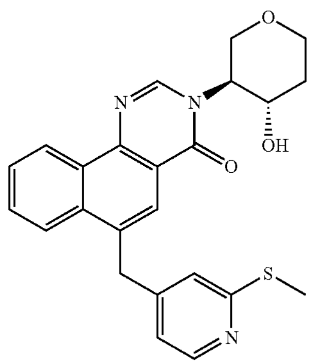 [SMILES: CSc1cc(Cc2cc3c(=O)n([C@H]4COCC[C@@H]4O)cnc3c3ccccc23)ccn1] | 433.8 | Example 2 |
| 158 | 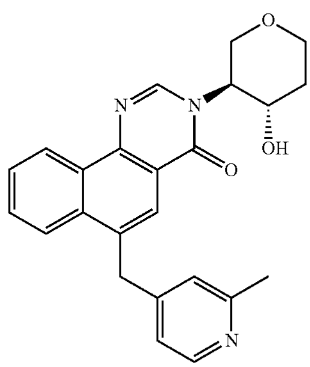 [SMILES: Cc1cc(Cc2cc3c(=O)n([C@H]4COCC[C@@H]4O)cnc3c3ccccc23)ccn1] | 401.9 | Example 3 |
| 159 | 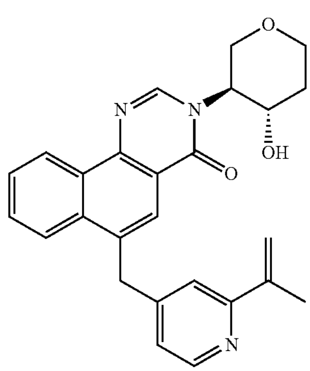 [SMILES: C=C(C)c1cc(Cc2cc3c(=O)n([C@H]4COCC[C@@H]4O)cnc3c3ccccc23)ccn1] | 427.9 | Example 4 |

TABLE 1-continued

| Example | Structure | MW | Synthesis Method |
|---|---|---|---|
| 160 | 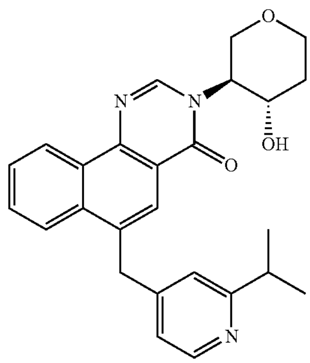 [SMILES: CC(C)c1cc(Cc2cc3c(=O)n([C@H]4COCC[C@@H]4O)cnc3c3ccccc23)ccn1] | 430.0 | Example 9 |
| 161 | 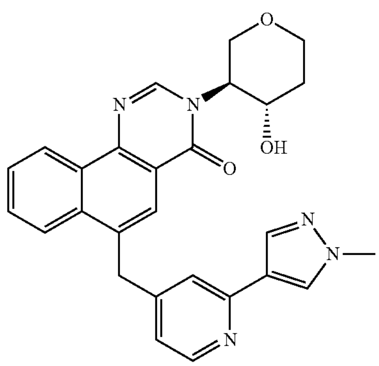 [SMILES: Cn1cc(-c2cc(Cc3cc4c(=O)n([C@H]5COCC[C@@H]5O)cnc4c4ccccc34)ccn2)cn1] | 467.9 | Example 4 |
| 162 | 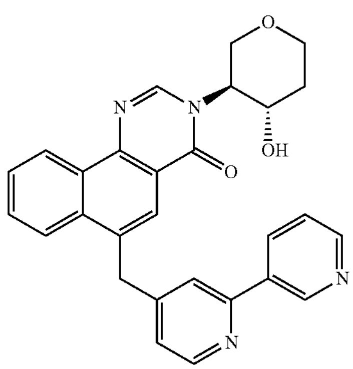 [SMILES: O=c1c2cc(Cc3ccnc(-c4cccnc4)c3)c3ccccc3c2ncn1[C@H]1COCC[C@@H]1O] | 464.9 | Example 4 |
| 163 | 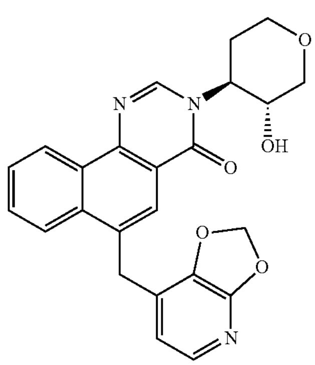 [SMILES: O=c1c2cc(Cc3ccnc4c3OCO4)c3ccccc3c2ncn1[C@H]1CCOC[C@@H]1O] | 431.5 | Example 26 |

TABLE 1-continued

| Example | Structure | MW | Synthesis Method |
|---|---|---|---|
| 164 | 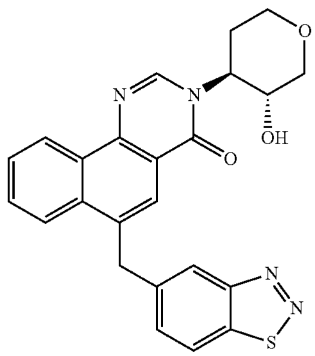 [SMILES: O=c1c2cc(Cc3ccc4snnc4c3)c3ccccc3c2ncn1[C@H]1CCOC[C@@H]1O] | 444.5 | Example 26 |
| 165 | 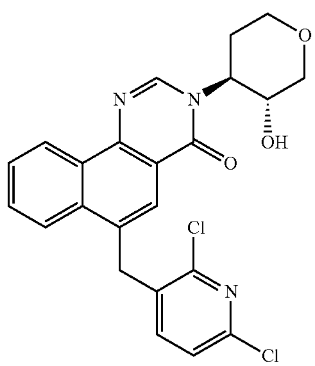 [SMILES: O=c1c2cc(Cc3ccc(Cl)nc3Cl)c3ccccc3c2ncn1[C@H]1CCOC[C@@H]1O] | 456.3 | Example 26 |
| 166 | 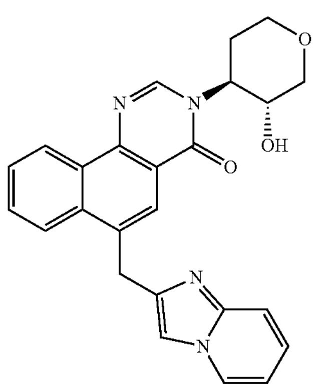 [SMILES: O=c1c2cc(Cc3cn4ccccc4n3)c3ccccc3c2ncn1[C@H]1CCOC[C@@H]1O] | 426.5 | Example 26 |
| 167 | 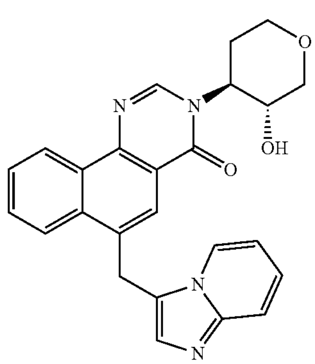 [SMILES: O=c1c2cc(Cc3cnc4ccccn34)c3ccccc3c2ncn1[C@H]1CCOC[C@@H]1O] | 426.5 | Example 26 |

TABLE 1-continued

| Example | Structure | MW | Synthesis Method |
|---------|-----------|------|------------------|
| 168 | 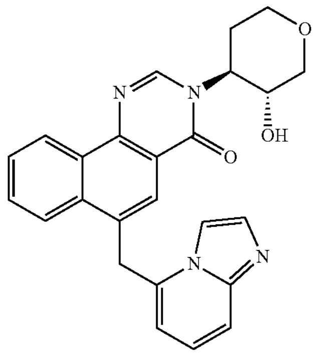 [SMILES: O=c1c2cc(Cc3cccc4nccn34)c3ccccc3c2ncn1[C@H]1CCOC[C@@H]1O] | 426.5 | Example 26 |
| 169 | 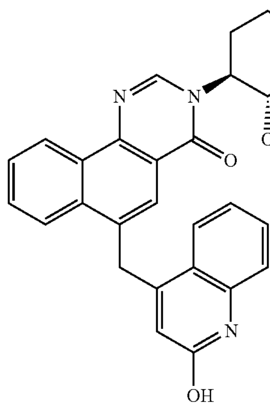 | 453.5 | Example 26 |
| 170 | 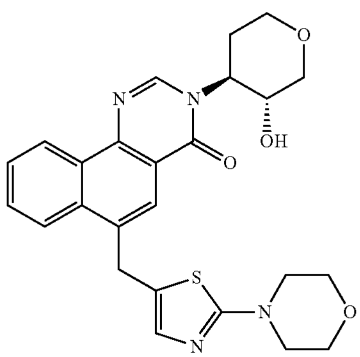 [SMILES: O=c1c2cc(Cc3cnc(N4CCOCC4)s3)c3ccccc3c2ncn1[C@H]1CCOC[C@@H]1O] | 478.6 | Example 26 |
| 171 | 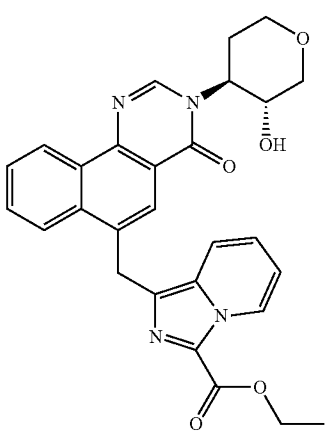 [SMILES: CCOC(=O)c1nc(Cc2cc3c(=O)n([C@H]4CCOC[C@@H]4O)cnc3c3ccccc23)c2ccccn12] | 498.5 | Example 26 |

TABLE 1-continued

| Example | Structure | MW | Synthesis Method |
|---------|-----------|------|------------------|
| 172 | 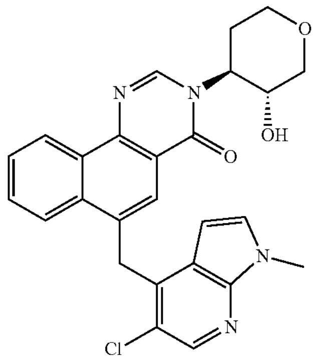 [SMILES: Cn1ccc2c(Cc3cc4c(=O)n([C@H]5CCOC[C@@H]5O)cnc4c4ccccc34)c(Cl)cnc21] | 475.0 | Example 26 |
| 173 | 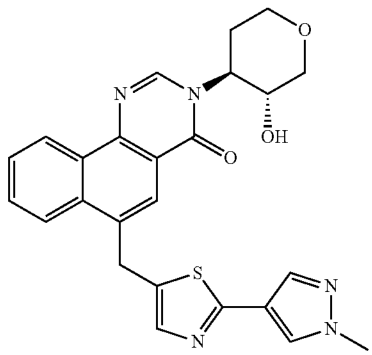 [SMILES: Cn1cc(-c2ncc(Cc3cc4c(=O)n([C@H]5CCOC[C@@H]5O)cnc4c4ccccc34)s2)cn1] | 473.6 | Example 26 |
| 174 | 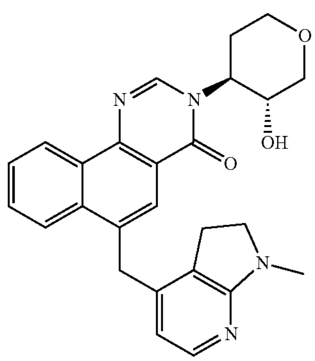 [SMILES: CN1CCc2c(Cc3cc4c(=O)n([C@H]5CCOC[C@@H]5O)cnc4c4ccccc34)ccnc21] | 442.5 | Example 26 |

Biological Utility

The utility of the compounds as M1 receptor positive allosteric modulators may be demonstrated by methodology known in the art, including by the assay described below. The assay is designed to select compounds that possess modulator activity at the acetylcholine muscarinic M1 receptor or other muscarinic receptors expressed in CHOnfat cells by measuring the intracellular calcium with a FLIPR[384] Fluorometric Imaging Plate Reader System. The assay studies the effect of one or several concentrations of test compounds on basal or acetylcholine-stimulated $Ca^{2+}$ levels using FLIPR.

Compounds are prepared and subjected to a preincubation period of 4 min. Thereafter, a single $EC_{20}$ concentration of acetylcholine is added to each well (3 nM final). The intracellular $Ca^{2+}$ level of each sample is measured and compared to an acetylcholine control to determine any modulatory activity.

Cells: CHOnfat/hM1, hM2, hM3 or hM4 cells are plated 24 hr before the assay at a density of 18,000 cells/well (100 µL) in a 384 well plate. CHOnfat/hM1 and CHOnfat/hM3 Growth Medium: 90% DMEM (Hi Glucose); 10% HI FBS; 2 mM L-glutamine; 0.1 mM NEAA; Pen-Strep; and 1 mg/ml Geneticin, are added. For M2Gqi5CHOnfat and M4Gqi5CHOnfat cells, an additional 600 ug/ml hygromycin is added.

Equipment: 384 well plate, 120 µL addition plate; 96-well Whatman 2 ml Uniplate Incubator, 37° C., 5% $CO_2$; Skatron EMBLA-384 Plate Washer; Multimek Pipetting System; Genesis Freedom 200 System; Mosquito System; Temo Nanoliter Pipetting System; and FLIPR[384]Fluorometric Imaging Plate Reader System are used.

Buffers. Assay Buffer: Hanks Balanced Salt Solution, with 20 mM Hepes, 2.5 mM Probenecid (Sigma P-8761) first dissolved in 1 N NaOH, 1% Bovine Serum Albumin (Sigma A-9647). Dye Loading Buffer: Assay Buffer plus 1% Fetal Bovine Serum and Fluo-4AM/Pluronic Acid Mixture. 2 mM Fluo-4AM ester stock in DMSO (Molecular Probes F-14202) Concentration of 2 µM in buffer for a final concentration of 1 µM in Assay. 20% Pluronic Acid Solution stock, with concentration of 0.04% in Buffer, 0.02% in Assay.

65 µL of 2 mM Fluo-4AM are mixed with 130 µL of 20% Pluronic Acid. The resulting solution and 650 µL FBS is added to the assay buffer for a total volume of 65 mL. Positive Controls: 4-Br-A23187: 10 mM in DMSO; final concentration 10 µM. Acetylcholine: 10 mM in water, working stock at both 20 µM and 30 µM in assay buffer, final concentration of 10 µM. This is used to check the maximum stimulation of the CHOK1/hM1 cells. 20 µM (2×) acetylcholine is added in the preincubation part of the assay, and the 30 µM (3×) stock is added in the second part. (EC$_{20}$) Acetylcholine: 10 mM in water, working stock of 9 nM (3×), and final concentration in assay is 3 nM. This is used after the preincubation with test compounds. Addition of the EC$_{20}$ Acetylcholine to each well with a test compound will ascertain any modulator activity. 24 wells contain 3 nM Acetylcholine alone as a control.

Determining Activity of Putative Compounds:
Screening Plate Compounds are titrated in 96-well plates (columns 2-11), 100% DMSO, started at a concentration of 15 mM (150× stock concentration), and 3-fold serial dilutions using Genesis Freedom200 System. Four 96-well plates are combined into a 384-well plate using Mosquito Nanoliter Pipetting System by transferring 1 µA of serial diluted compounds to each well, and 1 mM acetylcholine (100× stock concentration) were added as a control. Using Temo, 49 µl assay buffer is added to each well of the 384-well plate right before assay.

In a 96-well Whatman 2 ml Uniplate, 9 nM Acetylcholine (3×) is pipetted into wells corresponding to the screening compounds, and into control wells. The 30 µM acetylcholine control (3×) is added into control wells, and the 3× agonist plate is transferred into a 384 well plate.

Cells are washed three times with 100 µL of buffer, leaving 30 µL of buffer in each well. Using Multimek, 30 µL of Dye Loading Buffer is added into each well and incubated at 37° C., 5% CO$_2$ for up to one hr.

After 60 min, the cells are washed three times with 100 µL of buffer, leaving 30 µL of buffer in each well. The cell plate, screening plate, and agonist addition plates are placed on the platform in the FLIPR and the door closed. A signal test to check background fluorescence and basal fluorescence signal is performed. Laser intensity is adjusted if necessary.

4 mM of preincubation with the test compounds is provided to determine any agonist activity on the M1 receptor by comparison to the 1 mM acetylcholine control. After preincubation, the EC$_{20}$ value of acetylcholine (3 nM final) is added to determine any modulator activity.

A further description of the muscarinic FLIPR assay can be found in International patent application WO2004/073639.

In particular, the compounds of the following examples had activity in the aforementioned assay, generally with an IP (inflection point) of 10 µM (10,000 nM) or less. The inflection point is calculated from the FLIPR values, and is a measure of activity. Such a result is indicative of the intrinsic activity of the compounds in use as M1 allosteric modulators.

IP values from the aforementioned assay for representative exemplary compounds of the invention (as described herein) are provided below in Table 1 below:

| Example | IP Value (nM) |
|---|---|
| 1 | 13 |
| 2 | 14 |
| 3 | 15 |
| 4 | 2.5 |
| 5 | 15 |
| 6 | 23 |
| 7 | 16.8 |
| 8 | 31 |
| 9 | 16 |
| 10 | 30 |
| 11 | 76 |
| 12 | 21 |
| 13 | 5.8 |
| 14 | 59 |
| 15 | 12 |
| 16 | 53 |
| 17 | 90 |
| 18 | 124 |
| 19 | 318 |
| 20 | 45 |
| 21 | 28 |
| 22 | 23 |
| 23 | 14 |
| 24 | 58 |
| 25 | 15 |
| 26 | 34 |
| 27 | 27 |
| 28 | 27 |
| 29 | 39 |
| 30 | 77 |
| 31 | 275 |
| 32 | 32 |
| 33 | 10 |
| 34 | 7.1 |
| 35 | 54 |
| 36 | 120 |
| 37 | 4800 |

The following abbreviations are used throughout the text:
Me: methyl
Et: ethyl
Bu: butyl
t-Bu: tert-butyl
Ar: aryl
Ph: phenyl
Bn: benzyl
Ac: acetyl
RB: round bottom
DMF: dimethylformamide
DMSO: dimethylsulfoxide
DMEM: Dulbecco's Modified Eagle Medium (High Glucose)
FBS: fetal bovine serum
dppa: diphenylphosphoryl azide
dppf: (diphenylphosphino)ferrocene
THF: tetrahydrofuran
mCPBA: meta-chloroperoxybenzoic acid
TEA: triethylamine
THF: tetrahydrofuran
BOP: Benzotriazolyloxytris(dimethylamino)phosphonium hexafluorophosphate
SEM: β-(trimethylsilyl)ethoxy]methyl
DMFDMA: N,N-dimethylformamide dimethylacetal
TBAF: tetra-n-butylammonium fluoride
NBS: N-bromosuccinimide
TFAA: trifluoroacetic anhydride
TBSO: tert-butyl-dimethylsilyloxy
DDQ: 2,3-dichloro-5,6-dicyanobenzoquinone
NAD: nicotinamide adenine dinucleotide
TBAI: tetrabutylammonium iodide
KRED: Ketoreductase
NADP: Nicotinamide Adenine Dinucleotide Phosphate
LDH: Lactate dehydrogenase FDH: Formate dehydrogenase
PLP: Pyridoxal phosphate
rt: room temperature
aq: aqueous
HPLC: high performance liquid chromatography
MS: mass spectrometry
CDX TA P1G5 Codex Transaminase panel enzyme P1G5 (commercially available from Codex (Redwood City, Calif., USA) panel products.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:

1. A compound of formula (I):

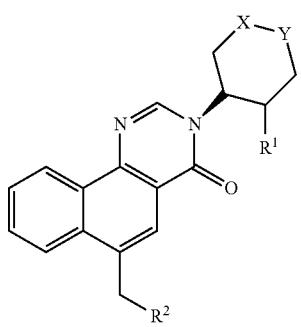

(I)

or a pharmaceutically acceptable salts thereof, wherein
X—Y is selected from the group consisting of
(1) —O—$CR^A R^B$—,
(2) —$CR^A R^B$—O—,
(3) —$CR^A R^B$—$SR^C$—,
(4) —$CR^A R^B$—$NR^C$—, and
(5) —$NR^C$—$CR^A R^B$—;
wherein $R^A$ and $R^B$ are each independently selected from the group consisting of,
(a) hydrogen, and
(b) —$C_{1-6}$ alkyl, and
$R^C$ is selected from the group consisting of,
(a) hydrogen,
(b) —C(=O)—$C_{1-6}$ alkyl,
(c) —$C_{1-6}$ alkyl,
(d) —C(=O)—$CH_2$—$C_6H_5$,
(e) —S(=O)$_2$—$C_{1-6}$ alkyl;
$R^1$ is selected from the group consisting of
(1) hydrogen, and
(2) hydroxy,
provided that when X—Y is —O—$CR^A R^B$—, —$CR^A R^B$—O— or —$CR^A R^B$—$SR^C$—, then $R^1$ is hydroxy in the isomeric position:

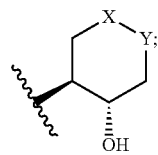

$R^2$ is selected from the group consisting of
(1) —$C_{6-10}$ aryl, and
(2) -heteroaryl, which is an aromatic cyclic group, having from five to twelve ring atoms, the ring atoms selected from C, O, N, N→O or S, at least one of which is O, N, N→O or S,
wherein the aryl or heteroaryl $R^2$ group is optionally substituted with one or more
(a) halogen,
(b) hydroxy,
(c) —$NR^3R^4$,
(d) —$C_{1-6}$ alkyl,
(e) —O—$C_{1-6}$ alkyl,
(f) —$C_{2-8}$ alkenyl,
(g) —C(=O)—(O)$_m$—$R^5$,
(h) —C(=O)—$NR^5$,
(i) —S(=O)$_2$—$R^5$,
(j) —$SR^5$,
(k) —CN;
(l) —$C_{6-10}$ aryl,
(m) heteroaryl, which is an aromatic cyclic group, having from five to twelve ring atoms, the ring atoms selected from C, O, N, N→O or S, at least one of which is O, N, N→O or S,
(n) Si($R^6$)$_3$,
(o) =S,
wherein the alkyl, alkenyl, aryl or heteroaryl moiety is optionally substituted with one or more
(a) halogen,
(b) hydroxyl,
(c) —$C_{1-6}$ alkyl,
(d) —S—$R^6$,
(e) —$NR^8R^9$,
(f) —O—$C_{1-6}$ alkyl,
wherein the alkyl moiety is optionally substituted with one or more halogen;
$R^3$ and $R^4$, or $R^8$ and $R^9$, are independently selected from the group consisting of
(1) hydrogen, and
(2) —$C_{1-6}$ alkyl,
wherein the alkyl is optionally substituted with one or more
(a) halogen,
(b) hydroxyl,
(c) —O—$C_{1-6}$ alkyl,
(d) —$NR^{10}R^{11}$,
(e) —C(=O)—(O)$_n$—$C_{1-6}$ alkyl,
or $R^3$ and $R^4$, or $R^8$ and $R^9$, are linked together with the nitrogen to which they are attached to form a 4-6 membered carbocyclic ring, wherein one or two of the ring carbon atoms is optionally replaced by a nitrogen, oxygen or sulfur, and the ring is optionally substituted with one or more
(a) halogen,
(b) hydroxyl,
(c) $C_{1-6}$ alkyl,
(d) —O—$C_{1-6}$ alkyl,
(e) —C(=O)—(O)$_n$—$C_{1-6}$ alkyl;

R⁵ is selected from the group consisting of
(1) hydrogen,
(2) —$C_{1-6}$ alkyl,
(3) —$C_{3-8}$ cycloalkyl,
(4) —$C_{2-8}$ alkenyl, and
(5) —$C_{6-10}$ aryl,
wherein the alkyl, cycloalkyl, alkenyl or aryl is optionally substituted with one or more
(a) halogen,
(b) hydroxyl,
(c) —$C_{1-6}$ alkyl,
(d) —O—$C_{1-6}$ alkyl,
(e) —$C_{3-8}$ cycloalkyl, or
(f) —$C_{6-10}$ aryl;
R⁶ is selected from the group consisting of
(1) hydrogen, and
(2) —$C_{1-6}$ alkyl;
R¹⁰ and R¹¹ are independently selected from the group consisting of
(1) hydrogen, and
(2) —$C_{1-6}$ alkyl,
wherein the alkyl is optionally substituted with one or more
(a) halogen,
(b) hydroxyl,
(c) —O—$C_{1-6}$ alkyl,
(d) —C(=O)—(O)$_n$—$C_{1-6}$ alkyl,
or R¹⁰ and R¹¹ are linked together with the nitrogen to which they are attached to form a 4-6 membered carbocyclic ring, wherein one or two of the ring carbon atoms is optionally replaced by a nitrogen, oxygen or sulfur, and the ring is optionally substituted with one or more
(a) halogen,
(b) hydroxyl,
(c) $C_{1-6}$ alkyl,
(d) —O—$C_{1-6}$ alkyl,
(e) —C(=O)—(O)$_n$—$C_{1-6}$ alkyl;
m is 0 or 1;
n is 0, 1 or 2.

2. The compound of claim 1, wherein R¹ is hydroxy.
3. The compound of claim 2, wherein the R¹ hydroxy group is in the isomeric position:

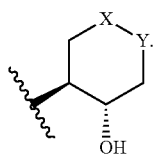

4. The compound of claim 1, wherein X—Y is —O—CR$^A$R$^B$— or —CR$^A$R$^B$—O—, wherein R$^A$ and R$^B$ are each hydrogen.
5. The compound of claim 1, wherein R² is optionally substituted —$C_{6-10}$ aryl.
6. The compound of claim 1, wherein R² is optionally substituted heteroaryl, the heteroaryl group having five ring atoms, the ring atoms selected from C, N, N→O and S, wherein one or two of the ring atoms is N, N→O or S.
7. The compound of claim 1, wherein R² is optionally substituted heteroaryl, the heteroaryl group having six ring atoms, the ring atoms selected from C, N and N→O, wherein one or two of the ring atoms is N or N→O.
8. The compound of claim 1, wherein R² is optionally substituted heteroaryl, the heteroaryl group having nine or ten ring atoms, the ring atoms selected from C, O, N, N→O and S, wherein one, two or three of the ring atoms is N, N→O, O or S.

9. The compound of claim 1, wherein the compound of formula (I) is a compound of formula (II):

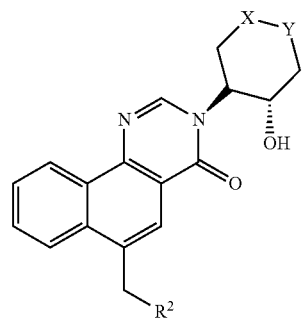

or a pharmaceutically acceptable salt thereof, wherein X, Y and R² are as defined in claim 1.

10. The compound of claim 9, wherein X—Y is —O—CR$^A$R$^B$— or —CR$^A$R$^B$—O—, wherein R$^A$ and R$^B$ are each hydrogen.
11. The compound of claim 9, wherein R² is optionally substituted —$C_{6-10}$ aryl.
12. The compound of claim 9, wherein R² is optionally substituted heteroaryl, the heteroaryl group having five ring atoms, the ring atoms selected from C, N, N→O and S, wherein one or two of the ring atoms is N, N→O or S.
13. The compound of claim 9, wherein R² is optionally substituted heteroaryl, the heteroaryl group having six ring atoms, the ring atoms selected from C, N and N→O, wherein one or two of the ring atoms is N or N→O.
14. The compound of claim 9, wherein R² is optionally substituted heteroaryl, the heteroaryl group having nine or ten ring atoms, the ring atoms selected from C, O, N N→O and S, wherein one, two or three of the ring atoms is N, N→O, O or S.
15. The compound of claim 1, wherein the compound of formula (I) is a compound of formula (III):

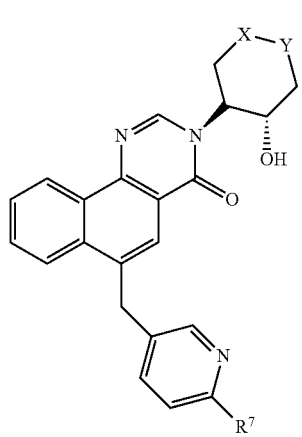

or a pharmaceutically acceptable salt thereof, wherein X, Y and R² are as described above, and R⁷ is selected from the group consisting of (1) halogen,
(2) hydroxy,
(3) —NR³R⁴,
(4) —C$_{1-6}$ alkyl,
(5) —O—C$_{1-6}$ alkyl,
(6) —C$_{2-8}$ alkenyl,
(7) —C(=O)—(O)$_m$—R⁵,
(9) —C(=O)—NR⁵,
(10) —S(=O)$_2$—R⁵,
(11) —SR⁵,
(12) —CN;
(13) —C$_{6-10}$aryl,
(14) heteroaryl, which is an aromatic cyclic group, having from five to twelve ring atoms, the ring atoms selected from C, O, N, N→O or S, at least one of which is O, N, N→O or S,
(15) Si(R⁶)$_3$,
(16) =S, and
(17) hydrogen,
wherein the alkyl, alkenyl, aryl or heteroaryl moiety is optionally substituted with one or more
(a) halogen,
(b) —C$_{1-6}$ alkyl,
(c) —S—R⁶,
(d) —NR⁸R⁹,
(e) —O—C$_{1-6}$ alkyl,
wherein the alkyl moiety is optionally substituted with one or more halogen.

16. The compound of claim 15, wherein R⁷ is selected from the group consisting of
(1) halogen,
(2) hydroxy,
(3) —NR³R⁴,
(4) —C$_{1-6}$ alkyl,
(5) —O—C$_{1-6}$ alkyl,
(6) —S(=O)$_2$—R⁵, and
(7) —SR⁵.

17. The compound of claim 15, wherein X—Y is selected from the group consisting of
(1) —O—CR$^A$R$^B$—, and
(2) —CR$^A$R$^B$—O—.

18. The compound of claim 1, wherein the compound of formula (I) is a compound of formula (IV):

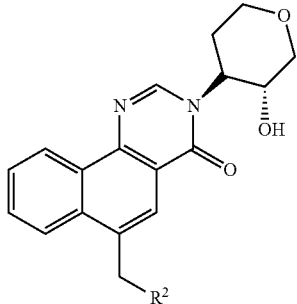

(IV)

wherein R² is as defined in claim 1.

19. The compound of claim 18, wherein R² is optionally substituted —C$_{6-10}$ aryl.

20. The compound of claim 18, wherein R² is optionally substituted heteroaryl, the heteroaryl group having five ring atoms, the ring atoms selected from C, N, N→O and S, wherein one or two of the ring atoms is N, N→O or S.

21. The compound of claim 18, wherein R² is optionally substituted heteroaryl, the heteroaryl group having six ring atoms, the ring atoms selected from C, N and N→O, wherein one or two of the ring atoms is N or N→O.

22. The compound of claim 18, wherein R² is optionally substituted heteroaryl, the heteroaryl group having nine or ten ring atoms, the ring atoms selected from C, O, N, N→O and S, wherein one, two or three of the ring atoms is N, N→O, O or S.

23. The compound of claim 1, which is selected from the group consisting of

6-[(6-Chloropyridin-3-yl)methyl]-3-[(3R,4S)-3-hydroxytetrahydro-2H-pyran-4-yl]benzo[h]quinazolin-4(3H)-one;

3-[(3R,4S)-3-Hydroxytetrahydro-2H-pyran-4-yl]-6-{[(6-methylthio)pyridin-3-yl)methyl]benzo[h]quinazolin-4(3H)-one;

3-[(3R,4S)-3-Hydroxytetrahydro-2H-pyran-4-yl]-6-[(6-methylpyridin-3-yl)methyl]benzo[h]quinazolin-4(3H)-one;

3-[(3R,4S)-3-Hydroxytetrahydro-2H-pyran-4-yl]-6-{[6-(1-methyl-1H-pyrazol-4-yl)pyridine-3-yl]methyl}benzo[h]quinazolin-4(3H)-one;

3-[(3R,4S)-3-Hydroxytetrahydro-2H-pyran-4-yl]-6-{[6-(1H-pyrazol-1-yl)pyridine-3-yl]methyl}benzo[h]quinazolin-4(3H)-one;

3-[(3R,4S)-3-Hydroxytetrahydro-2H-pyran-4-yl]-6-(pyridine-3-ylmethyl)benzo[h]quinazolin-4(3H)-one;

3-[(3R,4S)-3-Hydroxytetrahydro-2H-pyran-4-yl]-6-[(6-methoxypyridin-3-yl)methyl]benzo[h]quinazolin-4(3H)-one;

5-({3-[(3R,4S)-3-Hydroxytetrahydro-2H-pyran-4-yl]-4-oxo-3,4-dihydrobenzo[h]quinazolin-6-yl}methyl)pyridine-2-carbonitrile;

6-[(6-Ethylpyridin-3-yl)methyl]-3-[(3R,4S)-3-hydroxytetrahydro-2H-pyran-4-yl]benzo[h]quinazolin-4(3H)-one;

6-[(6-Acetylpyridin-3-yl)methyl]-3-[(3R,4S)-3-hydroxytetrahydro-2H-pyran-4-yl]benzo[h]quinazolin-4(3H)-one;

6-{[6-(1-Hydroxy-1-methylethyl)pyridine-3-yl]methyl}-3-[(3R,4S)-3-hydroxytetrahydro-2H-pyran-4-yl]benzo[h]quinazolin-4(3H)-one;

3-[(3R,4S)-3-Hydroxytetrahydro-2H-pyran-4-yl]-6-(4-morpholin-4-ylbenzyl)benzo[h]quinazolin-4(3H)-one;

3-[(3R,4S)-3-Hydroxytetrahydro-2H-pyran-4-yl]-6-{[6-(1,3-thiazol-4-yl)pyridine-3-yl]methyl}benzo[h]quinazolin-4(3H)-one;

6-[(6-Chloro-1-oxidopyridin-3-yl)methyl]-3-[(3R,4S)-3-hydroxytetrahydro-2H-pyran-4-yl]benzo[h]quinazolin-4(3H)-one;

6-[(2-Chloropyridin-4-yl)methyl]-3-[(3R,4S)-3-hydroxytetrahydro-2H-pyran-4-yl]benzo[h]quinazolin-4(3H)-one;

3-[(3R,4S)-3-Hydroxytetrahydro-2H-pyran-4-yl]-6-{[6-(methylsulfonyl)pyridine-3-yl]methyl}benzo[h]quinazolin-4(3H)-one;

3-[(3R,4S)-3-Hydroxytetrahydro-2H-pyran-4-yl]-6-{[6-(methylsulfinyl)pyridine-3-yl]methyl}benzo[h]quinazolin-4(3H)-one;

5-({3-[(3R,4S)-3-Hydroxytetrahydro-2H-pyran-4-yl]-4-oxo-3,4-dihydrobenzo[h]quinazolin-6-yl}methyl)pyridine-2-carboxylic acid;

5-({3-[(3R,4S)-3-Hydroxytetrahydro-2H-pyran-4-yl]-4-oxo-3,4-dihydrobenzo[h]quinazolin-6-yl}methyl)-N,N-dimethylpyridine-2-carboxamide;

3-[(3R,4S)-3-Hydroxytetrahydro-2H-pyran-4-yl]-6-{[6-(1-methoxy-1-methylethyl)pyridine-3-yl]methyl}benzo[h]quinazolin-4(3H)-one;

6-{[6-(Hydroxymethyl)pyridine-3-yl]methyl}-3-[(3R,4S)-3-hydroxytetrahydro-2H-pyran-4-yl]benzo[h]quinazolin-4(3H)-one;

6-{[6-(Fluoromethyl)pyridine-3-yl]methyl}-3-[(3R,4S)-3-hydroxytetrahydro-2H-pyran-4-yl]benzo[h]quinazolin-4(3H)-one;

6-{[6-(Difluoromethyl)pyridine-3-yl]methyl}-3-[(3R,4S)-3-hydroxytetrahydro-2H-pyran-4-yl]benzo[h]quinazolin-4(3H)-one;

6-[(2-Chloro-1-oxidopyridin-4-yl)methyl]-3-[(3R,4S)-3-hydroxytetrahydro-2H-pyran-4-yl]benzo[h]quinazolin-4(3H)-one;

6-[(2-Fluoropyridin-4-yl)methyl]-3-[(3R,4S)-3-hydroxytetrahydro-2H-pyran-4-yl]benzo[h]quinazolin-4(3H)-one;

3-[(3R,4S)-3-Hydroxytetrahydro-2H-pyran-4-yl]-6-[(2-methoxypyridin-4-yl)methyl]benzo[h]quinazolin-4(3H)-one;

6-[(6-Ethyoxypyridin-3-yl)methyl]-3-[(3R,4S)-3-hydroxytetrahydro-2H-pyran-4-yl]benzo[h]quinazolin-4(3H)-one;

6-[(6-Hydroxypyridin-3-yl)methyl]-3-[(3R,4S)-3-hydroxytetrahydro-2H-pyran-4-yl]benzo[h]quinazolin-4(3H)-one;

6-{[6-(Difluoromethoxy)pyridine-3-yl]methyl}-3-[(3R,4S)-3-hydroxytetrahydro-2H-pyran-4-yl]benzo[h]quinazolin-4(3H)-one;

6-{[2-(Difluoromethoxy)pyridine-4-yl]methyl}-3-[(3R,4S)-3-hydroxytetrahydro-2H-pyran-4-yl]benzo[h]quinazolin-4(3H)-one;

6-[(3-Bromo-1-methyl-1H-pyrrolo[2,3-b]pyridine-4-yl)methyl]-3-[(3R,4S)-3-hydroxytetrahydro-2H-pyran-4-yl]benzo[h]quinazolin-4(3H)-one;

6-[(1-Ethyl-1H-pyrrolo[2,3-b]pyrdin-4-yl)methyl]-3-[(3R,4S)-3-hydroxytetrahydro-2H-pyran-4-yl]benzo[h]quinazolin-4(3H)-one;

6-[(6-Chloropyridin-3-yl)methyl]-3-[(3R,4S)-3-hydroxytetrahydro-2H-thiopyran-4-yl]benzo[h]quinazolin-4(3H)-one;

3-[(3S,4S)-4-Hydroxytetrahydro-2H-pyran-3-yl]-6-[(6'-methyl-2,3-bipyridin-5-yl)methyl]benzo[h]quinazolin-4(3H)-one;

rac-6-[(6-Chloropyridin-3-yl)methyl]-3-[(3R,4R)-3-hydroxypiperidin-4-yl]benzo[h]quinazolin-4(3H)-one;

rac-3-[(3R,4R)-1-acetyl-3-hydroxypiperidin-4-yl]-6-[(6-chloropyridin-3-yl)methyl]benzo[h]quinazolin-4(3H)-one;

6-[(6-Chloropyridin-3-yl)methyl]-3-piperidin-4-ylbenzo[h]quinazolin-4(3H)-one;

or a pharmaceutically acceptable salt thereof.

24. The compound of claim 1, which is selected from the group consisting of

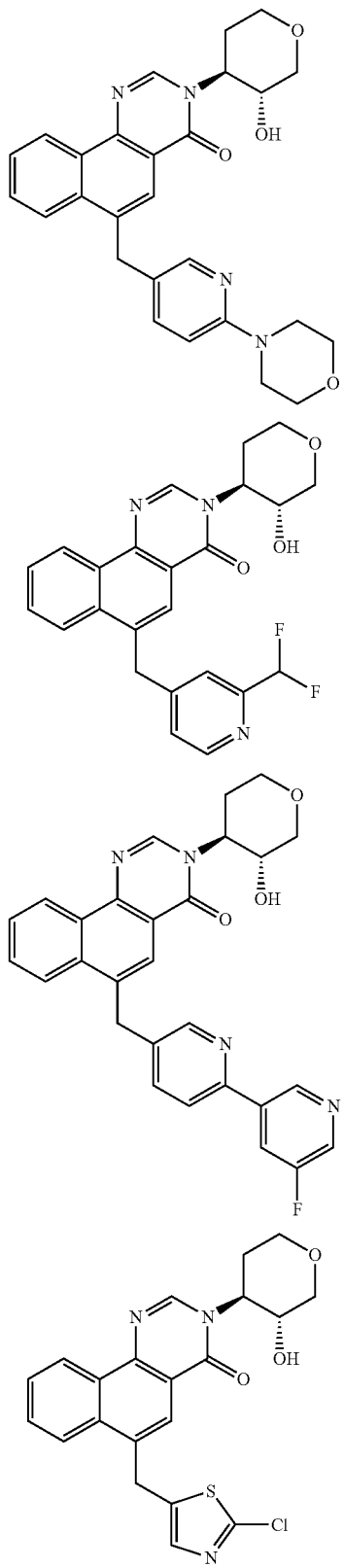

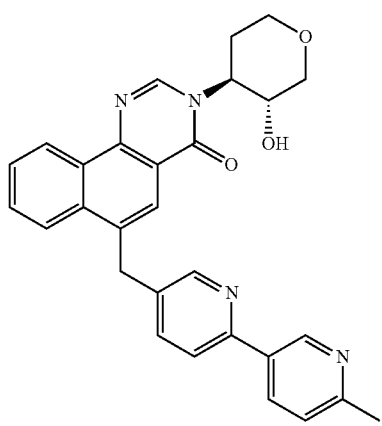
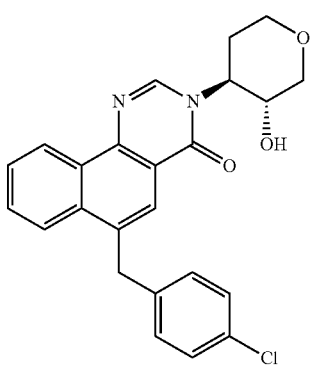
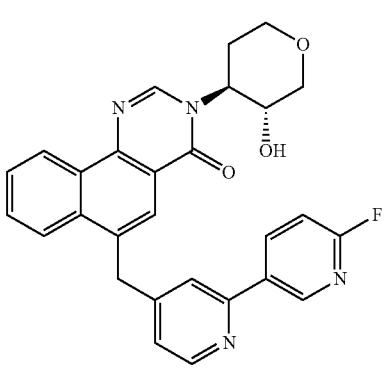
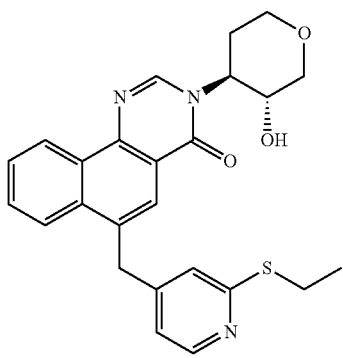
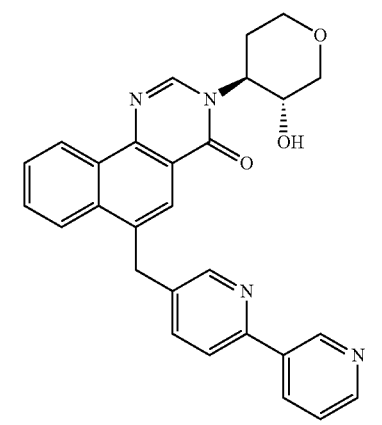
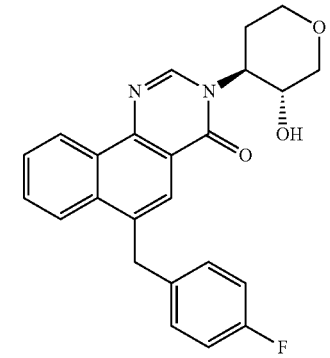
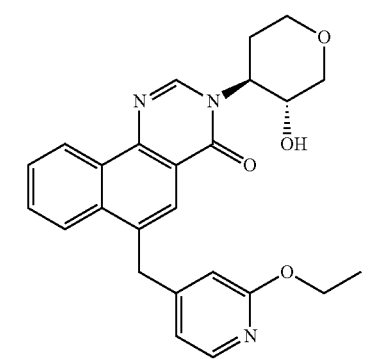
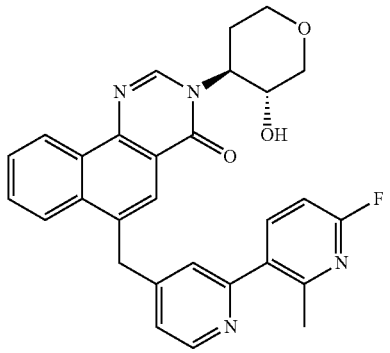

187
-continued
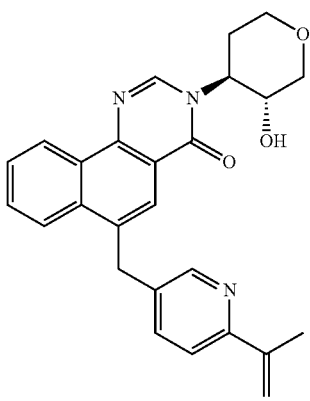
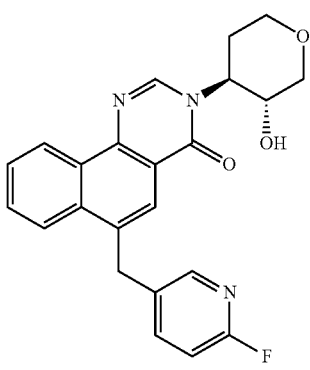
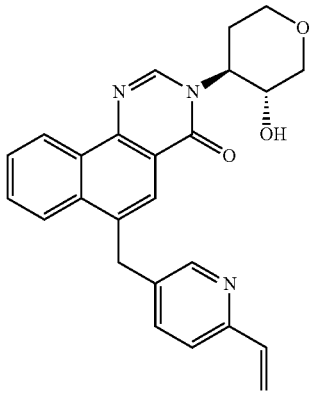
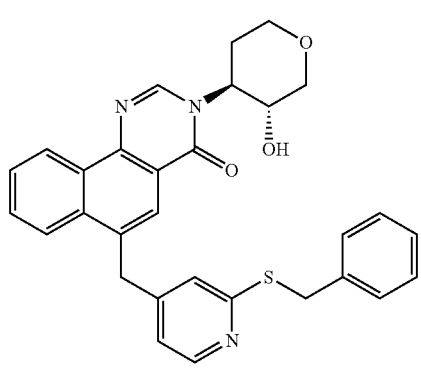
188
-continued
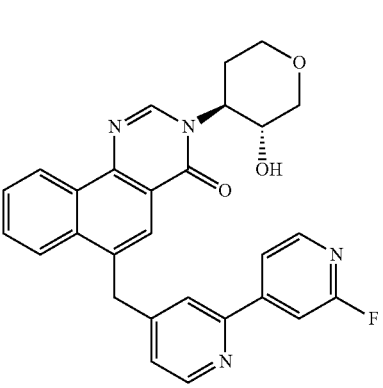
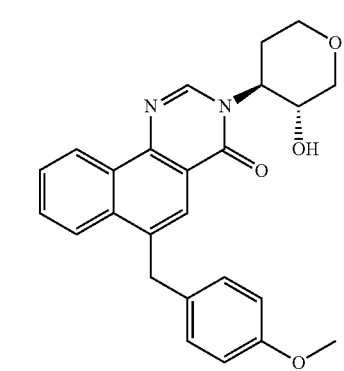
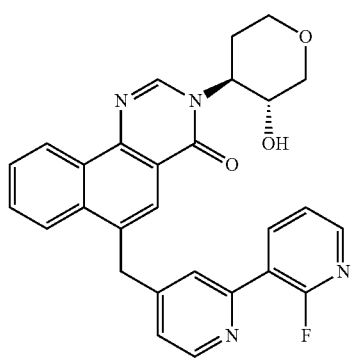

189
-continued
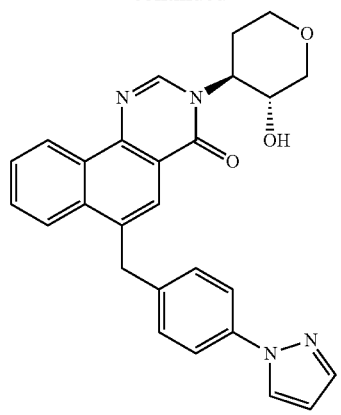
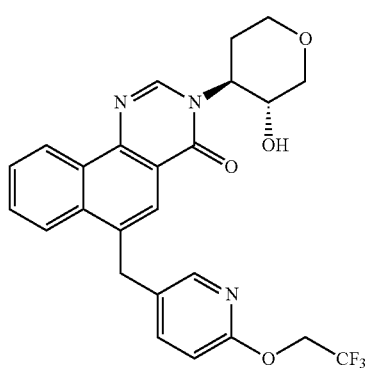
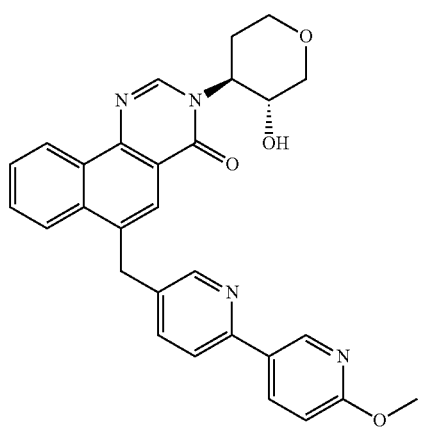
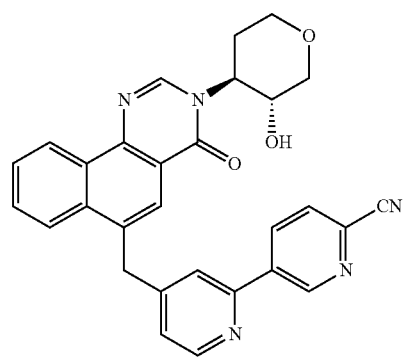
190
-continued
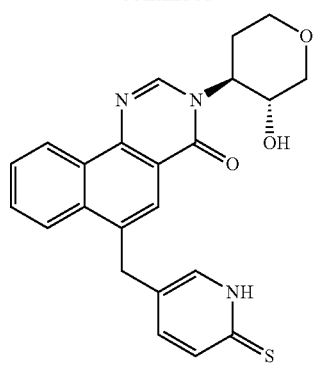
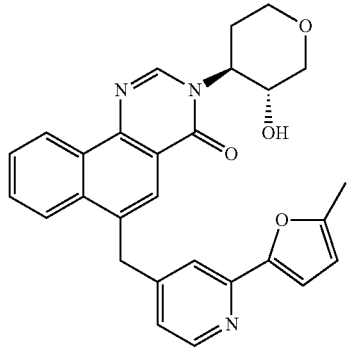
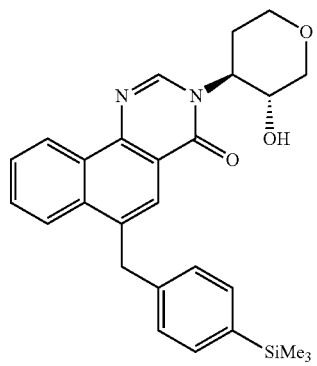
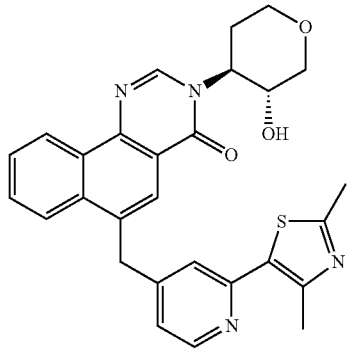

| 191 | 192 |
|---|---|
| -continued | -continued |
| 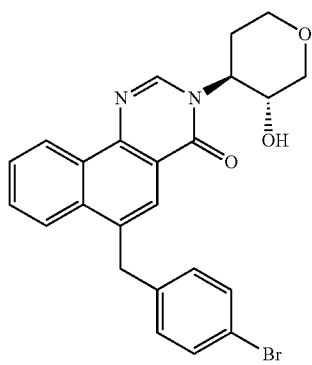 | 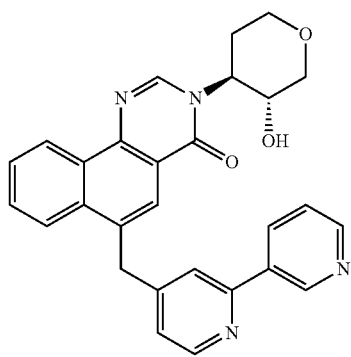 |
| 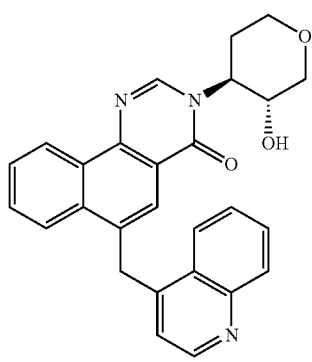 | 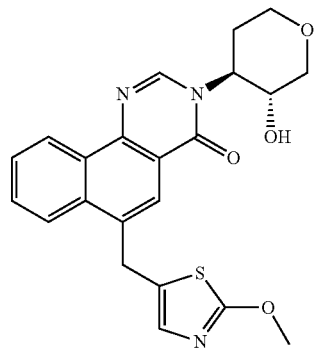 |
| 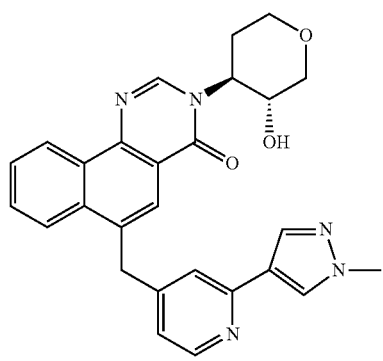 | 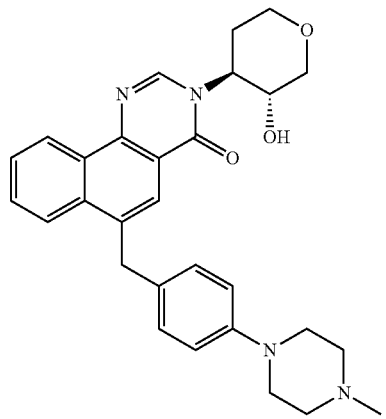 |
| 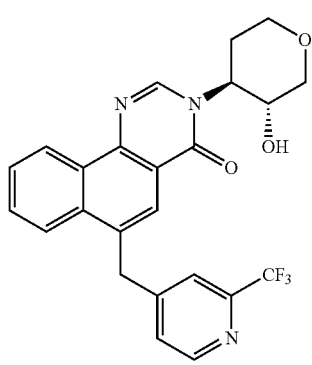 | 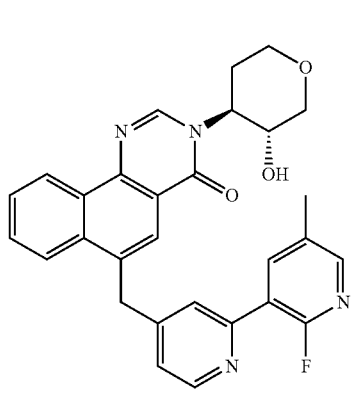 |

193
-continued
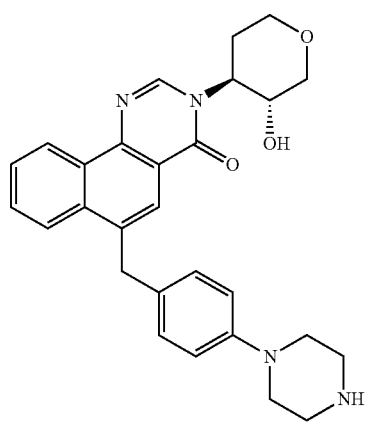
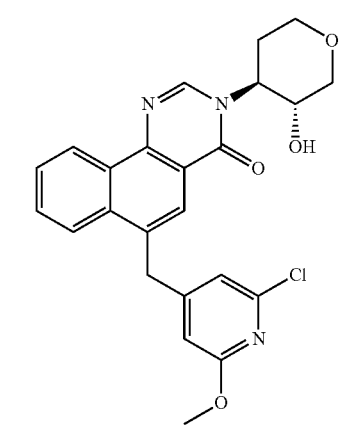
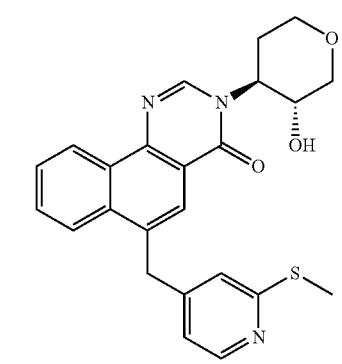
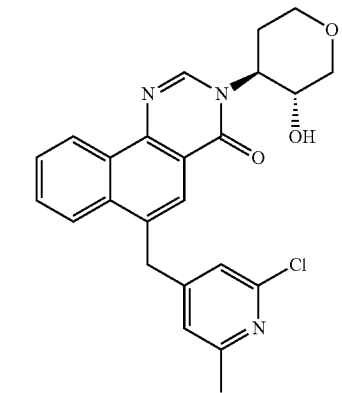
194
-continued
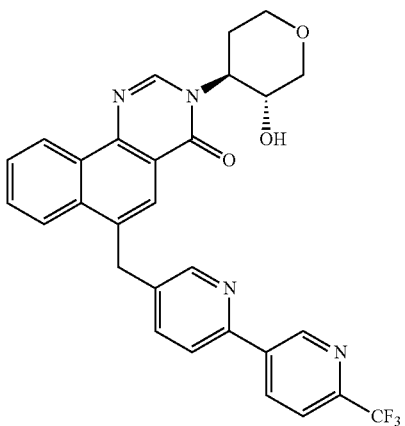
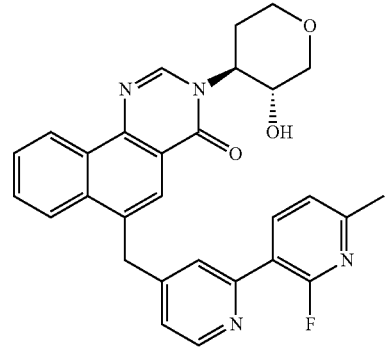
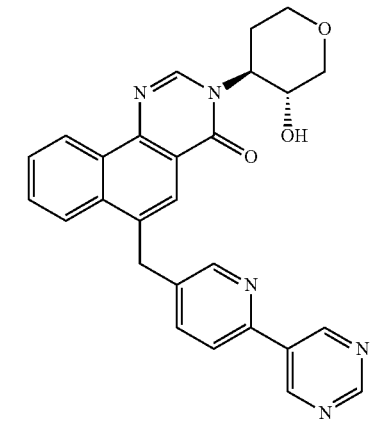
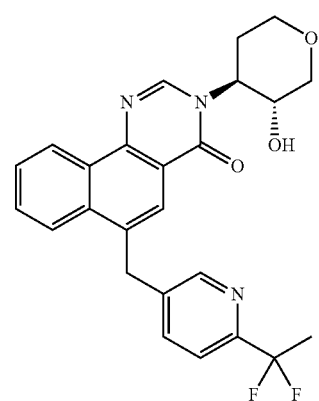

195
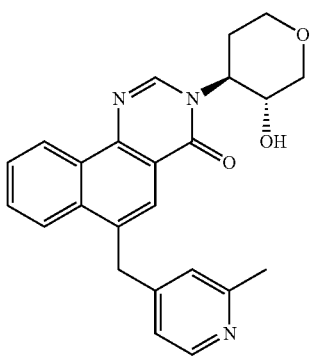
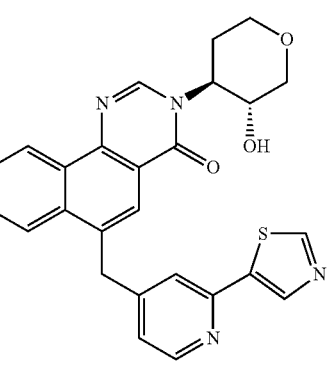
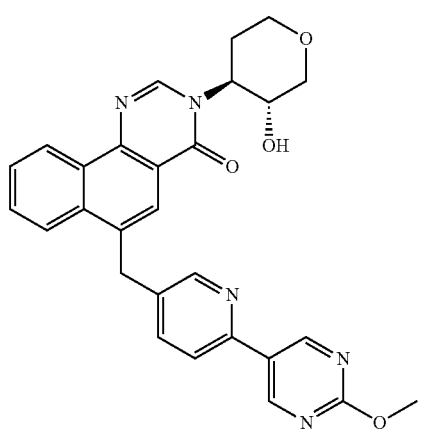
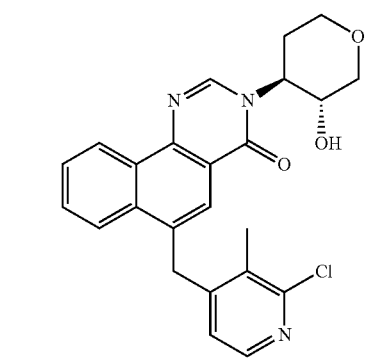
196
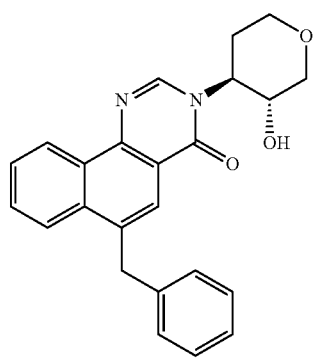
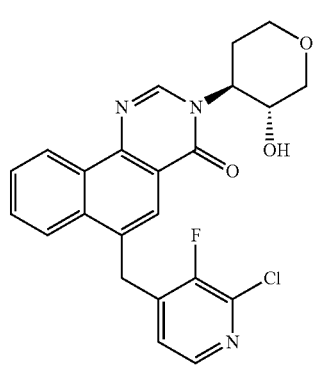
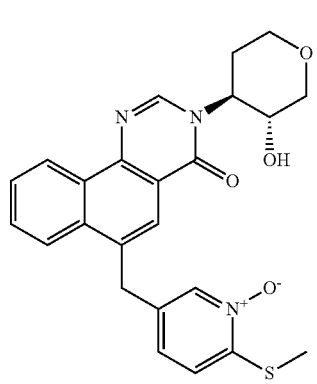
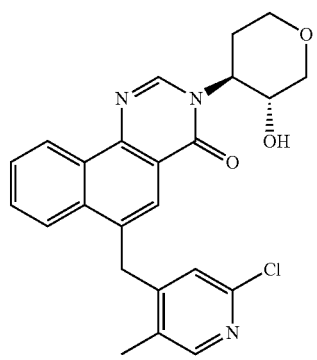

197
-continued
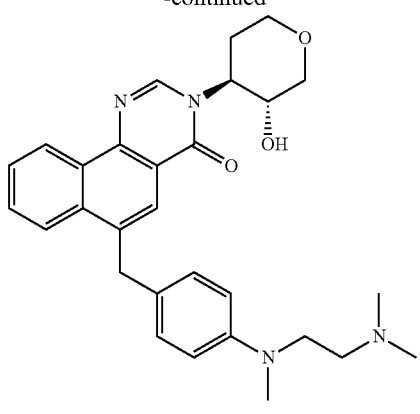
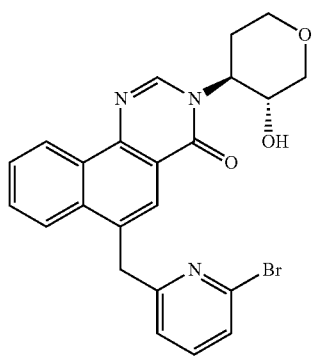
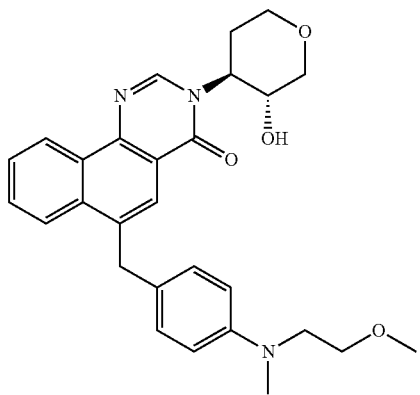
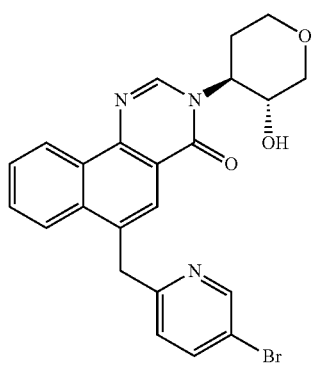
198
-continued
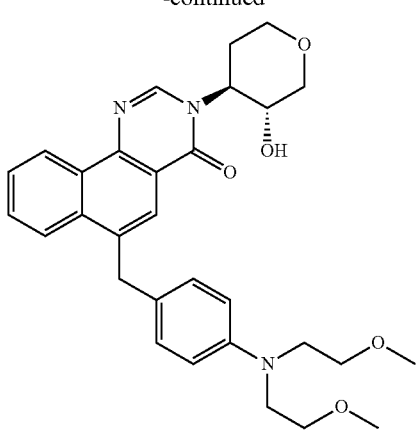
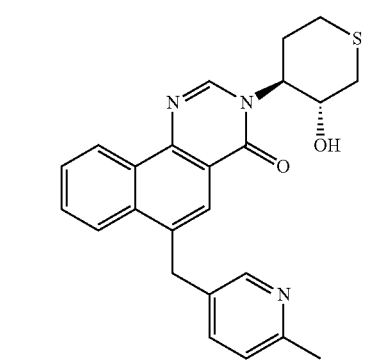
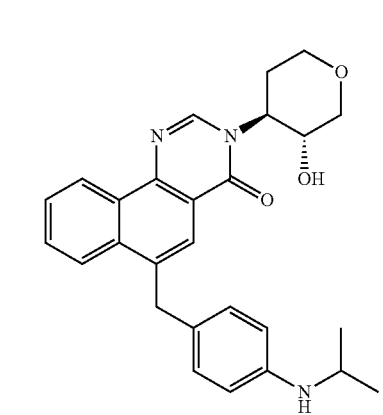
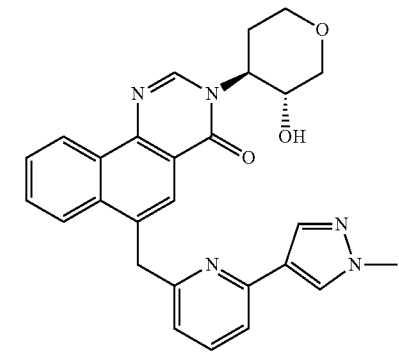

199
-continued
200
-continued
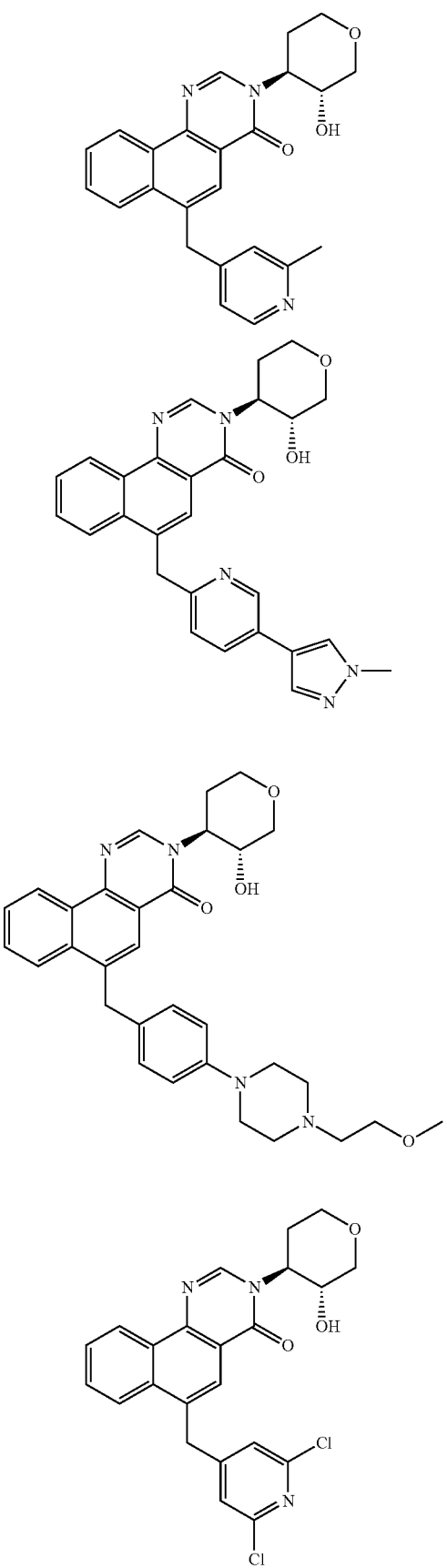
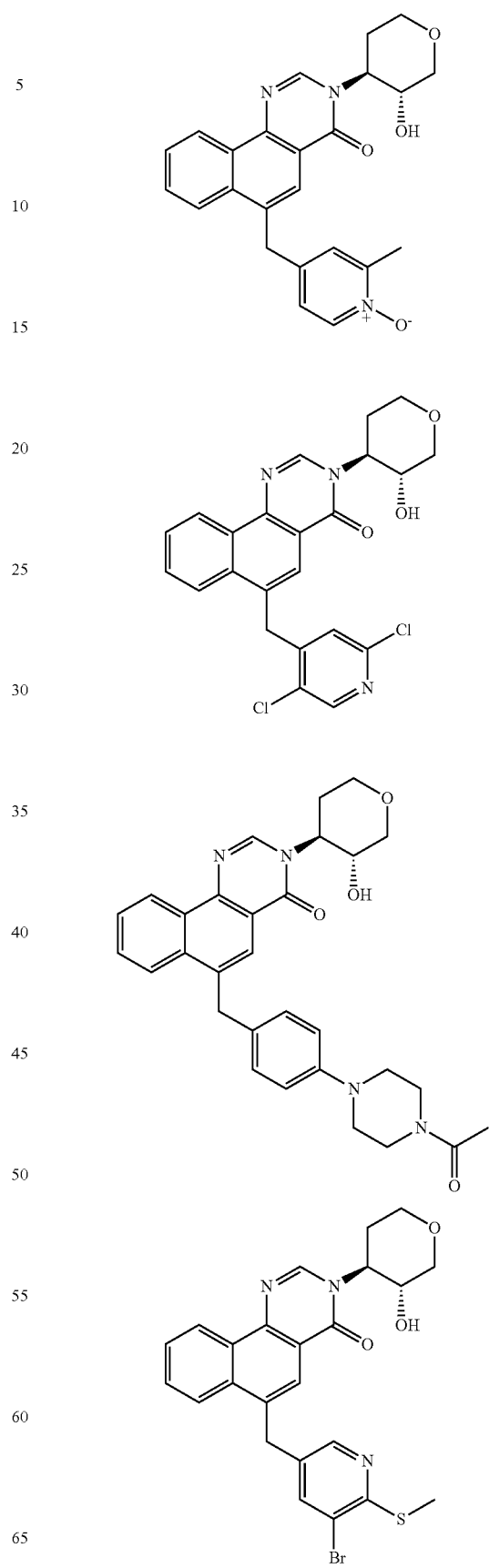

201
-continued
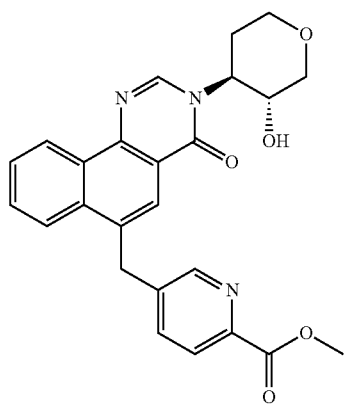
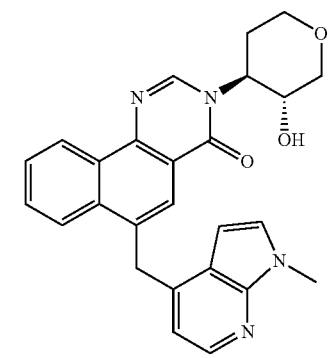
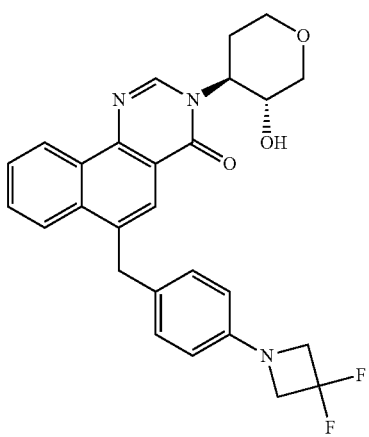
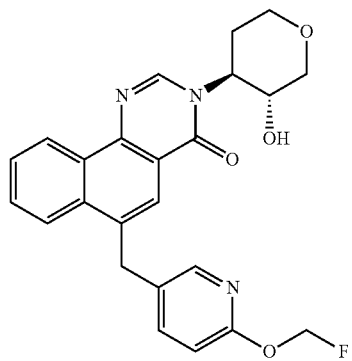
202
-continued
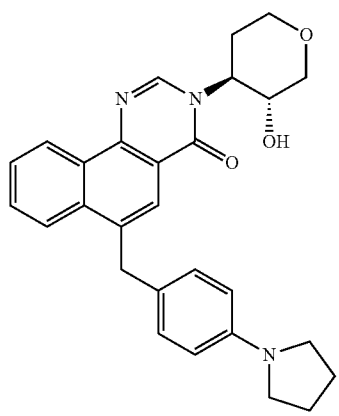
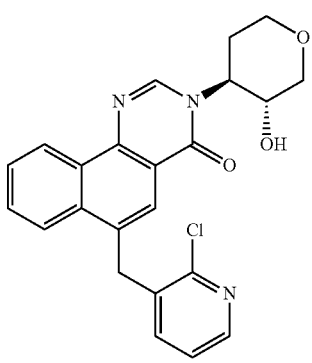
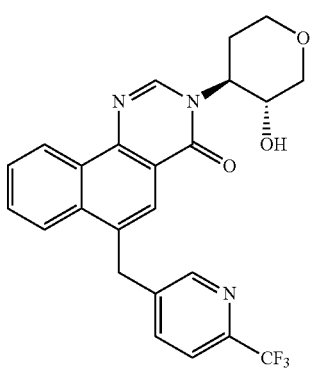
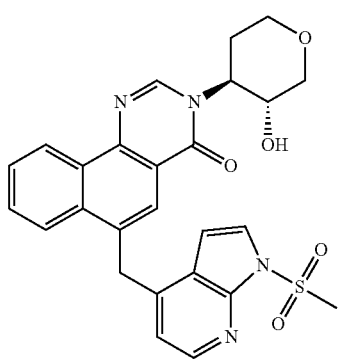

| 203 -continued | 204 -continued |
|---|---|
| 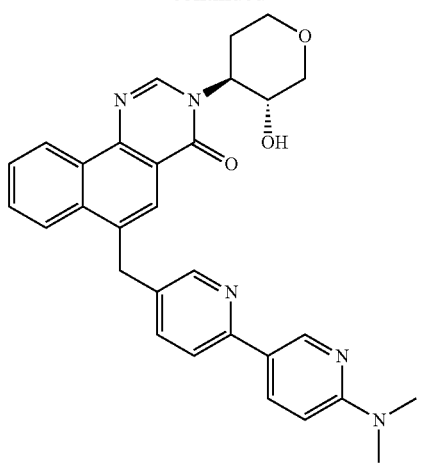 | 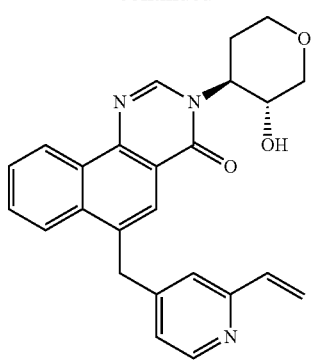 |
| 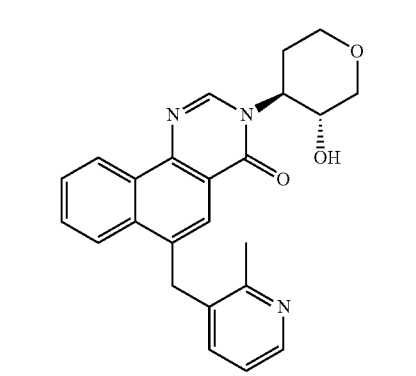 | 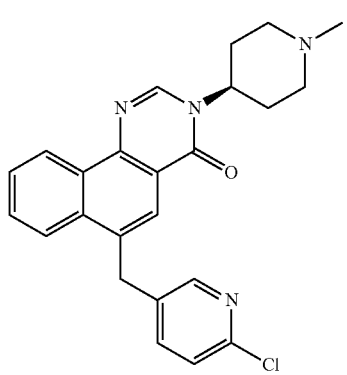 |
| 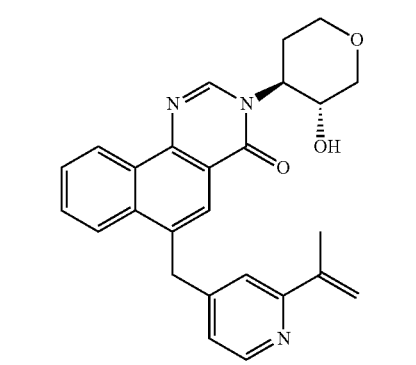 | 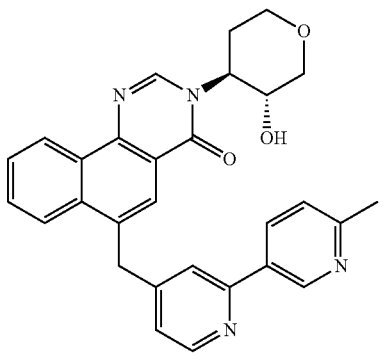 |
| 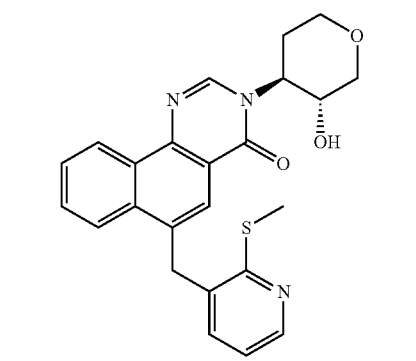 | 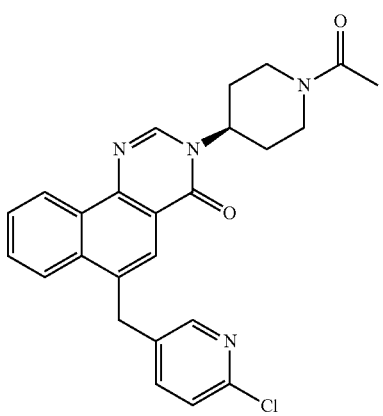 |

205
-continued
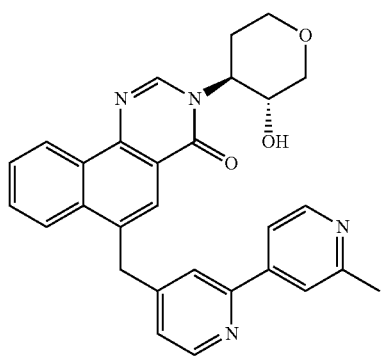
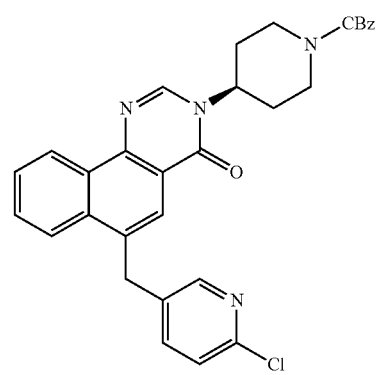
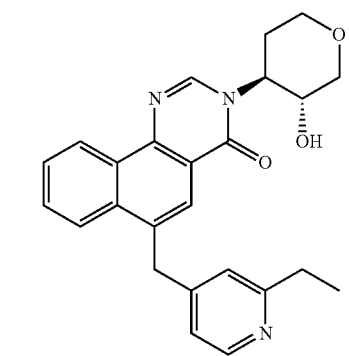
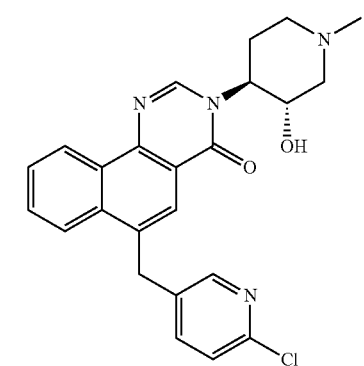
206
-continued
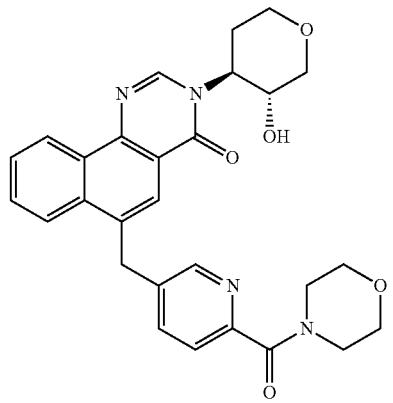
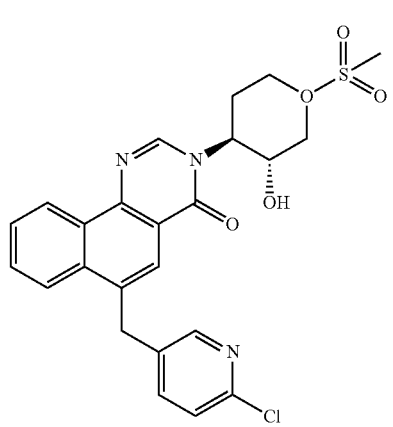
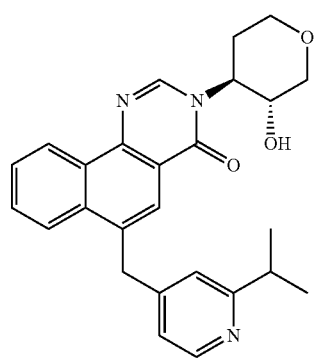
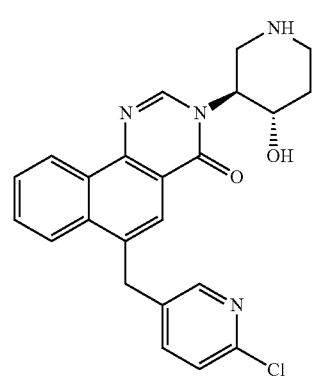

207
-continued
208
-continued
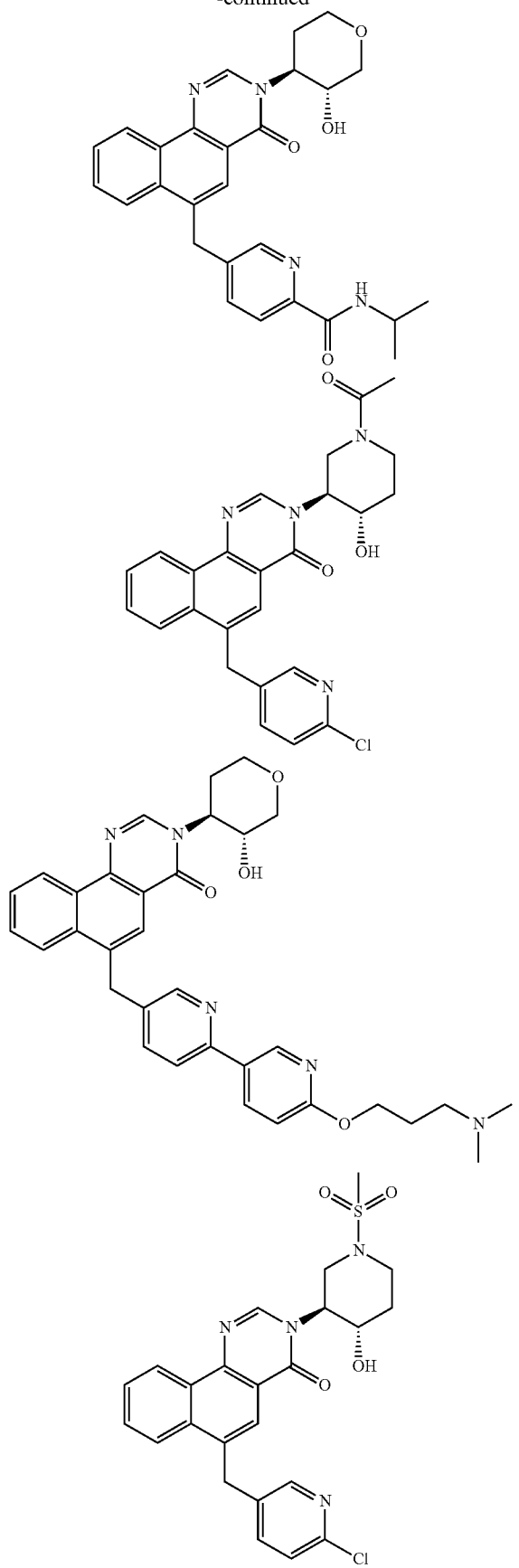
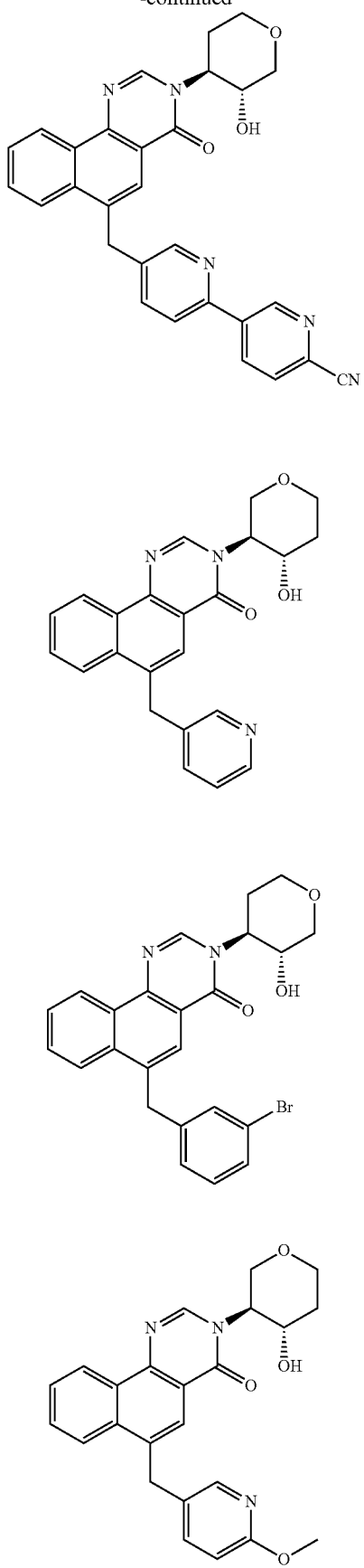

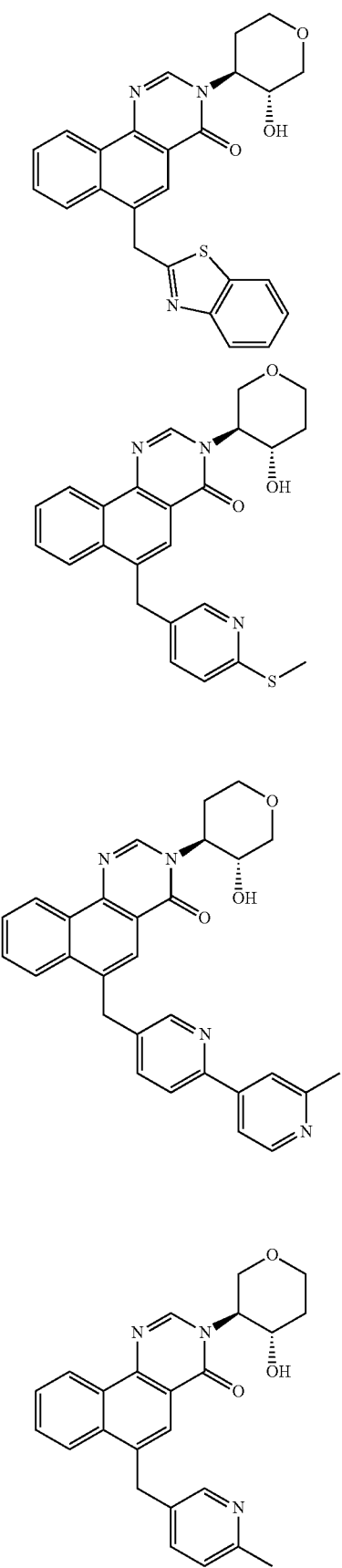
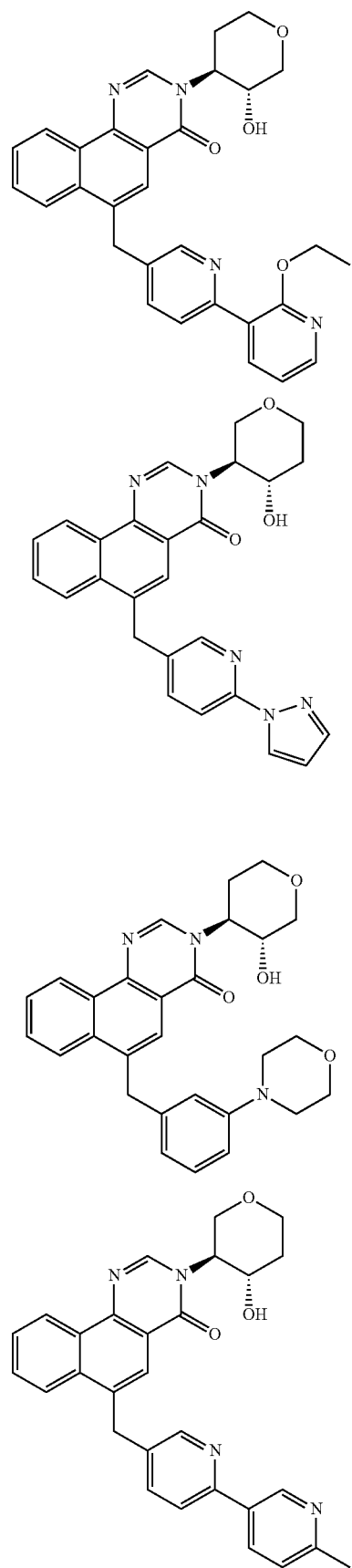

211
-continued
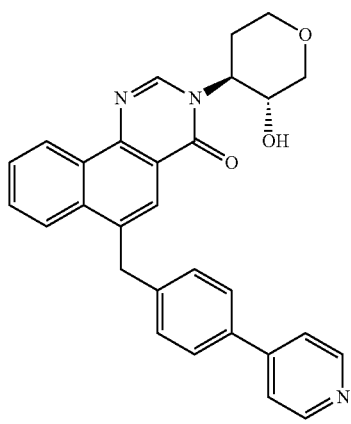
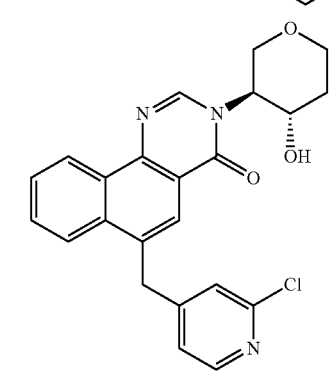
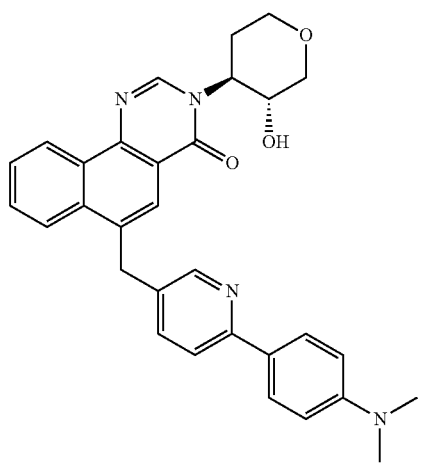
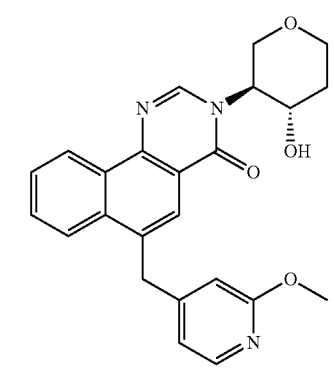
212
-continued
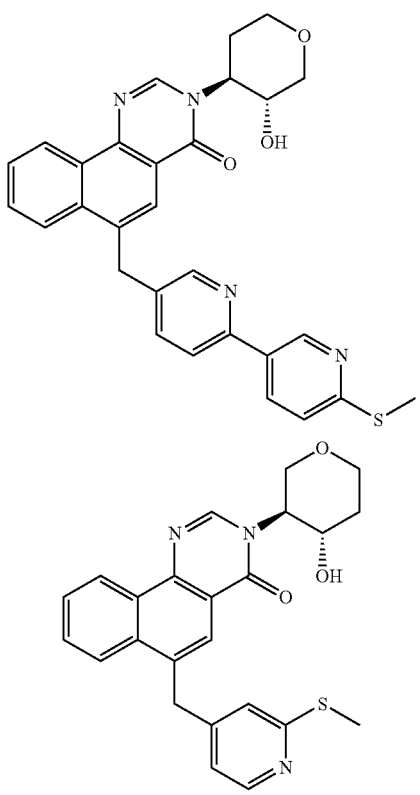
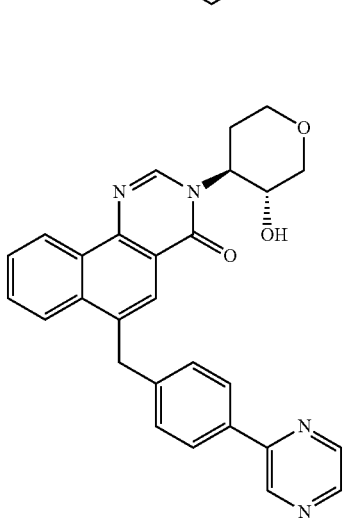
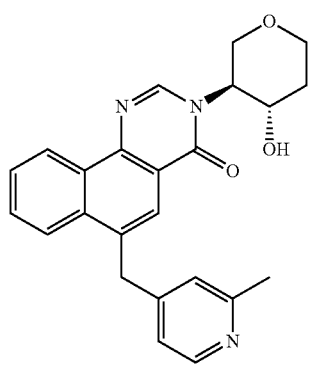

213
-continued
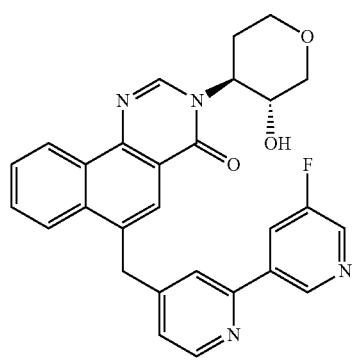
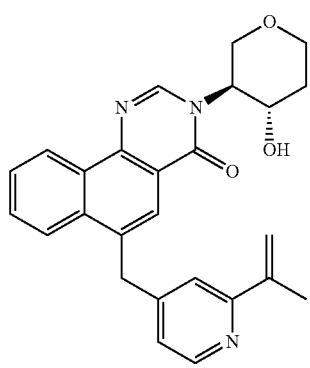
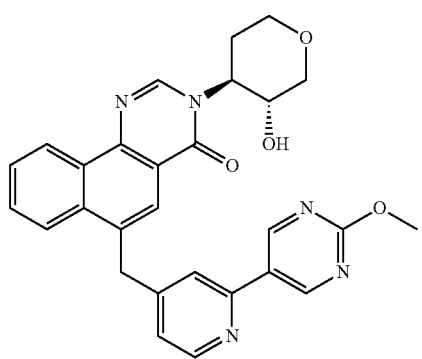
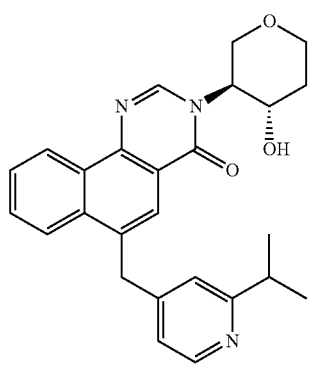
214
-continued
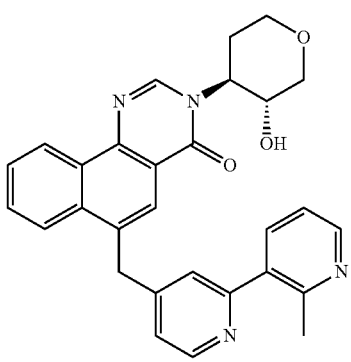
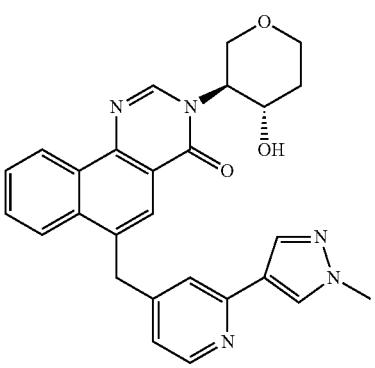
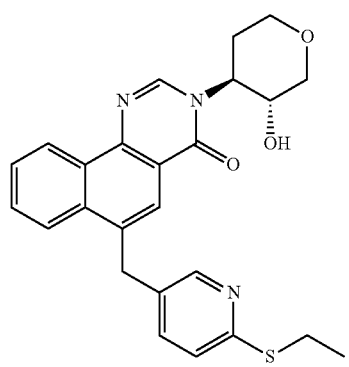
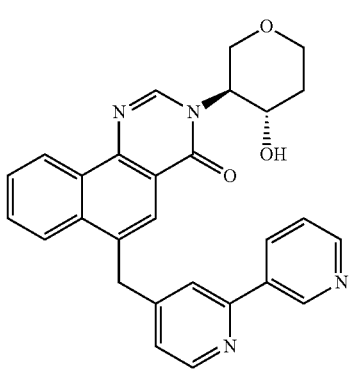

-continued
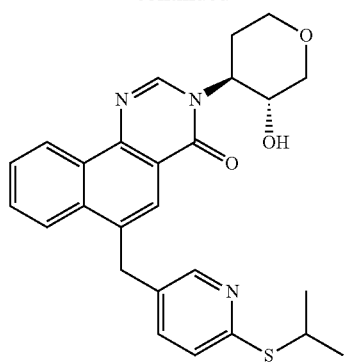
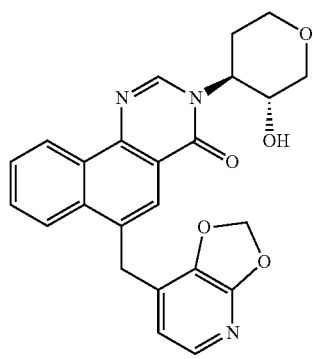
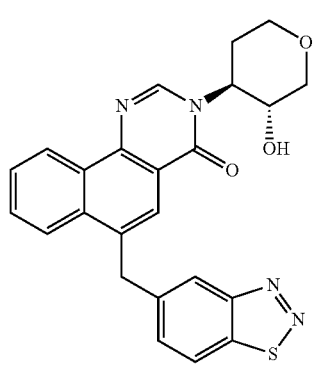
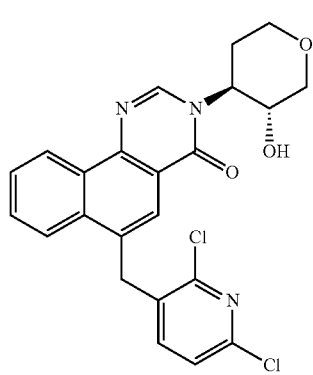
-continued
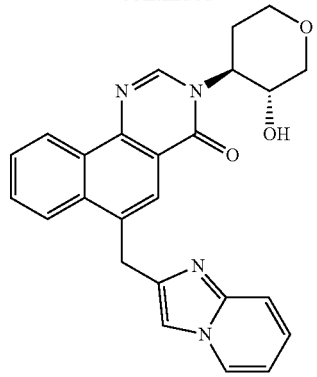
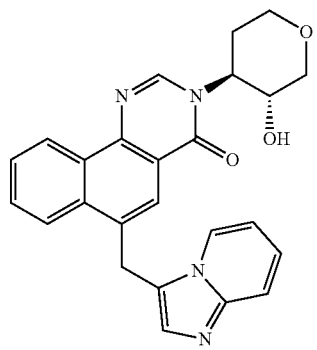
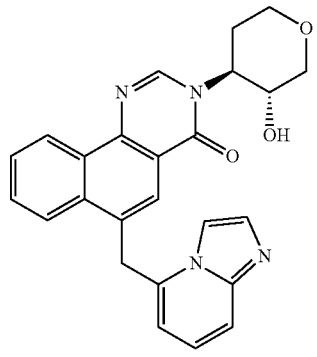
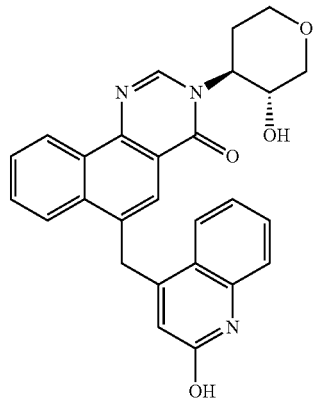

217
-continued

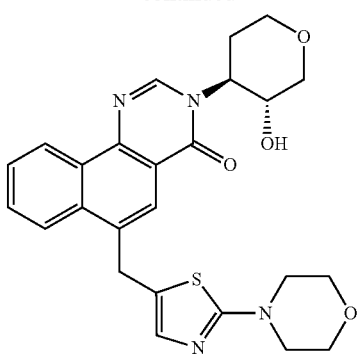

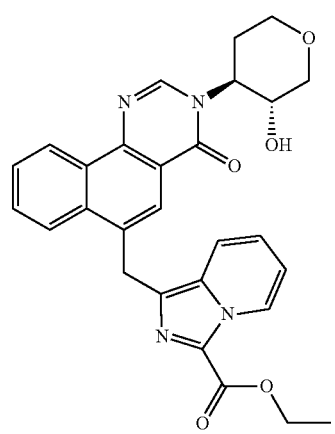

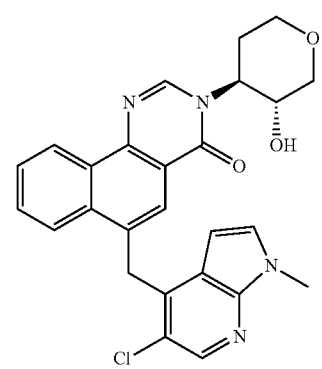

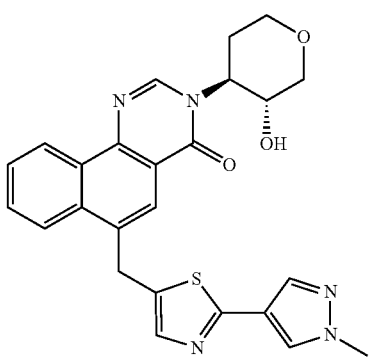

218
-continued

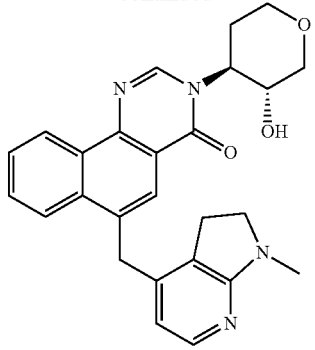

or a pharmaceutically acceptable salt thereof.

25. A pharmaceutical composition comprising a therapeutically effective amount of a compound of claim 1, or a pharmaceutically acceptable salt thereof, and a pharmaceutically acceptable carrier.

26. A compound which is 6-[(6-Chloropyridin-3-yl)methyl]-3-[(3R, 4S)-3-hydroxytetrahydro-2H-pyran-4-yl]benzo[h]quinazolin-4(3H)-one; or a pharmaceutically acceptable salt thereof.

27. The compound according to claim 26 which is 6-[(6-Chloropyridin-3-yl)methyl]-3-[(3R, 4S)-3-hydroxytetrahydro-2H-pyran-4-yl]benzo[h]quinazolin-4(3H)-one.

28. The compound according to claim 26 which is a salt of 6-[(6-Chloropyridin-3-yl)methyl]-3-[(3R, 4S)-3-hydroxytetrahydro-2H-pyran-4-yl]benzo[h]quinazolin-4(3H)-one.

29. A compound which is 3-[(3R, 4S)-3-Hydroxytetrahydro-2H-pyran-4-yl]-6-{[(6-methylthio)pyridin-3-yl)methyl]benzo[h]quinazolin-4(3H)-one; or a pharmaceutically acceptable salt thereof.

30. The compound according to claim 29 which is 3-[(3R, 4S)-3-Hydroxytetrahydro-2H-pyran-4-yl]-6-{[(6-methylthio)pyridin-3-yl)methyl]benzo[h]quinazolin-4(3H)-one.

31. The compound according to claim 29 which is a salt of 3-[(3R, 4S)-3-Hydroxytetrahydro-2H-pyran-4-yl]-6-{[(6-methylthio)pyridin-3-yl)methyl]benzo[h]-quinazolin-4(3H)-one.

32. A compound which is 3-[(3R, 4S)-3-Hydroxytetrahydro-2H-pyran-4-yl]-6-[(6-methylpyridin-3-yl)methyl]benzo[h]quinazolin-4(3H)-one; or a pharmaceutically acceptable salt thereof.

33. The compound according to claim 32 which is 3-[(3R, 4S)-3-Hydroxytetrahydro-2H-pyran-4-yl]-6-[(6-methylpyridin-3-yl)methyl]benzo [h]quinazolin-4(3H)-one.

34. The compound according to claim 32 which is a salt of 3-[(3R, 4S)-3-Hydroxytetrahydro-2H-pyran-4-yl]-6-[(6-methylpyridin-3-yl)methyl]benzo [h]quinazolin-4(3H)-one.

35. A compound which is 3-[(3R, 4S)-3-Hydroxytetrahydro-2H-pyran-4-yl]-6-{[6-(1-methyl-1H-pyrazol-4-yl)pyridine-3-yl]methyl}benzo[h]quinazolin-4(3H)-one; or a pharmaceutically acceptable salt thereof.

36. The compound according to claim 35 which is 3-[(3R, 4S)-3-Hydroxytetrahydro-2H-pyran-4-yl]-6- {[6-(1-methyl-1H-pyrazol-4-yl)pyridine-3-yl]methyl}benzo[h]quinazolin-4(3H)-one.

37. The compound according to claim 35 which is a salt of 3-[(3R, 4S)-3-Hydroxytetrahydro-2H-pyran-4-yl]-6-{[6-(1-methyl-1H-pyrazol-4-yl)pyridine-3-yl]methyl}benzo[h]quinazolin-4(3H)-one.

38. A compound which is 3-[(3R, 4S)-3-Hydroxytetrahydro-2H-pyran-4-yl]-6-{[6-(1H-pyrazol-1-yl)pyridine-3-yl]methyl}benzo[h]quinazolin-4(3H)-one; or a pharmaceutically acceptable salt thereof.

39. The compound according to claim 38 which is 3-[(3R,4S)-3-Hydroxytetrahydro-2H-pyran-4-yl]-6-{[6-(1H-pyrazol-1-yl)pyridine-3-yl]methyl}-benzo[h]quinazolin-4(3H)-one.

40. The compound according to claim 38 which is a salt of 3-[(3R, 4S)-3-Hydroxytetrahydro-2H-pyran-4-yl]-6-{[6-(1H-pyrazol-1-yl)pyridine-3-yl]methyl}benzo-[h]quinazolin-4(3H)-one.

* * * * *